United States Patent
Kerr et al.

(10) Patent No.: US 7,704,963 B2
(45) Date of Patent: Apr. 27, 2010

(54) **LPS-RESPONSIVE *CHS1/BEIGE*-LIKE ANCHOR GENE AND THERAPEUTIC APPLICATIONS THEREOF**

(75) Inventors: William G. Kerr, Tampa, FL (US); Jia-Wang Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 1351 days.

(21) Appl. No.: 10/473,741

(22) PCT Filed: Apr. 2, 2002

(86) PCT No.: PCT/US02/10350

§ 371 (c)(1),
(2), (4) Date: Mar. 18, 2004

(87) PCT Pub. No.: WO02/078614

PCT Pub. Date: Oct. 10, 2002

(65) Prior Publication Data

US 2004/0235765 A1    Nov. 25, 2004

Related U.S. Application Data

(60) Provisional application No. 60/280,107, filed on Apr. 2, 2001.

(51) Int. Cl.
*A01N 43/04* (2006.01)
*C12Q 1/68* (2006.01)
*C12P 19/34* (2006.01)
*C07H 21/02* (2006.01)
*C07H 21/04* (2006.01)

(52) U.S. Cl. .......................... 514/44; 435/6; 435/91.31; 435/455; 536/23.1; 536/24.31; 536/24.5

(58) Field of Classification Search ..................... 435/6, 435/91.1, 91.31, 455, 375; 514/1, 2, 44; 536/23.1, 24.5, 24.31
See application file for complete search history.

(56) References Cited

OTHER PUBLICATIONS

Webb et al. Bcl-2 antisense therapy in patients with non-Hodkin lymphoma. Lancet, 1997 vol. 349:1137-1141.*
Peracchi, A. et al., Rev. Med. Virol., vol. 14, pp. 47-64 (2004).*
Chirila, T. et al., Biomaterials, vol. 23, pp. 321-342 (2002).*
Agrawal, S. et al., MOlecular Med. Today, vol. 6, pp. 72-81 (2000).*
Crooke, S. Antisense Research & Application, Chapter 1, pp. 1-50 (Springer-Verlag, Publ.) S. Crooke, Ed.) (1998).*
Opalinska, J.B., et al., Nature Reviews, vol. 1, pp. 503-514 (2002).*
Bransh, A., Trends in Biochem. Sci., vol. 23, pp. 45-50 (1998).*
Holen, T. et al., Nucleic Acids Res., vol. 30, No. 8, pp. 1757-1766 (2002).*
Karim, M.A. et al. "Mutations in the Chediak-Hiagashi Syndrome Gene (CHS1) indicate requirement for the complete 3801 amino acid CHS protein" *Human Molecular Genetics*, 1997, pp. 1087-1089,vol. 6, No. 7.
Nagle, D.H. et al. "Identification and mutation analysis of the complete gene for Chediak-Higashi Syndrome" *Nature Genetics*, 1996, pp. 307-311, vol. 14.
Perou, C.M. et al. "The Beige/Chediak-Higashi Syndrome Gene encodes a widely expressed cytosolic protein" *J. Biol. Chem.*, 1997, pp. 29790-29794, vol. 272, No. 47.
Shiflett, S.L. et al. "Chediak-Higashi Syndrome: A rare disorder of lysosomes and lysosome related organelles" *Pigment Cell Res.*, 2002, pp. 251-257, vol. 15.
Spritz, R.A. "Genetic defects in Chediak-Higashi Syndrome and the beige mouse" *J. Clin. Immun.*, 1998, pp. 97-105, vol. 18, No. 2.
Wang, J-W. et al. "Identification of a novel LPS-inducible gene that involves in apoptosis and has key features of both protein kinase A anchor and chs1/beige genes" *FASEB J.*, 2001, p. A1175, vol. 15, No. 5.
Wang, J-W. et al. "Identification of a novel lipopolysaccharide-inducible gene with key features of both a kinase anchor proteins and chs1/beige proteins" *J. Immun.*, 2001, pp. 4586-4595, vol. 166.
Wang, J-W. et al. "Inhibition of apoptosis by the BEACH domain and WD repeats of *lba* gene that has key features of both protein kinase A anchor and *CHS1/Beige* genes" *ScientificWorldJournal*, 2001 (B), vol. 1 (1 Suppl 3), No. 96.
Wang, J.W. et al. "Identification of a Novel Lipopolysaccharide-Inducible Gene with Key Features of Both a Kinase Anchor Proteins and chs1/beige Proteins" *The Journal of Immunology*, Apr. 1, 2001, pp. 4586-4595, vol. 166, No. 7, published online Mar. 19, 2001.
Examination Report dated Dec. 28, 2006 in European Application No. 02731226.3, pp. cover page, 1-7.
Examination Report dated Dec. 18, 2007 in European Application No. 02731226.3, pp. cover page, 1-4.
Examination Report dated Dec. 8, 2008 in European Application No. 02731226.3, pp. cover page, 1-2.

* cited by examiner

*Primary Examiner*—Jane Zara
(74) *Attorney, Agent, or Firm*—Saliwanchik, Lloyd & Saliwanchik

(57) ABSTRACT

The present invention relates to a novel LPS-responsive and Beige-like Anchor gene (lrba), variants of the lrba gene, fragments of the lrba gene, and polypeptides encoded thereby. The subject invention also pertains to lrba interfering RNA, and uses thereof. In another aspect, the present invention also includes methods of inhibiting tumor growth in a patient by suppressing lrba function.

11 Claims, 21 Drawing Sheets

FIG. 1A

MASEDNRAPSRPFTGDDGGGGKEETPTEGGALSLKPGLPIRGIRMKFAVLTG
LVEVGEVSNRDIVETVFNLLVGGQFDLEMNFIIQEGESIMCMVELLEKCDVTC
QAEVWSMFTAILKKSIRNLQVCTEVGLVEKVLGKIEKVDSMIADLLVDMLGVL
ASYNLTVRELKLFFSKLQGDKGQWPPHAGKLLSVLKHMPQKYGPDAFFNFPGK
SAAAIALPPIARWPYQNGFTFHTWLRMDEVNNINVDKDKPYLYCFRTSKGLGY
SAHFVGGCLITTSIKSKGKGFQHCVKEDFKPQKWYMVTIVHIYNRWKNSELRC
YVNGELASYGEITWFVNTSDTFDKCFLGSSETADANRVFCGQMTAVYLFSDAL
NBAQIFAIYQLGLGYKGTFKFKAESDLFLAEHHKLLLYDGKLSSAIAEMYNPR
ATDAQLCLESSPKDNPSIFVHSPHALMLQDVKAVLTHSIQSAMHSIGGVQVLF
PLFAQLDYKQYLSDEVDLTICTTLLAFIMELLKNSIAMQEQMLACKGFLVIGY
SLEKSSKSHVSRAVLELCLAPSKYLSNLQNGMPLLKQLCDHILLNPAVWIHTP
AKVQLMLYTYLSTEFIGTVHIYNTIRRVGTVLLIMHTLKYYWAVNPQDRSGI
TPKGLDGPRPNQKEILSLRAFLLMFIKQLVMKDSGVKEDELQAILNYLLTMHE
DDNLMDVLQLLVALMAEHPNSMIPAFDQRNGLRVIYKLLASKSEGIRVQALKA
LGYFLKHLAPKRKAEVMLGHGLFSLLAERLMLQTNLITMTMYNVLFEILIEQI
CTQVIHKQRPDPDSTVKIQNPQILKVIATLLRNSPQCPESMEVRRAFLSDMIK
LFNNSRENRRSLLQCSVWQEWMLSLCYFNPKNSDEQKITEMVYAIFRILLYHA
VKYEWGGWRVWVDTLSITHSKVTFEIHKENLANIFREEQRKGDEETGPCSSSL
VPEGTGATRGVDVSVGSQHEDRKDSPISPHFTRNSDENSSIGRASSIDSASNT
ELQTHDMSSDEKKVERENQELLDQATVEETATNGAKDDLETSSDAAEPVTINS
NSLEPGKDTVTISEVSASISSPSEEDAAEMPELLEKSGVEEKEDDDYVELKVE
GSPTEEAGLPTELQGEGLVSAASGGREEPDMCGHGCEVQVEAPITKIHNDPET
TDSEDSRFPTVATAGSLATSSEVPVPQATVQSDSPEMLDGGMKATNLAGETES
VSDCADNVSEAPATSEQKITKLDVSSVASDTERFELKASTSTEAPQPQRHGLE
ISRQQEQTAQGTAPDAVDQQRRDSRSTMFRIPEFKWSQMRQRLLTDLLFSIET
DIQMWRSHSTKTVMDFVNSSDNVL[...]GGILPLLSA
ATSATHELENIEPTQGLSIE[...]SLGFTEIEAEKNM
SSGGILRQCLRLVCAVAVRNCLECQQHSQLKARGDTAKSSKTIHSLIPMGKSA
AKSPVDIVTGGISSVRDLDRLPARTWTLIGLRAVVFRDIEDSKQAQFLALAVV
YFISVLMVSKYRDILEPQDERHSQSLKETSSDNGNASLPDAENTPAEFSSLTL
SSVEESLEGTSCTRRRDSGLGEETASGLGSGLVSASPAAPLGVSAGPDAISEV
LCTLSLEVNKSQETRIDGGNELDRKVTPSVPVSKNVNVKDILRSLVNMPADGV
TVDPALLPPACLGALGDLSVDPPMQFRSFDRSVIIATKKSSVLPSALTTSAPS
SAVSVVSSVDPTHASDTGGESPGSRSPKCKTALSCKQLAPSHKTPAAHMSITE
RLEHALEKAAPLLREIFVDFAPFLSRTLLGSHGQELLIEGTSLVCMKSSSSVV
ELVMLLCSQEWQNSIQKNAGLAFIELVNEGRLLSQTMKDHLVRVANEAEFILS
RQRAEDIHRHAEFESLCAQYSADKREEEKMCDHLIRAAKYRDHVTATQLIQKI
INLLTDKHGAWGSSAVSRPREFWRLDYWEDDLRRRRRFVRNPLGSTHPEATLK
TAVEHAADEDILAKGKQSIKSQALGNQNSENEALLEGDDDTLSSVDEKDLENL
AGPVSLSTPAQLVAPSVVVKGTLSVTSSELYFEVDEEDPNFKKIDPKILAYTE
GLHGKWLFTEIRSIFSRRYLLQNTALEIFMANRVAVMFNFPDPATVKKVVNYL
PRVGVGTSFGLPQTRRISLATPRQLFKASNM[...]QRWQRREISNFEYLMFLNTIA
GRSYNDLNQYIPVFFWVITNYESEELDLTLPSNFRDLSKPIGALNPKRAAFFAE
RFESWEDDQVPKFHYGTHYSTASPVLAWLLRIEPFTTYFLNLQGGKFDHADRT
FSSVSRAWHNSQRDTSDIKELIPEFYILPEMFVNFNNYNLGVMDDGTVVSDVE
LPPWAKTSEEFVRINRLALESEFVSCQLHQWIDLIFGYKQQGPEAVRALNVFY
YLTYEGAVNLNSITDPVLREAVEAQIRSFGQTPSQLLIEPHPPRGSAMQASPL
MFTDQAQQDVIMVLKFPSNSPVTHVAANTQPGLAMPAVITVTANRLFAVNKWH
NLPAHQGAVQDQPYQLPVEIDPL[...]ACGTGTHRRQVTDLLDQSIQVHSQCFVIT
SDNRYILVCGFWDKSFRVYSTDTGKLIQVVEGHWDVVTCLARSESYIGGNCYI
LSGSRDATLLLWYWNGKSSGIGDNPGGETATPRAILTGHDYEITCAAVCAELG
LVLSGSQEGPCLIHSMNGDLLRTLEGPENCLKPKLIQASREGHCVIFYENGCF
CTFSVNGKLQATVETDDHI[...]AIQLSRDGQYLLTGGDNGVVIVRQVSDLKQLFA
YPGCDAGIRAMALSFDQRCIISGMASGSIVLFYNDFNRWHHEYQTRY

FIG. 1B

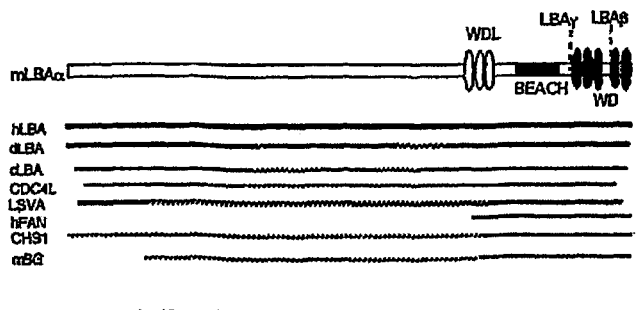

— significant homology    ---- no significant homology

FIG. 3

G peptide
MASEDNRVPSPPPTGDDGGGGGREETFTEGGALSLKFGDEIRGIRMKFAV 50
ITGLVEVGEVSNRDIVETVFMI*  ε    HSH domain
         ⇨LVGGQFDLEMNFIIQEGESINEMVDLLE 100
KCDITCQAEVWSMFTATLKKSIRNLQVCTEVGLVEKVLGKIEKVDNMIAD 150
LLVDMLGVLASYNLTVRELKLPFSKLQGDKGRWPPHAGKLLSVLKHMPQK 200
YGPDAFFNFPGKSAAAIALPPIAKWPYQNGFTFRTWLRMDPVNNINVDKD 250
KFYLYCFRTSKGLGYSAHFVGGCLIVTSIKSKGKGFQHCVKFDFKPQKWY 300
MVTIVHIYNRWKNSELRGYVNGRLASYGEITWFVNTSDTFDKCFLGSSET 350
ADANRVFGGQMIAVYLFSEALNAAQIFAIYQLGLGYKGTFKFKAESDLFL 400
AEHHKLLLYDGKLSSAIAFTYNPRATDAQLCLESSPKDNPSIFVHSPHAL 450
MLQDVKAVLTHSIQSAMHSIGGVQVLFPLFAQLDYRQYLSDEIDLTICST 500
LLAFIMELLKNSIAMQEQMLACKGFLVIGYSLEKSSKSHVSRAVLELCLA 550
FSKYLSNLQNGMPLLKQLCDHVLLNPAIWIHTPAKVQLMLYTYLSTEFIG 600
TVNIYNTIRRVGTVLLIMHTLKYYYWAVNPQDRSGITPKGLDGPRPNQKE 650
MLSLRAFLLMFIKQLVMKDSGVKEDELQAILNYLLTMHEDDNLMDVLQLL 700
VALMSEHPNSMIPAFDQRNGLRVIYKLLASKSEGIRVQALKAMGYFLKHR 750
PPKRKAEVMLGHGLFSLLAERLMLQTNLITMTTYNVLFEILIEQIGTQVI 800
HKQHPDPDSSVKIQNPQILKVIATLLRNSPQCPESMEVRRAFLSDMIKLF 850
NNSRENRRSLLQCSVWQEWMLSLCYFNPKNSDEQKITEMVYAIFRILLYH 900
AVKYEWGGWRVWVDTLSITHSKVTFEIHKENLANIFREQQGKVDEEIGLC 950
              SET domain
SSTSVQAASGIRRDINVSVGSQQPDTKDSPVGPHFTTNGNENSSTEKTSS 1000
EESASNIELQTTNFTSYEEMKAEQENQELPDEGTLEETITNETRNADDLEV 1050
SSDIIEAVAISSNSRITTGKDSMTVSEVTASISSPSEEDASEMPEFLDKS 1100
LVEEEEDDDYVELKVEGSPTEPANLPTELQDNSLSPAASEAGEKLDMFGN 1150
DDKLIFQEGKPVTEKQTDTETQDSKDSGIQTMTASGSSAMSPETTVSQTA 1200
VESDLGQMLEEGKKATNITRETKLINDCHGSVSEASSEQKIAKLDVSNVA 1250
IDTERDELKASPNVEAPQEHRHVLEISRQHEQPGQGIAPDAVNGQRRDSR 1300
STVFRIPEFNWSQMHQRLLTDLLFSIETDIQMWRSHSTKTVMDFVNSSDN 1350
VIFVHNTIHLISQVMDNMVMACGGILPLLSAATSATHELENIEPTQGLSI 1400
EASVTFLQRLISLVDVLIFASSLGFTEIEAEKSMSSGGILRQCLRLVCAV 1450
AVRNCLECQQHSQLKTRGDKALKPMHSLIPLGKSAAKSPVDIVTGGISPV 1500
RDLDRLLQDMDINRLRAVVFRDIEDSKQAQFLALAVVYFISVLMVSKYRD 1550
ILEPQNERHSQSCTETGSENENVSLSEITPAAFSTLTTASVEESESTSSA 1600
RRRDSGIGEETATGLGSHVEVTPHTAPPGVSAGPDAISEVLSTLSLEVNK 1650
SPETKNDRGNDLDTKATPSVSVSKNVNVKDILRSLVNIPADGVTVDPALL 1700
PPACLGALGDLSVEQPVQFRSFDRSVIVAAKKSAVSPSTFNTSIPTNAVS 1750
VVSSVDSAQASDMGGESPGSRSSNAKLPSVPTVDSVSQDPVSNMSITERL 1800
EHALEKAAPLLREIFVDFAPFLSRTLLGSHGQELLIEGTSLVCMKSSSSV 1850
VELVMLLCSQEWQNSIQKNAGLAFIELVNEGRLLSQTMKDHLVRVANEAE 1900
FILSRQRAEDIHRHAEFESLCAQYSADKREDEKMCDHLIRAAKYRDHVTA 1950
TQLIQKIINILTDKHGAWGNSAVSRPLEFWRLDYWEDDLRRRRRPVRNPL 2000
              WDL domain
GSTHPEATLKTAVEHVCIFKLRENSKATDEDILAKGKQSIRSQALGNQNS 2050
ENEILLEGDDDTLSGVDEKDLENLAGPVSLSTFAQLVAPSVVVKGTLSVI 2100
SSELIFEVDEEDPNFKKIDPKLLAYTEGLHGKWLFTEIRSIFSRRYLLQN 2150
IALEIFMANRVAVMFNFPDPATVKKVVNFLPRVGVGTSFGLPQTRRISLA 2200
              BEACH domain
SPRQLFKASNMTQRWQHREISNFFYLMFLNTIAGRSYNDLNQYPVFPWVT 2250
TNYESEELDLTLPTNFRDLSKPIGALNPKRAAFFAERYESSWEDDQVPKFH 2300
YGTHYSTASFVLAWLLRIEPFTTYFENLQGGKFDHADRTFSSISRAWRMS 2350
QRDTSDIKELIPEFYLPEMEVNFNNYNLGVMDDGTVVSDVELPPWAKTS 2400
SEFVHINRLVR* δ
          ⇨ALESEFVSCQLHQWIDLIFGYKQQGPEAVRALNVFYYLTYE 2450
GAVNLNSITDPVLREAVEAQIRSFGQTPSQLLIEPHPPRGSAMQVYLLLQ  γ
                                        ⇨SPLMF 2500
TDKAQQDVIMVLKFPSNSPVTHVAANTQPGLATPAVITVTANRLFAVNKW 2550
HNLPAHQGAVQDQPYQLPVEIDPLIGLSLPSLFAIH* β
     WD1            ⇨ASNTGMHRRQITDLLDQSIQVHSQC 2600
FVITSDNRYILVCGFWDKSFRVYSTDTGRLIQVVEGHWDVVTCLARSESY 2650
    WD2                              WD3
IGGNCYILSGSRDATLLLWYWNGKCSGIGDNPGSETAAPRAILTGHDYEV 2700
TCAAVCAELGLVLSGSQEGPCLIHSMNGDLLRTLEGPENCLKPKDIQASR 2750
EGHCVIFYENGLFCTFSVNGKLQATMETDDNIRAIQLSRDGQYLLTGGDR 2800
    WD4                    WD5

FIG. 9

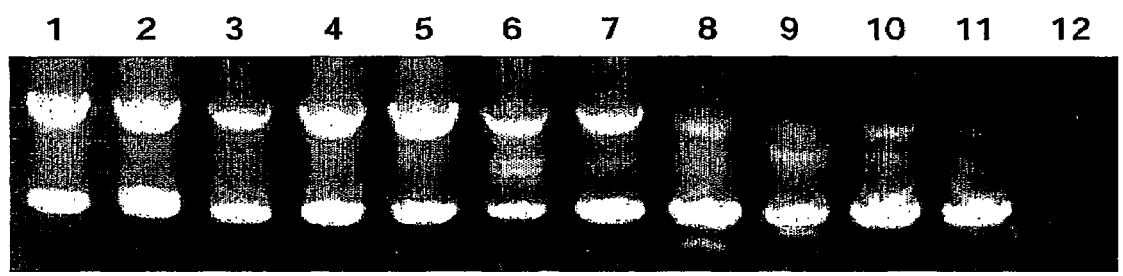
FIG. 14
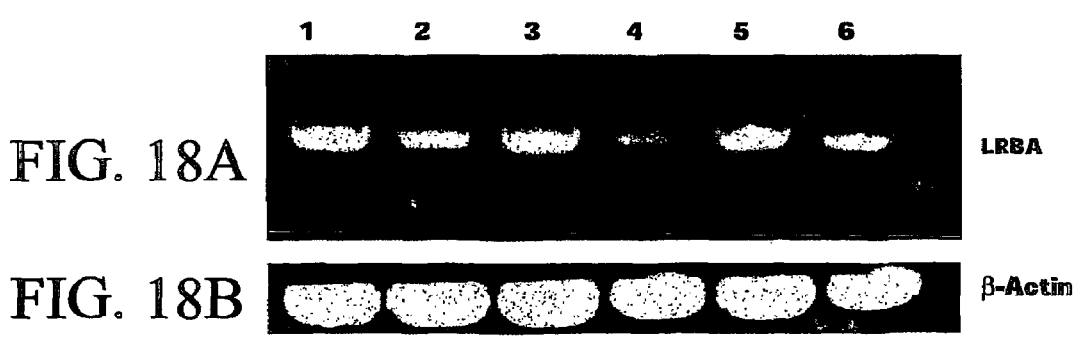

```
GGGGTGAGGACGAGTCCGGAGTATCTGGGGTTGGCGTGTGTCAGCCTCGGGAGAGA    60
GATTGGACAAATATTCTCCAAGAGGAGGAGGGCGACGCCAAGGACTTTCCACATCAACTG  120
CTTTGGGTATCTCCACAAGTGGAAGAGAGGACCCTTCGTTTGCATTGCGTGTGTTGT   180
GCTCATTACCAGTGCAGCGACTGCCGTCCCAGGGTGACTCTGAGTTGTCCTTTATCGTGA  240
GCTAGCA ATG GCT AGC GAT GAA GAC AAT CGT GTC CCT TCC CCG CCA CCA  286
         M   A   S   D   E   D   N   R   V   P   S   P   P   P>
ACA GGT GAT GAC GGG GGA GGT GGA GGG AGA GAA GAA ACC CCT ACT    331
 T   G   D   D   G   G   G   G   G   R   E   E   T   P   T>
GAA GGG GGT GCA TTG TCT CTG AAA CCA GGG CTC CCC ATC AGG GGC    376
 E   G   G   A   L   S   L   K   P   G   L   P   I   R   G>
ATC AGA ATG AAA TTT GCC GTG TTG ACC GTT GGT TTG GTT GAA GTT GGA  421
 I   R   M   K   F   A   V   L   T   V   G   L   V   E   V   G>
GAA GTA TCC AAT AGG GAT ATT GAA ACT GTC TTT AAC CTG            466
 E   V   S   N   R   D   I   E   T   V   F   N   L   *
GAA ACA GAA ATT TGT GGT AGT AAT ACA ATC CAT AAT TAC TTA TTT    511
  *                  *                  *
GTG TGT GAA GAC ACA ACA TCN TTT GGC AGA AGG AGT ATT TGA TTT ACT  556
  *                  *                  *
CCT GTT CTT TAG AAT GTG CTG TGT TGT AGT GGA TGA CCA AAC TTG    601
  *                  *                  *                    L
GTA GGA GGA CAG TTT GAT CTG GAA ATG AAT TTC ATT ATC CAA GAA    646
  *              M   N   F   I   Q   E>
V   G   G   Q   F   D   L   E
```

FIG. 15

```
CCCGGCTTCTGTCCACTTCTCAAGGCCATCTCAAATAACTTTTTCTTCAGGAAACTATTT   -1561
CTCAAACCACTATAATTTTTTCCTAAGTTCTCTAGAATTCTTCCTTTGTTTAATCCCACT   -1501
TTTTGCTTCACTTTCATTTTAGGAGCTAGGCGTATTTTTAAAAAGGCCCTTTGACCTCAA   -1441
AGGATACACGTGGGTGAAAAACCACCTTCCTCTAAATTTATTTTTCACTCACTAGGAAGA   -1381
ATGGTTTACTGTTAATAGCGGGTGGAAAGAAGGGACACTGAGTATGAGGACCTATCTGTA   -1321
CTACCTAATATAATTTATCTTTTGATCTACTCTGAGAATGACGCGAGCCTAATCTTCACA   -1261
TTGGAAAATCACGAGAGGAAAAAACCCTTCGGAGGTCTACAGGCACAAGGAACCCTGTCT   -1201
CCACGCTGTTTATAGCAGCTGTCTCAGGAATCCTCTGCCTAGAATGAATGTGGGAGAGGT   -1141
TTCGTGGCGCGGCAGCTGCAAAGCAAGGAATCTTTCCCATTCCTCGTCGACTCGGTCCCC   -1081
TCCCCTCCCCTCCCGAATGGCGGCAGCTGCCGAGGTATCCCAGTGGAAATCTCCAAGTCT   -1021
CCGCCGAGAGCGGCGGGCGGGCAACAGCTGAAAGCAGCCAGGGGTGGGGACTCCTCGCTC   -961
CCATTGGGCAGGGACAGCAGCCTCACTGGCTCCAGCGCCGTCACCTCTCTGGCTCGTAGA   -901
GGTGCCTCAGGTGTTCTTCTCCAAGTCCAATGAGACACCTAGGCAACGCAGCGCGTGTTC   -841
         E2F                                       E2F
CCTCCGCGCCAAGAGACCCTACGGTAACTTAACAACAGCAGGAGCGCCAAAATCCCCGCC   -781
TCAGGACTTGGCAGAAGCACCTCCCGAGGTCCGAGAGTGGGAGAGGGGAAAGTGTAGGCC   -721
CTCGGACGGAAGGGTCTCTCCTCGCCGGGCCGGGTACACACCTGGTGCTACCAGAGCAGC   -661
GCGCCTAGTGCAGCCGGAAGCCCCAGCCCAGCACTCCGGCTGGCTCGGGGCCCCCTTGGC   -601
                                         E2F
TGTCCGCGCGTGTAACCGCGCCCCGGCCGCGCGGGTGGCTCCGCTTGGCGGCCTCCCC   -541
GCCCGCGCACTCGCGCTCGCGCACGCGCACGCCGCGCCCGGCAGCACTCGGCGCTGTCAT   -481
                                            Sp1
GGCGGCCGGGAGCAGCTTCAGTGGGCACACGACAGCCGCGCGACCCGTGGCGGGGCGAGC   -421
TGTGGCAGTAGCATCCTCACCACTCGCAGCAGCCTCAGCCGCGGCGCCCGTAGCGCCAGC   -361
                       Sp1   Sp1       c-Ets-
AGCGGCTGCTTTTGCAAAGGCTGAGCGCAGGGGCGGGGCGGGCCAGGAAGCCATGGAGTT   -301
                                                Exon|Intron
CTGTGCAGCCGCGGACTCCCGGGGAGCGGACTAGGGAAACTTGGAGGCTGCGACCAG|TG   -241
            AML-1a
CACTGACCTCTCTGTCCTCCCTTCTCTCCCTGCGGTGGCCGCTGGGTTTCTCTGGCCGCT   -181
CCCCTCCCTTCCTGCCACCACACACACCTCCCCACCCCTTCCCGTCGAATCTCAGGTGCC   -121
                   Tst-1   HSF2
TGAGAGAGGTGCTTCACTCCTCCCACTGGGCCGAGCATTTAGAATAATCACCGCCCCCTT   -61
                            CdxA   CdxA
                                                       Sp1
CCCCCGCCTTTTCCTGCCCTGGATCTCCGCCGCCACCTCGGTCTCGCTGCTCCTGGGCGG   -1
  +1            Exon1  Exon2
         AML-1a       E2F                     C/EBPa
GGGGTGAGGACGAGTCCGGAGTATCTGGGTTTGGCGGTGTTGTCAGCCTCGGGGAGACA   +60
GATA-3,
GATTGGACAAATATTCTCCAAGAGGAGGAGGGCGACGCCAAGGACTTTCCACATCAACTG   +120

CTTTGGGGTATCTCCACAAGTTGGAAGAGGGACCCTTCGTTTTGCATTGCGTGTGTTGT   +180
GCTCATTACCAGTGCAGCGACTGCCGTCCCAGGGTGACTCTGAGTTGTCCTTTATCGTGA   +240
GCTAGCAATGGCTAGCGAAGACAATCGTGTCCCTTCCCCGCCACCAACAGGTGATGACGG   +300
```

FIG. 17

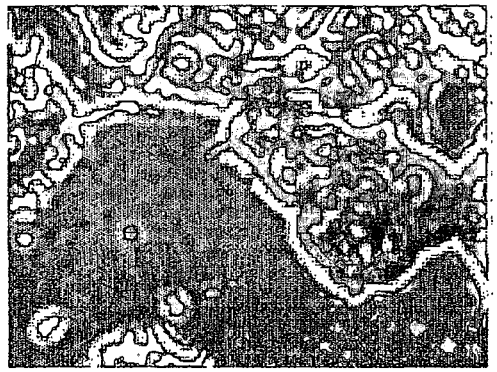 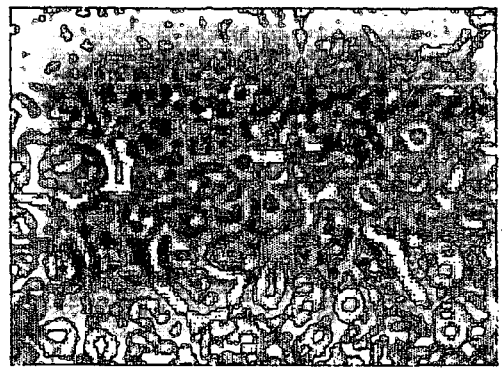
FIG. 21A  FIG. 21B
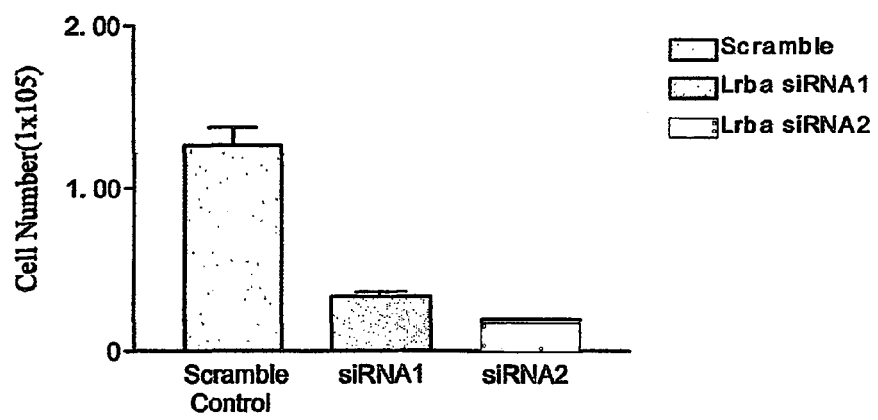
FIG. 21C
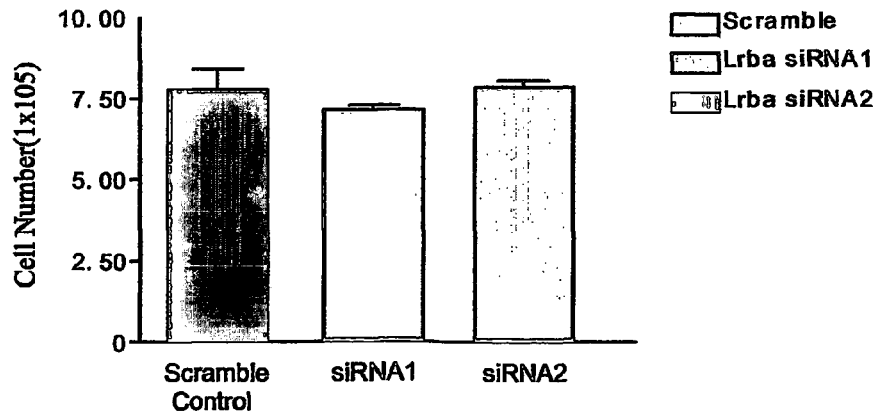
FIG. 21D

LPS-RESPONSIVE *CHS1/BEIGE*-LIKE ANCHOR GENE AND THERAPEUTIC APPLICATIONS THEREOF

CROSS-REFERENCE TO RELATED APPLICATION(S)

This application is a National Stage filing of International Application No. PCT/US02/10350, filed Apr. 2, 2002, which claims the benefit of provisional patent application Ser. No. 60/280,107, filed Apr. 2, 2001, which is hereby incorporated by reference in its entirety, including all nucleic acid sequences, amino acid sequences, figures, tables, and drawings.

The subject invention was made with government support under a research project supported by the National Institutes of Health Grant Nos. RO1 DK54767, R21 AI44333, and PO1 NS27405. The government may have certain rights in this invention.

BACKGROUND OF THE INVENTION

Mutations in chs1/beige result in a deficiency in intracellular transport of vesicles that leads to a generalized immune deficiency in mouse and man. The function of NK cells, CTL, and granulocytes is impaired by these mutations indicating that polarized trafficking of vesicles is controlled by chs1/beige proteins. However, a molecular explanation for this defect has not been identified.

Lipopolysaccharide (LPS) is a potent inducer of maturation in B cells, monocytes, and dendritic cells that facilitates production of inflammatory cytokines, nitric oxide, and antigen presentation so that these cells can participate in the immune response to bacterial pathogens (Harris, M. R. et al. *Journal of Immunology*, 1984, 133:1202; Tobias, P.S. et al. *Progress in Clinical & Biol. Res.*, 1994, 388:31; Inazawa, M. et al. *Lymphokine Res.*, 1985, 4:343). In an attempt to identify genes involved in the maturation of immune cells, a gene-trapping strategy was developed to identify mammalian genes whose expression is altered by cellular stimuli (Kerr, W. G. et al. *Cold Spring Harbor Symposia on Quantitative Biology*, 1989, 54:767). Several novel LPS-responsive genes were successfully trapped (Kerr, W. G. et al. *Proc. Natl. Acad. of Sci. USA*, 1996, 93:3947), including the SHIP gene that plays a role in controlling the maturation and proliferation of B cells and monocytes/macrophages in vivo (Huber, M. et al. *Prog. in Biophysics and Molecular Biol.*, 1999, 71:423; Ono, M. et al. *Nature*, 1996, 383:263; Ono, M. et al. *Cell*, 1997, 90:293).

Chediak-Higashi Syndrome (CHS[3]) patients suffer from a systematic immune deficiency characterized by a severe immune defect, hypopigmentation, progressive neurologic dysfunction and a bleeding diathesis (Spritz, R. A. *Jour. of Clinical Immun.*, 1998, 18:97). Specific defects in immune cells include defects in T cell cytotoxicity (Abo, T. et al. *Jour. of Clinical Investigation*, 1982, 70:193; Baetz, K. et al. *Jour. of Immun.*, 1995, 154:6122), killing by NK cells (Haliotis, T. et al. *Jour. of Exper. Med.*, 1980, 151:1039), defective bactericidal activity and chemotaxis by granulocytes and monocytes (Clark, R. A. and H. R. Kimball *Jour. of Clinical Investigation*, 1971, 50:2645). CHS and beige lysosomes also exhibit compartmental missorting of proteins (Takeuchi, K. et al. *Jour. of Exper. Med.*, 1986, 163:665). Other studies have found that beige macrophages are defective for class II surface presentation (Faigle, W. et al. *J. Cell Biol.*, 1998, 141: 1121; Lem, L. et al. *Jour. of Immun.*, 1999, 162:523) and that T cells in CHS patients are defective for CTLA4 surface expression (Barrat, F. J. et al. *Proc. Natl. Acad. of Sci. USA*, 1999, 96:8645). All cells in beige mice and CHS patients bear giant vesicles that cluster around the nucleus. Affected vesicles include lysosomes, platelet dense granules, endosomes, and cytolytic granules. These giant vesicles seem normal in several aspects except for their failure to release their contents, probably resulting from inability of the giant granules to mobilize and/or fuse with the membrane upon stimulation (Baetz, K. et al. *Jour. of Immun.*, 1995, 154:6122). However, despite these very provocative findings there still remains no direct evidence that BG(beige)/CHS1 proteins associate with intracellular vesicles and thus a molecular explanation for defective vesicle trafficking and protein missorting in these diseases is still sought.

BRIEF SUMMARY OF THE INVENTION

The present invention relates to a novel LPS-responsive and Beige-like Anchor gene (lrba), its transcriptional/translational products, and the targeting of the lrba gene for the treatment of cancer. Thus, the present application is directed to the lrba gene, variants of the lrba gene, fragments of the lrba gene, corresponding polypeptides encoding by such nucleotides, and uses thereof. The mouse lrba gene product is disclosed herein in FIG. 1 and the human lrba gene product is disclosed herein in FIG. 9. The lrba gene is associated with the vesicular system, such as the Golgi complex, lysosomes, endoplasmic reticulum, plasma membrane and perinuclear ER, and plays an important role in coupling signal transduction and vesicle trafficking to enable polarized secretion and/or membrane deposition of immune effector molecules. In one aspect, the lrba variants of the subject invention include five isoforms of the lrba gene, including lrba-α, lrba-β, lrba-δ, lrba-γ, and lrba-ε. The sequences of the mouse lrba cDNAs have been deposited in GENBANK with the following GENBANK accession numbers: lrba-α: AF187731, lrba-β: AF188506, lrba-γ AF188507.

The subject invention also relates to cloning and expression vectors containing the lrba gene, and fragments and variants thereof, and cells transformed with such vectors.

In one aspect, the subject invention concerns lrba small interfering RNA (siRNA) sequences useful for the treatment of cancer. Preferably, the siRNA duplex is formed by annealing single-stranded RNA sequences (ssRNA) of 5'CCAG-CAAAGGUCUUGGCUAdTdT3' (SEQ ID NO. 1) and 5'CAGUCGGGUUUGCGACUGGdTdT3' (SEQ ID NO. 2) from the lrba gene.

In a further aspect, the subject invention concerns methods of inhibiting the growth of tumors in a patient by suppressing lrba function. According to the method of the subject invention, suppression of lrba function can be carried out at various levels, including the levels of gene transcription, translation, expression, or post-expression. For example, suppression of lrba gene expression can be carried out using a variety of modalities known in the art for interfering with the production of a functional product of a target gene. For example, siRNA sequences, such as those described above, can be administered to a patient in need thereof. The siRNA can be produced and administered exogenously, or the siRNA can be inserted into an appropriate vector and the vector can be administered to the patient for production of the siRNA in vivo, for example.

The subject invention also provides methods of detecting the presence of lrba nucleic acids, transcriptional products, or polypeptides in samples suspected of containing lrba genes, transcriptional products, or polypeptides.

Another aspect of the subject invention provides kits for detecting the presence of lrba genes, lrba variants, lrba polypeptides, or lrba transcriptional products obtained from the polynucleotide sequences.

BRIEF DESCRIPTION OF DRAWINGS

FIGS. 1A and 1B show the sequence and structure of the mouse lrba gene. FIG. 1A shows the predicted full-length amino acid sequence of the lrba-α (SEQ ID NO. 3) and lrba-β (SEQ ID NO. 4) (stopped at the boxed "R" with the additional sequence VSAVGSTLFLLLGSSK (SEQ ID NO. 5)) and lrba-γ (SEQ ID NO. 6) cDNAs (stopped at the boxed "I" with the additional sequence GLPLLSLFAIH (SEQ ID NO. 7)). Bold amino acids indicate the BEACH domain (2204-2482) based on alignment with 20 other BEACH domains. Eight WD repeats predicted by an algorithm available at http://bmerc-www.bu.edu/psa/request.htm, are underlined or dotted-underlined. The first three WD repeats are not predicted by other programs but resemble WD repeats and thus are referred to herein as WDL (WD-like) repeats. Two putative protein kinase A RII binding sites are shaded. The sequences of the mouse lrba cDNAs have been deposited in GENBANK with the following GENBANK accession numbers: lrba-α: AF187731, lrba-β: AF188506, lrba-γ. AF188507. FIG. 1B shows a schematic diagram of mLRBA protein and alignment of the predicted mLRBA protein with its orthologues and some paralogues. The stop sites for the lrba-β and lrba-γ are indicated by dashed lines. The human LRBA protein (SEQ ID NO. 8) was predicted from a 9.9 kb "hybrid" cDNA sequence with the first 5' 2577 nucleotides from this work (GENBANK accession numbers AF216648) and the rest from the CDC4L partial cDNA sequence (GENBANK accession numbers M83822) (Feuchter, A. E. et al. (1992) *Genomics* 13:1237) except one G was added after position 5696 for two reasons: (i) the G base is present in the cDNA sequence (GENBANK accession numbers AF217149); and (ii) this addition extended the CDC4L ORF by an additional 165 AA that had high homology with mLRBA and other proteins shown in this figure. The dLRBA was predicted from the *drosophila melanogaster* genomic sequence (GENBANK accession number AE003433). cLRBA (GENBANK accession number T20719, *Caenorhabditis elegans*), aCDC4L (GENBANK accession number T00867, *Arabidopsis thaliana*), LSVA (GENBANK accession number AAD52096, *Dictyostelium discoideum*), hFAN (GENBANK accession number NP_0035711, *Homo sapiens*), CHS1 (Chediak-Higashi Syndrome 1, GENBANK accession number NP_000072, *Homo sapiens*), mBG (GENBANK accession number AAB60778, *Mus musculus*).

In FIG. 2A, the conservation of hydrophobic amino acids of putative PKA binging sites in mLRBA (SEQ ID NO. 9), hLRBA (SEQ ID NO. 10), dLRBA (SEQ ID NOs. 11-12), and cLRBA (SEQ ID NO. 13) are shown by aligning with the known B1 and B2 PKA RII tethering sites (underlined) in DAKAP550 (a partial cDNA sequence for dLRBA) along with other sequences in these regions. FIG. 2B shows the predicted secondary structure of the putative PKA binding sites in mLRBA (mLRBAb1, mLRBAb2). The hydrophobic amino acids on the hydrophobic side of the predicted amphipathic helices are boxed.

FIG. 3 shows the alignment of the C-terminal sequences of mLRBA (SEQ ID NO. 14), hLRBA (SEQ ID NO. 15), dLRBA (SEQ ID NO. 16), CHS1 (SEQ ID NO. 17), and hFAN (SEQ ID NO. 18), which include the BEACH domains (in the middle, boxed), 5 WD repeats and the 3 WDL repeats predicted in mLRBA and hLRBA. The predicted SH3, SH2 binding sites and tyrosine kinase recognition sites are also boxed. The C-terminal difference of the three isoforms of the mLRBA, α (SEQ ID NO. 14), β (SEQ ID NO. 19), and γ (SEQ ID NO. 20), are shown here (and FIG. 1B in more detail).

FIG. 4A shows Northern blot hybridization of mRNA from B cell line 70Z/3 and the macrophage cell line J774. Both cell lines were cultured with or without LPS for 20 hours. The poly A+RNA was purified from these cells, run on a denaturing formaldehyde agarose gell, and transferred to a Hybond-N+ filter. The filter was hybridized with the 2.5 kb probe that corresponds to the coding region of the lrba gene including the BEACH and WD domains, as described in the Materials and Methods section. The hybridized filter was exposed to X-ray film for 24 hours. Similar amounts of β-actin mRNA were found in all mRNA tested (Actin panels). FIGS. 4B and 4C show expression of mRNA of three lrba isoforms (α, β, and γ) in B cell lines (FIG. 4B) and tissues (FIG. 4C). Three isoform-specific primer pairs were used to detect the expression of the three isoforms by RT-PCR, the expected product size of the RT-PCR product for the α form is 1344 bp, for the β form 836 bp, and for the γ form 787 bp. Total RNA is analyzed. Aliquots (10 μl) of the PCR products were resolved on 0.8% agarose gels. Three independent experiments were performed and yielded similar results.

FIG. 5A shows the RAW 267.4 macrophage cell line (R7) stably transfected with a BEACH-WD-GFP fusion construct. Most cells have diffuse, cytosolic GFP fluorescence, but some cells show vesicle association of the GFP fusion protein. In FIG. 5B, the same cell line from FIG. 5A was plated on glass-covered plates and stimulated with LPS (100 ng/ml) for 24 hours. Extensive vesicle association of the fusion protein was observed. FIG. 5C shows RAW 267.4 macrophages stably transfected with the control vector pEGFP-N2 that were cultured with 100 ng/ml LPS stimulation. No obvious vesicle association of native GFP was observed. Magnification: 400×. FIG. 5D shows part of an R7 macrophage cell, showing GFP fluorescence. FIG. 5E shows the same part of an R7 macrophage cell as in FIG. 5D, showing acidic lysosomes specifically labeled by LysoTracker Red in living cells. FIG. 5F shows lysosome co-localization (white part) of GFP fusion protein by overlapping pictures of FIGS. 5D and 5E; N=nucleus. FIG. 5G shows R7 macrophage cells, showing GFP fluorescence. FIG. 5H shows the same R7 macrophage cells as in FIG. 5G, showing prominent labeling of the Golgi complex (between the two nuclei) specifically labeled by BODIPY TR ceramide. Other intracellular membranes are weakly labeled. FIG. 5I shows Golgi co-localization (white part) of GFP fusion protein by overlapping pictures shown in FIGS. 5G and 5H. Co-localization was determined by Zeiss LSM 510 software, which allows for a reliability of 99% for actual pixels with both fluorophores. Co-localization mask pixels are converted to white color for clarity. All cells were stimulated with LPS (100 ng/ml) for 24 hours except for FIG. 5A.

FIG. 6A shows a clathrin-coated pit (endocytic, or coated vesicle) labeled with gold particles (open arrow). This is a vesicle forming on the cell surface. The fact that there is clathrin around this vacuole indicates that it is involved in endocytosis and not exocytosis. FIG. 6B shows intense labeling of a primary lysosome (open arrow) and a vesicle on the cell surface (closed arrow). In FIG. 6C, the black arrows show ribosomes lining a profile of endoplasmic reticulum (er). There are three gold particles labeling the ER (open arrow). The gray structure next to the ER is a mitochondrion (m), which is not labeled. FIG. 6D shows a Golgi region of a cell labeled for GFP. The open arrows show gold particles on a Golgi cisterna. FIG. 6E shows labeling of endoplasmic reticulum comprising the perinuclear cisterna (open arrows), and labeling of the plasma membrane of the cell (closed arrows). FIG. 6F shows gold particles surrounding a secondary lysosome in a cell (*). At the top of the lysosome is a coated vesicle (closed arrow) fusing with the lysosome. A portion of ER surrounds the bottom of the lysosome, which is also labeled with gold particles (open arrow). Labeling of the perimeter of the secondary lysosome shows routing of GFP from the cell surface to the lysosome limiting membrane. In FIGS. 6A-6F, e=extracellular space; n=nucleus; er=endoplasmic reticulum; g=Golgi; m=mitochondrion; c=cytoplasm. The size of gold particles is 10 nm.

FIG. 9 shows the predicted full-length amino acid sequence and structure of the human LRBA gene and its five isoforms (SEQ ID NO:182). Each isoform is shown by α (SEQ ID NO. 8), β (SEQ ID NO. 21), γ (SEQ ID NO. 22), δ (SEQ ID NO. 23), ε (SEQ ID NO. 24) at the right of each C-terminus or the five amino acid insertion(γ). Residues in italic letters indicate isoform-specific sequences. Asterisk *=stop codon. Sequences are connected by arrows. The numbers at the right are for the α form. The domains are shaded and named above each domain. Five WD repeats predicted by an algorithm available on the protein sequence analysis (PSA) server at the Boston University website are also shaded or boxed. HSH (helix-sheet-helix); SET: Rich in Serine(S), Glutamic acid(E) and Threonine(T). G peptide has five consecutive glycine. The two potential start codons are boxed. The sequences of the LRBA cDNAs have been deposited in GenBank (accession number NM_006726).

FIG. 12 is based on the BEACH domain. All the sequences are from GeneBank. The numbers in parenthesis are GI numbers.

FIG. 14 shows results of a 5'RACE (rapid amplification of cDNA end) procedure and 3'RACE procedure, respectively, conducted on the human lrba gene. In FIG. 14, the lower band contains an AluSx repeat sequence 312 bp long. RNAs were from: (1.) pre-B (6417); (2.) Raji B cells; (3.) 293 cells; (4.) MCF7 breast cells; (5.) HTB4 lung cancer; (6.) H322 human lung cancer; (7.) A539 human lung cancer; (8.) human lung carcinoma; (9.) human lung carcinoma adjacent tissue; (10.) B-cell lymphoma; (11.) B-cell lymphoma; and (12.) normal adjacent tissue.

FIG. 15 shows the 5' end of the human lrbaϵ isoform with a long 5' UTR (SEQ ID NO. 33). There are four small ORFs before the major ORF of the human lrba gene. The longest small ORF encodes the first 73 amino acids of the hlrba protein (SEQ ID NO. 34) and is in frame with the major ORF, though there are four in-frame stop codons and 6 out-of-frame stop codons, in between which would prevent potential read-through that makes a fusion protein. The other three ORFs encode 20 amino acids, 18 amino acids, and 15 amino acids, respectively. The partial major coding sequence is in bold (SEQ ID NO. 35). The amino acid sequence in italics is present in the main form of the LRBA gene but absent in the delta form of the LRBA gene (SEQ ID NO. 36). The grey shaded sequence is the extra exon that has interrupted the LRBA sequence.

FIG. 17 shows the promoter and part of the 5' cDNA sequence of the human lrba gene (SEQ ID NO. 37). Transcription start sites as determined by 5'RACE procedure are indicated by arrows. Sequence for a CpG island is in bold. The DNA consensus binding motifs for various transcription factors shown in the region −1561 to +1 were identified using the TFSEARCH (version 1.3) software (Yukata Akiyama (Kyoto Univ.)), the first nucleotide of the most 5' cDNA denoted as 1. The initiator methionine is in bold. The transcription binding sites are shaded, boxed, or underlined. The genomic sequences have GenBank accession number AC104796.

FIGS. 18A and 18B show RT-PCR of human prostate tumor tissue and adjacent normal tissue, demonstrating that LRBA expression is increased in human prostate cancer relative to matched normal tissue controls. FIG. 18A shows RT-PCR detection of human LRBA mRNA. FIG. 18B shows RT-PCR detection of human β-Actin mRNA to control for the amounts of mRNA present. The PCR cycle parameters were as follows: 94° C. for 30 seconds, 68° C. for 30 seconds, 72° C. for 1 minute, 25 cycles. The sources from the matched samples are (from left to right) 1, 3, and 5: prostate adenocarcinoma tissue; 2, 4, and 6: normal prostate tissue. Samples 1 & 2, 3 & 4, and 5 & 6, are matched pairs from three different prostate cancer patients.

FIG. 20C shows absolute cell numbers recovered as determined by Coulter Counter. Students' T-test: P<0.0006 for mock versus Lrba siRNA; P<0.0036 for Blank versus Lrba siRNA; P<0.2271 for mock versus blank. The siRNA treated cultures show a statistically significant decrease in cell number as compared to either mock or blank cultures, but there is no significant difference in the number of cells recovered from the mock and blank cultures. The RNA sequences that were annealed to make the Lrba siRNA were: Lrba sense-strand: 5'CCAGCAAAGGUCUUGGCUAdTdT3' (SEQ ID NO. 1); Lrba antisense-strand: 5'UAGCCAAGACCUUUGCUGGdTdT3' (SEQ ID NO. 38).

FIGS. 21A-21D show silencing of the Lrba gene in MCF7 human breast cancer cells and MCF10A human breast normal cells by two pairs of Lrba siRNA (siRNA1 and siRNA2), demonstrating that Lrba siRNAs selectively kill human breast cancer cells but not normal cells. MCF7 cells (FIG. 21A-21C) and MCF10A cells (FIG. 21D) were seeded at $2 \times 10^4$ cells per well in 24-well plates. One day later, the cells were transfected with Lrba siRNAs or with scramble siRNA as a negative control using oligofectamine. After 72 hours of siRNA treatment, the photos (FIG. 21A, MCF7 transfected with siRNA1; FIG. 21B, MCF7 transfected with scramble siRNA negative control; magnification 400×) were taken and the cell numbers were counted by a Coulter counter. T-test: FIG. 21C (MCF7), P=0.0009 for scramble negative control versus siRNA1; P=0.0005 for scramble negative control 1 versus Lrba siRNA2; P=0.004 for siRNA1 versus siRNA2. FIG. 21D (MCF10A), P=0.4070 for scramble negative control versus siRNA1; P=0.9456 for scramble negative control 1 versus Lrba siRNA2; P=0.0514 for siRNA1 versus siRNA2. The siRNA sequences: siRNA1: CCAGCAAAGGUCUUGGC-UAdTdT (SEQ ID NO. 1); siRNA2: GGGCACUCUUUCU-GUCACCdTdT (SEQ ID NO. 39); scramble negative control: CAGUCGGGUUUGCGACUGGdTdT (SEQ ID NO. 2).

BRIEF DESCRIPTION OF THE SEQUENCES

SEQ ID NO. 1 is the human lrba siRNA (siRNA1), including 3' two-dT overhang.

SEQ ID NO. 2 is the human lrba siRNA, including 3' two-dT overhang.

SEQ ID NO. 3 is the murine LRBA-α amino acid sequence (FIG. 1A).

SEQ ID NO. 4 is the murine LRBA-β amino acid sequence (FIG. 1A).

SEQ ID NO. 5 is the additional amino acid sequence at end of LRBA-β protein sequence (FIG. 1A).

SEQ ID NO. 6 is the murine LRBA-γ amino acid sequence (FIG. 1A).

SEQ ID NO. 7 is the additional amino acid sequence at end of LRBA-γ protein sequence (FIG. 1A).

Figure 3:
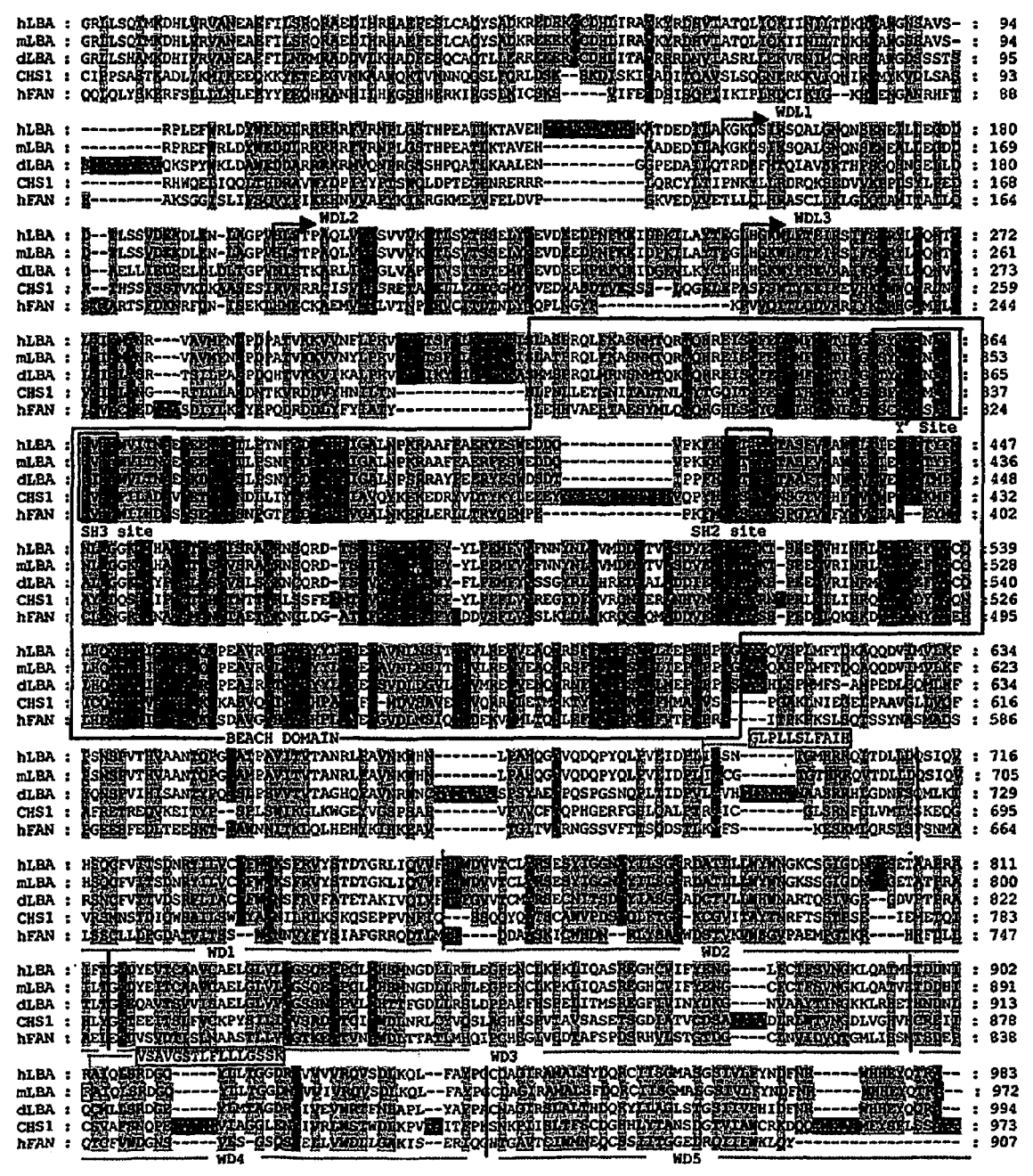

SEQ ID NO. 8 is the human LRBA amino acid sequence also termed LRBA-α (FIGS. 9 and 3).

Figures 2A, 2B:
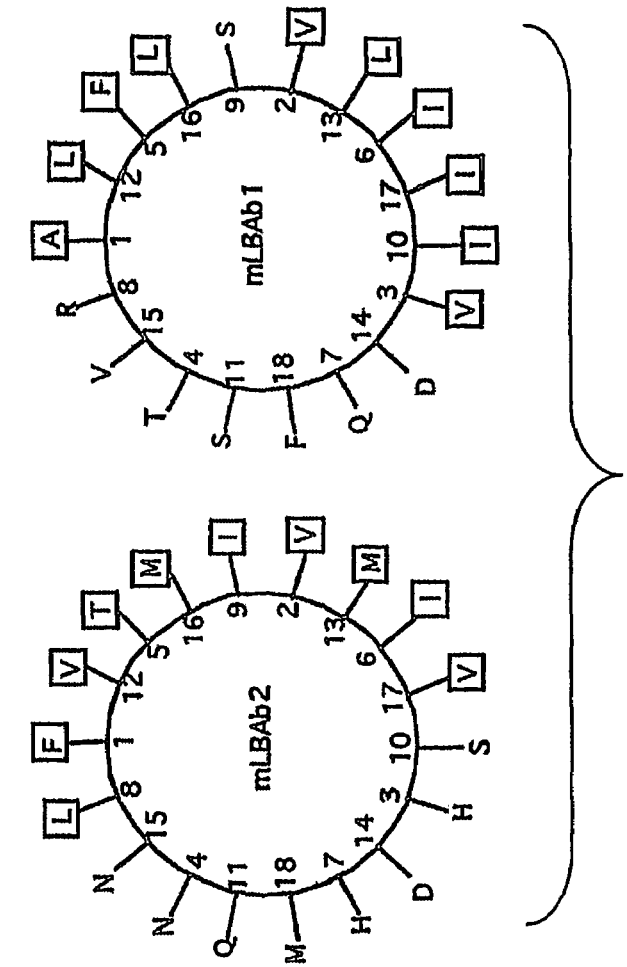
FIGS. 2A and 2B show the PKA binding sites in LRBA.

SEQ ID NO. 9 is the amino acid sequence of murine LRBA putative PKA binding sites (FIG. 2A).

SEQ ID NO. 10 is the amino acid sequence of human LRBA putative PKA binding sites (FIG. 2A).

SEQ ID NO. 11 is the amino acid sequence of *drosophila* LRBA putative PKA binding sites (FIG. 2A).

SEQ ID NO. 12 is the amino acid sequence of *drosophila* LRBA2 putative PKA binding sites (FIG. 2A).

SEQ ID NO. 13 is the amino acid sequence of *C. elegans* LRBA putative PKA binding sites (FIG. 2A).

SEQ ID NO. 14 is the C-terminal amino acid sequence of murine LRBA also termed LRBA-α (FIG. 3).

SEQ ID NO. 15 is the C-terminal amino acid sequence of human LRBA (FIG. 3).

SEQ ID NO. 16 is the C-terminal amino acid sequence of *drosophila* LRBA (FIG. 3).

SEQ ID NO. 17 is the C-terminal amino acid sequence of human CHS1 (FIG. 3).

SEQ ID NO. 18 is the C-terminal amino acid sequence of human FAN (FIG. 3).

SEQ ID NO. 19 is the C-terminal amino acid sequence of murine LRBA-β (FIG. 3).

SEQ ID NO. 20 is the C-terminal amino acid sequence of murine LRBA-γ (FIG. 3).

SEQ ID NO. 21 is the human LRBA-β amino acid sequence (FIG. 9).

SEQ ID NO. 22 is the human LRBA-γ amino acid sequence (FIG. 9).

SEQ ID NO. 23 is the human LRBA-δ amino acid sequence (FIG. 9).

SEQ ID NO. 24 is the human LRBA-ε amino acid sequence (FIG. 9).

Figure 10:
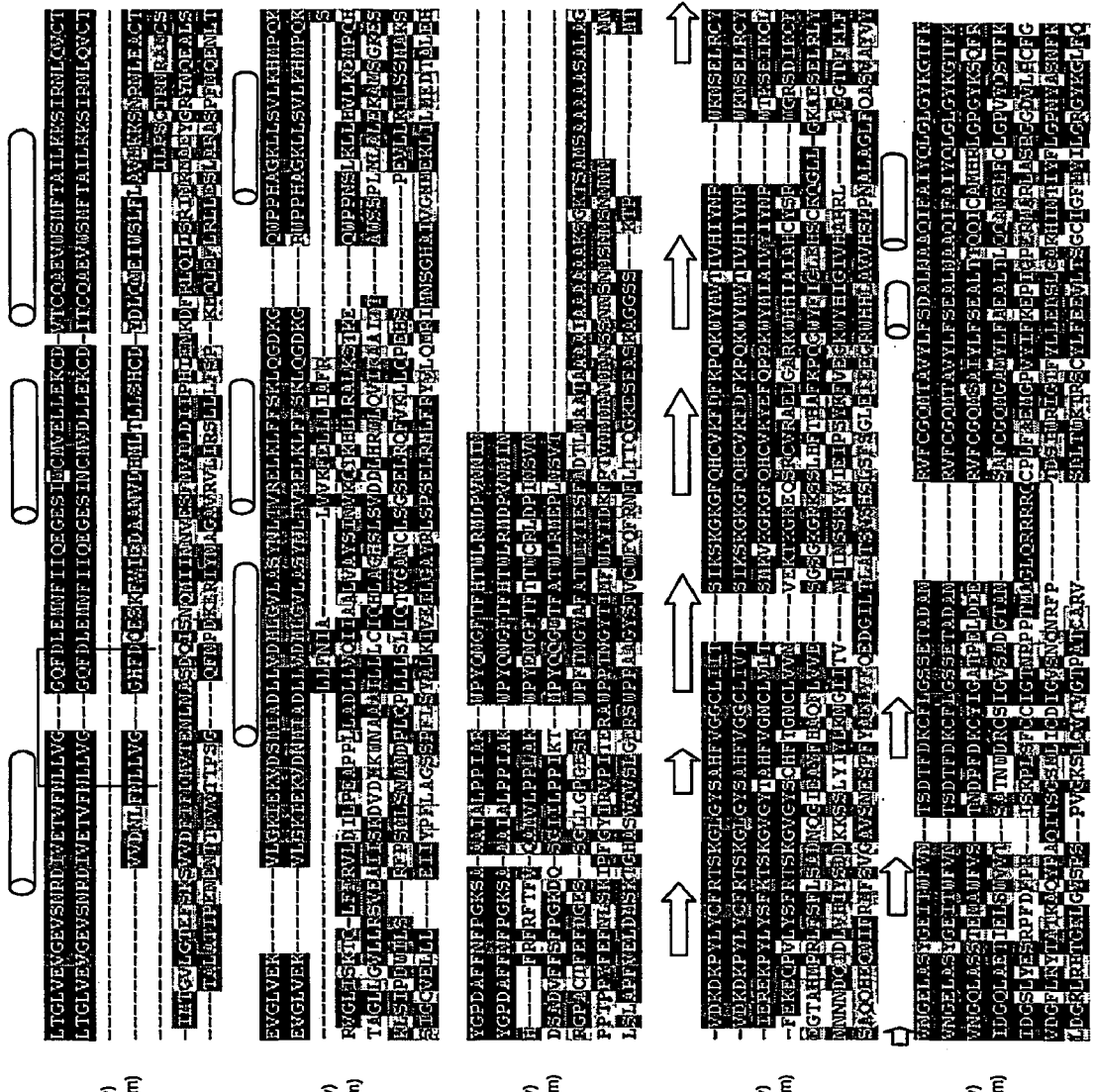
FIG. 10 shows secondary structure prediction and alignment of the HSH domain in several WBW proteins (SEQ ID NOs. 25-31). Sequence positions highlighted in magenta and yellow correspond, respectively, to helices and strands. Sequence positions highlighted in blue are potential glycosylation sites. Squared positions correspond to conserved residues found in the three WBW protein. The positions of the predicted helical regions of the HSH structure are indicated as tubes at the top of the sequences. Sequences having homologues in FIG. 9 were analyzed as multiple sequence alignments using the Jpred[2] method (Cuff, J. A. et al. (1998) *Bioinformatics* 14:892-893; Cuff J. A. and Barton, G. J. (1999) *Proteins: Structure, Function and Genetics* 34:508-519; Cuff, J. A. and Barton, G. J. (1999) *Proteins: Structure, Function and Genetics* 40:502-511). Several sequences that, after a first prediction run, were found to have more than 25% homology in one of the three conserved helical regions were reprocessed together as a multiple sequence alignment using Jpred[2] to refine the prediction of that particular region. Secondary structure predictions were performed by the Jpred[2] method. Rectangles indicate -helices and arrows indicate -strands. HSH (helix-sheet-helix) domain: Several WBW proteins have a high homology and a common predicted protein secondary structure (HSH structure) over an 100 amino acid stretch near their N-terminus, as shown in FIG. 10. Becuase the HSH domain exists in evolutionarily very distant species (*Dictyostelium* is a cellular slime mold, more ancient than yeast), it may have important function in a cell's life. SET domain: rich in serine (S, 13.70%), glutamic acid (E, 13.40%) and threonine (T, 9.03%). Its function is still unknown. This domain is very hydrophobic and has a very high antigenic index. PI is 3.96.
Figure 11:
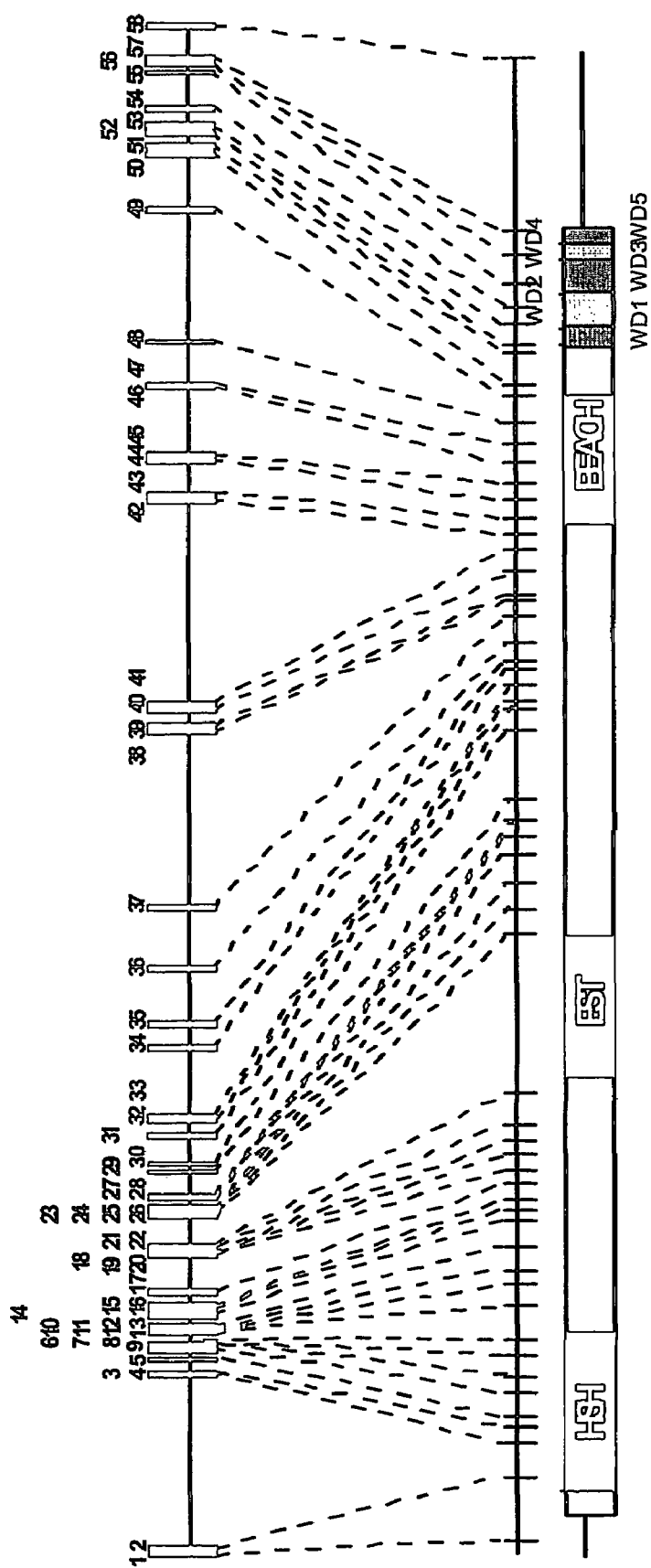
FIG. 11 shows the genomic structure of the human LRBA gene. The gene contains 59 exons, which span more than 700 kb. The exon/intron structure of the LRBA gene is mapped to the corresponding cDNA regions encoded by each exon. Location and size of exons and introns are drawn to scale (GenBank accession number NM_006726).

SEQ ID NO. 25 is the amino acid sequence of HSH domain of murine LRBA (FIG. 10).

SEQ ID NO. 26 is the amino acid sequence of HSH domain of human LRBA (FIG. 10).

SEQ ID NO. 27 is the amino acid sequence of HSH domain of *drosophila* AKAP550 (FIG. 10).

SEQ ID NO. 28 is the amino acid sequence of HSH domain of *C. elegans* F10F2.1 (FIG. 10).

SEQ ID NO. 29 is the amino acid sequence of HSH domain of arabidopsis CDC4L (FIG. 10).

SEQ ID NO. 30 is the amino acid sequence of HSH domain of dictyostelium LysA (FIG. 10).

SEQ ID NO. 31 is the amino acid sequence of HSH domain of arabidopsis LYSTL.

SEQ ID NO. 32 is the inserted amino acid sequence in human LRBA-γ.

SEQ ID NO. 33 is the 5' end of human lrba-ε isoform with a long 5' UTR (FIG. 15).

SEQ ID NO. 34 is the first 73 amino acids of the human LRBA (FIG. 15).

SEQ ID NO. 35 is the partial major coding sequence of human LRBA (FIG. 15).

SEQ ID NO. 36 is the amino acids encoded by the extra exon interrupting the lrba gene (FIG. 15).

SEQ ID NO. 37 is the promoter and part of the 5' cDNA sequence of the human lrba gene (FIG. 17).

SEQ ID NO. 38 is the human lrba siRNA antisense strand, including 3' two-dT overhang.

SEQ ID NO. 39 is the human lrba siRNA (siRNA2), including 3' two-dT overhang.

SEQ ID NOs. 40-46 are the primers used in cloning and sequencing of murine lrba cDNA.

SEQ ID NOs. 47-50 are the primers used in cloning and sequencing of human lrba cDNA.

SEQ ID NOs. 51-56 are the primers used in RT-PCR analysis of murine lrba expression.

SEQ ID NOs. 48, 57-61 are the primers used for amplification of human lrba.

SEQ ID NOs. 62-118 are the human lrba 5' splice donor sites (exons 1-57) (Table 2).

SEQ ID NOs. 119-175 are the human lrba 3' splice acceptor sites (introns 1-57) (Table 2).

SEQ ID NO. 176 is the amino acid sequence of p21 RAS motif.

SEQ ID NO. 177 is the human lrba siRNA (siRNA1).

SEQ ID NO. 178 is the human lrba siRNA.

SEQ ID NO. 179 is the human lrba siRNA antisense strand.

SEQ ID NO. 180 is the human lrba siRNA (siRNA2).

Figure 16:
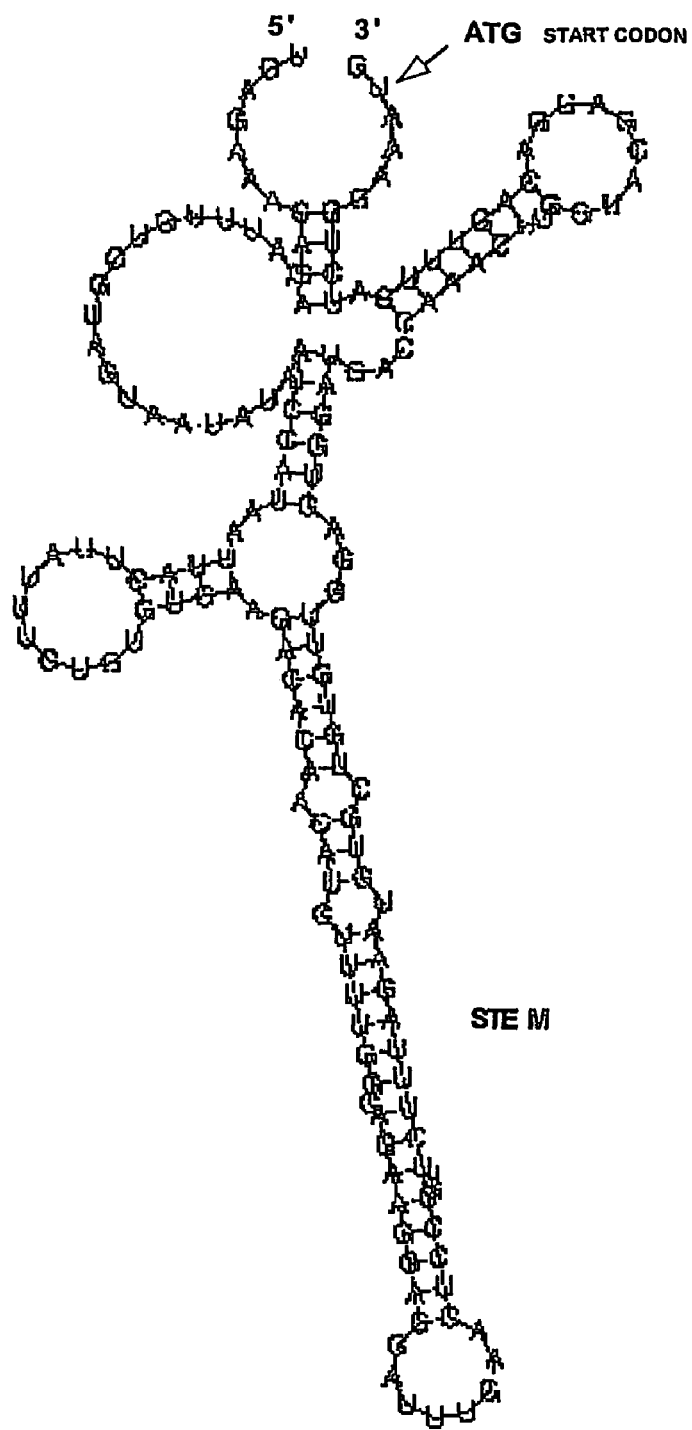
FIG. 16 shows the predicted secondary structure of RNA sequence between the two ORF of human lrbaδ (SEQ ID NO:181). The free energy for the structure is −40.29 kcal/mol. This suggests a potential IRES (internal ribosome entry signal). There is no homologous sequence between IRES, however they all have complex secondary structure like long stem structure.
Figure 19:
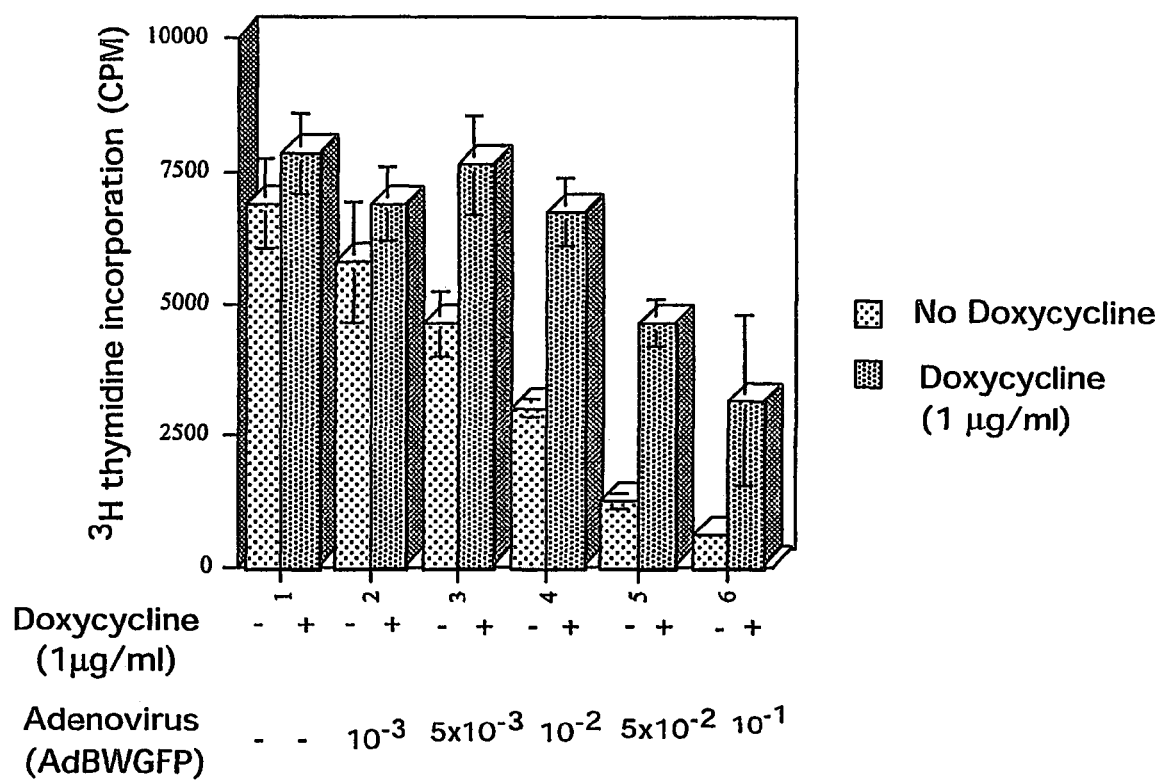
FIG. 19 shows growth inhibition of human breast cancer cells by expression of a dominant negative human LRBA mutant. MCF7 human breast cancer cells were seeded ($1 \times 10^4$/well) into a 96-well plate. On the second day, cells were infected with various titers of a recombinant adenovirus that contains a dominant negative LRBA mutant, in the presence or absence of doxycycline. The BW-GFP mutant comprises the BEACH and WD domains of LRBA fused to GFP. The adenoviral vector has a tetracycline-responsive promoter that is repressed in the presence of doxycycline and, thus, the BW-GFP mutant is expressed in the absence of doxycycline. Three days post-infection, the cells were labeled with $^3$H-thymidine, the cells harvested and CPM incorporated into high molecular weight DNA counted as a measure of cell proliferation (DNA synthesis).
Figures 20A, 20B:
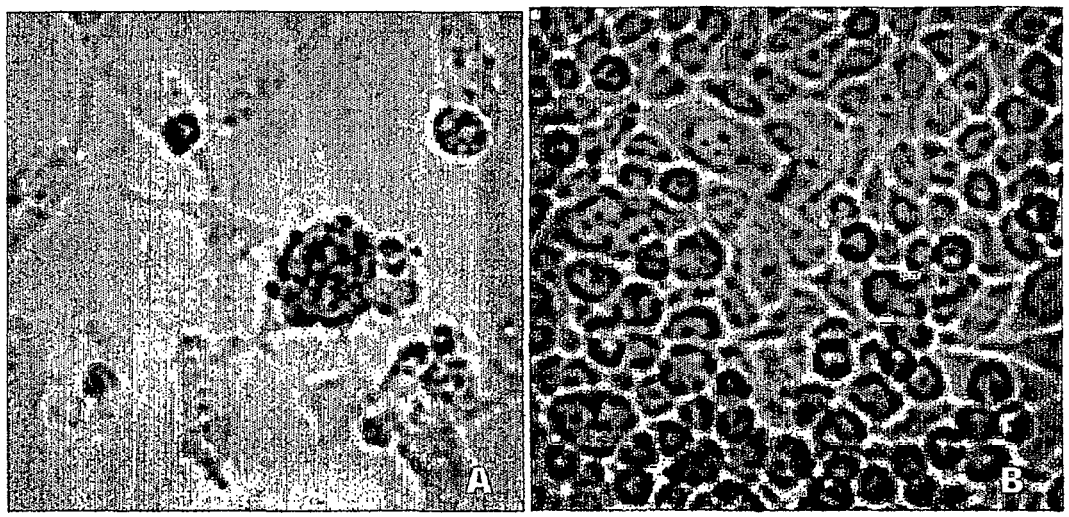
FIGS. 20A-20C show the knock-down of Lrba expression by LRBA siRNA treatment and death of cancer cells. HeLa cells were plated $2 \times 10^4$ cells/well of a 24-well dish. The next day, cells were transfected as indicated or were left untreated (Blank). The cells were photographed 72 hours after transfected and the wells harvested for cell counting. HeLa cells (human adenocarcinoma) transfected with Lrba siRNA and lipofectamine (FIG. 20A) or mock transfected with $H_2O$ and lipofectamine (FIG. 20B). Magnification is 400×. Note the presence of apoptotic or necrotic cell bodies as well as the spindly, stressed morphology of the remaining adherent cells in the siRNA Lrba-treated well.
Figure 20C:
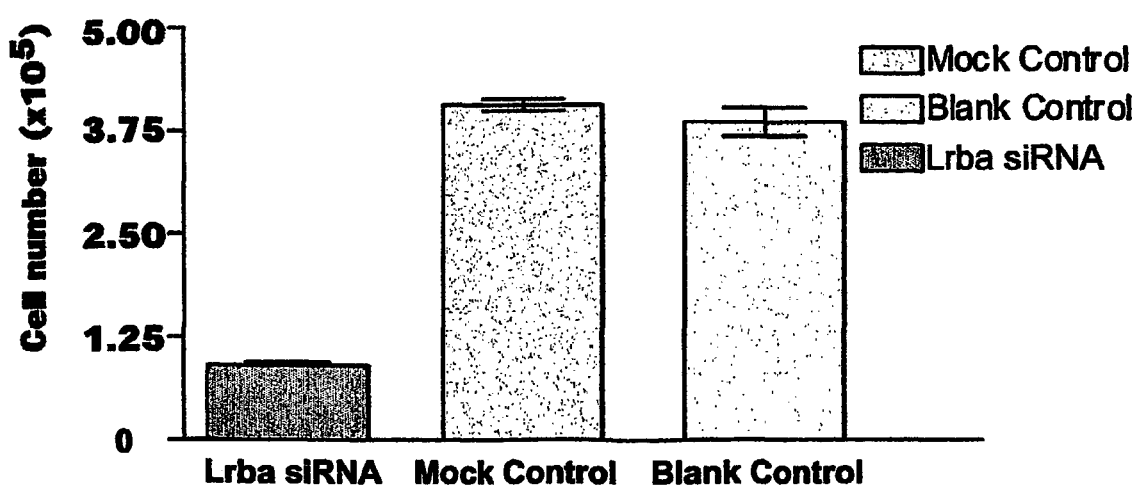
Figures 22A, 22B, 22C:
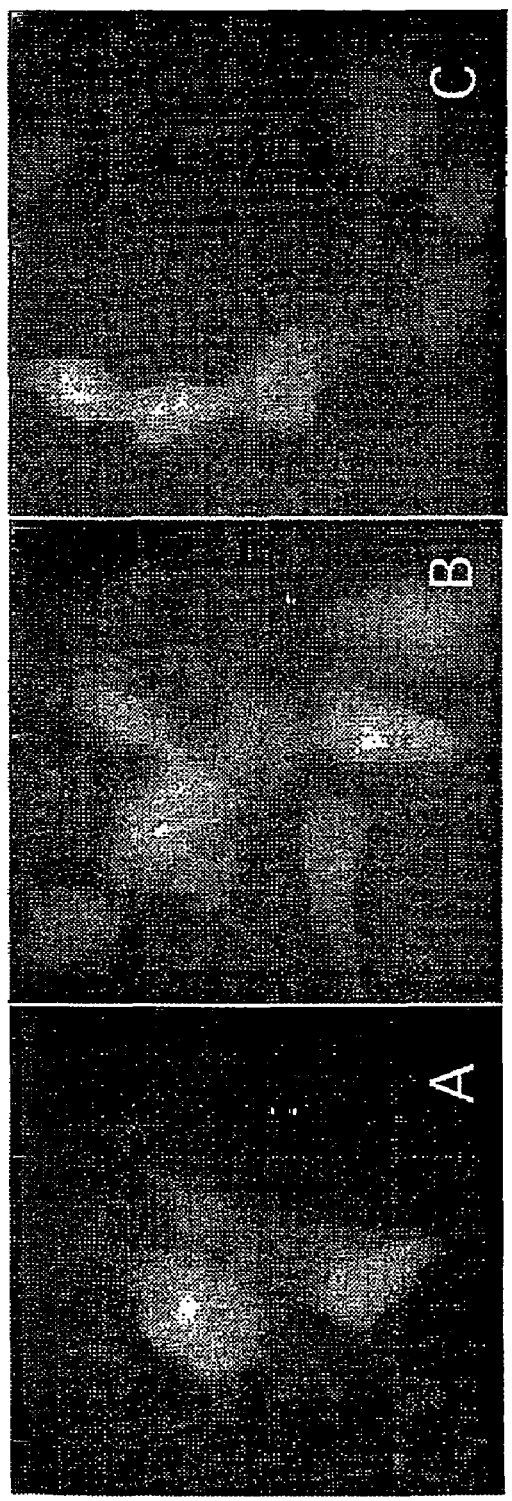
FIGS. 22A-22F show upregulation of lrba promoter activity by p53 and E2F transcription factors. The GFP reporter (GFP gene is placed downstream of the lrba gene promoter, designated pLP-GFP) construct was transfected into 293T cells with or without p53 or E2F wild type vector. The pictures were taken one day after transfection. FACS analysis was carried out 60 hours after transfection. The results show that there is 0.7% GFP positive cells in pLP-GFP only (FIGS. 22A and 22D), 6.88% in pLP-GFP+p53 vector (FIGS. 22B and 22E), 2.06% in pLP-GFP+pE2F1 vector (FIGS. 22C and 22F), suggesting that only a small fraction of cells have detectable lrba promoter activity, p53 and E2F can induce the lrba promoter activity to 9.8, 3-fold respectively. p53 and E2F are important cell cycle and apoptosis mediators. All or most tumors can be characterized as being defective in p53 function.
Figures 22D, 22E, 22F:
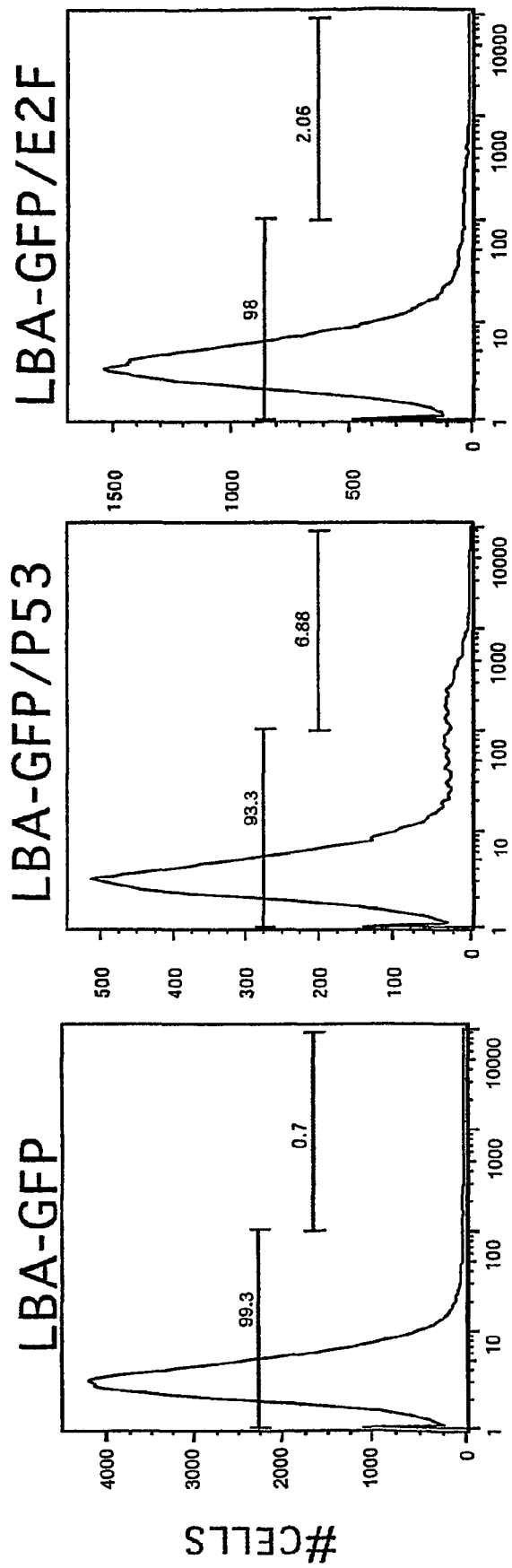

SEQ ID NO:181 is the RNA sequence between the two open reading frames of human lrbaδ (FIG. 16).

SEQ ID NO:182 is the predicted full-length amino acid sequence of human LRBA (all five isoforms) (FIG. 9).

DETAILED DISCLOSURE OF THE INVENTION

The subject invention concerns a method of inhibiting cancerous tumor growth in a patient by suppressing lrba function. Preferably, the method comprises suppressing the functional expression of the lrba gene. Various methods known in the art for suppressing the functional expression of a gene can be utilized to carry out this method of the subject invention. The lrba gene can be disrupted partially (e.g., a leaky mutation), resulting, for example, in reduced expression, or the lrba gene can be fully disrupted (e.g., complete gene ablation). Such mutations can include, for example, point mutations, such as transitions or transversions, or insertions and/or deletions, and the mutation can occur in the coding region encoding lrba or merely in its regulatory sequences. According to the method of the subject invention, functional expression of the lrba gene can be suppressed at any level. In another aspect, the subject invention includes methods of disrupting expression of the lrba gene in vivo or in vitro.

Using the method of the subject invention, lrba function is suppressed, which causes inhibition of tumor growth. Preferably, the suppression of lrba function results in death of tumor cells. More preferably, lrba function is suppressed to an extent that normal (non-cancerous) cells are not killed.

Various means for suppression of lrba function can be utilized according to the method of the subject invention. For example, suppression of lrba function can be carried by administration of an agent that directly or indirectly causes suppression of lrba function. Agents suitable for the method of the subject invention include nucleic acids, such as a genetic construct or other genetic means for directing expression of an antagonist of lrba function. Nucleic acid molecules suitable for the method of the invention include, for example, anti-sense polynucleotides, or other polynucleotides that bind to lrba mRNA, for example. Preferably, the nucleic acid molecules administered to the patient are those disclosed herein. Other agents that can be utilized to carry out suppression of lrba function include, for example, peptidomimetics, ribozymes, and RNA aptamers.

According to the method of the subject invention, polypeptides can be administered to a patient in order to suppress lrba function and inhibit tumor growth. Preferably, the polypeptides utilized are those disclosed herein. More preferably, the polypeptides comprise fragments of the full-length lrba amino acid sequence (including fragments of full-length amino acid sequences of lrba orthologs). Most preferably, the polypeptides comprise amino acid sequences corresponding to the BEACH domain, WD domain, or BEACH and WD domains, of the lrba gene (including lrba gene orthologs). Various means for delivering polypeptides to a cell can be utilized to carry out the method of the subject invention. For example, protein transduction domains (PTDs) can be fused to the polypeptide, producing a fusion polypeptide, in which the PTDs are capable of transducing the polypeptide cargo across the plasma membrane (Wadia, J. S. and Dowdy, S. F., *Curr. Opin. Biotechnol.*, 2002, 13(1)52-56). Examples of PTDs include the *Drosophila* homeotic transcription protein antennapedia (Antp), the herpes simples virus structural protein VP22, and the human immuno-deficiency virus 1 (HIV-1) transcriptional activator Tat protein.

According to the method of tumor inhibition of the subject invention, recombinant cells can be administered to a patient, wherein the recombinant cells have been genetically modified to express an lrba gene product, such as a portion of the amino acid sequences set forth in FIG. 1 (SEQ ID NOs. 3-7) or FIG. 9 (SEQ ID NOs. 8 and 21-24), or variants thereof.

The method of tumor inhibition of the subject invention can be used to treat patient suffering from cancer or as a cancer preventative. The method of tumor inhibition of the subject invention can be used to treat patients suffering from a variety of cancers including, but not limited to, cancer of the breast, prostate, melanoma, chronic myelogenous leukemia, cervical cancer, adenocarcinoma, lymphoblastic leukemia, colorectal cancer, and lung carcinoma.

In another aspect, the subject invention provides isolated and/or purified nucleotide sequences comprising: (i) a polynucleotide sequence encoding the amino acid sequence set forth in FIG. 1 (SEQ ID NOs. 3-7) or FIG. 9 (SEQ ID NOs. 8 and 21-24), or a complement thereof; (ii) a polynucleotide sequence having at least about 20% to 99.99% identity to the polynucleotide sequence of (i); (iii) a polynucleotide encoding a fragment of the amino acid sequence shown in FIG. 1 (SEQ ID NOs 3-7) or FIG. 9 (SEQ ID NOs. 8 and 21-24); or (iv) an interfering RNA sequence corresponding to the transcript of the polynucleotide set forth in FIG. 1 (SEQ ID NOs. 3-7) or FIG. 9 (SEQ ID NOs. 8 and 21-24), or a fragment of the transcript.

Nucleotide, polynucleotide, or nucleic acid sequences(s) are understood to mean, according to the present invention, either a double-stranded DNA, a single-stranded DNA, or products of transcription of the said DNAs (e.g., RNA molecules). It should also be understood that the present invention does not relate to the genomic nucleotide sequences encoding lrba in their natural/native environment or natural/native state. The nucleic acid, polynucleotide, or nucleotide sequences of the invention have been isolated, purified (or partially purified), by separation methods including, but not limited to, ion-exchange chromatography, molecular size exclusion chromatography, affinity chromatography, or by genetic engineering methods such as amplification, cloning or subcloning.

Optionally, the polynucleotide sequences of the instant invention can also contain one or more polynucleotides encoding heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental Biology* 203:19-28, The Co. of Biologists, Ltd., G.B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A.* 707:3-22, Elsevier Science B.V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B.V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or INVITROGEN (San Diego, Calif.).

Other aspects of the invention provide vectors containing one or more of the polynucleotides of the invention. The vectors can be vaccine, replication, or amplification vectors. In some embodiments of this aspect of the invention, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations of the aforementioned vector sources, such as those derived from plasmid and bacteriophage genetic elements (e.g., cosmids and phagemids).

As indicated above, vectors of this invention can also comprise elements necessary to provide for the expression and/or the secretion of a polypeptide encoded by the nucleotide sequences of the invention in a given host cell. The vector can contain one or more elements selected from the group consisting of a promoter, signals for initiation of translation, signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, a vector comprises a promoter operably linked to a protein or peptide-encoding nucleic acid sequence, one or more origins of replication, and, optionally, one or more selectable markers (e.g., an antibiotic resistance gene). Non-limiting exemplary vectors for the expression of the polypeptides of the invention include pBr-type vectors, pET-type plasmid vectors (Promega), pBAD plasmid vectors (Invitrogen) or those provided in the examples below. Furthermore, vectors according to the invention are useful for transforming host cells for the cloning or expression of the nucleotide sequences of the invention.

Promoters which may be used to control expression include, but are not limited to, the CMV promoter, the SV40 early promoter region (Bemoist and Chambon [1981] *Nature* 290:304-310), the promoter contained in the 3' long terminal repeat of *Rous sarcoma* virus (Yamamoto, et al. [1980] *Cell* 22:787-797), the herpes thymidine kinase promoter (Wagner et al. [1981] *Proc. Natl. Acad. Sci. USA* 78:1441-1445), the regulatory sequences of the metallothionein gene (Brinster et al. [1982] *Nature* 296:39-42); prokaryotic vectors containing promoters such as the β-lactamase promoter (Villa-Kamaroff, et al. [1978] *Proc. Natl. Acad. Sci. USA* 75:3727-3731), or the tac promoter (DeBoer, et al. [1983] *Proc. Natl. Acad. Sci. USA* 80:21-25); see also, "Useful Proteins from Recombinant Bacteria" in *Scientific American,* 1980, 242:74-94; plant expression vectors comprising the nopaline synthetase promoter region (Herrera-Estrella et al. [1983] *Nature* 303: 209-213) or the cauliflower mosaic virus 35S RNA promoter (Gardner, et al. [1981] *Nucl. Acids Res.* 9:2871), and the promoter of the photosynthetic enzyme ribulose biphosphate carboxylase (Herrera-Estrella et al. [1984] *Nature* 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The subject invention also provides for "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological or serological activity as the native (naturally occurring) LRBA polypeptides. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85(8):2444-2448; Altschul et al. [1990] *J. Mol. Biol.* 215(3): 403-410; Thompson et al. [1994] *Nucleic Acids Res.* 22(2): 4673-4680; Higgins et al. [1996] *Methods Enzymol.* 266:383-402; Altschul et al. [1990] *J. Mol. Biol.* 215(3):403-410; Altschul et al. [1993] *Nature Genetics* 3:266-272).

The subject invention also provides nucleotide sequences complementary to any of the polynucleotide sequences disclosed herein. Thus, the invention is understood to include any DNA whose nucleotides are complementary to those of the sequence of the invention, and whose orientation is reversed (e.g., an antisense sequence).

The present invention further provides fragments of the polynucleotide sequences provided herein. Representative fragments of the polynucleotide sequences according to the invention will be understood to mean any nucleotide fragment having at least 8 or 9 successive nucleotides, preferably at least 12 successive nucleotides, and still more preferably at least 15 or at least 20 successive nucleotides of the sequence from which it is derived. The upper limit for such fragments is the total number of polynucleotides found in the full-length sequence (or, in certain embodiments, of the full length open reading frame (ORF) identified herein). It is understood that such fragments refer only to portions of the disclosed polynucleotide sequences that are not listed in a publicly available database or prior art references. However, it should be understood that with respect to the method for inhibiting tumor growth of the subject invention, disclosed nucleotides (and polypeptides encoded by such nucleotides) that are listed in a publicly available database or prior art reference can also be utilized. For example, nucleotide sequences that are lrba orthologs, or fragments thereof, which have been previously identified, can be utilized to carry out the method for inhibiting tumor growth of the subject invention. Thus sequences from the *drosophila melanogaster* genomic sequence (GENBANK accession number AE003433), cLRBA (GENBANK accession number T20719, *Caenorhabditis elegans*), aCDC4L (GENBANK accession number T00867, *Arabidopsis thaliana*), LSVA (GENBANK accession number AAD52096, *Dictyostelium discoideum*), hFAN (GENBANK accession number NP_0035711, *Homo sapiens*), CHS1 (Chediak-Higashi Syndrome 1, GENBANK accession number NP_000072, *Homo sapiens*), or mBG (GENBANK accession number AAB60778, *Mus musculus*) can be utilized to carry out the method of tumor growth inhibition of the subject invention.

In other embodiments, fragments contain from one nucleotide less than the full length polynucleotide sequence (1249 nucleotides) to fragments comprising up to, and including 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, . . . and up to, for example, 1,245 consecutive nucleotides of a particular sequence disclosed herein.

Yet other embodiments provide fragments (or detection probes) comprising nucleotides within the lrba cDNA sequence, such as the human lrba cDNA sequence (GenBank accession number NM_006726), including 245 to 458 (G-peptide), 488 to 1424 (HSH domain), 2573-2627 (siRNA1) (SEQ ID NO. 5), 3179 to 4148 (SET domain), 4301 to 4505 (PKA RII binding sites), 6347 to 6749 (WDL repeats), 6878 to 7709 (BEACH domain), 8018 to 8831 (WD repeats).

Among these representative fragments, those capable of hybridizing under stringent conditions with a nucleotide sequence according to the invention are preferred. Conditions of high or intermediate stringency are provided infra and are chosen to allow for hybridization between two complementary DNA fragments. Hybridization conditions for a polynucleotide of about 300 bases in size will be adapted by persons skilled in the art for larger- or smaller-sized oligonucleotides, according to methods well known in the art (see, for example, Sambrook et al. [1989]).

The subject invention also provides detection probes (e.g., fragments of the disclosed polynucleotide sequences) for hybridization with a target sequence or an amplicon generated from the target sequence. Such a detection probe will advantageously have as sequence a sequence of at least 9, 12, 15, 20, 25, 30, 35, 40, 45, 50, 55, 60, 65, 70, 75, 80, 85, 90, 95, or 100 nucleotides. Alternatively, detection probes can comprise 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, . . . and up to, for example, 1245 consecutive nucleotides of the disclosed nucleic acids. The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromodeoxyuridine, or fluorescein to provide probes that can be used in numerous applications.

The nucleotide sequences according to the invention may also be used in analytical systems, such as DNA chips. DNA chips and their uses are well known in the art and (see for example, U.S. Pat. Nos. 5,561,071; 5,753,439; 6,214,545; Schena et al. [1996] *BioEssays* 18:427-431; Bianchi et al. [1997] *Clin. Diagn. Virol.* 8:199-208; each of which is hereby incorporated by reference in their entireties) and/or are provided by commercial vendors such as AFFYMETRIX, Inc. (Santa Clara, Calif.).

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] *DNA Probes*, Stockton Press, New York, N.Y., pp. 169-170.

By way of example, hybridization of immobilized DNA on Southern blots with $^{32}P$-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20-25° C. below the melting temperature (Tm) of the DNA hybrid in 6× SSPE, 5× Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$T_m$=81.5° C.+16.6 Log[*Na+*]+0.41(% *G+C*)−0.61(% formamide)−600/length of duplex in base pairs.

Washes are typically carried out as follows:
(1) twice at room temperature for 15 minutes in 1× SSPE, 0.1% SDS (low stringency wash);
(2) once at $T_m$-20° C. for 15 minutes in 0.2× SSPE, 0.1% SDS (moderate stringency wash).

For oligonucleotide probes, hybridization can be carried out overnight at 10-20° C. below the melting temperature ($T_m$) of the hybrid in 6× SSPE, 5× Denhardt's solution, 0.1% SDS, 0.1 mg/ml denatured DNA. $T_m$ for oligonucleotide probes can be determined by the following formula:

$T_m$ (° C.)=2(number T/A base pairs)+4(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:
(1) twice at room temperature for 15 minutes 1× SSPE, 0.1% SDS (low stringency wash;
2) once at the hybridization temperature for 15 minutes in 1× SSPE, 0.1% SDS (moderate stringency wash).

In general, salt and/or temperature can be altered to change stringency. With a labeled DNA fragment >70 or so bases in length, the following conditions can be used:

| | |
|---|---|
| Low: | 1 or 2X SSPE, room temperature |
| Low: | 1 or 2X SSPE, 42° C. |
| Moderate: | 0.2X or 1X SSPE, 65° C. |
| High: | 0.1X SSPE, 65° C. |

By way of another non-limiting example, procedures using conditions of high stringency can also be performed as follows: Pre-hybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in pre-hybridization mixture containing 100 μg/ml denatured salmon sperm DNA and 5-20×10$^6$ cpm of $^{32}$P-labeled probe. Alternatively, the hybridization step can be performed at 65° C. in the presence of SSC buffer, 1× SSC corresponding to 0.15M NaCl and 0.05 M Na citrate. Subsequently, filter washes can be done at 37° C. for 1 h in a solution containing 2× SSC, 0.01% PVP, 0.01% Ficoll, and 0.01% BSA, followed by a wash in 0.1× SSC at 50° C. for 45 min. Alternatively, filter washes can be performed in a solution containing 2× SSC and 0.1% SDS, or 0.5× SSC and 0.1% SDS, or 0.1× SSC and 0.1% SDS at 68° C. for 15 minute intervals. Following the wash steps, the hybridized probes are detectable by autoradiography. Other conditions of high stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al. [1989] *Current Protocols in Molecular Biology*, Green Publishing Associates and Wiley Interscience, N.Y., each incorporated herein in its entirety).

A further non-limiting example of procedures using conditions of intermediate stringency are as follows: Filters containing DNA are pre-hybridized, and then hybridized at a temperature of 60° C. in the presence of a 5× SSC buffer and labeled probe. Subsequently, filters washes are performed in a solution containing 2× SSC at 50° C. and the hybridized probes are detectable by autoradiography. Other conditions of intermediate stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al. [1989] *Current Protocols in Molecular Biology*, Green Publishing Associates and Wiley Interscience, N.Y., each of which is incorporated herein in its entirety).

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512. The nucleic acid sequences of the subject invention can also be used as molecular weight markers in nucleic acid analysis procedures.

The invention also provides host cells transformed by a polynucleotide according to the invention and the production of LRBA (or LRBA ortholog) polypeptides by the transformed host cells. In some embodiments, transformed cells comprise an expression vector containing LRBA, or LRBA ortholog, polynucleotide sequences. Other embodiments provide for host cells transformed with nucleic acids. Yet other embodiments provide transformed cells comprising an expression vector containing fragments of lrba, or lrba ortholog, polynucleotide sequences. Transformed host cells according to the invention are cultured under conditions allowing the replication and/or the expression of the nucleotide sequences of the invention. Expressed polypeptides are recovered from culture media and purified, for further use, according to methods known in the art.

The host cell may be chosen from eukaryotic or prokaryotic systems, for example bacterial cells (Gram negative or Gram positive), yeast cells, animal cells, plant cells, and/or insect cells using baculovirus vectors. In some embodiments, the host cell for expression of the polypeptides include, and are not limited to, those taught in U.S. Pat. Nos. 6,319,691; 6,277,375; 5,643,570; 5,565,335; Unger [1997] *The Scientist* 11(17):20; or Smith [1998] *The Scientist* 12(22):20, each of which is incorporated by reference in its entirety, including all references cited within each respective patent or reference. Other exemplary, and non-limiting, host cells include *Staphylococcus* spp., *Enterococcus* spp., *E. coli*, and *Bacillus subtilis*; fungal cells, such as *Streptomyces* spp., *Aspergillus* spp., *S. cerevisiae*, *Schizosaccharomyces pombe*, *Pichia pastoris*, *Hansela polymorpha*, *Kluveromyces lactis*, and *Yarrowia lipolytica*; insect cells such as *Drosophila* S2 and *Spodoptera* Sf9 cells; animal cells such as CHO, COS, HeLa, C127, 3T3, BHK, 293 and Bowes melanoma cells; and plant cells. A great variety of expression systems can be used to produce the polypeptides of the invention and polynucleotides can be modified according to methods known in the art to provide optimal codon usage for expression in a particular expression system.

Furthermore, a host cell strain may be chosen that modulates the expression of the inserted sequences, modifies the gene product, and/or processes the gene product in the specific fashion. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product whereas expression in yeast will produce a glycosylated product. Expression in mammalian cells can be used to provide "native" glycosylation of a heterologous protein. Furthermore, different vector/host expression systems may effect processing reactions to different extents.

Nucleic acids and/or vectors can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection (see, for example, Sambrook et al.

[1989] *Molecular Cloning: A Laboratory Manual*, 2$^{nd}$ Ed., Cold Spring Harbor Laboratory Press, Cold Spring Harbor, N.Y.).

The subject invention also provides for the expression of a polypeptide, derivative, or a variant (e.g., a splice variant) encoded by a polynucleotide sequence disclosed herein. Alternatively, the invention provides for the expression of a polypeptide fragment obtained from a polypeptide, derivative, or a variant encoded by a polynucleotide fragment derived from the polynucleotide sequences disclosed herein. In either embodiment, the disclosed sequences can be regulated by a second nucleic acid sequence so that the polypeptide or fragment is expressed in a host transformed with a recombinant DNA molecule according to the subject invention. For example, expression of a protein or peptide may be controlled by any promoter/enhancer element known in the art.

The subject invention also provides nucleic acid based methods for the identification of the presence of the lrba gene, or orthologs thereof, in a sample. These methods can utilize the nucleic acids of the subject invention and are well known to those skilled in the art (see, for example, Sambrook et al. [1989] or Abbaszadega [2001] "Advanced Detection of Viruses and Protozoan Parasites in Water," *Reviews in Biology and Biotechnology*, 1(2):21-26). Among the techniques useful in such methods are enzymatic gene amplification (or PCR), Southern blots, Northern blots, or other techniques utilizing nucleic acid hybridization for the identification of polynucleotide sequences in a sample. The nucleic acids can be used to screen individuals for cancers, tumors, or malignancies associated with dysregulation of the lrba gene or its transcriptional products.

The subject invention also provides polypeptides encoded by nucleotide sequences of the invention. The subject invention also provides fragments of at least 5 amino acids of a polypeptide encoded by the polynucleotides of the instant invention.

In the context of the instant invention, the terms polypeptide, peptide and protein are used interchangeably. Likewise, the terms variant and homologous are also used interchangeably. It should be understood that the invention does not relate to the polypeptides in natural form or native environment. Peptides and polypeptides according to the invention have been isolated or obtained by purification from natural sources (or their native environment), chemically synthesized, or obtained from host cells prepared by genetic manipulation (e.g., the polypeptides, or fragments thereof, are recombinantly produced by host cells). Polypeptides according to the instant invention may also contain non-natural amino acids, as will be described below.

"Variant" or "homologous" polypeptides will be understood to designate the polypeptides containing, in relation to the native polypeptide, modifications such as deletion, addition, or substitution of at least one amino acid, truncation, extension, or the addition of chimeric heterologous polypeptides. Optionally, "variant" or "homologous" polypeptides can contain a mutation or post-translational modifications. Among the "variant" or "homologous" polypeptides, those whose amino acid sequence exhibits 20.00% to 99.99% (inclusive) identity to the native polypeptide sequence are preferred. The aforementioned range of percent identity is to be taken as including, and providing written description and support for, any fractional percentage, in intervals of 0.01%, between 50.00% and, up to, including 99.99%. These percentages are purely statistical and differences between two polypeptide sequences can be distributed randomly and over the entire sequence length.

"Variant" or "homologous" polypeptide sequences exhibiting a percentage identity with the polypeptides of the present invention can, alternatively, have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 91, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides and as provided below.

By way of example, amino acid substitutions can be carried out without resulting in a substantial modification of the biological activity of the corresponding modified polypeptides; for example, the replacement of leucine with valine or isoleucine; aspartic acid with glutamic acid; glutamine with asparagine; arginine with lysine; and the reverse substitutions can be performed without substantial modification of the biological activity of the polypeptides.

In other embodiments, homologous polypeptides according to the subject invention also include various splice variants identified within the lrba coding sequence.

The subject invention also provides biologically active fragments of a polypeptide according to the invention and includes those peptides capable of eliciting an immune response. The immune response can provide components (either antibodies or components of the cellular immune response (e.g., B-cells, helper, cytotoxic, and/or suppressor T-cells) reactive with the biologically active fragment of a polypeptide, the intact, full length, unmodified polypeptide disclosed herein, or both the biologically active fragment of a polypeptide and the intact, full length, unmodified polypeptides disclosed herein. Biologically active fragments according to the invention comprise from five (5) amino acids to one amino acid less than the full length of any polypeptide sequence provided herein. Alternatively, fragments comprising 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, . . . and up to 2845 consecutive amino acids of a disclosed polypeptide sequence are provided herein.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector containing nucleic acids encoding polypeptide fragments according to the invention. The transformed host cells contain a nucleic acid and are cultured according to well-known methods; thus, the invention allows for the expression of these fragments, under the control of appropriate elements for regulation and/or expression of the polypeptide fragments.

Modified polypeptides according to the invention are understood to designate a polypeptide obtained by variation in the splicing of transcriptional products of the lrba gene, genetic recombination, or by chemical synthesis as described below. Modified polypeptides contain at least one modification in relation to the normal polypeptide sequence. These modifications can include the addition, substitution, deletion of amino acids contained within the polypeptides of the invention.

Conservative substitutions whereby an amino acid of one class is replaced with another amino acid of the same type fall within the scope of the subject invention so long as the substitution does not materially alter the biological activity of the polypeptide. For example, the class of nonpolar amino acids include Ala, Val, Leu, Ile, Pro, Met, Phe, and Trp; the class of uncharged polar amino acids includes Gly, Ser, Thr, Cys, Tyr, Asn, and Gln; the class of acidic amino acids includes Asp and Glu; and the class of basic amino acids includes Lys, Arg, and His. In some instances, non-conservative substitutions can be made where these substitutions do not significantly detract from the biological activity of the polypeptide.

In order to extend the life of the polypeptides of the invention, it may be advantageous to use non-natural amino acids, for example in the D form, or alternatively amino acid analogs, such as sulfur-containing forms of amino acids. Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. Nos. 6,319,691; 6,277,375; or 5,643,570, each of which is incorporated by reference in its entirety, including all references cited within each respective patent. Alternatively, the polynucleotides and genes of the instant invention can be recombinantly fused to elements that are useful in the preparation of immunogenic constructs for the purposes of vaccine formulation or elements useful for the isolation of the polypeptides of the invention.

The polypeptides, fragments, and immunogenic fragments of the invention may further contain linkers that facilitate the attachment of the fragments to a carrier molecule for the stimulation of an immune response or diagnostic purposes. The linkers can also be used to attach fragments according to the invention to solid support matrices for use in affinity purification protocols. In this aspect of the invention, the linkers specifically exclude, and are not to be considered anticipated, where the fragment is a subsequence of another peptide, polypeptide, or protein as identified in a search of protein sequence databases as indicated in the preceding paragraph. In other words, the non-identical portions of the other peptide, polypeptide, of protein is not considered to be a "linker" in this aspect of the invention. Non-limiting examples of "linkers" suitable for the practice of the invention include chemical linkers (such as those sold by Pierce, Rockford, Ill.), peptides that allow for the connection of the immunogenic fragment to a carrier molecule (see, for example, linkers disclosed in U.S. Pat. Nos. 6,121,424; 5,843,464; 5,750,352; and 5,990,275, hereby incorporated by reference in their entirety). In various embodiments, the linkers can be up to 50 amino acids in length, up to 40 amino acids in length, up to 30 amino acids in length, up to 20 amino acids in length, up to 10 amino acids in length, or up to 5 amino acids in length.

In other specific embodiments, the polypeptides, peptides, derivatives, or analogs thereof may be expressed as a fusion, or chimeric protein product (comprising the protein, fragment, analog, or derivative joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental Biology* 203:19-28, The Co. of Biologists, Ltd., G.B.; Baneyx [1999] "Recombinant Protein Expression in *Escherichia coli*," *Biotechnology* 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. Chromatography A*. 707:3-22, Elsevier Science B.V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," *TibTech* 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: The Strep-tag", *Biomolecular Engineering* 16:79-86, Elsevier Science, B.V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11(17):20, each of which is hereby incorporated by reference in their entireties). Alternatively, such a chimeric product may be made by protein synthetic techniques, e.g., by use of a peptide synthesizer. Fusion peptides can comprise polypeptides of the subject invention and one or more protein transduction domains, as described above. Such fusion peptides are particularly useful for delivering the cargo polypeptide through the cell membrane.

The expression of the lrba gene or lrba gene product (e.g., DNA, RNA, or polypeptide) is disregulated in a variety of cancers, tumors, and/or malignancies. Non-limiting examples of such cancers, tumors, and/or malignancies include prostate cancer, breast cancer, melanoma, chronic myelogenous leukemia, cervical cancer, adenocarcinomas, lymphoblastic leukemia, colorectal cancer, and lung carcinoma. Accordingly, the present invention provides a method for screening, or aiding in the diagnosis of, an individual suspected of having a malignancy or cancer. The subject invention provides methods comprising the steps of determining the amount of lrba in a biological sample obtained from said individual and comparing the measured amount of lrba to the amount of lrba found in the normal population. The presence of a significantly increased amount of lrba is associated with an indication of a malignancy or cancer. Lrba gene product can be detected by well-known methodologies including, and not limited to, Western blots, enzyme linked immunoassays (ELISAs), radioimmunoassays (RIAs), Northern blots, Southern blots, PCR-based assays, or other assays for the quantification of gene product known to the skilled artisan. This information, in conjunction with other information available to the skilled practitioner, assists in making a diagnosis.

Antisense technology can also be used to interfere with expression of the disclosed polynucleotides. For example, the transformation of a cell or organism with the reverse complement of a gene encoded by a polynucleotide exemplified herein can result in strand co-suppression and silencing or inhibition of a target gene, e.g., one involved in the infection process.

Polynucleotides disclosed herein are useful as target genes for the synthesis of antisense RNA or dsRNA useful for RNA-mediated gene interference. The ability to specifically inhibit gene function in a variety of organisms utilizing antisense RNA or ds RNA-mediated interference is well known in the fields of molecular biology (see for example C. P. Hunter, Current Biology [1999] 9:R440-442; Hamilton et al., [1999] Science, 286:950-952; and S. W. Ding, Current Opinions in Biotechnology [2000] 11:152-156, hereby incorporated by reference in their entireties). dsRNA (RNAi) typically comprises a polynucleotide sequence identical or homologous to a target gene (or fragment thereof) linked directly, or indirectly, to a polynucleotide sequence complementary to the sequence of the target gene (or fragment thereof). The dsRNA may comprise a polynucleotide linker sequence of sufficient length to allow for the two polynucleotide sequences to fold over and hybridize to each other; however, a linker sequence is not necessary. The linker sequence is designed to separate the antisense and sense strands of RNAi significantly enough to limit the effects of steric hindrances and allow for the formation of dsRNA molecules and should not hybridize with sequences within the hybridizing portions of the dsRNA molecule. The specificity of this gene silencing mechanism appears to be extremely high, blocking expression only of targeted genes, while leaving other genes unaffected. Accordingly, one method for controlling gene expression according to the subject invention provides materials and methods using double-stranded interfering RNA (dsRNAi), or RNA-mediated interference (RNAi). The terms "dsRNAi", "RNAi", "iRNA", and "siRNA" are used interchangeably herein unless otherwise noted.

RNA containing a nucleotide sequence identical to a fragment of the target gene is preferred for inhibition; however, RNA sequences with insertions, deletions, and point mutations relative to the target sequence can also be used for inhibition. Sequence identity may optimized by sequence comparison and alignment algorithms known in the art (see Gribskov and Devereux, *Sequence Analysis Primer*, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands); the promoters may be known inducible promoters such as baculovirus. Inhibition may be targeted by specific transcription in an organ, tissue, or cell type. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593, 874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

Preferably and most conveniently, dsRNAi can be targeted to an entire polynucleotide sequence set forth herein. Preferred RNAi molecules of the instant invention are highly homologous or identical to the polynucleotides of the sequence listing. The homology may be greater than 70%, preferably greater than 80%, more preferably greater than 90% and is most preferably greater than 95%.

Fragments of genes can also be utilized for targeted suppression of gene expression. These fragments are typically in the approximate size range of about 20 nucleotides. Thus, targeted fragments are preferably at least about 15 nucleotides. In certain embodiments, the gene fragment targeted by the RNAi molecule is about 20-25 nucleotides in length. In a more preferred embodiment, the gene fragments are at least about 25 nucleotides in length. In an even more preferred embodiment, the gene fragments are at least 50 nucleotides in length.

Thus, RNAi molecules of the subject invention are not limited to those that are targeted to the full-length polynucleotide or gene. Gene product can be inhibited with an RNAi molecule that is targeted to a portion or fragment of the exemplified polynucleotides; high homology (90-95%) or greater identity is also preferred, but not necessarily essential, for such applications.

In another aspect of the invention, the dsRNA molecules of the invention may be introduced into cells with single stranded (ss) RNA molecules which are sense or anti-sense RNA derived from the nucleotide sequences disclosed herein. Methods of introducing ssRNA and dsRNA molecules into cells are well-known to the skilled artisan and includes transcription of plasmids, vectors, or genetic constructs encoding the ssRNA or dsRNA molecules according to this aspect of the invention; electroporation, biolistics, or other well-known methods of introducing nucleic acids into cells may also be used to introduce the ssRNA and dsRNA molecules of this invention into cells.

As used herein, the term "administration" or "administering" refers to the process of delivering an agent to a patient, wherein the agent directly or indirectly suppresses lrba function and inhibits the growth of tumors. The process of administration can be varied, depending on the agent, or agents, and the desired effect. Administration can be accomplished by any means appropriate for the therapeutic agent, for example, by parenteral, mucosal, pulmonary, topical, catheter-based, or oral means of delivery. Parenteral delivery can include for example, subcutaneous intravenous, intramuscular, intra-arterial, and injection into the tissue of an organ, particularly tumor tissue. Mucosal delivery can include, for example, intranasal delivery. Oral or intranasal delivery can include the administration of a propellant. Pulmonary delivery can include inhalation of the agent. Catheter-based delivery can include delivery by iontropheretic catheter-based delivery. Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid. Gene therapy protocol is also considered an administration in which the therapeutic agent is a polynucleotide capable of accomplishing a therapeutic goal when expressed as a transcript or a polypeptide into the patient.

As used herein, the term "biological activity" with respect to the nucleotides and polypeptides of the subject invention refers to the inhibition of tumor cell growth or proliferation. Thus, cell-based assays can be utilized to determine whether an agent, such as nucleotide or polypeptide, can be utilized to carry out the method of tumor growth inhibition of the subject invention, as shown in FIGS. 18A-21D.

The term "means for inhibiting or suppressing lrba function" comprises genetic and non-genetic means for inhibiting or suppressing lrba function. Among the genetic constructs inhibiting lrba function are various "gene delivery vehicles" known to those of ordinary skill in the art, that facilitate delivery to a cell of, for example, a coding sequence for expression of a polypeptide, such as an lrba inhibitor, an anti-sense oligonucleotide, an RNA aptamer capable of inhibiting lrba function, or other genetic construct capable of inhibiting lrba function at the transcription, translation, or post-translation level. Methods of gene silencing and/or knock-down, as described herein, and as known to those of ordinary skill in the art, can be utilized to suppress lrba function, for example. For example, gene therapy comprising administration of a dominant negative lrba mutant can be utilized to carry out the method of tumor inhibition of the subject invention.

Among the non-genetic means for inhibiting lrba function are pharmaceutical agents, or pharmaceutically acceptable salts thereof, which are preferably administered in a pharmaceutically acceptable carrier.

The term "patient", as used herein, refers to any vertebrate species. Preferably, the patient is of a mammalian species. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales.

The terms "lrba", "LRBA", and "Lrba" (italicized and unitalicized) are used herein interchangeably to refer to the LPS-responsive CHS1/beige-like gene or its polypeptide product, and includes lrba homologs (such as human and mouse orthologs), unless otherwise noted.

The terms "comprising", "consisting of", and "consisting essentially of" are defined according to their standard meaning and may be substituted for one another throughout the instant application in order to attach the specific meaning associated with each term.

Materials and Methods

Murine RNA Isolation and cDNA Synthesis. Total RNA was prepared using the RNEASY kit (QIAGEN, Valencia, Calif.). Poly(A)$^+$ RNA was prepared using the FAST TRACK mRNA isolation kit (INVITROGEN, Calsbad, Calif.). RNA was prepared from murine cell lines as well as liver and thymus of C57BL6/J mice per the manufacturers' instructions. RNAs were treated with Rnase-free Dnase I (AMERSHAM PHARMACIA BIOTECH, Piscataway, N.J.) at 10 U/μg of RNA for 30 minutes at 37° C. to destroy genomic DNA. First-strand cDNA synthesis was primed with random DNA hexamers or oligo(dT) primers at 42° C. for 1 hour using the SUPERSCRIPT II RNase H Reverse Transcriptase cDNA Synthesis System (Life Technologies, Inc., Rockville, Md.).

Cloning and Sequencing of Murine lrba Gene cDNAs. Primers (5'AGAGAAGAGGAGAAGATGTGTGATC3' (SEQ ID NO. 40); and 5'CCAGGCTCCATGCTTGTCTGT-GAG3' (SEQ ID NO. 41) forward and reverse, respectively) were designed from a 143 bp cDNA fragment obtained from previous gene-trap experiments (Kerr, W. G. et al. *Proc. Natl. Acad. of Sci. USA,* 1996, 93:3947) and combined with Lambda GT10 forward and reverse primers (5'AGCAAGT-TCAGCCTGGTTAAGT3' (SEQ ID NO. 42) and 5'TTAT-GAGTATTTCTTCCAGGG3' (SEQ ID NO. 43), respectively) to amplify the lrba gene cDNA from a mouse B lymphocyte cDNA library (Mouse lymphocyte 5' stretch cDNA library, CLONTECH, Palo Alto, Calif.). These PCR products were then cloned and sequenced. New primers were then designed from these sequences and further RT-PCR reactions were carried out to extend the cDNA sequence to the 5' or 3' direction. The SMART RACE amplification kit (CLONTECH, Palo Alto, Calif.) was used to amplify 5' cDNA ends using the following lrba-specific primers: 5'ACT-GCAGCAAGCTCCTCCTGTTTTCTC3' (SEQ ID NO. 44) and a nested primer: 5'TGGGCGAAGAGCGGAAACA-GAAC3' (SEQ ID NO. 45), while for 3' cDNA clones the following primers were used: 5'AGAGAAGAGGAGAA-GATGTGTGATC3' (SEQ ID NO. 40) and a nested primer: 5'GAGTGATGGATGATGGGACAGTGGTG3' (SEQ ID NO. 46). PCR conditions for the 5'-RACE and 3'-RACE were as follows using the ADVANTAGE polymerase mix (CLON-TECH, Palo Alto, Calif.): 94° C. for 30 seconds, followed by 5 cycles at 94° C. for 30 seconds, 70° C. for 30 seconds, and 72° C. for 3-5 minutes; 5 cycles at 94° C. for 30 seconds, 68° C. for 30 seconds, and 72° C. for 3-5 minutes; 20 cycles at 94° C. for 30 seconds, 65° C. for 30 seconds, and 72° C. for 3-5 minutes; and a final extension at 72° C. for 30 minutes. After the full-length cDNA sequence of the lrba gene was obtained, several primers were designed to amplify the region of the lrba gene cDNA containing its major open reading frame (ORF). The region containing the major ORF of the lrba gene was then amplified from a single source of C57BL6/J liver mRNA and resequenced to confirm that the lrba cDNAs obtained from liver cells were identical to that amplified from the aligned cDNA fragments amplified from primary and transformed B lymphocytes, indicating that these represent the major mRNAs expressed from the lrba locus. All RT-PCR and RACE products were isolated and purified from agarose gels using the QIAEX II Gel Extraction Kit (QIAGEN; Valencia, Calif.). The purified products were sequenced directly to avoid detecting the mutations introduced during PCT. Both strands of each template were sequenced and the sequence was confirmed by sequence analysis of at least two independent PCR products. PCR products and RACE products were cloned into PCRII vector (TA cloning kit; INVITROGEN, Carlsbad, Calif.) and multiple clones were sequenced. Plasmids were purified from liquid cultures using the QIAGEN plasmid Maxi preparation kit (QIAGEN; Valencia, Calif.).

Human lrba cDNA Cloning and Sequencing. A search of GENBANK indicated that the murine lrba gene has a high degree of homology to a 7.3 kb human partial cDNA sequence (GENBANK accession numbers M83822) called BGL (Feuchter, A. E. et al. *Genomics,* 1992, 13:1237), which was thereby tentatively identified as possibly a small fragment of a human lrba gene. The 5' end of the human lrba gene was obtained by using a 5' primer (5'GCCACCTC-CGTCTCGCTGC3' (SEQ ID NO. 47)) from the mouse lrba gene cDNA sequence and a 3' primer (5'GGGCACTGGG-GAGAATTTCGAAGTAGG3' (SEQ ID NO. 48)) from the human BGL sequence. Human lung, brain, and kidney cDNA libraries (MARATHON cDNA Libraries, CLONTECH, Palo Alto, Calif.) were used as templates for the amplification of the 5' and 3' ends of the human cDNA under the following PCR conditions: 35 cycles at 95° C. for 45 seconds; 60° C. for 15 seconds; 72° C. for 3 minutes. The PCR products were cloned into a TA cloning vector and multiple clones were sequenced. Additional PCRs were carried out with the primers from the 3' cDNA clones obtained as described above to complete the sequence of the human lrba cDNA. The primer pairs used for these additional 3' cDNA clones were 5'TTCAGGCAGTTTTCAGGACCCTCCAAG3' (SEQ ID NO. 49) and 5'TAGTGTCTGATGTTGAACTTCCTCCTG3' (SEQ ID NO. 50). Overlapping regions of the 5' and 3' human lrba cDNAs were compared and merged with the human BGL cDNA in GENBANK to construct, for the first time, a complete sequence for the human lrba gene (GenBank accession number AF216648). The human lrba gene encodes a 319KD protein that has 2863 amino acids. The amino acid homology between the human and murine lrba gene is 93% (identity 89%, similarity 4%). Like the murine lrba gene, the human lrba gene contains BEACH domain, five WD40 repeats and two novel domains that are defined as followed (FIGS. 9 and 10).

Northern Blot Analysis. 70Z/3 B lymphoma cells were maintained in RPMI1640 supplemented with $10^{-5}$M 2-mercaptoethanol and 10% fetal bovine serum (FBS). J774 cells were maintained in DMEM supplemented with 10% FBS. 70Z/3 cells were stimulated with 10 ng/ml LPS (Sigma, St. Louis, Mo.) and J774 cells were stimulated with 1 ng/ml LPS for 20 hours. Poly(A)$^+$ RNA was prepared from $10^8$ stimulated or unstimulated cells using the FASTRACK isolation kit (INVITROGEN, Carlsbad, Calif.). Poly(A)$^+$ RNA (5 µg/lane) was size-fractionated by electrophoresis on a 6% formaldehyde/1% agarose gel buffered with MOPS, transferred to a nylon membrane (STRATAGENE, La Jolla, Calif.) by capillary action in 20× SSC and immobilized by UV cross-linking. The filter was probed with a uniformly labeled $^{32}$P probe using the READY-TO-GO DNA labeling kit (AMERSHAM PHARMACIA BIOTECH, Piscataway, N.J.). The probe corresponds to a 2.5 kb PCR product that spans nucleotides 3545-6040 of the murine lrba cDNA. The filter was hybridized with the probe in 2× SSC, 0.5% SDS, 5× Denhardt's containing 100 µg/ml heat denatured salmon sperm DNA at 68° C. overnight. Filters were washed 2 times for 5 minutes at room temperature in 2× SSC/0.5% SDS and 2 times for 30 minutes at 68° C. in 0.1× SSC/0.1% SDS. Hybridization signals were detected and quantitated using a Molecular Dynamics PHOSPHORIMAGER and IMAGEQUANT software.

RT-PCR Analysis of lrba Expression. The cell lines (70Z/3, BAL17, A20, WEHI231, and S194) used for the RT-PCR were obtained from ATCC (Rockville, Md.). Spleen, brain, lung, and bone marrow were obtained from C57BL6/J mice. The preparation of total RNA and cDNA synthesis were carried out as described above. First strand cDNA reaction products (2 µl) were amplified in a 25 µl PCR reaction using primers that detect three of the lrba isoforms ("5'GGCA-CAACCTTCCTGCTCAC3'" (SEQ ID NO. 51) and "5'CCT-GTCCCCCATTTGAACCC3'" (SEQ ID NO. 52) for the α form: "5'ACGGCTGCTTCTGCACCTTC3'" (SEQ ID NO. 53) and "5'TTTTGGGACAGGGCTTCTCTG3'" (SEQ ID NO. 54) for the β form; "5'GGCACAACCTTCCTGCT-CAC3'" (SEQ ID NO. 55) and "5'GCAGATGCTCTC-CTCGCTCC3'" (SEQ ID NO. 56) for the γ form). The cycling program was: 94° C. for 30 seconds, followed by 5 cycles at 94° C. for 30 seconds, 70° C. for 30 seconds, and 72° C. for 4 minutes; 5 cycles at 94° C. for 30 seconds, 68° C. for 30 seconds, and 72° C. for 4 minutes; 30 cycles at 94° C. for 30 seconds, 62° C. for 30 seconds, and 72° C. for 4 minutes; and a final extension at 72° C. for 10 minutes.

Gene and Protein Structure Prediction. Analyses of the nucleotide and amino acid sequences for the murine and human lrba gene were performed using MACVECTOR (Oxford Molecular Group Inc., Oxford, UK). Nucleotide sequence alignments and other analyses were carried out using BLAST (Altschul, S. F. and E. V. Koonin *Trends in Biochemical Sciences,* 1998, 23:444). SMART (Schultz, J. et al. *Nucleic Acids Res.,* 2000, 28:231), and CLUSTLX (Thompson, J. D. et al. *Clinical Orthopaedics & Related Res.,* 1997, 241) were used for protein secondary structure predictions. For WD repeat prediction, an algorithm developed by Neer et al (Neer, E. J. and T. F. Smith *Cell,* 1996, 84:175; Garcia-Higuera, I. et al. *Biochemistry,* 1996, 35:13985; Neer, E. J. et al. *Nature, October* 1994, 371(6500):812; Smith, T. F. et al. *Trends Biochem.,* 1999, 24:181; Neer, E. J. and T. F. Smith *Proc. Natl. Acad. Sci. USA,* 2000, 97:960) is used.

Construction, Expression, and Fluorescence Microscopy of the Lrba-GFP Fusion Protein. A region from the murine lrba cDNA that includes the BEACH and the WD domains 3' to the BEACH domain was inserted "in-frame" and upstream of the coding region of a modified GFP gene cloned in a mammalian expression vector pEGFP-N2 (CLONTECH, Palo Alto, Calif.). Recombinant clones (called pBWEGFP) were picked, plasmid DNAs prepared and sequenced to confirm that no mutations were introduced during these manipulations. Murine 3T3 cells, the macrophage RAW264.7 cells, and human 293 cells were transfected by the FUGEN transfection kit (ROCHE Molecular Biochemicals, Indianapolis, Ind.) or by electroporation (Gene Pulser; BIO-RAD Laboratories, Hercules, Calif.) with 20 µg of linearized recombinant plasmid pBWEGFP DNA as well as the control vector pEGFP at 250V, 500 µF. One day later, cells were cultured in DMEM containing 0.8 µg/ml of G418 (LIFE TECHNOLOGIES, Inc., Rockville, Md.). This medium was changed every day for the first four days. The surviving G418 resistant colonies were isolated and used for further experimentation. For subcellular localization, cells were plated in glass-covered plates at 2.5×10$^5$ cells/ml in 2 ml DMEM media with or without LPS at 100 ng/ml. After 12 hours, cells were directly examined by fluorescence microscopy using a fluorescein isothiocyanate filter to detect expression of GFP fusion proteins. Fluorescent photomicrography was performed using Nikon photomicrographic equipment model H-III and image software (NIKON, Tokyo, Japan).

Confocal Laser Scanning Microscopy. The RAW 264.7 cells stably transfected with the pBWEGFP construct were grown on glass coverslips and stimulated with 100 ng/ml LPS for 24 hours. Golgi and lysosomes were specifically labeled with BODIPY TR ceramide and LysoTracker Red DND-99 (MOLECULAR PROBE, Eugene, Oreg.), respectively, following the manufacturer's protocols. Briefly, for Golgi labeling, cells were washed with PBS three times and incubated for 30 minutes at 4° C. with 5 μM BODIPY TR ceramide, rinsed several times with ice-cold medium, and then incubated in fresh medium at 37° C. for another 30 minutes. For lysosome labeling, medium was changed with pre-warmed fresh medium containing 60-75 nM lysosome probe and the cell sample was incubated for 30 minutes. Finally, the medium was removed, washed with PBS three times, fixed with 3.7% formaldehyde for 10-20 minutes, washed again, and the slides were mounted with DAPI-containing VECTASHIELD medium (VECTOR LABORATORIES, Burlingame, Calif.). Cells were observed on a Zeiss inverted Axiovert 100 M laser scanning confocal microscope. Fluorescence of GFP was excited using a 458/488 nm argon/krypton laser, and emitted fluorescence was detected with 505-530 nm band pass filter. For LysoTracker Red and BODIPY TR, a 633-nm helium/neon laser was used for excitation, and fluorescence was detected with a 585 nm band pass filter, using a 100× oil immersion lens. The co-localization function of LSM510 software (EMBO Laboratory) allows for a reliability of 99% for actual pixels with both fluorophores. The co-localization mask pixels were converted to white color for clarity.

Immunoelectron Microscopy. The RAW 264.7 cells stably transfected with the pBWEGFP construct were grown in the presence of 100 ng/ml LPS for 24 hours, washed with PBS three times, fixed with 2% paraformaldehyde in phosphate buffer for 1 hour and 4° C., and processed for postembedding immunocytochemistry. The cells were scraped from the dishes they were grown in and pelleted by low speed centrifugation. The pellets were dehydrated in a graded series of ethanol dilutions and embedded in gelatin capsules in LR White resin. The resin was polymerized for 48 hours at 50° C. Ultrathin sections of LR White embedded cells were collected on nickel grids and immunolabeled according to the technique of Haller et al. (Haller, E. M. et al. *J. Histochem Cytochem*, 1992, 40:1491) with rabbit-anti-GFP (CLONTECH, Palo Alto, Calif.) at 1:20 ration for 1 hour at room temperature, followed by extensive rinsing and then labeling with 10 nm goat-anti-rabbit IgG-gold (AURION, Wageningen, The Netherlands) for 1 hour at room temperature. Control grids were labeled by replacing the primary antibody with normal rabbit serum. After extensive washing, thin sections were stained with uranyl acetate and lead citrate before examination with EM.

Primers. The gene-specific primers were designed from the partial sequences of the human lrba that were obtained and from BGL sequence in the GenBank (GenBank accession numbers M83822). The sequences of synthetic oligonucleotides used for PCR amplification were as follows: cdc415mar2: CACACAGAGCATTGTAGCAAGCTCCTC (SEQ ID NO. 57); h65-56153: TGCAGACTTGAAGAT-TCCG (SEQ ID NO. 58); 3CDS: 5'-AAGCAGTGGTAT-CAACGCAGAGTACTTTTTTTTTTTTTTTTTTTTTTT-TTTTTTVN-3' (SEQ ID NO. 59); h6439: GAGTGATGGAT-GATGGGACAGTAGTG (SEQ ID NO. 60); cdc415mar1: GGGCACTGGGGAGAATTTCGAAGTAGG (SEQ ID NO. 48); and h5end65': CGAGAAGATGAGAAGATGTGT-GATC (SEQ ID NO. 61).

Human RNA isolation and cDNA synthesis. Total RNA was prepared using the RNeasy kit (QIAGEN, Valencia, Calif.). RNA was prepared from cell lines as well as human prostate tumor tissues and normal adjacent tissue per the manufacturers' instructions. First-strand cDNA synthesis was primed with gene-specific primers or oligo(dT) primers at 42° C. for 1 h-2 h using the SUPERSCRIPT II RNase H Reverse Transcriptase cDNA Synthesis System (Life TECH-NOLOGIES, Inc., Rockville, Md.) or PowerScript Reverse Transcriptase (CLONTECH, Palo Alto, Calif.).

5'-RACE, 3'-RACE and the Cloning of human lrba Gene cDNAs. 5'-RACE, 3'-RACE of hlrba gene were carried out by using the SMART RACE amplification kit (CLONTECH, Palo Alto, Calif.) and the following condition: 5'-RACE: cdc415mar2 as reverse transcription primer, 1-2.5 μg RNAs were used. cdc415mar1 was used for first PCR reaction, h65-56153 ( ) was used for nested primer; 3'-RACE: 3CDS from the kit was used as reverse transcription primer. h5end65' was used for first PCR reaction and h6439 was used for nested PCR primer. The PCR parameters are: 94° C. for 30 seconds, followed by 5 cycles at 94° C. for 30 s, 70° C. for 30 s, and 72° C. for 3-5 min; 5 cycles at 94° C. for 30 s, 68° C. for 30 s, and 72° C. for 3-5 min; 25 cycles at 94° C. for 30 s, 65° C. for 30 s, and 72° C. for 3-5 min; and a final extension at 72° C. for 10 min. All RT-PCR and RACE products were isolated and purified from agarose gels using the QIAEX II Gel Extraction Kit (QIAGEN; Valencia, Calif.). The purified products were sequenced directly to avoid detecting the mutations introduced during PCR. Both strands of each template were sequenced and the sequence was confirmed by sequence analysis of at least two independent PCR products. PCR products and RACE products were cloned into PCRII vector (TA cloning kit; INVITROGEN, Carlsbad, Calif.) and multiple clones were sequenced.

Mapping of the 5' end of the human lrba gene. The 5' end of the human lrba gene were determined by SMART 5' RACE (Clontech, Palo Alto, Calif.) in tumor tissues and adjacent tissues from prostate, human lung carcinoma, B-cell lymphoma and B-cell lymphoma (AMBION, Austin, Tex.). cdc415mar1 as reverse transcription primer were used. The lrba gene-specific primer cdc415mar2 was used to prime reverse transcription using 1-2.5 μg RNAs. Then first PCR reaction was performed using gene-specific primer cdc415mar2, h65-56153 was used for nested primer. Products were sequenced both directly and indirectly by first cloning into pCR2.1 vector (TA cloning kit; INVITROGEN, Carlsbad, Calif.).

Multiple Sequence Alignment. All amino acid sequences were obtained from the SWISS-PROT/TrEMBL database at the Expasy web site (www.expasy.ch). Homologous sequences were searched for using the BLAST server of Expasy. To gather tetraspanin and tetraspanin-like sequences from the data base, BLAST searches were performed using a number of sequences from well established members of the tetraspanin superfamily (i.e. CD81, CD82, CD9, CD53, CD63, UPK, RDS, and ROM). A multiple sequence alignment was initially achieved with the CLUSTAL1X software. The alignment was then improved manually using the GENE-DOC software.

Secondary Structure Prediction. To predict the secondary structure of the HSH domain, two methods (available on the World Wide Web) based on a consensus assignment were used. The first method, Jpred[2], takes a multiple sequence alignment as input and performs a consensus average of nine different alignment-based secondary structure prediction methods. Alignment-based prediction methods have been demonstrated to have a significantly better accuracy than those using single sequences, and consensus averaging by Jpred[2] has been shown to increase the accuracy to 72.9%. The use of alignment-based secondary structure prediction methods requires the sequences to have a degree of homology of at least ~25%.

RT-PCR Analysis of hlrba Expression. The cell lines MCF7 breast cancer cell line, 293 cell line, pre-B (6417); Raji B cells; HTB4 lung cancer; H322 human lung cancer; A539 human lung cancer used for the RT-PCR were obtained from ATCC (Rockville, Md.). The preparation of total RNA and cDNA synthesis were carried out as described above. First strand cDNA reaction products (2 µl) were amplified in a 25 µl PCR reaction using primers.

Following examples illustrate procedures for practicing the invention. These examples should not be construed as limiting. All percentages are by weight and all solvent mixture proportions are by volume unless otherwise noted.

EXAMPLE 1

Cloning and Sequencing of the Murine lrba cDNA

An LPS-inducible gene was identified by integration of Gensr1 gene-trap retrovirus (Kerr, W. G. et al. *Proc. Natl. Acad. of Sci. USA,* 1996, 93:3947). A partial cDNA sequence of the LPS-inducible gene-trap cell clone, 7a65, was used to design PCR primers to amplify the upstream and downstream regions of cDNA from a mouse B lymphocyte library. Initially, a 1.6 Kb cDNA sequence was obtained by this strategy. Sequence analysis confirmed that this 1.6 Kb cDNA sequence contains the original 142 bp sequence obtained by gene-trapping (Kerr, W. G. et al. *Proc. Natl. Acad. of Sci. USA,* 1996, 93:3947). 5' RACE reactions using anti-sense primers from the 5' end of this 1.6 Kb region yield additional 5' cDNA sequences including the 5' UTS of the lrba gene as well as the ATG of its major ORF. Sense strand primers were also designed from the 1.6 Kb cDNA sequence and three 3' RACE fragments of 2.5 Kb, 2 Kb, and 1.4 Kb were obtained that have identical 5' end sequence; however, their 3' ends differ substantially. The amino acid sequence of the major ORF in the murine lrba cDNA is shown in FIG. 1A. The human lrba orthologue is obtained as described in the Experimental Procedures section.

Sequence analysis of the lrba cDNAs indicated the existence of three isoforms with identical 5' ends that differ at their 3' termini. These isoforms include a 9903 bp form (lrba-α), a 9396 bp form (lrba-β) and 8854 bp form (lrba-γ) encoding proteins of 2856, 2792, and 2779aa, respectively. All three ORFs begin with the same Kozak consensus ATG at nucleotide 308. The first 2776aa of the β form are identical to the first 2776aa of the α form, while the 16aa at its C-terminus are unique to it. The first 2769aa of the γ form are identical to the first 2769aa of the α and β forms with its C-terminal 10aa unique to it; the α form has its C-terminal 80aa unique to it (FIG. 1). Homology search indicates that all lrba isoforms have a BEACH domain (Nagle, D. L. et al *Nature Genetics,* 1996, 14:307); however, the lrba-α isoform has 5 WD repeats, lrba-β has 3 WD repeats while lrba-γ lacks WD repeats (FIG. 1B). The isoform specific unique coding sequences and the associated 3' untranslated sequence (totally 1267 bp for α form, 761 bp for β form, and 845 bp for γ form) show no significant homology with each other. Interestingly, only the α form has an AATAAA sequence for polyA recognition and a TGA stop codon, while the β and γ forms have TAA stop codons.

EXAMPLE 2

Lrba Orthologues Exist in Diverse Organisms and Belong to a Novel Gene Family

Homology analysis revealed that lrba has significant homology with the partial protein sequence DAKAP550 (Han, J. D. et al. *Jour. Biol. Chem.,* 1997, 272:26611), which is an AKAP, and with AKAP550 (GENBANK accession number AAF46011) predicted from the *Drosophila* genomic sequence (GENBANK accession number AE003433). A longer sequence for this gene is predicted from the genomic sequence and is designated dLRBA, which is identical to AKAP550 except that it has an additional 160aa at its N-terminus. As used herein, the first letter of the genus is placed before the gene's name to distinguish the lrba genes of different species. Thus, DAKAP550 is a partial sequence of dLRBA and AKAP550. Amino acid alignment analysis shows that the murine LRBA protein has 85% aa identity with human LRBA, 51% aa identity with dLRBA and 35% aa identity with the *C. elegans* CDC4L gene (GENBANK accession number T20719) (designated cLRBA for clarity) (FIG. 1B). This homology analysis shows that the lrba and DAKAP550 genes are othologues based on their high homology that extends from their N terminus to the C terminus (FIGS. 1-3 and Table 1). Furthermore, two putative PKA binding sites are found in all lrba orthologues (FIGS. 2A and 2B) and are structurally similar to the B1 and B2 RII binding sites of DAKAP550, a protein that has been demonstrated to bind PKA in vitro and in vivo (Han, J. D. et al. *Jour. Biol. Chem.,* 1997, 272:26611 ). This region is highly conserved in lrba orthologues in mice, man, *Drosophila,* and *C. elegans* (FIG. 2A) and potentially provides another two PKA binding sites for DAKAP550. Unexpectedly, the B1 and B2 sites of DAKAP550 are not found in other LRBA proteins; they may be species-specific and these potential RII binding sites need to be confirmed by biochemical studies.

TABLE 1

|  | Identities | Positives | | Length (aa) |
| --- | --- | --- | --- | --- |
| mLBA dLBA | | | | |
| 92-405 | 47-394 | 51% | 73% | 314 |
| 405-959 | 601-1160 | 55% | 75% | 555 |
| 998-1576 | 1542-2127 | 36% | 53% | 579 |
| 1793-2856 | 2642-3727 | 56% | 74% | 1064 |
| mLBA cLBA | | | | |
| 65-946 | 164-1057 | 42% | 61% | 882 |
| 1300-1571 | 1065-1333 | 39% | 59% | 271 |
| 1787-2856 | 1436-22512 | 47% | 64% | 1070 |
| mLBA hLBA | | | | |
| 1-2856 | 1-2863 | 85% | 88% | 2856 |
| mLBA mBG | | | | |
| 1934-2839 | 1460-2335 | 27% | 43% | 906 |
| mLBA hFAN | | | | |
| 2038-2841 | 163-913 | 29% | 45% | 803 |

Table 1 shows the protein homology between LRBA and dLRBA, mBG, and HFAN, showing the percentage of identity, and positive gaps. The positions of each fragment are also indicated.

These lrba orthologues also have a highly conserved long C-terminal region (around 1000 amino acids) shared with a group of proteins including CHS1/BG (Perou, C. M. et al. *Nature Genetics*, 1996, 13:303; Kingsmore, S. F. et al. *Jour. Invest. Med.*, 1996, 44:454), FAN (Adam-Klages, S. et al. *Cell*, 1996, 86:937), LVSA (Kwak, E. et al. *Cell*, 1999, 10:4429) proteins (FIGS. 2A and 2B), and a number of anonymous ORFs. They constitute a new gene family. The conserved region contains an unidentified region followed by one BEACH domain and several WD repeats. Several WD repeats are found in the unidentified region of homology in these genes when about 1000 aa of C-terminal sequence is searched for WD repeats; however, no WD repeat is predicted when this region is analyzed alone (data not shown). Thus, this region is designated herein as WD repeat-like domain (WDL). In aggregate, and not to be limited by theory, the entire WDL-BEACH-WD (WBW) structure may have a precise functional role since the WD repeats found in the WBW structures of different beige-like genes have a higher degree of homology with each other than with other WD repeats in proteins that lack a BEACH domain (FIG. 3). This homology analysis suggests the evolutionary conservation of the WBW structure in a gene family that includes lrba, chs1/beige, FAN, lvsA, and other unidentified ORFs in GENBANK. However, the BEACH domain can exist without WD motifs as in the case of lrba-γ (FIGS. 1A, 1B and 3). It is shown herein that all BEACH domains have an SH3 binding site (consensus sequence PXXP), an SH2 binding site (consensus sequence YXXhy) (Pawson, T. and J. D. Scott *Science*, 1997, 278: 2075), and a tyrosine kinase phosphorylation site (consensus sequence: (RK)-x(2,3)-(DE)-x(2,3)-Y) (Patschinsky, T. et al. *Proc. Natl. Acad. Sci. USA*, 1982, 79:973; Hunter, T. *J. Biol. Chem.*, 1982, 257:4843; Cooper, J. A. et al. *J. Biol. Chem.*, 1984, 259:7835), as shown in FIG. 3. These putative binding sites show that WBW proteins may interact with multiple signal transduction components.

EXAMPLE 3

Analysis of lrba mRNA Expression

Figure 4A:
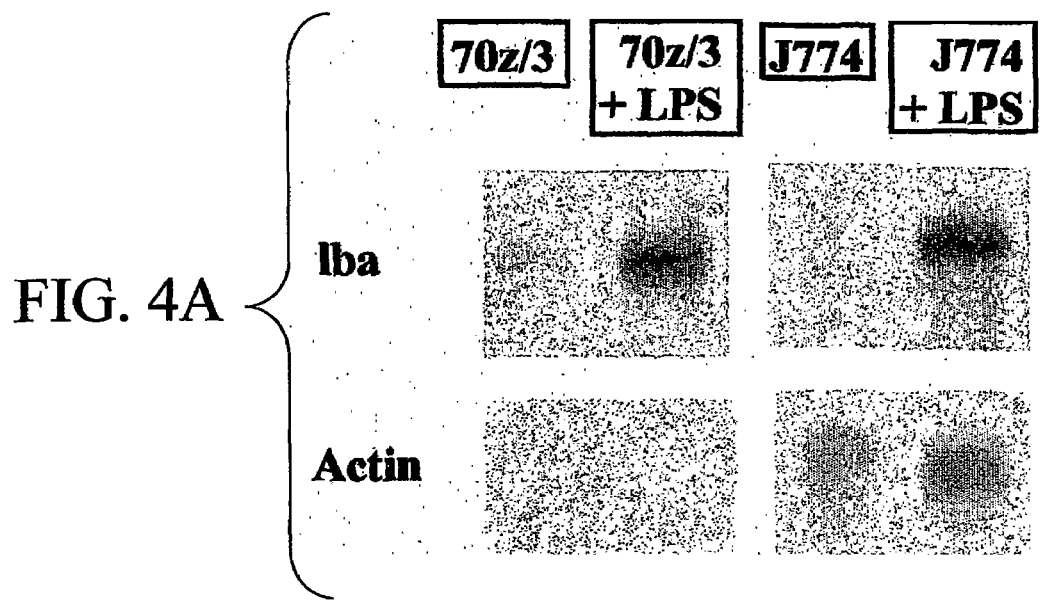
FIGS. 4A and 4B show that expression of lrba is inducible in B cells and macrophages.

Northern blot analysis indicates a single mRNA of about 10 Kb encoding the lrba gene is present in LPS-induced J774 macrophages and 70Z/3 B cells (FIG. 4A), as well as in other B cell lines (WEHI231, BCL1) and the macrophage cell line, RAW264.7 [RAW267.4]. The size (~10 Kb) of the transcript is consistent with the cDNA sequence analysis described herein (9903 bp for lrba-α). The expression of the lrba gene is significantly up-regulated in LPS-induced J774 macrophage cells as the lrba mRNA is nearly undetectable in J774 cells in the absence of LPS stimulation. The level of lrba mRNA is increased by 3 fold in 70Z/3 B cells (FIG. 4A) using β-actin mRNA as an internal standard. The upregulation of lrba expression in the B cell lines is consistent with the FACS analysis of lacZ induction in the 7a65 gene-trap cell clone (Kerr, W. G. et al. *Proc. Natl. Acad. of Sci. USA*, 1996, 93:3947).

Figure 4B:
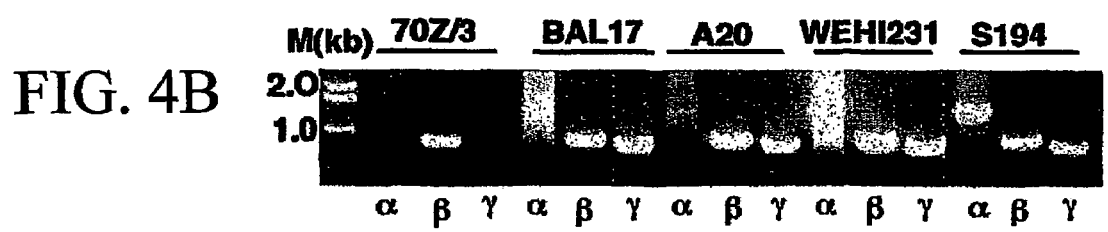
Figure 4C:
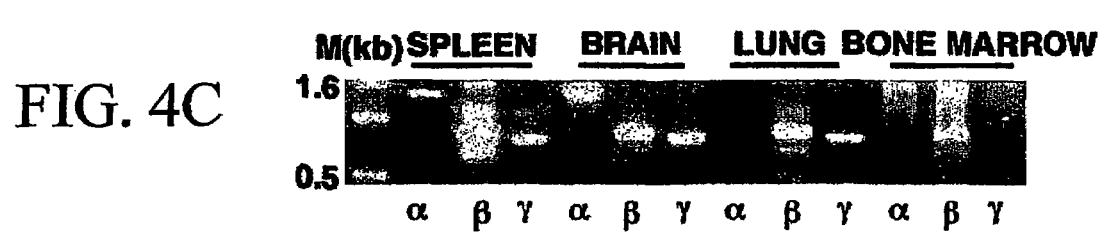

A multiplex RT-PCR assay was also developed that can simultaneously detect the expression of the lrba mRNA isoforms. RT-PCR analysis of lrba mRNA (FIGS. 4B and 4C) shows that lrba-β mRNA is expressed in all cell lines and tissues analyzed; however, lrba-α mRNA is absent in 70Z/3, lung and bone marrow and is less abundant in spleen and lung, suggesting that these different isoforms may have discrete functions in different tissues.

EXAMPLE 4

Subcellular Localization of LRBA-GFP Fusion Protein Shifts Upon LPS Stimulation

Figure 5A:
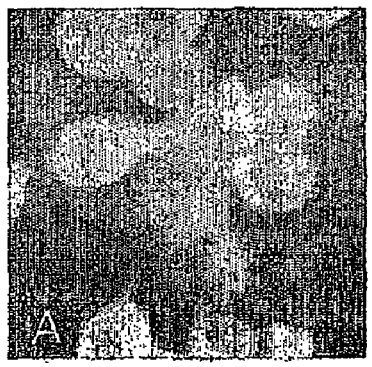
FIGS. 5A-5I show subcellular localization of GFP-LRBA fusion proteins revealed by UV-fluorescence microscopy and laser-scan confocal microscopy.
Figure 5B:
Figure 5C:
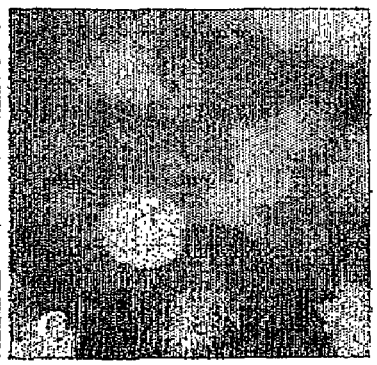
Figure 5D:
Figure 5E:
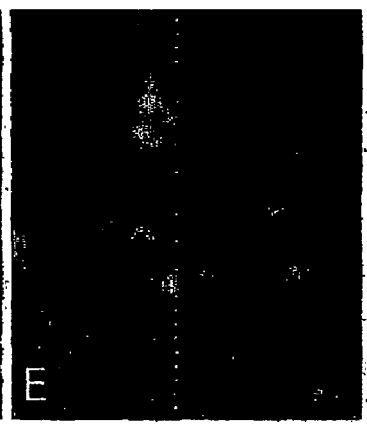
Figure 5F:
Figure 5G:
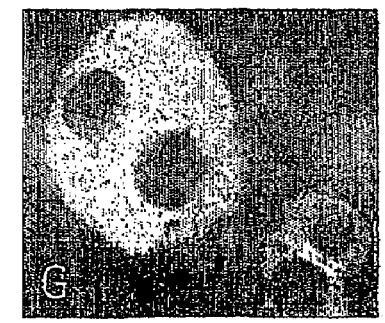
Figure 5H:

All mutations in beige or chs1 genes result in truncated proteins that lack the BEACH and COOH terminal WD repeats (Certain, S. et al. *Blood*, 2000, 95:979). This region may contain sequences critical to the function of chs1/beige and lrba genes. In particular, the ability of their gene products to associate with intracellular vesicles to influence their trafficking may be lost in these truncated mutants. Therefore, a GFP fusion with the BEACH-WD region of lrba called BW-GFP was created. As shown in FIGS. 5A-5I, fluorescence microscopy of RAW 267.4 cells stably transfected with an expression vector encoding the BW-GFP fusion shows that the BW-GFP protein is present in the cytosol with rare cells showing a vesicular staining pattern in the absence of LPS stimulation (FIG. 5A). However, this vesicular staining pattern is dramatically increased in these cells following LPS stimulation (FIG. 5B). Both the percentage of cells and the degree of vesicular staining in each cell are increased following LPS stimulation. RAW267.4 cells stably transfected with a GFP control construct show no change in their GFP fluorescence pattern upon LPS stimulation (FIG. 5C).

Figure 5I:
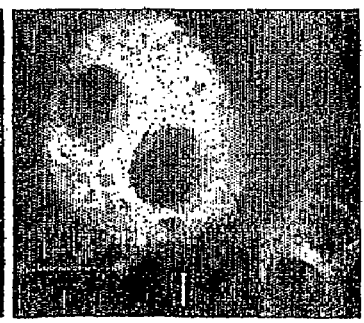

To determine which vesicular compartments the BW-GFP fusion localizes to, the RAW264.7 cells stably transfected with the pBWEGFP construct stained with a lysosome specific dye (FIG. 5E) and trans-Golgi specific dye (FIG. 5H) were analyzed with confocal microscopy. The merged pictures show that some LRBA-GFP proteins are co-localized with lysosomes (FIG. 5F, white area) and co-localization with the trans-Golgi complex (FIG. 5I, white peri-nucleus area).

Figure 6:
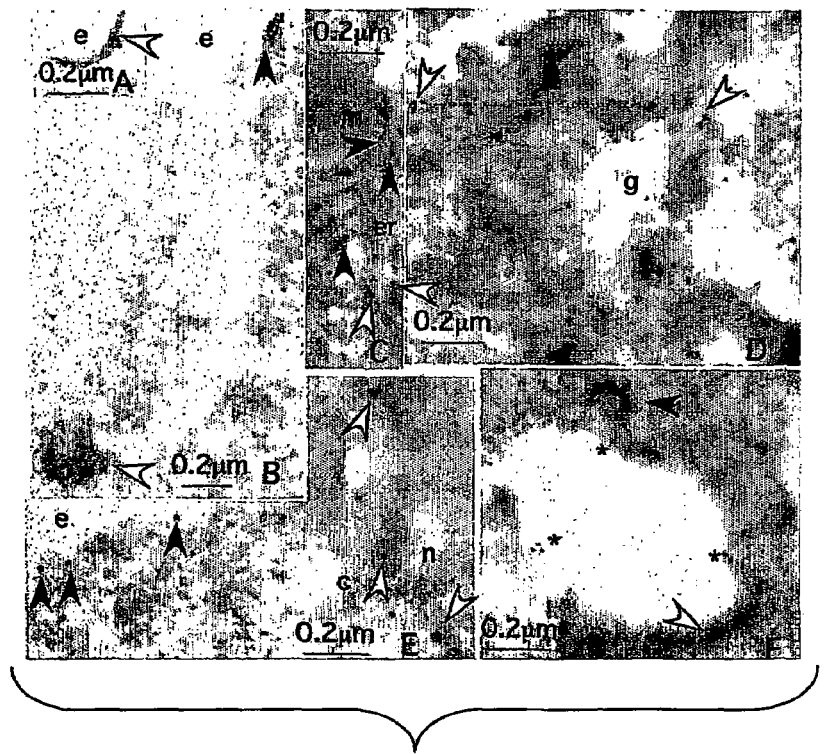
FIGS. 6A-6F show immunoelectron microscopy of LRBA-GFP fusion protein. The LPS-stimulated R7 macrophage cells were fixed and processed for postembedding immunocytochemistry. The cells were dehydrated and embedded in gelatin capsules in LR White resin. Ultrathin sections of LR White embedded cells were collected on nickel grids and immunolabeled with rabbit-anti-GFP followed by labeling with anti-rabbit IgG-gold secondary antibody, and finally stained with uranyl acetate and lead citrate before examination with EM.
Figure 8:
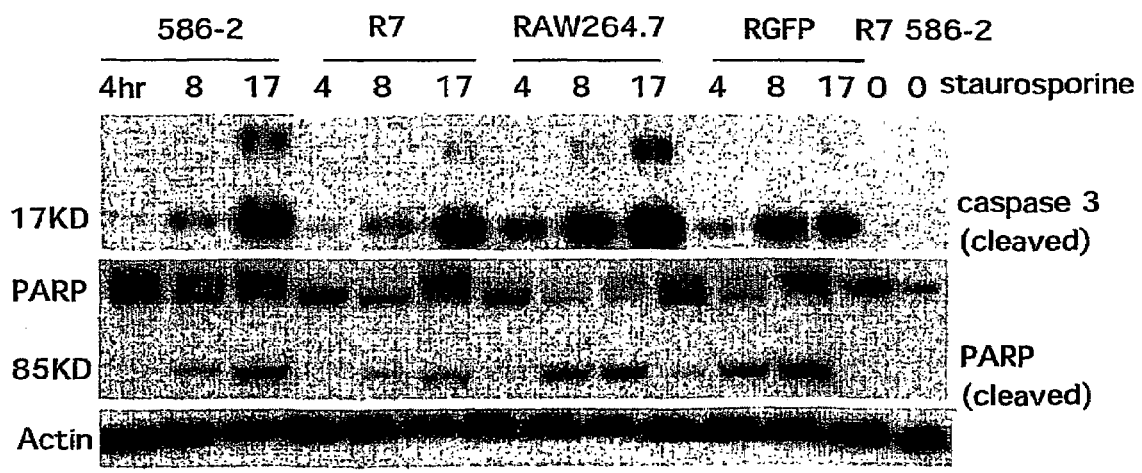
FIG. 8 shows a Western blot of a Raw 264.7 macrophage cell line and stably transfected Raw 264.7 cell lines, demonstrating inhibition of apoptosis by LRBA fusion proteins. 586-2 cells were transfected with BEACH-GFP construct; R7 cells were transfected with BEACH-WD-GFP construct; and RGFP cells were transfected with pEGFP vector. The level of both cleaved PARP (poly(ADP-ribose) polymerase and cleaved caspase 3 are higher in control cell lines (Raw 264.7 and RGFP) than in LRBA transfected Raw 264.7 cell lines (586-2 and R7), suggesting LRBA constructs can prevent cells from apoptosis induced by staursporine.

Immunogold labeling experiments were also performed that show the LRBA-GFP fusion protein can be found in association with the Golgi complex (FIG. 6D), lysosomes (FIGS. 6B and 6F), endoplasmic reticulum (FIG. 6C), plasma membrane (FIG. 6E), perinuclear ER (FIG. 6E), and endocytic vacuole (FIG. 6A, as the gold particles are labeling a clathrin coated endocytic vacuole, which indicates that it is involved in endocytosis and not exocytosis). The immunoelectron microscopy results agree well with the observations made by fluorescence microscopy and confocal fluorescence microscopy.

EXAMPLE 5

Exon/Intron Structure of the Human lrba Gene

The genomic locus of lrba gene is composed of 58 exons and 57 introns, spinning over a 700 K bps genomic sequence. Exon 1 and exon 2 contain the first part of the 5' UTR, exon 2 contains the rest of the 5'UTR and the start methione, while exon 58, the final exon, contains part of the WD5 and the whole 3'UTR. There are two considerably large exons—exon 24 (1059 bps) and exon 58 (1148 bps). The entire SET domain is encoded by one exon—exon 24, while other domains are econded by multiple exons. The remaining exons range in size from 33 to 435 bps, most are below 200 bps. All exon/intron junctions conform to the GT-donor/AG-acceptor rule (Breathnach and Chambon, 1981)(Table 1). The function of the lrba gene is defined by its domain structure consisting of BEACH domain, WD repeats, HSH domain and SET domain and potential RII binding sites. The BEACH domain is encoded by exons 45 to 51. The 5-WD repeat domain is encoded by exons 54 to 58. Isoforms are formed by splicing with splicing site inside the exons of the other isoforms.

Table 2 shows the exon/intron organization of the human lrba gene.

TABLE 2

Exon/Intron Organization of the Human lrba Gene

| Exon No | Exon size (bp) | 5'Splice donor | SEQ ID NO. | Intron No | Intron size (kb) | 3'Splice acceptor | SEQ ID NO. |
|---|---|---|---|---|---|---|---|
| 1 | ~67 | AGT ATC TGG gtgaggaag | 62 | I | 0.340 | tccaataag GGT TTG GCG | 119 |
| 2 | 435 | TTT AAC CTG gtaagtcca | 63 | II | 85.572 | ccttgtaag TTG GTA GGA | 120 |
| 3 | 232 | TGA TAG CAG gtatgatttt | 64 | III | 0.217 | tgtttccag ATC TTT TGG | 121 |
| 4 | 101 | GGA CGA TCG gtaaaaaaa | 65 | IV | 7.224 | tcttcatag CCT CCA CAT | 122 |
| 5 | 96 | AGT GCT GCA gtaagtaa | 66 | V | 4.458 | ttcctttag GCT ATT GCA | 123 |
| 6 | 122 | TTT GTA TTG gtatgtatt | 67 | VI | 0.089 | tctttatag TTT CAG AAC | 124 |
| 7 | 127 | CCA CAA AAG gtacatgat | 68 | VII | 0.674 | cttctgcag TGG TAT ATG | 125 |
| 8 | 120 | ACT AGC GAT gtaagtagt | 69 | VIII | 1.266 | cttttacag ACC TTT GAC | 126 |
| 9 | 147 | GGA TAC AAG gtagtttgc | 70 | IX | 5.537 | ttcttagag GGT ACA TTT | 127 |
| 10 | 198 | ATG CTC CAG gtactaact | 71 | X | 0.192 | tcttacaag GAT GTA AAG | 128 |
| 11 | 134 | GAC TAT ATG gtgagtgcc | 72 | XI | 1.971 | aaattctag TTC AAC CTT | 129 |
| 12 | 109 | CTT GAA AAG gtaaagtat | 73 | XII | 0.306 | tttttgcag TCT TCC AAA | 130 |
| 13 | 153 | CCA GCC AAG gtaatatat | 74 | XIII | 5.619 | attctgtag GTT CAA CTG | 131 |
| 14 | 169 | AAG GAT TAG gtatataat | 75 | XIV | 2.233 | ttttaaaag ATG GAC CGC | 132 |
| 15 | 80 | GTG ATG AAG gtaggttca | 76 | XV | 1.282 | tttttgaag GAT TCT GGA | 133 |
| 16 | 63 | ATG CAT GAG gtaatatat | 77 | XVI | 3.245 | tgattatag GAT GAC AAT | 134 |
| 17 | 98 | TGG GTT ACG gtaagagtt | 78 | XVII | 20.299 | ttcattcag TGT TAT CTA | 135 |
| 18 | 93 | GGC CCC AAA gtaagtatg | 79 | XVIII | 1.209 | taattgcag GAG GAA AGC | 136 |
| 19 | 109 | CTG TTT GAG gtaggaatg | 80 | XIX | 0.738 | cttctgtag ATT CTT ATA | 137 |
| 20 | 82 | AAA CCC CTC gtatgtatg | 81 | XX | 2.220 | agattacag AGA TAC TAA | 138 |
| 21 | 124 | AAA CAG GAG gtaagctga | 82 | XXI | 0.318 | aattttcag GAG CTT GCT | 139 |
| 22 | 193 | CAT TCA AAG gtaagtttc | 83 | XXII | 14.688 | ttcacctag GTC ACT TTT | 140 |
| 23 | 1059 | GTG CTT GAG gtgatttta | 84 | XIII | 0.982 | tgtattaag ATA TCA AGG | 141 |
| 24 | 179 | GTG GAG AAG gtttgtcta | 85 | XXIV | 1.148 | tttggacag CCA TTC AAC | 142 |
| 25 | 154 | TCG GCT ACA gtaaggact | 86 | XXV | 0.423 | tctttacag CAT GAA CTG | 143 |
| 26 | 181 | TCC GAC TAG gtgagctgc | 87 | XXVI | 4.039 | aaattacag TTT GTG CAG | 144 |
| 27 | 122 | GCA GCG AAG gtaagtata | 88 | XXVII | 0.450 | cttaaatag AGC CCA GTG | 145 |
| 28 | 108 | AGA GAC ATA gtaagttac | 89 | XXVIII | 12.124 | ttttcccag GAG GAT AGC | 146 |
| 29 | 160 | CAC TCT CTG gtaagtttg | 90 | XXIX | 3.193 | atgatatag AAA TCA CAC | 147 |
| 30 | 442 | TTT TGA CAG gtactgata | 91 | XXX | 10.928 | ttattacag AAG TGT CAT | 148 |
| 31 | 134 | AAT CAC CAG gtgagttag | 92 | XXXI | 8.713 | cttttatag GCA GTA GAT | 149 |
| 32 | 79 | AAA TAT GAG gtatttaag | 93 | XXXII | 1.909 | tttccttag TAT TAC AGA | 150 |
| 33 | 134 | AAG GAA CAA gtaagtggt | 94 | XXXIII | 7.964 | ttaaaatag GTC TGG TTT | 151 |
| 34 | 62 | TGT TCT CAG gtgagtggc | 95 | XXXIV | 35.939 | tttttatag GAG TGG CAA | 152 |
| 35 | 65 | ATG AGG AAG gtaatttat | 96 | XXXV | 26.429 | ttcttacag GTT GCT TAG | 153 |
| 36 | 109 | GAA TTT GAG gtaggttac | 97 | XXXVI | >28.963 | ctctccaag TCA CTG TGT | 154 |
| 37 | 167 | TGC AGT GAG gtaaaggga | 98 | XXXVII | 83.886 | cattgtag TCG TCC TCT | 155 |

TABLE 2-continued

Exon/Intron Organization of the Human lrba Gene

| Exon No | Exon size (bp) | 5'Splice donor | SEQ ID NO. | Intron No | Intron size (kb) | 3'Splice acceptor | SEQ ID NO. |
|---|---|---|---|---|---|---|---|
| 38 | 125 | TGG AAC ATG gtcagtgg | 99 | XXXVIII | 1.891 | atgttttag TGT GCA TTT | 156 |
| 39 | 33 | ACA GCA AAG gtaagcatt | 100 | XXXIX | 6.179 | tcatttcag CCA CAG ATG | 157 |
| 40 | 147 | ATC TTG CCG gtaaatttg | 101 | XXXX | 2.515 | ttttggcag GTC CTG TTA | 158 |
| 41 | 137 | GAC CCC AAG gt | 102 | XXXXI | 96.572 | cctcattag ATC TTG GCA | 159 |
| 42 | 118 | CAA ACA GAG gtaatgtgt | 103 | XXXXII | 3.088 | ctgttgtag TTG CTG TGA | 160 |
| 43 | 103 | TCA AAC CAG gtactgttt | 104 | XXXXIII | 15.997 | ttcttgcag ACG TAT TTC | 161 |
| 44 | 116 | CGA TAG CAG gtaacctaa | 105 | XXXXIV | 3.840 | ccctatcag GAC GGA GTT | 162 |
| 45 | 113 | TTG TCC AAG gtaatttct | 106 | XXXXV | 30.846 | tattggcag CCA ATA GGA | 163 |
| 46 | 141 | CTA AGA ATA gtaagttca | 107 | XXXXVI | 1.015 | attttttag GAA CCC TTT | 164 |
| 47 | 120 | GAT ATT AAG gtacagaaa | 108 | XXXXVII | 19.536 | tttatatag GAG TTG ATC | 165 |
| 48 | 153 | AAC AGA TTG gtaagataa | 109 | XXXXVIII | 65.358 | tttttcag GCC CTG GAG | 166 |
| 49 | 169 | TTG AGA GAG gtaa9ttat | 110 | XXXXIX | 24.093 | cctttcag GCT GTT GAA | 167 |
| 50 | 90 | ATG CAA GTG gtaagtgct | 111 | XXXXX | 4.443 | ctcctgcag AGT CCA TTG | 168 |
| 51 | 178 | ACC TTC CTG gtaagtaaa | 112 | XXXXXI | 5.563 | gaattccag CTC ATC AAG | 169 |
| 52 | 63 | CTC TCA TAG gtctgtcac | 113 | XXXXXII | 5.176 | ttcttacag CCA GCA ATA | 170 |
| 53 | 156 | CAG ACA CAG gtaattttc | 114 | XXXXXIII | 7.441 | gcattacag GAA GAT TGA | 171 |
| 54 | 168 | ACC CAG GCA gtaagtatg | 115 | XXXXXIV | 16.043 | ttcctaaag GTG AGA CTG | 172 |
| 55 | 102 | GTT CAC AAG gtaaacctg | 116 | XXXXXV | 3.286 | tcttctcag AAG GAC CAT | 173 |
| 56 | 197 | AAC ATA AGA gtgagtgcc | 117 | XXXXXVI | 4.444 | gtctcacag GCC ATC CAG | 174 |
| 57 | 152 | CGA CCA GAG gtaacactg | 118 | XXXXXVII | 12.028 | ttctcctag GTG CAT CAT | 175 |
| 58 | 1148 | | | | | | |
| Total | 9936 | | | | >716.138 | | |

EXAMPLE 6

Molecular Phylogenic Relationship of hlrba Proteins with Other WBWs

Figure 12:
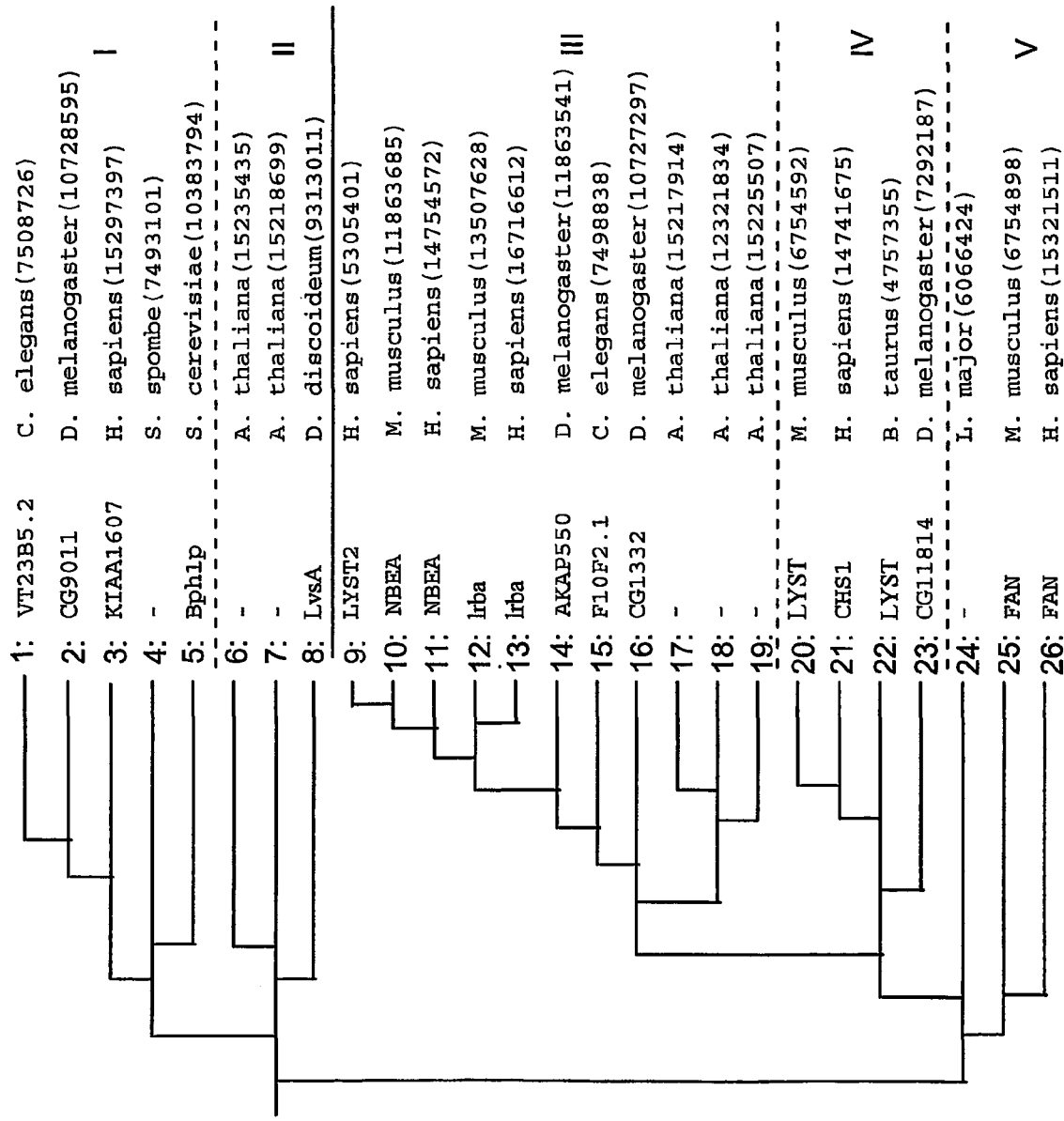
FIG. 12 shows a molecular phylogenic tree of the amino acid sequences of WBW genes from various species. The tree was constructed by the neighbor joining method, based on sequence alignment conducted by CLUSTALX software using either whole length sequence or only the BEACH domain, which gave very similar results. This indicates that the BEACH domain is co-evolving with the rest sequence of the gene and, as the whole sequences of some WBW genes are still unavailable (moreover, the length of the BEACH domain is relatively consistent (around 278 amino acids)), using the BEACH domain seems more reasonable. Thus.

Phylogenic analysis of the WBW family reveals that the members can be grouped into two major families, as shown in FIG. 12. One family is composed of proteins from *C. elegans*, *D. melanogaster*, *H. sapiens*, *S. pombe*, *S. cerevisiae*, *A. thaliana*, *D. discoideum*, and the other family contains proteins from *H. sapiens*, *M. musculus*, *Dr. melanogaster*, *C. elegans*, *A. thaliana*, *B. taurus*, *L. major*. These can be further sub-grouped into five distinct subfamilies, each of which may contains every species from the very ancient unicellular eukaryote to human. Lrba in human and murine, AKAP550 in fruit fly, F10F2.1 in *C. elegans* are orthologs as indicated previously, while NBEA and CG1332 are very close to lrba gene. Lrba, CHS1/beige and FAN belong to the same family. Despite the divergence of these species over several hundred million years, there is a high degree of sequence conservation in the BEACH domain, which may suggest an important role in the life of the cell concerning the BEACH domain.

EXAMPLE 7

The Human lrbaε Alternative Transcript has Two In-frame ORF

The ORF prediction shows there are two in frame ORFs in the human lrbaε alternative transcript. One ORF encodes a 72 amino acid protein, another encodes a 2782 amino acid protein. A very conserved motif (p21 RAS motif IV(LLGVG-GFD (SEQ ID NO. 176))) is missing from both proteins as a result of the disruption. Both ATGs are in the Kozak sequence and thus could serve as translation initiation sites. According to the translation scanning theory, the translation of the first ORF should not be a problem. There are three possibilities for the translation of the second ORF. The first possibility is leaking scanning, meaning that some ribosomes do not recognize the first ATG, but recognize the later ATG. However, there are four ATGs before the main ATG, and there is a long stem secondary structure between the two ORFs. Therefore, it is unlikely that the leaking model is the mechanism of translation. The second possibility is reading through translation, meaning that the translation machinery ignores the stop codon and reads through it. However, there are 10 stop codons between the two ORFs. Likewise, this is unlikely. A third possibility is that IRES (internal ribosome entry signal) translation is cap-independent. There is no homologous sequence between IRES, but they have complex secondary structure, such as long stem secondary structure. The RNA sequence between the two ORFs of human lrbaε can form a long stem structure, which could further make the leaking scanning or reading through impossible. Some mRNAs encoding pro-apoptic proteins, including Apaf-1 and DAP5 are also translated via an IRES element. IRES-independent initiation is sometimes utilized during mitosis. The numberous mRNAs whose 5' UTR structures likely interfere with the 5' cap-dependent ribosome are good candidates for the presence of an IRES. However, the prediction of an IRES from only looking at the 5' UTR could be strengthened by a better understanding of the structural components that comprise these IRES elements.

Figure 13:
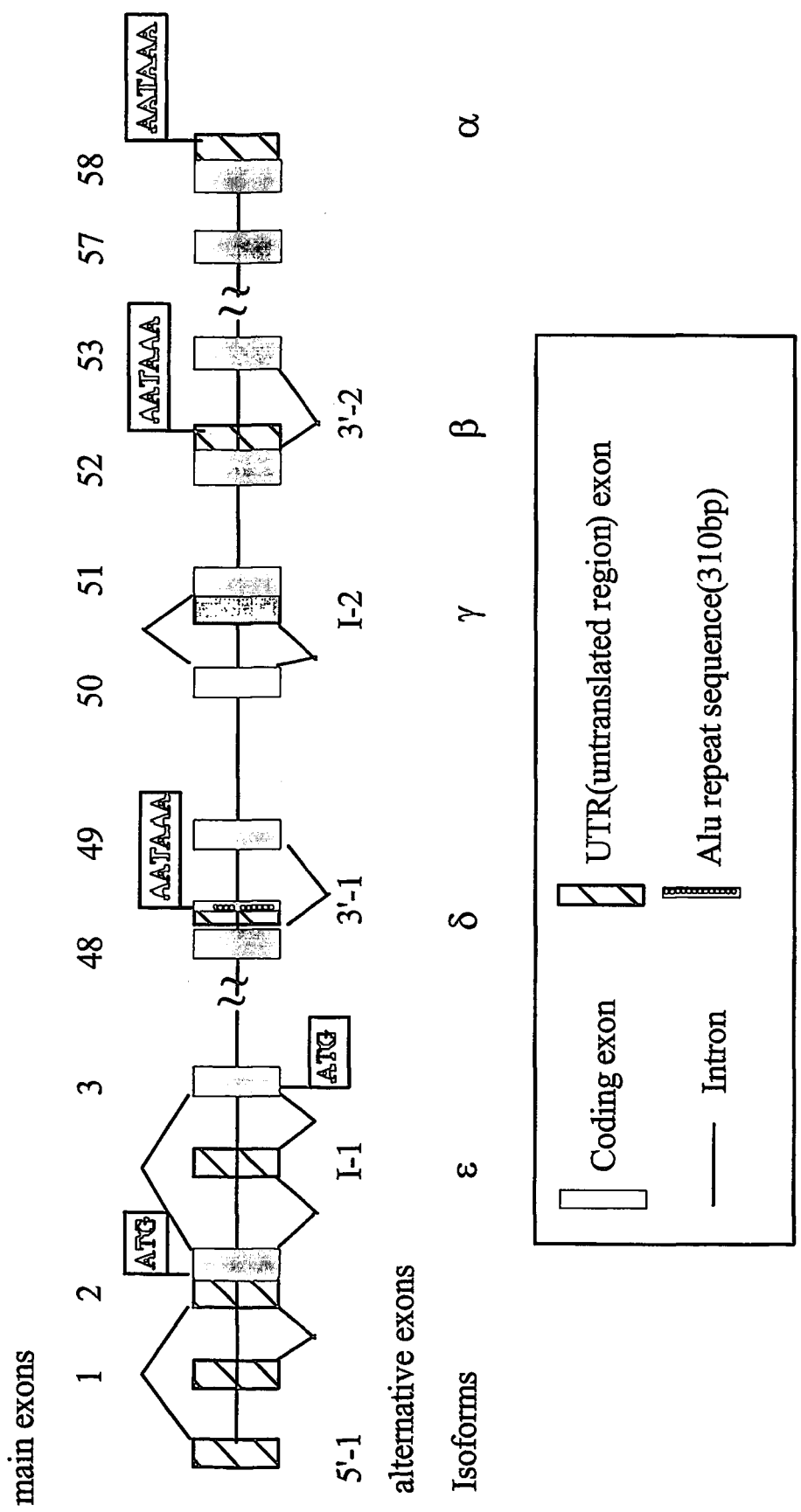
FIG. 13 shows alternative splicing of the human LRBA gene. The solid or gray box indicates coding exon, and the hatched box indicates UTR (untranslated region). The top numbers indicate exons in the main form (constitutive isoform versus alternative isoform) of human lrba, while the bottom numbers indicate alternative splicing isoforms of the human LRBA gene. The single Greek letters denote the five isoforms. The LRBAδ has a 310 bp Alu sequence at its poly (A) tail. 5'-1, 3'-1 and 3'-2 indicate 5' end and 3' end splicing, while I-1 and I-2 represent internal splicing. 5'-1 splicing gives alternative transcription start site and suggests alternative promoter for human LRBA gene. The internal splicing I-1 interrupts the coding sequence of LRBA, splitting LRBA into two open reading frames (ORF), and thus alternative potential start codon ATG (the meaning of this splicing is further described and discussed later). Another internal alternative splicing I-2 is a 15 bp sequence in frame with the main ORF, inserting a YLLLQ (SEQ ID NO. 32) insertion into the human LRBA protein (noting that the l and w are hydrophobic amino acids). AATAAA indicate a polyadenine signal. 3'-1 and 3'-2 splicing generate two additional different 3' UTR tails for human LRBA gene. The isoform identification was conducted by using the following cultured cells and tissues: (1.) human pre-B (6417) cells; (2.) human Raji B cells; (3.) 293 cells; (4.) human MCF7 breast cancer cells; (5.) human HTB4 lung cancer; (6.) human H322 human lung cancer; (7.) human A539 human lung cancer; (8.) human lung carcinoma; (9.) human lung carcinoma adjacent tissue; (10.) human B-cell lymphoma; (11.) human B-cell lymphoma; and (12.) normal adjacent tissue (3 pairs of tumor tissue and adjacent tissue of human prostate).

(SEQ ID NO. 32) additional sequence between BEACH domain and WD repeats. This insertion isoform also exists in murine LRBA gene, and the 15 bp nucleotide sequence insertion remains unchanged. All the isoforms are summarized as shown in FIG. 13.

TABLE 3

| Isoforms | Positions | Features | Implications | Pattern of alternative splicing* |
|---|---|---|---|---|
| 1α | There is one extra exon between Exon2 and Exon 3 | Disrrupt the coding sequence of the lrba gene at the N-terminus | Bicistron may exist in eukaryotes. Ribosome Internal entry sequence. | Cassette |
| 2β | Poly(A) alternative splicing after Exon 48 | There is a 312 bp Alu repeat sequence at the 5'UTR, splitting the BEACH domain at two third into two potential domains | 1. The BEACH domain is not a minimum domain, could be actually composed of two domains. 2. The Alu sequence may regulate the translation of LRBA gene or other gene. | Multiple Polyadenylation Site |
| 3γ | 15 bp insertion before Exon 51, just after BEACH domain and before WD repeats | The insertion encodes a YLLLQ peptide insertion into the LRBA protein. | Leucine (L) is a hydrophobic amino acid and may be involved in protein-protein interaction(as Leucine Zipper structure). That there are three consecutive Ls in a short sequence is unusual and Y could be a potential target for phosphorilation. | Retained intron |
| 4δ | Poly(A) alternative splicing after Exon 52 | The isoform doesn't have WD repeats but BEACH domain | Although BEACH domain and WD repeats often stay together, they are separate domain and can exist and function separately. | Multiple Polyadenylation Site |
| 5ε | An additional exon at 5' end (Exon 5'-1) before Exon 1 | Alternative promoter and transcription start site | LRBA may use different promoters to regulate the expression of LRBA. | Multiple Promoters |

EXAMPLE 8

Identification of the Five Isoforms of the Human lrba Gene

Four isoforms that encode four different proteins are present in human lrba gene, among which three isoforms differ at C-terminal: h-lrbaα has five WD repeats, h-lrbaβ lacks WD repeats, h-lrbaδ lacks WD repeats and part of BEACH domain. The fourth isoform h-lrbaγ has a YLLLQ The LRBA gene and five isoforms of the LRBA gene are disclosed and characterized herein. Northern blot experiments show that expression of lrba is upregulated 2-4 fold following LPS stimulation of B cells and macrophages. A homology search of GENBANK reveals that lrba gene has othologues in C. elegans, Drosophila, mice and humans and paralogues in diverse species ranging from yeast to human. These genes define a new protein family that are designated the WBW gene family herein because the members share an evolutionarily conserved structure over a long protein sequence (around 1000 aa). The analysis of subcellular localization with a BEACH-WD-GFP fusion protein described herein provides the first direct evidence that the lrba member of the WBW family can physically associate with various vesicular compartments in cells. Furthermore, it is proposed that the lrba gene is also an AKAP, suggesting that WBW family proteins may have microtubule and PKA binding properties like AKAPs (Colledge, M. and J. D. Scott *Trends in Cell Biology*, 1999, 9:216). Studies of FAN suggest that WBW proteins can bind to cytoplasmic tails of activated receptors via their WE repeats (Adam-Klages, S. et al. *Cell*, 1996, 86:937).

The evidence suggests that WBW proteins are involved in intracellular vesicle trafficking. For example, the strikingly enlarged vesicles in beige/CHS cells occur in membrane-bound organelles. The CHS1/BG protein has a similar modular architecture to the VPS15 and Huntington proteins that are associated with the membrane fraction (Nagle, D. L. et al. *Nature Genetics,* 1996, 14:307) and the lvsA gene that is essential for cytokinesis (Kwak, E. et al. *Cell,* 1999, 10:4429)-a process that also involves fusion of intracellular vesicles (Jantsch-Plunger, V. and M. Glotzer *Curr. Biol.,* 1999, 9:738; Heese, M. et al. *Curr. Opin. Plant Biol.,* 1998, 1:486). FAN may also be involved in vesicle trafficking since FAN-deficient mice, after cutaneous barrier disruption, have delayed kinetics of skin recovery that requires secretion of vesicles (Kreder, D. et al. *EMBO Journal,* 1999, 18:2472; Elias, P. M. *J. Invest. Dermatol.,* 1983, 80:44s). However, there is no direct evidence that these WBW proteins directly associate with vesicles. In contrast, others found unexpectedly by Western blot that the BG, LVSA, and DAKAP550 proteins are present in the cytosolic fraction of cells and not in the membrane fraction (Kwak, E. et al. *Cell,* 1999, 10:4429; Perou, C. M. et al. *Jour. Biol. Chem.,* 1997, 272:29790) or cytoskeleton (Han, J. D. et al. *Jour. Biol. Chem.,* 1997, 272: 26611). This paradox can be explained by hypothesizing (without being limited by theory) that these proteins are not constitutively associated with vesicles, but rather associate with vesicles under certain conditions like LPS stimulation. This hypothesis agrees well with the observation that an LRBA-GFP fusion protein is located in the cytosol; however, it becomes associated with vesicles following activation of the cells by LPS stimulation. Confocal microscopy also shows this fusion protein co-localizes with the trans-Golgi and lysosomes. Immunoelectron microscopy further demonstrates that it is also localized to endoplasmic reticulum and the plasma membrane as well as the trans-Golgi complex and lysosomes. Therefore, it is established herein that the BEACH-WD-GFP fusion protein is associated with the vesicular system. This may be true for the intact LRBA protein as well as for other WBW proteins like CHS1/BG, LVSA, and FAN, since they share high homology with the region in mouse lrba that was used for the GFP fusion experiment. The activation-triggered vesicle trafficking hypothesis is further supported by the following: (1) BEACH domain contains a tyrosine phosphorylation site, (2) the WD repeats binding site of FAN contains a serine residue (Adam-Klages, S. et al. *Cell,* 1996, 86:937), it is possible that this serine is a target of serine kinases, as some experiments suggest that the WD repeats binding requires phosphorylation of the WD binding sites (Skowyra, D. et al. *Cell,* 1997, 91:209) and (3) MAPK was suggested to control the movement of lytic granules of NK cells (Wei, S. et al. *Jour. Exper. Med.,* 1998, 187:1753). Potentially, WBW protein functions are activated by tyrosine and/or serine/threonine kinases following stimulation by agents like LPS. Although the GFP fusion experiment previously described does not demonstrate that the BEACH domain and/or the WD repeats in LRBA directly associate with intracellular vesicles, it is proposed that the BEACH domain binds to vesicles while the WD repeat domains bind to a membrane-associated protein. It is proposed that because BEACH domains and WD repeats exist separately in some proteins, they have separate functions. For instance, the WD repeats of the FAN protein bind to the cytoplasmic tail of the TNFR55 receptor independent of the BEACH domain (Adam-Klages, S. et al. *Cell,* 1996, 86:937). It is worth noting that the FAN gene is made up almost entirely of the sequence in the highly conserved WBW structure (FIG. 3), therefore other WBW-containing proteins may act like FAN and bind the cytoplasmic tails of TNFR55 or TNFR55-like receptors.

Figure 7:
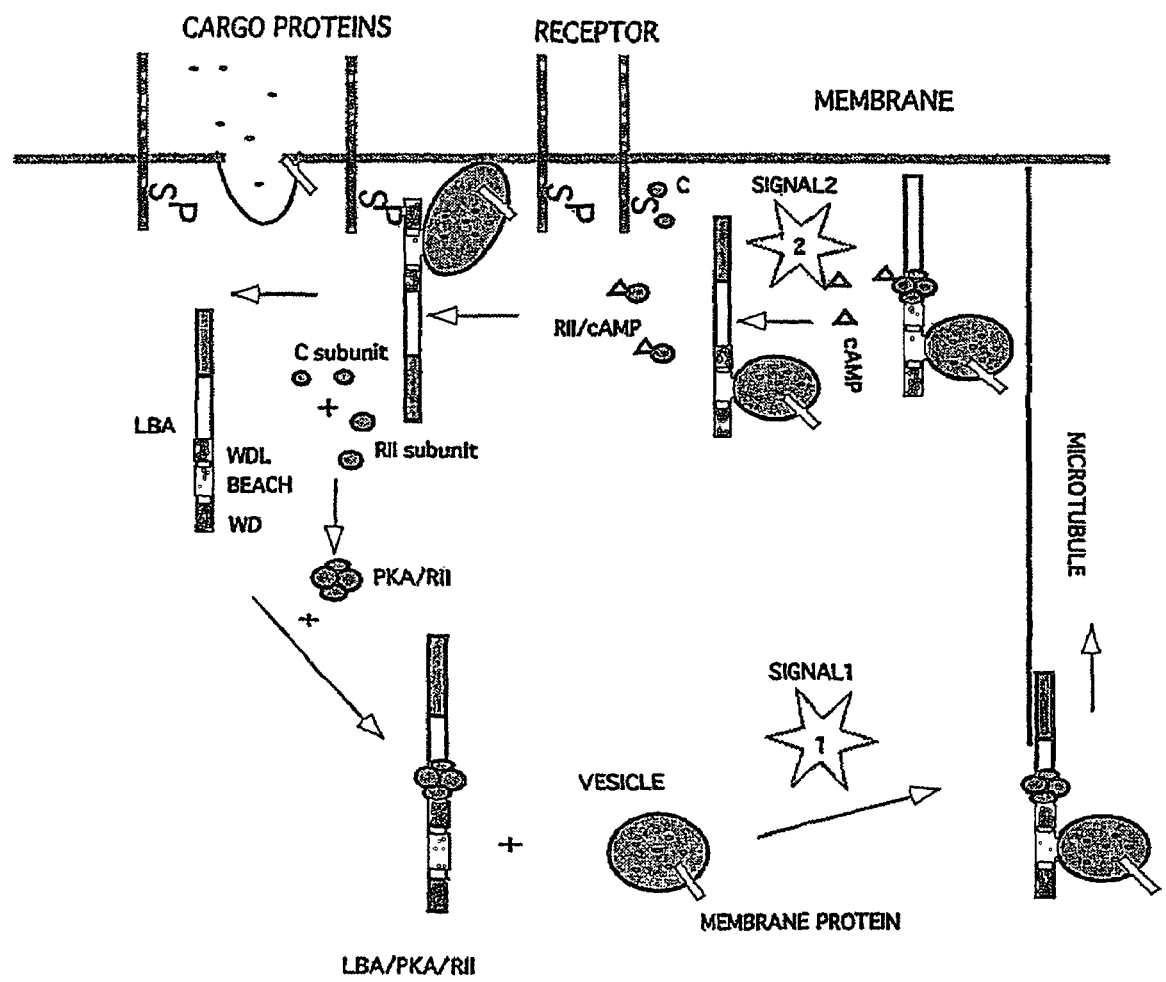
FIG. 7 shows a model of vesicle secretion for WBW protein family using the lrba gene as a prototype. Following immune cell activation, the BEACH domain binds to vesicles containing cargo proteins and membrane proteins for secretion or deposition in the plasma membrane. The anchor domain binds to microtubules to move the vesicles to the membrane where the WD domain binds to phosphorylated sequences of membrane receptor complexes to mediate the fusion of the vesicles with the membrane, thus releasing the cargo proteins or depositing membrane proteins on the plasma membrane of immune cells.

As indicated above, the lrba gene is a potential AKAP. The recently completed genomic sequence of *Drosophila* indicates that lrba has an orthologue in *Drosophila* (DAKAP550) that is capable of binding to protein kinase A (Han, J. D. et al. *Jour. Biol. Chem.,* 1997, 272:26611). The DAKAP550 gene is expressed in all tissues throughout development and is the principal A-kinase anchor protein in adult flies; it is enriched in secretory tissues such as neurons and salivary glands, and is found concentrated in the apical cytoplasm of some cells (Han, J. D. et al. *Jour. Biol. Chem.,* 1997, 272:26611), in agreement with the proposed function in secretion of lrba. Although the B1 and B2 RII binding sites of DAKAP550 are not present in mLRBA, hLRBA, and cLRBA, two sequences are disclosed that are very similar to the B1 and B2 RII binding sites in all lrba orthologues. The two sequences are predicted to form two adjacent amphipathic helices characteristic of PKA binding sites, satisfying the requirement of the hydrophobic interaction mechanism of RII peptide binding to the RII subunits of PKA revealed recently (Newlon, M. G. et al. *Nat. Struct. Biol.,* 1999, 6:222). Thus, lrba may serve as an AKAP that is involved in cAMP-mediated signaling secretory processes by translocating PKA to specific membrane sites. This translocation may require microtubule binding as suggested by the recent finding that another WBW protein, human CHS1, can associate with microtubules (Faigle, W. et al. *J. Cell Biol.,* 1998, 141:1121). Based on these findings, it is proposed a two-signal model for the function of the WBW protein family using the lrba gene as a prototype: LRBA is constitutively associated with PKA like other AKAPs and following LPS stimulation (signal one) the BEACH domain is phosphorylated. This enables the LRBA/PKA complex to bind to intracellular vesicles and tether vesicles to microtubules for transport to the plasma membrane. At the membrane, a second signal is required that generates cAMP. Binding of locally generated cAMP to the LRBA/PKA complex releases PKA, allowing it to phosphorylate cytoplasmic tails of activated receptors to enable binding of LRBA via its WD repeats. This final step would result in vesicle fusion with the plasma membrane (FIG. 7). Many immune processes need a second signal such as in the case of co-stimulators. Without being bound by theory, it proposed that a first signal activates an immune cell to transport enough vesicles to the plasma membrane area that contact another cell. A second signal generated by the contact with the target cell produces cAMP that stimulates PKA activity resulting in membrane fusion of vesicles. Thus, LRBA and other WBW proteins may provide a means for eukaryotic cells to direct the fusion of membrane-bound vesicles in a polarized fashion, in coordination with signal transduction complexes at the plasma membrane as is required of many different effector cell types in the immune system (Stinchcombe, J. C. and G. M. Griffiths *Jour. Cell Biol.,* 1999, 147:1).

Increasing evidence suggests that all clinical symptoms of CHS/beige patients could be explained by a secretion malfunction. The cytolytic proteins (granzymes A/B and perforin) in CHS CTL are expressed normally, but are not secreted upon stimulation (Baetz, K. et al. *Jour. of Immun.,* 1995, 154:6122). Secretion of other enzymes are also defective in macrophages and neutrophils (Barak, Y. and E. Nir *American Journal of Pediatric Hematology-Oncology,* 1987, 9:42) as are the membrane deposition of class II molecules (Faigle, W. et al. *J. Cell Biol.,* 1998, 141:1121) and CTL-4 (Barrat, F. J. et al. *Proc. Natl. Acad. of Sci. USA,* 1999, 96:8645). However, there is a dispute over whether giant lysosomes in beige/CHS disease are a result of abnormalities in the fusion or fission of lysosomes (Baetz, K. et al. *Jour. of Immun.,* 1995, 154:6122; Barrat, F. J. et al. *Proc. Natl. Acad. of Sci. USA,* 1999, 96:8645; Perou, C. M. et al. *Jour. Biol. Chem.,* 1997, 272:29790; Cervero, C. et al. *Sangre,* 1994, 39:135; Barbosa, M. D. et al. *Nature,* 1996, 382:262; Menard, M. and K. M. Meyers *Blood,* 1988, 72:1726). How the secretion pathway is impaired is unclear. The characterization of the lrba gene and the model for its function, described herein, may provide a molecular explanation for these two major cellular dysfunctions of CHS/beige: giant vesicles and secretion malfunction. Vesicles may require association with the BEACH domain of CHS1 for fission and/or movement to the plasma membrane. After reaching the plasma membrane, they then require recognition of certain membrane proteins by the WD repeats to mediate fusion with the plasma membrane. This requires CHS1 proteins to be full-length for proper function since the WD repeats are at the COOH terminus. Thus, truncated beige/CHS protein molecules (or perhaps LRBA proteins) that lack the COOH terminal WD repeats would be expected to cause disease (Certain, S. et al. *Blood,* 2000, 95:979). The giant lysosomes in the affected cells may come from the failure of vesicle movement and/or fusion with the membrane. Similar disorders of beige/CHS have also been described in mink, cattle, cats, and killer whales. Given the structural similarity of the WBW gene family, it is proposed that the genetic mutations in these species also involve other WBW genes. There are also other lysosomal trafficking mutants in mice with similar phenotypes to beige that may also involve mutation of other WBW gene family members.

In summary, the existence of a novel gene family, the WBW family, is demonstrated herein, which includes the lrba gene that: (1) is associated with the vesicular system, including the Golgi complex, lysosomes, endoplasmic reticulum, plasma membrane, and perinuclear ER, (2) is LPS inducible, (3) is an A kinase anchor protein (AKAP), and (4) has 5 different isoforms that differ in WD repeat number. These findings suggest an important role for lrba in coupling signal transduction and vesicle trafficking to enable polarized secretion and/or membrane deposition of immune effector molecules. This disclosure provides novel tools and methods that can be used to further the understanding of the mechanism of CHS and other related diseases as well as general immune cell function.

The cell membrane system not only delimits and protects cell and intracellular organelles, maintaining the essential differences between the cell interior and the environment, but also transports various molecules back and forth between the membrane-bound compartments in the cell, and between the cell and the environment through vesicle trafficking processes. These processes are critical for the correct biological functioning of a eukaryotic cell. A novel gene family, WBW, may play an essential role in vesicle trafficking has been identified in eukaryotic organisms from the very ancient unicellular organism Dictyostelium to human, but not in prokaryotes, which have no vesicle system (Wang, J. W. et al. *Journal of Immunology,* 2001, 166(7):4586-4595; Kwak, E. et al. *Mol. Biol. Cell,* 1999, 10(12):4429-4439; Adam-Klages, S. et al. *Cell,* 1996, 86(6):937-947; Barbosa, M. D. et al *Nature,* 1996, 382(6588):262-265; Nagle, D. L. et al. *Nat. Genet.,* 1996, 14(3):307-311). The WBW proteins all have a highly conserved long WBW(WDL-BEACH-WD) structure composed of three domains at their C-termini (Wang, J. W. et al. *Journal of Immunology,* 2001, 166(7):4586-4595). WD domain is present in over two thousand proteins and is thought to be involved in protein-protein interaction (Smith, T. F. et al. *Trends Biochem. Sci.,* 1999, 24(5):181-185). The WD repeats of FAN bind to NSD motif of TNFR55 to mediate the activation of the plasma membrane-bound neutral sphingomyelinase, producing the secondary messenger ceramide to activate raf-1 and MAP kinases, leading to cell growth and inflammation responses (Adam-Klages, S. et al. *Cell,* 1996, 86(6):937-947). The function of the BEACH domain is unclear, it potentially has SH3 and SH2 binding sites and a tyrosine kinase phosphorylation site, and those sites may interact with multiple signal transduction proteins (Wang, J. W. et al. *Journal of Immunology,* 2001, 166(7):4586-4595). The WDL domain was first described in a previous publication, and its function also remains unknown (Wang, J. W. et al. *Journal of Immunology,* 2001, 166(7):4586-4595). However, the WBW structure is very conserved and the WBW structure of FAN represents most of its ORF, and thus it is reasonable to propose that the WBW structure has a similar function to that of FAN. Another interesting question is if WBW proteins are also AKAPs (A kinase anchor protein), as DAKAP550 and Neurobeachin have been experimentally proved to be AKAPs, which can direct protein kinase A to discrete intracellular locations, where PKA may be activated by the secondary messenger cAMP (Han, J. D. et al. *J. Biol. Chem.,* 1997, 272(42):26611-26619; Wang, X. et al *J. Neurosci.,* 2000, 20(23):8551-8565). The subcellular localizations of the WBW proteins are not restricted to the plasma membrane, but are found in the Golgi complex, lysosomes, ER, perinuclear ER and clathrin-coated endocytosis pits (Wang, J. W. et al. *Journal of Immunology,* 2001, 166(7):4586-4595; Wang, X. et al. *J. Neurosci.,* 2000, 20(23):8551-8565), moreover are associated with microtubules (Faigle, W. et al. *J. Cell Biol.,* 1998, 141(5):1121-1134).

In the WBW family chs1/beige gene is the most extensively studied. The mutations of the gene can cause a generalized immunodeficiency in mice and humans with the impairment of NK cells, CTL, and granulocytes and often cause premature death in humans due to a second disease phase characterized by a lymphoproliferative syndrome, probably as a result of defective intracellular trafficking of vesicles (Spritz, R. A. et al. *J. Clin. Immunol.,* 1998, 18(2): 97-105). For example, the deposition of some membrane proteins (HLA-DR) and antigen presentation are affected (Faigle, W. et al. *J. Cell Biol.,* 1998, 141(5):1121-1134). FAN has a role in TNF pathway by binding to a cytoplasmic motif upstream of the death domain of some TNF family receptors (TNFR55 and CD40) (Adam-Klages, S. et al. *Cell,* 1996, 86(6):937-947; Segui, B. et al. *J. Biol. Chem.,* 1999, 274(52): 37251-37258). FAN knockout or FAN dominant-negative form can protect cell from apoptosis mediated by CD40 or TNF receptor (Segui, B. et al. *J. Clin. Invest.,* 2001, 108(1): 143-151; Segui, B. et al. *J. Biol. Chem.,* 1999, 274(52): 37251-37258). LvsA gene is essential for cytokinesis by possibly playing an important role in a membrane-processing pathway (Kwak, E. et al. *Mol. Biol. Cell,* 1999, 10(12):4429-4439). These studies suggest that the WBW proteins may play a role not only in vesicle trafficking, but also in some important cell processes like apoptosis and cell cycle.

However, the exact molecular mechanism of vesicle trafficking for the WBW proteins remains largely unclear. The mouse lrba (LPS-responsive beige-like PKA anchor gene) has its three isoforms, which differ at C-termini and have tissue-specific and development stage-specific expression pattern. LRBA gene is LPS inducible and can physically associate with various vesicular compartments in cells (Wang, J. W. et al. *Journal of Immunology,* 2001, 166(7): 4586-4695). Described herein is the cloning, genomic structure and promoter analysis of the human lrba gene and its five isoforms. Its genomic locus consists of 58 exons and 57 introns, spinning over 700 K bps. Three isoforms (α, β, δ) differ at BEACH domain and WD repeats at their C-termini. The fourth isoform(γ) has a YLLLQ insertion sequence. The mRNA of the fifth isoform (δ) has two ORFs and a potential IRES for the translation of the second ORF. In the promoter region, there are four E2F binding sites and a CpG island, and surprisingly a potential p53 binding site was found in the promoter, suggesting that lrba gene may be involved in p53 mediated apoptosis or cell arrest, and E2F regulated cell cycle progress, and is regulated developmentally by CpG island. These results show that the Lrba gene is highly regulated at both the transcriptional and translational level, indicating that lrba gene may have a critical role in the life of the cell.

All patents, patent applications, provisional applications, publications, and nucleic acid and amino acid sequences associated with the GenBank accession numbers referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method for inhibiting the growth of a tumor characterized by overexpression of the LPS-responsive CHS1/beige-like anchor gene (lrba) in a mammal, comprising directly administering an effective amount of an interfering RNA molecule to the tumor, wherein the interfering RNA is specific for lrba mRNA within the mammal and reduces lrba expression within the tumor, and wherein the interfering RNA inhibits growth of the tumor in the mammal.

2. The method according to claim 1, wherein the interfering RNA is single-stranded RNA selected from the group consisting of SEQ ID NO. 177, SEQ ID NO. 178, SEQ ID NO. 179, and SEQ ID NO. 180.

3. The method according to claim 1, wherein the interfering RNA is double-stranded RNA comprising SEQ ID NO. 177, SEQ ID NO. 178, SEQ ID NO. 179, or SEQ ID NO. 180.

4. The method of claim 1, wherein the mammal is a human.

5. The method according to claim 1, wherein the tumor is of a cancer type selected from the group consisting of breast, prostate, melanoma, cervical cancer, adenocarcinoma, colorectal cancer, and lung carcinoma.

6. The method according to claim 1, wherein the tumor is of a cancer type selected from breast cancer or prostate cancer.

7. A method for inhibiting the growth of mammalian cancer cells characterized by overexpression of the LPS-responsive CHS1/beige-like anchor gene (lrba), comprising directly administering an effective amount of an interfering RNA molecule to the cancer cells in vitro or in vivo, wherein the interfering RNA is specific for lrba mRNA within the cancer cells and reduces lrba expression within the cancer cells, and wherein the interfering RNA inhibits growth of the cancer cells.

8. The method according to claim 7, wherein the cancer cells are of a cancer type selected from the group consisting of breast, prostate, melanoma, cervical cancer, adenocarcinoma, colorectal cancer, and lung carcinoma.

9. The method according to claim 7, wherein the cancer cells are of a cancer type selected from breast cancer or prostate cancer.

10. The method according to claim 7, wherein the cancer cells are human cells.

11. The method according to claim 7, wherein said administering is carried out in vivo.

* * * * *

UNITED STATES PATENT AND TRADEMARK OFFICE
CERTIFICATE OF CORRECTION

PATENT NO. : 7,704,963 B2
APPLICATION NO. : 10/473741
DATED : April 27, 2010
INVENTOR(S) : William G. Kerr and Jia-Wang Wang It is certified that error appears in the above-identified patent and that said Letters Patent is hereby corrected as shown below:

Column 32,
Line 63, "HFAN," should read --hFAN,--.

Column 35, Table 2, row 4,
Column 5'Splice donor, "GGA CGA TCG gtaaaaaaa" should read
--GGA CGA TGG gtaaaaaaa--.

Column 37, Table 2, row 49,
Column 5'Splice donor, "TTG AGA GAG gtaa9ttat" should read
--TTG AGA GAG gtaagttat--.

Signed and Sealed this

Twenty-seventh Day of July, 2010

David J. Kappos
*Director of the United States Patent and Trademark Office*

SEQUENCE LISTING

```
<160> NUMBER OF SEQ ID NOS: 182

<210> SEQ ID NO 1
<211> LENGTH: 21
<212> TYPE: DNA
<213> ORGANISM: Artificial Sequence
<220> FEATURE:
<223> OTHER INFORMATION: lrba siRNA (siRNA1)
<220> FEATURE:
<221> NAME/KEY: misc_feature
<222> LOCATION: (1)..(21)
<223> OTHER INFORMATION: combined DNA/RNA sequence
<220> FEATURE:
<221> NAME/KEY: misc_feature
<222> LOCATION: (20)..(21)
<223> OTHER INFORMATION: deoxythymidine

<400> SEQUENCE: 1
ccagcaaagg ucuuggcuat t                                           21

<210> SEQ ID NO 2
<211> LENGTH: 21
<212> TYPE: DNA
<213> ORGANISM: Artificial Sequence
<220> FEATURE:
<223> OTHER INFORMATION: lrba siRNA
<220> FEATURE:
<221> NAME/KEY: misc_feature
<222> LOCATION: (1)..(21)
<223> OTHER INFORMATION: combined DNA/RNA sequence
<220> FEATURE:
<221> NAME/KEY: misc_feature
<222> LOCATION: (20)..(21)
<223> OTHER INFORMATION: deoxythymidine

<400> SEQUENCE: 2
cagucggguu ugcgacuggt t                                           21

<210> SEQ ID NO 3
<211> LENGTH: 2856
<212> TYPE: PRT
<213> ORGANISM: Mus musculus
<220> FEATURE:
<221> NAME/KEY: BINDING
<222> LOCATION: (1350)..(1369)
<223> OTHER INFORMATION: Putative Protein Kinase A RII binding site
<220> FEATURE:
<221> NAME/KEY: BINDING
<222> LOCATION: (1399)..(1418)
<223> OTHER INFORMATION: Putative Protein Kinase A RII binding site
<220> FEATURE:
<221> NAME/KEY: REPEAT
<222> LOCATION: (2028)..(2071)
<223> OTHER INFORMATION: WDL (WD-like) repeat
<220> FEATURE:
<221> NAME/KEY: REPEAT
<222> LOCATION: (2072)..(2121)
<223> OTHER INFORMATION: WDL (WD-like) repeat
```

```
<220> FEATURE:
<221> NAME/KEY: REPEAT
<222> LOCATION: (2122)..(2162)
<223> OTHER INFORMATION: WDL (WD-like) repeat
<220> FEATURE:
<221> NAME/KEY: DOMAIN
<222> LOCATION: (2204)..(2482)
<223> OTHER INFORMATION: BEACH domain
<220> FEATURE:
<221> NAME/KEY: REPEAT
<222> LOCATION: (2584)..(2628)
<223> OTHER INFORMATION: WD repeat
<220> FEATURE:
<221> NAME/KEY: REPEAT
<222> LOCATION: (2629)..(2687)
<223> OTHER INFORMATION: WD repeat
<220> FEATURE:
<221> NAME/KEY: REPEAT
<222> LOCATION: (2688)..(2769)
<223> OTHER INFORMATION: WD repeat
<220> FEATURE:
<221> NAME/KEY: REPEAT
<222> LOCATION: (2770)..(2811)
<223> OTHER INFORMATION: WD repeat
<220> FEATURE:
<221> NAME/KEY: REPEAT
<222> LOCATION: (2812)..(2856)
<223> OTHER INFORMATION: WD repeat

<400> SEQUENCE: 3
```

```
Met Ala Ser Glu Asp Asn Arg Ala Pro Ser Arg Pro Thr Gly Asp
 1               5                  10                  15

Asp Gly Gly Gly Gly Lys Glu Thr Pro Thr Glu Gly Gly Ala
            20                  25                  30

Leu Ser Leu Lys Pro Gly Leu Pro Ile Arg Gly Ile Arg Met Lys Phe
        35                  40                  45

Ala Val Leu Thr Gly Leu Val Glu Val Gly Glu Val Ser Asn Arg Asp
    50                  55                  60

Ile Val Glu Thr Val Phe Asn Leu Leu Val Gly Gly Gln Phe Asp Leu
65                  70                  75                  80

Glu Met Asn Phe Ile Ile Gln Glu Gly Glu Ser Ile Met Cys Met Val
                85                  90                  95

Glu Leu Leu Glu Lys Cys Asp Val Thr Cys Gln Ala Glu Val Trp Ser
            100                 105                 110

Met Phe Thr Ala Ile Leu Lys Lys Ser Ile Arg Asn Leu Gln Val Cys
        115                 120                 125

Thr Glu Val Gly Leu Val Glu Lys Val Leu Gly Lys Ile Glu Lys Val
    130                 135                 140

Asp Ser Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Gln Trp Pro Pro His Ala Gly Lys Leu Leu Ser
            180                 185                 190

Val Leu Lys His Met Pro Gln Lys Tyr Gly Pro Asp Ala Phe Phe Asn
        195                 200                 205

Phe Pro Gly Lys Ser Ala Ala Ala Ile Ala Leu Pro Pro Ile Ala Arg
    210                 215                 220

Trp Pro Tyr Gln Asn Gly Phe Thr Phe His Thr Trp Leu Arg Met Asp
225                 230                 235                 240

Pro Val Asn Asn Ile Asn Val Asp Lys Asp Lys Pro Tyr Leu Tyr Cys
                245                 250                 255
```

```
Phe Arg Thr Ser Lys Gly Leu Gly Tyr Ser Ala His Phe Val Gly Gly
            260                 265                 270

Cys Leu Ile Ile Thr Ser Ile Lys Ser Lys Gly Lys Gly Phe Gln His
            275                 280                 285

Cys Val Lys Phe Asp Phe Lys Pro Gln Lys Trp Tyr Met Val Thr Ile
            290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
            340                 345                 350

Ala Asn Arg Val Phe Cys Gly Gln Met Thr Ala Val Tyr Leu Phe Ser
            355                 360                 365

Asp Ala Leu Asn Ala Ala Gln Ile Phe Ala Ile Tyr Gln Leu Gly Leu
370                 375                 380

Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
                405                 410                 415

Ile Ala Phe Met Tyr Asn Pro Arg Ala Thr Asp Ala Gln Leu Cys Leu
            420                 425                 430

Glu Ser Ser Pro Lys Asp Asn Pro Ser Ile Phe Val His Ser Pro His
            435                 440                 445

Ala Leu Met Leu Gln Asp Val Lys Ala Val Leu Thr His Ser Ile Gln
            450                 455                 460

Ser Ala Met His Ser Ile Gly Gly Val Gln Val Leu Phe Pro Leu Phe
465                 470                 475                 480

Ala Gln Leu Asp Tyr Lys Gln Tyr Leu Ser Asp Glu Val Asp Leu Thr
                485                 490                 495

Ile Cys Thr Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
            515                 520                 525

Gly Tyr Ser Leu Glu Lys Ser Ser Lys Ser His Val Ser Arg Ala Val
            530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Ile Leu Leu Asn Pro
                565                 570                 575

Ala Val Trp Ile His Thr Pro Ala Lys Val Gln Leu Met Leu Tyr Thr
            580                 585                 590

Tyr Leu Ser Thr Glu Phe Ile Gly Thr Val Asn Ile Tyr Asn Thr Ile
            595                 600                 605

Arg Arg Val Gly Thr Val Leu Leu Ile Met His Thr Leu Lys Tyr Tyr
            610                 615                 620

Tyr Trp Ala Val Asn Pro Gln Asp Arg Ser Gly Ile Thr Pro Lys Gly
625                 630                 635                 640

Leu Asp Gly Pro Arg Pro Asn Gln Lys Glu Ile Leu Ser Leu Arg Ala
                645                 650                 655

Phe Leu Leu Met Phe Ile Lys Gln Leu Val Met Lys Asp Ser Gly Val
            660                 665                 670
```

-continued

```
Lys Glu Asp Glu Leu Gln Ala Ile Leu Asn Tyr Leu Leu Thr Met His
            675                 680                 685
Glu Asp Asp Asn Leu Met Asp Val Leu Gln Leu Leu Val Ala Leu Met
        690                 695                 700
Ala Glu His Pro Asn Ser Met Ile Pro Ala Phe Asp Gln Arg Asn Gly
705                 710                 715                 720
Leu Arg Val Ile Tyr Lys Leu Leu Ala Ser Lys Ser Glu Gly Ile Arg
                725                 730                 735
Val Gln Ala Leu Lys Ala Leu Gly Tyr Phe Leu Lys His Leu Ala Pro
            740                 745                 750
Lys Arg Lys Ala Glu Val Met Leu Gly His Gly Leu Phe Ser Leu Leu
        755                 760                 765
Ala Glu Arg Leu Met Leu Gln Thr Asn Leu Ile Thr Met Thr Met Tyr
770                 775                 780
Asn Val Leu Phe Glu Ile Leu Ile Glu Gln Ile Cys Thr Gln Val Ile
785                 790                 795                 800
His Lys Gln His Pro Asp Pro Asp Ser Thr Val Lys Ile Gln Asn Pro
                805                 810                 815
Gln Ile Leu Lys Val Ile Ala Thr Leu Leu Arg Asn Ser Pro Gln Cys
            820                 825                 830
Pro Glu Ser Met Glu Val Arg Arg Ala Phe Leu Ser Asp Met Ile Lys
        835                 840                 845
Leu Phe Asn Asn Ser Arg Glu Asn Arg Arg Ser Leu Leu Gln Cys Ser
850                 855                 860
Val Trp Gln Glu Trp Met Leu Ser Leu Cys Tyr Phe Asn Pro Lys Asn
865                 870                 875                 880
Ser Asp Glu Gln Lys Ile Thr Glu Met Val Tyr Ala Ile Phe Arg Ile
                885                 890                 895
Leu Leu Tyr His Ala Val Lys Tyr Glu Trp Gly Gly Trp Arg Val Trp
            900                 905                 910
Val Asp Thr Leu Ser Ile Thr His Ser Lys Val Thr Phe Glu Ile His
        915                 920                 925
Lys Glu Asn Leu Ala Asn Ile Phe Arg Glu Gln Arg Lys Gly Asp
930                 935                 940
Glu Glu Thr Gly Pro Cys Ser Ser Ser Leu Val Pro Glu Gly Thr Gly
945                 950                 955                 960
Ala Thr Arg Gly Val Asp Val Ser Val Gly Ser Gln His Glu Asp Arg
                965                 970                 975
Lys Asp Ser Pro Ile Ser Pro His Phe Thr Arg Asn Ser Asp Glu Asn
            980                 985                 990
Ser Ser Ile Gly Arg Ala Ser Ser  Ile Asp Ser Ala Ser  Asn Thr Glu
        995                 1000                1005
Leu Gln  Thr His Asp Met Ser  Ser Asp Glu Lys Lys  Val Glu Arg
        1010                1015                1020
Glu Asn  Gln Glu Leu Leu Asp  Gln Ala Thr Val Glu  Glu Thr Ala
        1025                1030                1035
Thr Asn  Gly Ala Lys Asp Asp  Leu Glu Thr Ser Ser  Asp Ala Ala
        1040                1045                1050
Glu Pro  Val Thr Ile Asn Ser  Asn Ser Leu Glu Pro  Gly Lys Asp
        1055                1060                1065
Thr Val  Thr Ile Ser Glu Val  Ser Ala Ser Ile Ser  Ser Pro Ser
        1070                1075                1080
```

-continued

```
Glu Glu Asp Ala Ala Glu Met Pro Glu Leu Leu Glu Lys Ser Gly
    1085                1090                1095

Val Glu Glu Lys Glu Asp Asp Tyr Val Glu Leu Lys Val Glu
1100                1105                1110

Gly Ser Pro Thr Glu Glu Ala Gly Leu Pro Thr Glu Leu Gln Gly
    1115                1120                1125

Glu Gly Leu Val Ser Ala Ala Ser Gly Gly Arg Glu Glu Pro Asp
    1130                1135                1140

Met Cys Gly His Gly Cys Glu Val Gln Val Glu Ala Pro Ile Thr
    1145                1150                1155

Lys Ile His Asn Asp Pro Glu Thr Thr Asp Ser Glu Asp Ser Arg
    1160                1165                1170

Phe Pro Thr Val Ala Thr Ala Gly Ser Leu Ala Thr Ser Ser Glu
    1175                1180                1185

Val Pro Val Pro Gln Ala Thr Val Gln Ser Asp Ser His Glu Met
    1190                1195                1200

Leu Asp Gly Gly Met Lys Ala Thr Asn Leu Ala Gly Glu Thr Glu
    1205                1210                1215

Ser Val Ser Asp Cys Ala Asp Asn Val Ser Glu Ala Pro Ala Thr
    1220                1225                1230

Ser Glu Gln Lys Ile Thr Lys Leu Asp Val Ser Ser Val Ala Ser
    1235                1240                1245

Asp Thr Glu Arg Phe Glu Leu Lys Ala Ser Thr Ser Thr Glu Ala
    1250                1255                1260

Pro Gln Pro Gln Arg His Gly Leu Glu Ile Ser Arg Gln Gln Glu
    1265                1270                1275

Gln Thr Ala Gln Gly Thr Ala Pro Asp Ala Val Asp Gln Gln Arg
    1280                1285                1290

Arg Asp Ser Arg Ser Thr Met Phe Arg Ile Pro Glu Phe Lys Trp
    1295                1300                1305

Ser Gln Met His Gln Arg Leu Leu Thr Asp Leu Leu Phe Ser Ile
    1310                1315                1320

Glu Thr Asp Ile Gln Met Trp Arg Ser His Ser Thr Lys Thr Val
    1325                1330                1335

Met Asp Phe Val Asn Ser Ser Asp Asn Val Ile Phe Val His Asn
    1340                1345                1350

Thr Ile His Leu Ile Ser Gln Val Met Asp Asn Met Val Met Ala
    1355                1360                1365

Cys Gly Gly Ile Leu Pro Leu Leu Ser Ala Ala Thr Ser Ala Thr
    1370                1375                1380

His Glu Leu Glu Asn Ile Glu Pro Thr Gln Gly Leu Ser Ile Glu
    1385                1390                1395

Ala Ser Val Thr Phe Leu Gln Arg Leu Ile Ser Leu Val Asp Val
    1400                1405                1410

Leu Ile Phe Ala Ser Ser Leu Gly Phe Thr Glu Ile Glu Ala Glu
    1415                1420                1425

Lys Asn Met Ser Ser Gly Gly Ile Leu Arg Gln Cys Leu Arg Leu
    1430                1435                1440

Val Cys Ala Val Ala Val Arg Asn Cys Leu Glu Cys Gln Gln His
    1445                1450                1455

Ser Gln Leu Lys Ala Arg Gly Asp Thr Ala Lys Ser Ser Lys Thr
    1460                1465                1470
```

-continued

```
Ile His Ser Leu Ile Pro Met Gly Lys Ser Ala Ala Lys Ser Pro
1475                1480                1485

Val Asp Ile Val Thr Gly Gly Ile Ser Ser Val Arg Asp Leu Asp
1490                1495                1500

Arg Leu Pro Ala Arg Thr Trp Thr Leu Ile Gly Leu Arg Ala Val
1505                1510                1515

Val Phe Arg Asp Ile Glu Asp Ser Lys Gln Ala Gln Phe Leu Ala
1520                1525                1530

Leu Ala Val Val Tyr Phe Ile Ser Val Leu Met Val Ser Lys Tyr
1535                1540                1545

Arg Asp Ile Leu Glu Pro Gln Asp Glu Arg His Ser Gln Ser Leu
1550                1555                1560

Lys Glu Thr Ser Ser Asp Asn Gly Asn Ala Ser Leu Pro Asp Ala
1565                1570                1575

Glu Asn Thr Pro Ala Glu Phe Ser Ser Leu Thr Leu Ser Ser Val
1580                1585                1590

Glu Glu Ser Leu Glu Gly Thr Ser Cys Thr Arg Arg Arg Asp Ser
1595                1600                1605

Gly Leu Gly Glu Glu Thr Ala Ser Gly Leu Gly Ser Gly Leu Val
1610                1615                1620

Ser Ala Ser Pro Ala Ala Pro Leu Gly Val Ser Ala Gly Pro Asp
1625                1630                1635

Ala Ile Ser Glu Val Leu Cys Thr Leu Ser Leu Glu Val Asn Lys
1640                1645                1650

Ser Gln Glu Thr Arg Ile Asp Gly Gly Asn Glu Leu Asp Arg Lys
1655                1660                1665

Val Thr Pro Ser Val Pro Val Ser Lys Asn Val Asn Val Lys Asp
1670                1675                1680

Ile Leu Arg Ser Leu Val Asn Met Pro Ala Asp Gly Val Thr Val
1685                1690                1695

Asp Pro Ala Leu Leu Pro Pro Ala Cys Leu Gly Ala Leu Gly Asp
1700                1705                1710

Leu Ser Val Asp Pro Pro Met Gln Phe Arg Ser Phe Asp Arg Ser
1715                1720                1725

Val Ile Ile Ala Thr Lys Lys Ser Ser Val Leu Pro Ser Ala Leu
1730                1735                1740

Thr Thr Ser Ala Pro Ser Ser Ala Val Ser Val Val Ser Ser Val
1745                1750                1755

Asp Pro Thr His Ala Ser Asp Thr Gly Gly Glu Ser Pro Gly Ser
1760                1765                1770

Arg Ser Pro Lys Cys Lys Thr Ala Leu Ser Cys Lys Gln Leu Ala
1775                1780                1785

Pro Ser His Lys Thr Pro Ala Ala His Met Ser Ile Thr Glu Arg
1790                1795                1800

Leu Glu His Ala Leu Glu Lys Ala Ala Pro Leu Leu Arg Glu Ile
1805                1810                1815

Phe Val Asp Phe Ala Pro Phe Leu Ser Arg Thr Leu Leu Gly Ser
1820                1825                1830

His Gly Gln Glu Leu Leu Ile Glu Gly Thr Ser Leu Val Cys Met
1835                1840                1845

Lys Ser Ser Ser Ser Val Val Glu Leu Val Met Leu Leu Cys Ser
1850                1855                1860
```

-continued

```
Gln Glu Trp Gln Asn Ser Ile Gln Lys Asn Ala Gly Leu Ala Phe
1865                1870                1875

Ile Glu Leu Val Asn Glu Gly Arg Leu Leu Ser Gln Thr Met Lys
1880                1885                1890

Asp His Leu Val Arg Val Ala Asn Glu Ala Glu Phe Ile Leu Ser
1895                1900                1905

Arg Gln Arg Ala Glu Asp Ile His Arg His Ala Glu Phe Glu Ser
1910                1915                1920

Leu Cys Ala Gln Tyr Ser Ala Asp Lys Arg Glu Glu Lys Met
1925                1930                1935

Cys Asp His Leu Ile Arg Ala Ala Lys Tyr Arg Asp His Val Thr
1940                1945                1950

Ala Thr Gln Leu Ile Gln Lys Ile Ile Asn Leu Leu Thr Asp Lys
1955                1960                1965

His Gly Ala Trp Gly Ser Ser Ala Val Ser Arg Pro Arg Glu Phe
1970                1975                1980

Trp Arg Leu Asp Tyr Trp Glu Asp Leu Arg Arg Arg Arg
1985                1990                1995

Phe Val Arg Asn Pro Leu Gly Ser Thr His Pro Glu Ala Thr Leu
2000                2005                2010

Lys Thr Ala Val Glu His Ala Ala Asp Glu Asp Ile Leu Ala Lys
2015                2020                2025

Gly Lys Gln Ser Ile Lys Ser Gln Ala Leu Gly Asn Gln Asn Ser
2030                2035                2040

Glu Asn Glu Ala Leu Leu Glu Gly Asp Asp Thr Leu Ser Ser
2045                2050                2055

Val Asp Glu Lys Asp Leu Glu Asn Leu Ala Gly Pro Val Ser Leu
2060                2065                2070

Ser Thr Pro Ala Gln Leu Val Ala Pro Ser Val Val Val Lys Gly
2075                2080                2085

Thr Leu Ser Val Thr Ser Ser Glu Leu Tyr Phe Glu Val Asp Glu
2090                2095                2100

Glu Asp Pro Asn Phe Lys Lys Ile Asp Pro Lys Ile Leu Ala Tyr
2105                2110                2115

Thr Glu Gly Leu His Gly Lys Trp Leu Phe Thr Glu Ile Arg Ser
2120                2125                2130

Ile Phe Ser Arg Arg Tyr Leu Leu Gln Asn Thr Ala Leu Glu Ile
2135                2140                2145

Phe Met Ala Asn Arg Val Ala Val Met Phe Asn Phe Pro Asp Pro
2150                2155                2160

Ala Thr Val Lys Lys Val Val Asn Tyr Leu Pro Arg Val Gly Val
2165                2170                2175

Gly Thr Ser Phe Gly Leu Pro Gln Thr Arg Arg Ile Ser Leu Ala
2180                2185                2190

Thr Pro Arg Gln Leu Phe Lys Ala Ser Asn Met Thr Gln Arg Trp
2195                2200                2205

Gln His Arg Glu Ile Ser Asn Phe Glu Tyr Leu Met Phe Leu Asn
2210                2215                2220

Thr Ile Ala Gly Arg Ser Tyr Asn Asp Leu Asn Gln Tyr Pro Val
2225                2230                2235

Phe Pro Trp Val Ile Thr Asn Tyr Glu Ser Glu Glu Leu Asp Leu
2240                2245                2250
```

-continued

```
Thr Leu Pro Ser Asn Phe Arg Asp Leu Ser Lys Pro Ile Gly Ala
2255                2260                2265

Leu Asn Pro Lys Arg Ala Ala Phe Phe Ala Glu Arg Phe Glu Ser
2270                2275                2280

Trp Glu Asp Asp Gln Val Pro Lys Phe His Tyr Gly Thr His Tyr
2285                2290                2295

Ser Thr Ala Ser Phe Val Leu Ala Trp Leu Leu Arg Ile Glu Pro
2300                2305                2310

Phe Thr Thr Tyr Phe Leu Asn Leu Gln Gly Gly Lys Phe Asp His
2315                2320                2325

Ala Asp Arg Thr Phe Ser Ser Val Ser Arg Ala Trp Arg Asn Ser
2330                2335                2340

Gln Arg Asp Thr Ser Asp Ile Lys Glu Leu Ile Pro Glu Phe Tyr
2345                2350                2355

Tyr Leu Pro Glu Met Phe Val Asn Phe Asn Asn Tyr Asn Leu Gly
2360                2365                2370

Val Met Asp Asp Gly Thr Val Val Ser Asp Val Glu Leu Pro Pro
2375                2380                2385

Trp Ala Lys Thr Ser Glu Glu Phe Val Arg Ile Asn Arg Leu Ala
2390                2395                2400

Leu Glu Ser Glu Phe Val Ser Cys Gln Leu His Gln Trp Ile Asp
2405                2410                2415

Leu Ile Phe Gly Tyr Lys Gln Gln Gly Pro Glu Ala Val Arg Ala
2420                2425                2430

Leu Asn Val Phe Tyr Tyr Leu Thr Tyr Glu Gly Ala Val Asn Leu
2435                2440                2445

Asn Ser Ile Thr Asp Pro Val Leu Arg Glu Ala Val Glu Ala Gln
2450                2455                2460

Ile Arg Ser Phe Gly Gln Thr Pro Ser Gln Leu Leu Ile Glu Pro
2465                2470                2475

His Pro Pro Arg Gly Ser Ala Met Gln Ala Ser Pro Leu Met Phe
2480                2485                2490

Thr Asp Gln Ala Gln Gln Asp Val Ile Met Val Leu Lys Phe Pro
2495                2500                2505

Ser Asn Ser Pro Val Thr His Val Ala Ala Asn Thr Gln Pro Gly
2510                2515                2520

Leu Ala Met Pro Ala Val Ile Thr Val Thr Ala Asn Arg Leu Phe
2525                2530                2535

Ala Val Asn Lys Trp His Asn Leu Pro Ala His Gln Gly Ala Val
2540                2545                2550

Gln Asp Gln Pro Tyr Gln Leu Pro Val Glu Ile Asp Pro Leu Ile
2555                2560                2565

Ala Cys Gly Thr Gly Thr His Arg Arg Gln Val Thr Asp Leu Leu
2570                2575                2580

Asp Gln Ser Ile Gln Val His Ser Gln Cys Phe Val Ile Thr Ser
2585                2590                2595

Asp Asn Arg Tyr Ile Leu Val Cys Gly Phe Trp Asp Lys Ser Phe
2600                2605                2610

Arg Val Tyr Ser Thr Asp Thr Gly Lys Leu Ile Gln Val Val Phe
2615                2620                2625

Gly His Trp Asp Val Val Thr Cys Leu Ala Arg Ser Glu Ser Tyr
2630                2635                2640
```

```
Ile Gly Gly Asn Cys Tyr Ile Leu Ser Gly Ser Arg Asp Ala Thr
2645                2650                2655

Leu Leu Leu Trp Tyr Trp Asn Gly Lys Ser Ser Gly Ile Gly Asp
2660                2665                2670

Asn Pro Gly Gly Glu Thr Ala Thr Pro Arg Ala Ile Leu Thr Gly
2675                2680                2685

His Asp Tyr Glu Ile Thr Cys Ala Ala Val Cys Ala Glu Leu Gly
2690                2695                2700

Leu Val Leu Ser Gly Ser Gln Glu Gly Pro Cys Leu Ile His Ser
2705                2710                2715

Met Asn Gly Asp Leu Leu Arg Thr Leu Glu Gly Pro Glu Asn Cys
2720                2725                2730

Leu Lys Pro Lys Leu Ile Gln Ala Ser Arg Glu Gly His Cys Val
2735                2740                2745

Ile Phe Tyr Glu Asn Gly Cys Phe Cys Thr Phe Ser Val Asn Gly
2750                2755                2760

Lys Leu Gln Ala Thr Val Glu Thr Asp Asp His Ile Arg Ala Ile
2765                2770                2775

Gln Leu Ser Arg Asp Gly Gln Tyr Leu Leu Thr Gly Gly Asp Asn
2780                2785                2790

Gly Val Val Ile Val Arg Gln Val Ser Asp Leu Lys Gln Leu Phe
2795                2800                2805

Ala Tyr Pro Gly Cys Asp Ala Gly Ile Arg Ala Met Ala Leu Ser
2810                2815                2820

Phe Asp Gln Arg Cys Ile Ile Ser Gly Met Ala Ser Gly Ser Ile
2825                2830                2835

Val Leu Phe Tyr Asn Asp Phe Asn Arg Trp His His Glu Tyr Gln
2840                2845                2850

Thr Arg Tyr
2855

<210> SEQ ID NO 4
<211> LENGTH: 2792
<212> TYPE: PRT
<213> ORGANISM: Mus musculus
<220> FEATURE:
<221> NAME/KEY: BINDING
<222> LOCATION: (1350)..(1369)
<223> OTHER INFORMATION: Putative Protein Kinase A RII binding site
<220> FEATURE:
<221> NAME/KEY: BINDING
<222> LOCATION: (1399)..(1418)
<223> OTHER INFORMATION: Putative Protein Kinase A RII binding site
<220> FEATURE:
<221> NAME/KEY: REPEAT
<222> LOCATION: (2028)..(2071)
<223> OTHER INFORMATION: WDL (WD-like) repeat
<220> FEATURE:
<221> NAME/KEY: REPEAT
<222> LOCATION: (2072)..(2121)
<223> OTHER INFORMATION: WDL (WD-like) repeat
<220> FEATURE:
<221> NAME/KEY: REPEAT
<222> LOCATION: (2122)..(2162)
<223> OTHER INFORMATION: WDL (WD-like) repeat
<220> FEATURE:
<221> NAME/KEY: DOMAIN
<222> LOCATION: (2204)..(2482)
<223> OTHER INFORMATION: BEACH domain
<220> FEATURE:
<221> NAME/KEY: REPEAT
<222> LOCATION: (2584)..(2628)
<223> OTHER INFORMATION: WD repeat
```

```
<220> FEATURE:
<221> NAME/KEY: REPEAT
<222> LOCATION: (2629)..(2687)
<223> OTHER INFORMATION: WD repeat
<220> FEATURE:
<221> NAME/KEY: REPEAT
<222> LOCATION: (2688)..(2769)
<223> OTHER INFORMATION: WD repeat

<400> SEQUENCE: 4

Met Ala Ser Glu Asp Asn Arg Ala Pro Ser Arg Pro Thr Gly Asp
 1               5                  10                  15

Asp Gly Gly Gly Gly Lys Glu Glu Thr Pro Thr Glu Gly Gly Ala
                20                  25                  30

Leu Ser Leu Lys Pro Gly Leu Pro Ile Arg Gly Ile Arg Met Lys Phe
                35                  40                  45

Ala Val Leu Thr Gly Leu Val Glu Val Gly Glu Val Ser Asn Arg Asp
 50                  55                  60

Ile Val Glu Thr Val Phe Asn Leu Leu Val Gly Gly Gln Phe Asp Leu
 65                  70                  75                  80

Glu Met Asn Phe Ile Ile Gln Glu Gly Glu Ser Ile Met Cys Met Val
                85                  90                  95

Glu Leu Leu Glu Lys Cys Asp Val Thr Cys Gln Ala Glu Val Trp Ser
                100                 105                 110

Met Phe Thr Ala Ile Leu Lys Lys Ser Ile Arg Asn Leu Gln Val Cys
                115                 120                 125

Thr Glu Val Gly Leu Val Glu Lys Val Leu Gly Lys Ile Glu Lys Val
                130                 135                 140

Asp Ser Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Gln Trp Pro Pro His Ala Gly Lys Leu Leu Ser
                180                 185                 190

Val Leu Lys His Met Pro Gln Lys Tyr Gly Pro Asp Ala Phe Phe Asn
                195                 200                 205

Phe Pro Gly Lys Ser Ala Ala Ala Ile Ala Leu Pro Pro Ile Ala Arg
                210                 215                 220

Trp Pro Tyr Gln Asn Gly Phe Thr Phe His Thr Trp Leu Arg Met Asp
225                 230                 235                 240

Pro Val Asn Asn Ile Asn Val Asp Lys Asp Lys Pro Tyr Leu Tyr Cys
                245                 250                 255

Phe Arg Thr Ser Lys Gly Leu Gly Tyr Ser Ala His Phe Val Gly Gly
                260                 265                 270

Cys Leu Ile Ile Thr Ser Ile Lys Ser Lys Gly Lys Gly Phe Gln His
                275                 280                 285

Cys Val Lys Phe Asp Phe Lys Pro Gln Lys Trp Tyr Met Val Thr Ile
                290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
                340                 345                 350

Ala Asn Arg Val Phe Cys Gly Gln Met Thr Ala Val Tyr Leu Phe Ser
                355                 360                 365
```

```
Asp Ala Leu Asn Ala Ala Gln Ile Phe Ala Ile Tyr Gln Leu Gly Leu
        370                 375                 380

Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
                405                 410                 415

Ile Ala Phe Met Tyr Asn Pro Arg Ala Thr Asp Ala Gln Leu Cys Leu
            420                 425                 430

Glu Ser Ser Pro Lys Asp Asn Pro Ser Ile Phe Val His Ser Pro His
        435                 440                 445

Ala Leu Met Leu Gln Asp Val Lys Ala Val Leu Thr His Ser Ile Gln
    450                 455                 460

Ser Ala Met His Ser Ile Gly Gly Val Gln Val Leu Phe Pro Leu Phe
465                 470                 475                 480

Ala Gln Leu Asp Tyr Lys Gln Tyr Leu Ser Asp Glu Val Asp Leu Thr
                485                 490                 495

Ile Cys Thr Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
        515                 520                 525

Gly Tyr Ser Leu Glu Lys Ser Ser Lys Ser His Val Ser Arg Ala Val
    530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Ile Leu Leu Asn Pro
                565                 570                 575

Ala Val Trp Ile His Thr Pro Ala Lys Val Gln Leu Met Leu Tyr Thr
            580                 585                 590

Tyr Leu Ser Thr Glu Phe Ile Gly Thr Val Asn Ile Tyr Asn Thr Ile
        595                 600                 605

Arg Arg Val Gly Thr Val Leu Leu Ile Met His Thr Leu Lys Tyr Tyr
    610                 615                 620

Tyr Trp Ala Val Asn Pro Gln Asp Arg Ser Gly Ile Thr Pro Lys Gly
625                 630                 635                 640

Leu Asp Gly Pro Arg Pro Asn Gln Lys Glu Ile Leu Ser Leu Arg Ala
                645                 650                 655

Phe Leu Leu Met Phe Ile Lys Gln Leu Val Met Lys Asp Ser Gly Val
            660                 665                 670

Lys Glu Asp Glu Leu Gln Ala Ile Leu Asn Tyr Leu Leu Thr Met His
        675                 680                 685

Glu Asp Asp Asn Leu Met Asp Val Leu Gln Leu Leu Val Ala Leu Met
    690                 695                 700

Ala Glu His Pro Asn Ser Met Ile Pro Ala Phe Asp Gln Arg Asn Gly
705                 710                 715                 720

Leu Arg Val Ile Tyr Lys Leu Leu Ala Ser Lys Ser Glu Gly Ile Arg
                725                 730                 735

Val Gln Ala Leu Lys Ala Leu Gly Tyr Phe Leu Lys His Leu Ala Pro
            740                 745                 750

Lys Arg Lys Ala Glu Val Met Leu Gly His Gly Leu Phe Ser Leu Leu
        755                 760                 765

Ala Glu Arg Leu Met Leu Gln Thr Asn Leu Ile Thr Met Thr Met Tyr
    770                 775                 780
```

```
-continued

Asn Val Leu Phe Glu Ile Leu Ile Glu Gln Ile Cys Thr Gln Val Ile
785                 790                 795                 800

His Lys Gln His Pro Asp Pro Asp Ser Thr Val Lys Ile Gln Asn Pro
            805                 810                 815

Gln Ile Leu Lys Val Ile Ala Thr Leu Leu Arg Asn Ser Pro Gln Cys
            820                 825                 830

Pro Glu Ser Met Glu Val Arg Arg Ala Phe Leu Ser Asp Met Ile Lys
            835                 840                 845

Leu Phe Asn Asn Ser Arg Glu Asn Arg Arg Ser Leu Leu Gln Cys Ser
        850                 855                 860

Val Trp Gln Glu Trp Met Leu Ser Leu Cys Tyr Phe Asn Pro Lys Asn
865                 870                 875                 880

Ser Asp Glu Gln Lys Ile Thr Glu Met Val Tyr Ala Ile Phe Arg Ile
                885                 890                 895

Leu Leu Tyr His Ala Val Lys Tyr Glu Trp Gly Gly Trp Arg Val Trp
            900                 905                 910

Val Asp Thr Leu Ser Ile Thr His Ser Lys Val Thr Phe Glu Ile His
            915                 920                 925

Lys Glu Asn Leu Ala Asn Ile Phe Arg Glu Gln Arg Lys Gly Asp
930                 935                 940

Glu Glu Thr Gly Pro Cys Ser Ser Ser Leu Val Pro Glu Gly Thr Gly
945                 950                 955                 960

Ala Thr Arg Gly Val Asp Val Ser Val Gly Ser Gln His Glu Asp Arg
                965                 970                 975

Lys Asp Ser Pro Ile Ser Pro His Phe Thr Arg Asn Ser Asp Glu Asn
            980                 985                 990

Ser Ser Ile Gly Arg Ala Ser Ser  Ile Asp Ser Ala Ser  Asn Thr Glu
            995                 1000                1005

Leu Gln  Thr His Asp Met Ser  Ser Asp Glu Lys Lys  Val Glu Arg
    1010                1015                1020

Glu Asn  Gln Glu Leu Leu Asp  Gln Ala Thr Val Glu  Glu Thr Ala
    1025                1030                1035

Thr Asn  Gly Ala Lys Asp Asp  Leu Glu Thr Ser Ser  Asp Ala Ala
    1040                1045                1050

Glu Pro  Val Thr Ile Asn Ser  Asn Ser Leu Glu Pro  Gly Lys Asp
    1055                1060                1065

Thr Val  Thr Ile Ser Glu Val  Ser Ala Ser Ile Ser  Ser Pro Ser
    1070                1075                1080

Glu Glu  Asp Ala Ala Glu Met  Pro Glu Leu Leu Glu  Lys Ser Gly
    1085                1090                1095

Val Glu  Glu Lys Glu Asp Asp  Tyr Val Glu Leu  Lys Val Glu
    1100                1105                1110

Gly Ser  Pro Thr Glu Glu Ala  Gly Leu Pro Thr Glu  Leu Gln Gly
    1115                1120                1125

Glu Gly  Leu Val Ser Ala Ala  Ser Gly Gly Arg Glu  Glu Pro Asp
    1130                1135                1140

Met Cys  Gly His Gly Cys Glu  Val Gln Val Glu Ala  Pro Ile Thr
    1145                1150                1155

Lys Ile  His Asn Asp Pro Glu  Thr Thr Asp Ser Glu  Asp Ser Arg
    1160                1165                1170

Phe Pro  Thr Val Ala Thr Ala  Gly Ser Leu Ala Thr  Ser Ser Glu
    1175                1180                1185
```

```
Val Pro Val Pro Gln Ala Thr Val Gln Ser Asp Ser His Glu Met
1190                1195                1200

Leu Asp Gly Gly Met Lys Ala Thr Asn Leu Ala Gly Glu Thr Glu
1205                1210                1215

Ser Val Ser Asp Cys Ala Asp Asn Val Ser Glu Ala Pro Ala Thr
1220                1225                1230

Ser Glu Gln Lys Ile Thr Lys Leu Asp Val Ser Ser Val Ala Ser
1235                1240                1245

Asp Thr Glu Arg Phe Glu Leu Lys Ala Ser Thr Ser Thr Glu Ala
1250                1255                1260

Pro Gln Pro Gln Arg His Gly Leu Glu Ile Ser Arg Gln Gln Glu
1265                1270                1275

Gln Thr Ala Gln Gly Thr Ala Pro Asp Ala Val Asp Gln Gln Arg
1280                1285                1290

Arg Asp Ser Arg Ser Thr Met Phe Arg Ile Pro Glu Phe Lys Trp
1295                1300                1305

Ser Gln Met His Gln Arg Leu Leu Thr Asp Leu Leu Phe Ser Ile
1310                1315                1320

Glu Thr Asp Ile Gln Met Trp Arg Ser His Ser Thr Lys Thr Val
1325                1330                1335

Met Asp Phe Val Asn Ser Ser Asp Asn Val Ile Phe Val His Asn
1340                1345                1350

Thr Ile His Leu Ile Ser Gln Val Met Asp Asn Met Val Met Ala
1355                1360                1365

Cys Gly Gly Ile Leu Pro Leu Leu Ser Ala Ala Thr Ser Ala Thr
1370                1375                1380

His Glu Leu Glu Asn Ile Glu Pro Thr Gln Gly Leu Ser Ile Glu
1385                1390                1395

Ala Ser Val Thr Phe Leu Gln Arg Leu Ile Ser Leu Val Asp Val
1400                1405                1410

Leu Ile Phe Ala Ser Ser Leu Gly Phe Thr Glu Ile Glu Ala Glu
1415                1420                1425

Lys Asn Met Ser Ser Gly Gly Ile Leu Arg Gln Cys Leu Arg Leu
1430                1435                1440

Val Cys Ala Val Ala Val Arg Asn Cys Leu Glu Cys Gln Gln His
1445                1450                1455

Ser Gln Leu Lys Ala Arg Gly Asp Thr Ala Lys Ser Ser Lys Thr
1460                1465                1470

Ile His Ser Leu Ile Pro Met Gly Lys Ser Ala Ala Lys Ser Pro
1475                1480                1485

Val Asp Ile Val Thr Gly Gly Ile Ser Ser Val Arg Asp Leu Asp
1490                1495                1500

Arg Leu Pro Ala Arg Thr Trp Thr Leu Ile Gly Leu Arg Ala Val
1505                1510                1515

Val Phe Arg Asp Ile Glu Asp Ser Lys Gln Ala Gln Phe Leu Ala
1520                1525                1530

Leu Ala Val Val Tyr Phe Ile Ser Val Leu Met Val Ser Lys Tyr
1535                1540                1545

Arg Asp Ile Leu Glu Pro Gln Asp Glu Arg His Ser Gln Ser Leu
1550                1555                1560

Lys Glu Thr Ser Ser Asp Asn Gly Asn Ala Ser Leu Pro Asp Ala
1565                1570                1575
```

-continued

```
Glu Asn Thr Pro Ala Glu Phe Ser Ser Leu Thr Leu Ser Ser Val
1580                1585                1590

Glu Glu Ser Leu Glu Gly Thr Ser Cys Thr Arg Arg Arg Asp Ser
1595                1600                1605

Gly Leu Gly Glu Glu Thr Ala Ser Gly Leu Gly Ser Gly Leu Val
1610                1615                1620

Ser Ala Ser Pro Ala Ala Pro Leu Gly Val Ser Ala Gly Pro Asp
1625                1630                1635

Ala Ile Ser Glu Val Leu Cys Thr Leu Ser Leu Glu Val Asn Lys
1640                1645                1650

Ser Gln Glu Thr Arg Ile Asp Gly Gly Asn Glu Leu Asp Arg Lys
1655                1660                1665

Val Thr Pro Ser Val Pro Val Ser Lys Asn Val Asn Val Lys Asp
1670                1675                1680

Ile Leu Arg Ser Leu Val Asn Met Pro Ala Asp Gly Val Thr Val
1685                1690                1695

Asp Pro Ala Leu Leu Pro Pro Ala Cys Leu Gly Ala Leu Gly Asp
1700                1705                1710

Leu Ser Val Asp Pro Pro Met Gln Phe Arg Ser Phe Asp Arg Ser
1715                1720                1725

Val Ile Ile Ala Thr Lys Lys Ser Ser Val Leu Pro Ser Ala Leu
1730                1735                1740

Thr Thr Ser Ala Pro Ser Ser Ala Val Ser Val Val Ser Ser Val
1745                1750                1755

Asp Pro Thr His Ala Ser Asp Thr Gly Gly Glu Ser Pro Gly Ser
1760                1765                1770

Arg Ser Pro Lys Cys Lys Thr Ala Leu Ser Cys Lys Gln Leu Ala
1775                1780                1785

Pro Ser His Lys Thr Pro Ala Ala His Met Ser Ile Thr Glu Arg
1790                1795                1800

Leu Glu His Ala Leu Glu Lys Ala Ala Pro Leu Leu Arg Glu Ile
1805                1810                1815

Phe Val Asp Phe Ala Pro Phe Leu Ser Arg Thr Leu Leu Gly Ser
1820                1825                1830

His Gly Gln Glu Leu Leu Ile Glu Gly Thr Ser Leu Val Cys Met
1835                1840                1845

Lys Ser Ser Ser Ser Val Val Glu Leu Val Met Leu Leu Cys Ser
1850                1855                1860

Gln Glu Trp Gln Asn Ser Ile Gln Lys Asn Ala Gly Leu Ala Phe
1865                1870                1875

Ile Glu Leu Val Asn Glu Gly Arg Leu Leu Ser Gln Thr Met Lys
1880                1885                1890

Asp His Leu Val Arg Val Ala Asn Glu Ala Glu Phe Ile Leu Ser
1895                1900                1905

Arg Gln Arg Ala Glu Asp Ile His Arg His Ala Glu Phe Glu Ser
1910                1915                1920

Leu Cys Ala Gln Tyr Ser Ala Asp Lys Arg Glu Glu Glu Lys Met
1925                1930                1935

Cys Asp His Leu Ile Arg Ala Ala Lys Tyr Arg Asp His Val Thr
1940                1945                1950

Ala Thr Gln Leu Ile Gln Lys Ile Ile Asn Leu Leu Thr Asp Lys
1955                1960                1965
```

```
His Gly Ala Trp Gly Ser Ser Ala Val Ser Arg Pro Arg Glu Phe
1970              1975              1980

Trp Arg Leu Asp Tyr Trp Glu Asp Asp Leu Arg Arg Arg Arg Arg
    1985              1990              1995

Phe Val Arg Asn Pro Leu Gly Ser Thr His Pro Glu Ala Thr Leu
2000              2005              2010

Lys Thr Ala Val Glu His Ala Ala Asp Glu Asp Ile Leu Ala Lys
    2015              2020              2025

Gly Lys Gln Ser Ile Lys Ser Gln Ala Leu Gly Asn Gln Asn Ser
    2030              2035              2040

Glu Asn Glu Ala Leu Leu Glu Gly Asp Asp Asp Thr Leu Ser Ser
    2045              2050              2055

Val Asp Glu Lys Asp Leu Glu Asn Leu Ala Gly Pro Val Ser Leu
    2060              2065              2070

Ser Thr Pro Ala Gln Leu Val Ala Pro Ser Val Val Val Lys Gly
    2075              2080              2085

Thr Leu Ser Val Thr Ser Ser Glu Leu Tyr Phe Glu Val Asp Glu
    2090              2095              2100

Glu Asp Pro Asn Phe Lys Lys Ile Asp Pro Lys Ile Leu Ala Tyr
    2105              2110              2115

Thr Glu Gly Leu His Gly Lys Trp Leu Phe Thr Glu Ile Arg Ser
    2120              2125              2130

Ile Phe Ser Arg Arg Tyr Leu Leu Gln Asn Thr Ala Leu Glu Ile
    2135              2140              2145

Phe Met Ala Asn Arg Val Ala Val Met Phe Asn Phe Pro Asp Pro
    2150              2155              2160

Ala Thr Val Lys Lys Val Val Asn Tyr Leu Pro Arg Val Gly Val
    2165              2170              2175

Gly Thr Ser Phe Gly Leu Pro Gln Thr Arg Arg Ile Ser Leu Ala
    2180              2185              2190

Thr Pro Arg Gln Leu Phe Lys Ala Ser Asn Met Thr Gln Arg Trp
    2195              2200              2205

Gln His Arg Glu Ile Ser Asn Phe Glu Tyr Leu Met Phe Leu Asn
    2210              2215              2220

Thr Ile Ala Gly Arg Ser Tyr Asn Asp Leu Asn Gln Tyr Pro Val
    2225              2230              2235

Phe Pro Trp Val Ile Thr Asn Tyr Glu Ser Glu Glu Leu Asp Leu
    2240              2245              2250

Thr Leu Pro Ser Asn Phe Arg Asp Leu Ser Lys Pro Ile Gly Ala
    2255              2260              2265

Leu Asn Pro Lys Arg Ala Ala Phe Phe Ala Glu Arg Phe Glu Ser
    2270              2275              2280

Trp Glu Asp Asp Gln Val Pro Lys Phe His Tyr Gly Thr His Tyr
    2285              2290              2295

Ser Thr Ala Ser Phe Val Leu Ala Trp Leu Leu Arg Ile Glu Pro
    2300              2305              2310

Phe Thr Thr Tyr Phe Leu Asn Leu Gln Gly Gly Lys Phe Asp His
    2315              2320              2325

Ala Asp Arg Thr Phe Ser Ser Val Ser Arg Ala Trp Arg Asn Ser
    2330              2335              2340

Gln Arg Asp Thr Ser Asp Ile Lys Glu Leu Ile Pro Glu Phe Tyr
    2345              2350              2355
```

```
Tyr Leu Pro Glu Met Phe Val Asn Phe Asn Asn Tyr Asn Leu Gly
    2360            2365                2370

Val Met Asp Asp Gly Thr Val Val Ser Asp Val Glu Leu Pro Pro
    2375            2380                2385

Trp Ala Lys Thr Ser Glu Glu Phe Val Arg Ile Asn Arg Leu Ala
    2390            2395                2400

Leu Glu Ser Glu Phe Val Ser Cys Gln Leu His Gln Trp Ile Asp
    2405            2410                2415

Leu Ile Phe Gly Tyr Lys Gln Gln Gly Pro Glu Ala Val Arg Ala
    2420            2425                2430

Leu Asn Val Phe Tyr Tyr Leu Thr Tyr Glu Gly Ala Val Asn Leu
    2435            2440                2445

Asn Ser Ile Thr Asp Pro Val Leu Arg Glu Ala Val Glu Ala Gln
    2450            2455                2460

Ile Arg Ser Phe Gly Gln Thr Pro Ser Gln Leu Leu Ile Glu Pro
    2465            2470                2475

His Pro Pro Arg Gly Ser Ala Met Gln Ala Ser Pro Leu Met Phe
    2480            2485                2490

Thr Asp Gln Ala Gln Gln Asp Val Ile Met Val Leu Lys Phe Pro
    2495            2500                2505

Ser Asn Ser Pro Val Thr His Val Ala Ala Asn Thr Gln Pro Gly
    2510            2515                2520

Leu Ala Met Pro Ala Val Ile Thr Val Thr Ala Asn Arg Leu Phe
    2525            2530                2535

Ala Val Asn Lys Trp His Asn Leu Pro Ala His Gln Gly Ala Val
    2540            2545                2550

Gln Asp Gln Pro Tyr Gln Leu Pro Val Glu Ile Asp Pro Leu Ile
    2555            2560                2565

Ala Cys Gly Thr Gly Thr His Arg Arg Gln Val Thr Asp Leu Leu
    2570            2575                2580

Asp Gln Ser Ile Gln Val His Ser Gln Cys Phe Val Ile Thr Ser
    2585            2590                2595

Asp Asn Arg Tyr Ile Leu Val Cys Gly Phe Trp Asp Lys Ser Phe
    2600            2605                2610

Arg Val Tyr Ser Thr Asp Thr Gly Lys Leu Ile Gln Val Val Phe
    2615            2620                2625

Gly His Trp Asp Val Val Thr Cys Leu Ala Arg Ser Glu Ser Tyr
    2630            2635                2640

Ile Gly Gly Asn Cys Tyr Ile Leu Ser Gly Ser Arg Asp Ala Thr
    2645            2650                2655

Leu Leu Leu Trp Tyr Trp Asn Gly Lys Ser Ser Gly Ile Gly Asp
    2660            2665                2670

Asn Pro Gly Gly Glu Thr Ala Thr Pro Arg Ala Ile Leu Thr Gly
    2675            2680                2685

His Asp Tyr Glu Ile Thr Cys Ala Ala Val Cys Ala Glu Leu Gly
    2690            2695                2700

Leu Val Leu Ser Gly Ser Gln Glu Gly Pro Cys Leu Ile His Ser
    2705            2710                2715

Met Asn Gly Asp Leu Leu Arg Thr Leu Glu Gly Pro Glu Asn Cys
    2720            2725                2730

Leu Lys Pro Lys Leu Ile Gln Ala Ser Arg Glu Gly His Cys Val
    2735            2740                2745
```

```
Ile Phe Tyr Glu Asn Gly Cys Phe Cys Thr Phe Ser Val Asn Gly
    2750                2755                2760

Lys Leu Gln Ala Thr Val Glu Thr Asp Asp His Ile Arg Val Ser
    2765                2770                2775

Ala Val Gly Ser Thr Leu Phe Leu Leu Leu Gly Ser Ser Lys
    2780                2785                2790

<210> SEQ ID NO 5
<211> LENGTH: 16
<212> TYPE: PRT
<213> ORGANISM: Mus musculus

<400> SEQUENCE: 5

Val Ser Ala Val Gly Ser Thr Leu Phe Leu Leu Leu Gly Ser Ser Lys
1               5                   10                  15

<210> SEQ ID NO 6
<211> LENGTH: 2579
<212> TYPE: PRT
<213> ORGANISM: Mus musculus
<220> FEATURE:
<221> NAME/KEY: BINDING
<222> LOCATION: (1350)..(1369)
<223> OTHER INFORMATION: Putative Protein Kinase A RII binding site
<220> FEATURE:
<221> NAME/KEY: BINDING
<222> LOCATION: (1399)..(1418)
<223> OTHER INFORMATION: Putative Protein Kinase A RII binding site
<220> FEATURE:
<221> NAME/KEY: REPEAT
<222> LOCATION: (2028)..(2071)
<223> OTHER INFORMATION: WDL (WD-like) repeat
<220> FEATURE:
<221> NAME/KEY: REPEAT
<222> LOCATION: (2072)..(2121)
<223> OTHER INFORMATION: WDL (WD-like) repeat
<220> FEATURE:
<221> NAME/KEY: REPEAT
<222> LOCATION: (2122)..(2162)
<223> OTHER INFORMATION: WDL (WD-like) repeat
<220> FEATURE:
<221> NAME/KEY: DOMAIN
<222> LOCATION: (2204)..(2482)
<223> OTHER INFORMATION: BEACH domain

<400> SEQUENCE: 6

Met Ala Ser Glu Asp Asn Arg Ala Pro Ser Arg Pro Thr Gly Asp
1               5                   10                  15

Asp Gly Gly Gly Gly Lys Glu Glu Thr Pro Thr Glu Gly Gly Ala
            20                  25                  30

Leu Ser Leu Lys Pro Gly Leu Pro Ile Arg Gly Ile Arg Met Lys Phe
            35                  40                  45

Ala Val Leu Thr Gly Leu Val Glu Val Gly Glu Val Ser Asn Arg Asp
        50                  55                  60

Ile Val Glu Thr Val Phe Asn Leu Leu Val Gly Gly Gln Phe Asp Leu
65                  70                  75                  80

Glu Met Asn Phe Ile Ile Gln Glu Gly Glu Ser Ile Cys Met Val
                85                  90                  95

Glu Leu Leu Glu Lys Cys Asp Val Thr Cys Gln Ala Glu Val Trp Ser
            100                 105                 110

Met Phe Thr Ala Ile Leu Lys Lys Ser Ile Arg Asn Leu Gln Val Cys
        115                 120                 125

Thr Glu Val Gly Leu Val Glu Lys Val Leu Gly Lys Ile Glu Lys Val
        130                 135                 140
```

-continued

```
Asp Ser Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Gln Trp Pro Pro His Ala Gly Lys Leu Leu Ser
            180                 185                 190

Val Leu Lys His Met Pro Gln Lys Tyr Gly Pro Asp Ala Phe Phe Asn
        195                 200                 205

Phe Pro Gly Lys Ser Ala Ala Ile Ala Leu Pro Pro Ile Ala Arg
    210                 215                 220

Trp Pro Tyr Gln Asn Gly Phe Thr Phe His Thr Trp Leu Arg Met Asp
225                 230                 235                 240

Pro Val Asn Asn Ile Asn Val Asp Lys Asp Lys Pro Tyr Leu Tyr Cys
                245                 250                 255

Phe Arg Thr Ser Lys Gly Leu Gly Tyr Ser Ala His Phe Val Gly Gly
            260                 265                 270

Cys Leu Ile Ile Thr Ser Ile Lys Ser Lys Gly Lys Gly Phe Gln His
        275                 280                 285

Cys Val Lys Phe Asp Phe Lys Pro Gln Lys Trp Tyr Met Val Thr Ile
    290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
            340                 345                 350

Ala Asn Arg Val Phe Cys Gly Gln Met Thr Ala Val Tyr Leu Phe Ser
        355                 360                 365

Asp Ala Leu Asn Ala Ala Gln Ile Phe Ala Ile Tyr Gln Leu Gly Leu
    370                 375                 380

Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
                405                 410                 415

Ile Ala Phe Met Tyr Asn Pro Arg Ala Thr Asp Ala Gln Leu Cys Leu
            420                 425                 430

Glu Ser Ser Pro Lys Asp Asn Pro Ser Ile Phe Val His Ser Pro His
        435                 440                 445

Ala Leu Met Leu Gln Asp Val Lys Ala Val Leu Thr His Ser Ile Gln
    450                 455                 460

Ser Ala Met His Ser Ile Gly Gly Val Gln Val Leu Phe Pro Leu Phe
465                 470                 475                 480

Ala Gln Leu Asp Tyr Lys Gln Tyr Leu Ser Asp Glu Val Asp Leu Thr
                485                 490                 495

Ile Cys Thr Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
        515                 520                 525

Gly Tyr Ser Leu Glu Lys Ser Ser Lys Ser His Val Ser Arg Ala Val
    530                 535                 540

Leu Glu Leu Cys Leu Ala Phe Ser Lys Tyr Leu Ser Asn Leu Gln Asn
545                 550                 555                 560
```

-continued

```
Gly Met Pro Leu Leu Lys Gln Leu Cys Asp His Ile Leu Leu Asn Pro
            565                 570                 575
Ala Val Trp Ile His Thr Pro Ala Lys Val Gln Leu Met Leu Tyr Thr
            580                 585                 590
Tyr Leu Ser Thr Glu Phe Ile Gly Thr Val Asn Ile Tyr Asn Thr Ile
            595                 600                 605
Arg Arg Val Gly Thr Val Leu Leu Ile Met His Thr Leu Lys Tyr Tyr
            610                 615                 620
Tyr Trp Ala Val Asn Pro Gln Asp Arg Ser Gly Ile Thr Pro Lys Gly
625                 630                 635                 640
Leu Asp Gly Pro Arg Pro Asn Gln Lys Glu Ile Leu Ser Leu Arg Ala
                    645                 650                 655
Phe Leu Leu Met Phe Ile Lys Gln Leu Val Met Lys Asp Ser Gly Val
                    660                 665                 670
Lys Glu Asp Glu Leu Gln Ala Ile Leu Asn Tyr Leu Leu Thr Met His
            675                 680                 685
Glu Asp Asp Asn Leu Met Asp Val Leu Gln Leu Leu Val Ala Leu Met
            690                 695                 700
Ala Glu His Pro Asn Ser Met Ile Pro Ala Phe Asp Gln Arg Asn Gly
705                 710                 715                 720
Leu Arg Val Ile Tyr Lys Leu Leu Ala Ser Lys Ser Glu Gly Ile Arg
                    725                 730                 735
Val Gln Ala Leu Lys Ala Leu Gly Tyr Phe Leu Lys His Leu Ala Pro
                    740                 745                 750
Lys Arg Lys Ala Glu Val Met Leu Gly His Gly Leu Phe Ser Leu Leu
            755                 760                 765
Ala Glu Arg Leu Met Leu Gln Thr Asn Leu Ile Thr Met Thr Met Tyr
770                 775                 780
Asn Val Leu Phe Glu Ile Leu Ile Glu Gln Ile Cys Thr Gln Val Ile
785                 790                 795                 800
His Lys Gln His Pro Asp Pro Asp Ser Thr Val Lys Ile Gln Asn Pro
                    805                 810                 815
Gln Ile Leu Lys Val Ile Ala Thr Leu Leu Arg Asn Ser Pro Gln Cys
            820                 825                 830
Pro Glu Ser Met Glu Val Arg Arg Ala Phe Leu Ser Asp Met Ile Lys
            835                 840                 845
Leu Phe Asn Asn Ser Arg Glu Asn Arg Arg Ser Leu Leu Gln Cys Ser
850                 855                 860
Val Trp Gln Glu Trp Met Leu Ser Leu Cys Tyr Phe Asn Pro Lys Asn
865                 870                 875                 880
Ser Asp Glu Gln Lys Ile Thr Glu Met Val Tyr Ala Ile Phe Arg Ile
                    885                 890                 895
Leu Leu Tyr His Ala Val Lys Tyr Glu Trp Gly Gly Trp Arg Val Trp
            900                 905                 910
Val Asp Thr Leu Ser Ile Thr His Ser Lys Val Thr Phe Glu Ile His
            915                 920                 925
Lys Glu Asn Leu Ala Asn Ile Phe Arg Glu Gln Arg Lys Gly Asp
930                 935                 940
Glu Glu Thr Gly Pro Cys Ser Ser Ser Leu Val Pro Glu Gly Thr Gly
945                 950                 955                 960
Ala Thr Arg Gly Val Asp Val Ser Val Gly Ser Gln His Glu Asp Arg
                    965                 970                 975
```

-continued

```
Lys Asp Ser Pro Ile Ser Pro His Phe Thr Arg Asn Ser Asp Glu Asn
            980                 985                 990

Ser Ser Ile Gly Arg Ala Ser Ser Ile Asp Ser Ala Ser Asn Thr Glu
            995                1000                1005

Leu Gln Thr His Asp Met Ser Ser Asp Glu Lys Lys Val Glu Arg
        1010                1015                1020

Glu Asn Gln Glu Leu Leu Asp Gln Ala Thr Val Glu Glu Thr Ala
    1025                1030                1035

Thr Asn Gly Ala Lys Asp Asp Leu Glu Thr Ser Ser Asp Ala Ala
    1040                1045                1050

Glu Pro Val Thr Ile Asn Ser Asn Ser Leu Glu Pro Gly Lys Asp
    1055                1060                1065

Thr Val Thr Ile Ser Glu Val Ser Ala Ser Ile Ser Ser Pro Ser
    1070                1075                1080

Glu Glu Asp Ala Ala Glu Met Pro Glu Leu Leu Glu Lys Ser Gly
    1085                1090                1095

Val Glu Glu Lys Glu Asp Asp Tyr Val Glu Leu Lys Val Glu
    1100                1105                1110

Gly Ser Pro Thr Glu Glu Ala Gly Leu Pro Thr Glu Leu Gln Gly
    1115                1120                1125

Glu Gly Leu Val Ser Ala Ala Ser Gly Gly Arg Glu Glu Pro Asp
    1130                1135                1140

Met Cys Gly His Gly Cys Glu Val Gln Val Glu Ala Pro Ile Thr
    1145                1150                1155

Lys Ile His Asn Asp Pro Glu Thr Thr Asp Ser Glu Asp Ser Arg
    1160                1165                1170

Phe Pro Thr Val Ala Thr Ala Gly Ser Leu Ala Thr Ser Ser Glu
    1175                1180                1185

Val Pro Val Pro Gln Ala Thr Val Gln Ser Asp Ser His Glu Met
    1190                1195                1200

Leu Asp Gly Gly Met Lys Ala Thr Asn Leu Ala Gly Glu Thr Glu
    1205                1210                1215

Ser Val Ser Asp Cys Ala Asp Asn Val Ser Glu Ala Pro Ala Thr
    1220                1225                1230

Ser Glu Gln Lys Ile Thr Lys Leu Asp Val Ser Ser Val Ala Ser
    1235                1240                1245

Asp Thr Glu Arg Phe Glu Leu Lys Ala Ser Thr Ser Thr Glu Ala
    1250                1255                1260

Pro Gln Pro Gln Arg His Gly Leu Glu Ile Ser Arg Gln Gln Glu
    1265                1270                1275

Gln Thr Ala Gln Gly Thr Ala Pro Asp Ala Val Asp Gln Gln Arg
    1280                1285                1290

Arg Asp Ser Arg Ser Thr Met Phe Arg Ile Pro Glu Phe Lys Trp
    1295                1300                1305

Ser Gln Met His Gln Arg Leu Leu Thr Asp Leu Leu Phe Ser Ile
    1310                1315                1320

Glu Thr Asp Ile Gln Met Trp Arg Ser His Ser Thr Lys Thr Val
    1325                1330                1335

Met Asp Phe Val Asn Ser Ser Asp Asn Val Ile Phe Val His Asn
    1340                1345                1350

Thr Ile His Leu Ile Ser Gln Val Met Asp Asn Met Val Met Ala
    1355                1360                1365
```

```
Cys Gly Gly Ile Leu Pro Leu Leu Ser Ala Ala Thr Ser Ala Thr
1370                1375                1380

His Glu Leu Glu Asn Ile Glu Pro Thr Gln Gly Leu Ser Ile Glu
1385                1390                1395

Ala Ser Val Thr Phe Leu Gln Arg Leu Ile Ser Leu Val Asp Val
1400                1405                1410

Leu Ile Phe Ala Ser Ser Leu Gly Phe Thr Glu Ile Glu Ala Glu
1415                1420                1425

Lys Asn Met Ser Ser Gly Gly Ile Leu Arg Gln Cys Leu Arg Leu
1430                1435                1440

Val Cys Ala Val Ala Val Arg Asn Cys Leu Glu Cys Gln Gln His
1445                1450                1455

Ser Gln Leu Lys Ala Arg Gly Asp Thr Ala Lys Ser Ser Lys Thr
1460                1465                1470

Ile His Ser Leu Ile Pro Met Gly Lys Ser Ala Ala Lys Ser Pro
1475                1480                1485

Val Asp Ile Val Thr Gly Gly Ile Ser Ser Val Arg Asp Leu Asp
1490                1495                1500

Arg Leu Pro Ala Arg Thr Trp Thr Leu Ile Gly Leu Arg Ala Val
1505                1510                1515

Val Phe Arg Asp Ile Glu Asp Ser Lys Gln Ala Gln Phe Leu Ala
1520                1525                1530

Leu Ala Val Val Tyr Phe Ile Ser Val Leu Met Val Ser Lys Tyr
1535                1540                1545

Arg Asp Ile Leu Glu Pro Gln Asp Glu Arg His Ser Gln Ser Leu
1550                1555                1560

Lys Glu Thr Ser Ser Asp Asn Gly Asn Ala Ser Leu Pro Asp Ala
1565                1570                1575

Glu Asn Thr Pro Ala Glu Phe Ser Ser Leu Thr Leu Ser Ser Val
1580                1585                1590

Glu Glu Ser Leu Glu Gly Thr Ser Cys Thr Arg Arg Arg Asp Ser
1595                1600                1605

Gly Leu Gly Glu Glu Thr Ala Ser Gly Leu Gly Ser Gly Leu Val
1610                1615                1620

Ser Ala Ser Pro Ala Ala Pro Leu Gly Val Ser Ala Gly Pro Asp
1625                1630                1635

Ala Ile Ser Glu Val Leu Cys Thr Leu Ser Leu Glu Val Asn Lys
1640                1645                1650

Ser Gln Glu Thr Arg Ile Asp Gly Gly Asn Glu Leu Asp Arg Lys
1655                1660                1665

Val Thr Pro Ser Val Pro Val Ser Lys Asn Val Asn Val Lys Asp
1670                1675                1680

Ile Leu Arg Ser Leu Val Asn Met Pro Ala Asp Gly Val Thr Val
1685                1690                1695

Asp Pro Ala Leu Leu Pro Pro Ala Cys Leu Gly Ala Leu Gly Asp
1700                1705                1710

Leu Ser Val Asp Pro Pro Met Gln Phe Arg Ser Phe Asp Arg Ser
1715                1720                1725

Val Ile Ile Ala Thr Lys Lys Ser Ser Val Leu Pro Ser Ala Leu
1730                1735                1740

Thr Thr Ser Ala Pro Ser Ser Ala Val Ser Val Val Ser Ser Val
1745                1750                1755
```

-continued

```
Asp Pro Thr His Ala Ser Asp Thr Gly Glu Ser Pro Gly Ser
    1760                1765                1770

Arg Ser Pro Lys Cys Lys Thr Ala Leu Ser Cys Lys Gln Leu Ala
    1775                1780                1785

Pro Ser His Lys Thr Pro Ala Ala His Met Ser Ile Thr Glu Arg
    1790                1795                1800

Leu Glu His Ala Leu Glu Lys Ala Ala Pro Leu Leu Arg Glu Ile
    1805                1810                1815

Phe Val Asp Phe Ala Pro Phe Leu Ser Arg Thr Leu Leu Gly Ser
    1820                1825                1830

His Gly Gln Glu Leu Leu Ile Glu Gly Thr Ser Leu Val Cys Met
    1835                1840                1845

Lys Ser Ser Ser Val Val Glu Leu Val Met Leu Leu Cys Ser
    1850                1855                1860

Gln Glu Trp Gln Asn Ser Ile Gln Lys Asn Ala Gly Leu Ala Phe
    1865                1870                1875

Ile Glu Leu Val Asn Glu Gly Arg Leu Leu Ser Gln Thr Met Lys
    1880                1885                1890

Asp His Leu Val Arg Val Ala Asn Glu Ala Glu Phe Ile Leu Ser
    1895                1900                1905

Arg Gln Arg Ala Glu Asp Ile His Arg His Ala Glu Phe Glu Ser
    1910                1915                1920

Leu Cys Ala Gln Tyr Ser Ala Asp Lys Arg Glu Glu Lys Met
    1925                1930                1935

Cys Asp His Leu Ile Arg Ala Ala Lys Tyr Arg Asp His Val Thr
    1940                1945                1950

Ala Thr Gln Leu Ile Gln Lys Ile Ile Asn Leu Leu Thr Asp Lys
    1955                1960                1965

His Gly Ala Trp Gly Ser Ser Ala Val Ser Arg Pro Arg Glu Phe
    1970                1975                1980

Trp Arg Leu Asp Tyr Trp Glu Asp Leu Arg Arg Arg Arg
    1985                1990                1995

Phe Val Arg Asn Pro Leu Gly Ser Thr His Pro Glu Ala Thr Leu
    2000                2005                2010

Lys Thr Ala Val Glu His Ala Ala Asp Glu Asp Ile Leu Ala Lys
    2015                2020                2025

Gly Lys Gln Ser Ile Lys Ser Gln Ala Leu Gly Asn Gln Asn Ser
    2030                2035                2040

Glu Asn Glu Ala Leu Leu Glu Gly Asp Asp Thr Leu Ser Ser
    2045                2050                2055

Val Asp Glu Lys Asp Leu Glu Asn Leu Ala Gly Pro Val Ser Leu
    2060                2065                2070

Ser Thr Pro Ala Gln Leu Val Ala Pro Ser Val Val Lys Gly
    2075                2080                2085

Thr Leu Ser Val Thr Ser Ser Glu Leu Tyr Phe Glu Val Asp Glu
    2090                2095                2100

Glu Asp Pro Asn Phe Lys Lys Ile Asp Pro Lys Ile Leu Ala Tyr
    2105                2110                2115

Thr Glu Gly Leu His Gly Lys Trp Leu Phe Thr Glu Ile Arg Ser
    2120                2125                2130

Ile Phe Ser Arg Arg Tyr Leu Leu Gln Asn Thr Ala Leu Glu Ile
    2135                2140                2145
```

```
Phe Met Ala Asn Arg Val Ala Val Met Phe Asn Phe Pro Asp Pro
    2150                2155                2160

Ala Thr Val Lys Lys Val Val Asn Tyr Leu Pro Arg Val Gly Val
    2165                2170                2175

Gly Thr Ser Phe Gly Leu Pro Gln Thr Arg Arg Ile Ser Leu Ala
    2180                2185                2190

Thr Pro Arg Gln Leu Phe Lys Ala Ser Asn Met Thr Gln Arg Trp
    2195                2200                2205

Gln His Arg Glu Ile Ser Asn Phe Glu Tyr Leu Met Phe Leu Asn
    2210                2215                2220

Thr Ile Ala Gly Arg Ser Tyr Asn Asp Leu Asn Gln Tyr Pro Val
    2225                2230                2235

Phe Pro Trp Val Ile Thr Asn Tyr Glu Ser Glu Glu Leu Asp Leu
    2240                2245                2250

Thr Leu Pro Ser Asn Phe Arg Asp Leu Ser Lys Pro Ile Gly Ala
    2255                2260                2265

Leu Asn Pro Lys Arg Ala Ala Phe Phe Ala Glu Arg Phe Glu Ser
    2270                2275                2280

Trp Glu Asp Asp Gln Val Pro Lys Phe His Tyr Gly Thr His Tyr
    2285                2290                2295

Ser Thr Ala Ser Phe Val Leu Ala Trp Leu Leu Arg Ile Glu Pro
    2300                2305                2310

Phe Thr Thr Tyr Phe Leu Asn Leu Gln Gly Gly Lys Phe Asp His
    2315                2320                2325

Ala Asp Arg Thr Phe Ser Ser Val Ser Arg Ala Trp Arg Asn Ser
    2330                2335                2340

Gln Arg Asp Thr Ser Asp Ile Lys Glu Leu Ile Pro Glu Phe Tyr
    2345                2350                2355

Tyr Leu Pro Glu Met Phe Val Asn Phe Asn Asn Tyr Asn Leu Gly
    2360                2365                2370

Val Met Asp Asp Gly Thr Val Val Ser Asp Val Glu Leu Pro Pro
    2375                2380                2385

Trp Ala Lys Thr Ser Glu Glu Phe Val Arg Ile Asn Arg Leu Ala
    2390                2395                2400

Leu Glu Ser Glu Phe Val Ser Cys Gln Leu His Gln Trp Ile Asp
    2405                2410                2415

Leu Ile Phe Gly Tyr Lys Gln Gln Gly Pro Glu Ala Val Arg Ala
    2420                2425                2430

Leu Asn Val Phe Tyr Tyr Leu Thr Tyr Glu Gly Ala Val Asn Leu
    2435                2440                2445

Asn Ser Ile Thr Asp Pro Val Leu Arg Glu Ala Val Glu Ala Gln
    2450                2455                2460

Ile Arg Ser Phe Gly Gln Thr Pro Ser Gln Leu Leu Ile Glu Pro
    2465                2470                2475

His Pro Pro Arg Gly Ser Ala Met Gln Ala Ser Pro Leu Met Phe
    2480                2485                2490

Thr Asp Gln Ala Gln Gln Asp Val Ile Met Val Leu Lys Phe Pro
    2495                2500                2505

Ser Asn Ser Pro Val Thr His Val Ala Ala Asn Thr Gln Pro Gly
    2510                2515                2520

Leu Ala Met Pro Ala Val Ile Thr Val Thr Ala Asn Arg Leu Phe
    2525                2530                2535
```

```
Ala Val Asn Lys Trp His Asn Leu Pro Ala His Gln Gly Ala Val
    2540            2545                2550

Gln Asp Gln Pro Tyr Gln Leu Pro Val Glu Ile Asp Pro Leu Ile
    2555            2560                2565

Gly Leu Pro Leu Leu Ser Leu Phe Ala Ile His
    2570            2575

<210> SEQ ID NO 7
<211> LENGTH: 11
<212> TYPE: PRT
<213> ORGANISM: Mus musculus

<400> SEQUENCE: 7

Gly Leu Pro Leu Leu Ser Leu Phe Ala Ile His
1               5                   10

<210> SEQ ID NO 8
<211> LENGTH: 2863
<212> TYPE: PRT
<213> ORGANISM: Homo sapiens
<220> FEATURE:
<221> NAME/KEY: DOMAIN
<222> LOCATION: (1)..(72)
<223> OTHER INFORMATION: G peptide
<220> FEATURE:
<221> NAME/KEY: DOMAIN
<222> LOCATION: (82)..(393)
<223> OTHER INFORMATION: HSH (helix-sheet-helix) domain
<220> FEATURE:
<221> NAME/KEY: DOMAIN
<222> LOCATION: (979)..(1302)
<223> OTHER INFORMATION: SET Domain (Rich in Serine, Glutamic acid and
      Threonine)
<220> FEATURE:
<221> NAME/KEY: DOMAIN
<222> LOCATION: (2035)..(2169)
<223> OTHER INFORMATION: WDL (WD-like) domain
<220> FEATURE:
<221> NAME/KEY: DOMAIN
<222> LOCATION: (2212)..(2489)
<223> OTHER INFORMATION: BEACH domain
<220> FEATURE:
<221> NAME/KEY: REPEAT
<222> LOCATION: (2592)..(2635)
<223> OTHER INFORMATION: WD repeat
<220> FEATURE:
<221> NAME/KEY: REPEAT
<222> LOCATION: (2636)..(2694)
<223> OTHER INFORMATION: WD repeat
<220> FEATURE:
<221> NAME/KEY: REPEAT
<222> LOCATION: (2695)..(2778)
<223> OTHER INFORMATION: WD repeat
<220> FEATURE:
<221> NAME/KEY: REPEAT
<222> LOCATION: (2779)..(2819)
<223> OTHER INFORMATION: WD repeat
<220> FEATURE:
<221> NAME/KEY: REPEAT
<222> LOCATION: (2820)..(2863)
<223> OTHER INFORMATION: WD repeat

<400> SEQUENCE: 8

Met Ala Ser Glu Asp Asn Arg Val Pro Ser Pro Pro Thr Gly Asp
1               5                   10                  15

Asp Gly Gly Gly Gly Arg Glu Glu Thr Pro Thr Glu Gly Gly Ala
                20                  25                  30

Leu Ser Leu Lys Pro Gly Leu Pro Ile Arg Gly Ile Arg Met Lys Phe
            35                  40                  45
```

-continued

```
Ala Val Leu Thr Gly Leu Val Glu Val Gly Glu Val Ser Asn Arg Asp
    50              55                  60

Ile Val Glu Thr Val Phe Asn Leu Leu Val Gly Gln Phe Asp Leu
65              70                  75                  80

Glu Met Asn Phe Ile Ile Gln Glu Gly Glu Ser Ile Asn Cys Met Val
                85                  90                  95

Asp Leu Leu Glu Lys Cys Asp Ile Thr Cys Gln Ala Glu Val Trp Ser
            100                 105                 110

Met Phe Thr Ala Ile Leu Lys Lys Ser Ile Arg Asn Leu Gln Val Cys
            115                 120                 125

Thr Glu Val Gly Leu Val Glu Lys Val Leu Gly Lys Ile Glu Lys Val
    130                 135                 140

Asp Asn Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Arg Trp Pro Pro His Ala Gly Lys Leu Leu Ser
            180                 185                 190

Val Leu Lys His Met Pro Gln Lys Tyr Gly Pro Asp Ala Phe Phe Asn
            195                 200                 205

Phe Pro Gly Lys Ser Ala Ala Ala Ile Ala Leu Pro Pro Ile Ala Lys
    210                 215                 220

Trp Pro Tyr Gln Asn Gly Phe Thr Phe His Thr Trp Leu Arg Met Asp
225                 230                 235                 240

Pro Val Asn Asn Ile Asn Val Asp Lys Asp Lys Pro Tyr Leu Tyr Cys
                245                 250                 255

Phe Arg Thr Ser Lys Gly Leu Gly Tyr Ser Ala His Phe Val Gly Gly
            260                 265                 270

Cys Leu Ile Val Thr Ser Ile Lys Ser Lys Gly Lys Gly Phe Gln His
            275                 280                 285

Cys Val Lys Phe Asp Phe Lys Pro Gln Lys Trp Tyr Met Val Thr Ile
    290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
            340                 345                 350

Ala Asn Arg Val Phe Cys Gly Gln Met Thr Ala Val Tyr Leu Phe Ser
            355                 360                 365

Glu Ala Leu Asn Ala Ala Gln Ile Phe Ala Ile Tyr Gln Leu Gly Leu
    370                 375                 380

Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
                405                 410                 415

Ile Ala Phe Thr Tyr Asn Pro Arg Ala Thr Asp Ala Gln Leu Cys Leu
            420                 425                 430

Glu Ser Ser Pro Lys Asp Asn Pro Ser Ile Phe Val His Ser Pro His
            435                 440                 445

Ala Leu Met Leu Gln Asp Val Lys Ala Val Leu Thr His Ser Ile Gln
    450                 455                 460
```

-continued

```
Ser Ala Met His Ser Ile Gly Val Gln Val Leu Phe Pro Leu Phe
465                 470                 475                 480

Ala Gln Leu Asp Tyr Arg Gln Tyr Leu Ser Asp Glu Ile Asp Leu Thr
            485                 490                 495

Ile Cys Ser Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
            515                 520                 525

Gly Tyr Ser Leu Glu Lys Ser Ser Lys Ser His Val Ser Arg Ala Val
        530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Val Leu Leu Asn Pro
            565                 570                 575

Ala Ile Trp Ile His Thr Pro Ala Lys Val Gln Leu Met Leu Tyr Thr
            580                 585                 590

Tyr Leu Ser Thr Glu Phe Ile Gly Thr Val Asn Ile Tyr Asn Thr Ile
        595                 600                 605

Arg Arg Val Gly Thr Val Leu Leu Ile Met His Thr Leu Lys Tyr Tyr
610                 615                 620

Tyr Trp Ala Val Asn Pro Gln Asp Arg Ser Gly Ile Thr Pro Lys Gly
625                 630                 635                 640

Leu Asp Gly Pro Arg Pro Asn Gln Lys Glu Met Leu Ser Leu Arg Ala
            645                 650                 655

Phe Leu Leu Met Phe Ile Lys Gln Leu Val Met Lys Asp Ser Gly Val
            660                 665                 670

Lys Glu Asp Glu Leu Gln Ala Ile Leu Asn Tyr Leu Leu Thr Met His
        675                 680                 685

Glu Asp Asp Asn Leu Met Asp Val Leu Gln Leu Leu Val Ala Leu Met
690                 695                 700

Ser Glu His Pro Asn Ser Met Ile Pro Ala Phe Asp Gln Arg Asn Gly
705                 710                 715                 720

Leu Arg Val Ile Tyr Lys Leu Leu Ala Ser Lys Ser Glu Gly Ile Arg
            725                 730                 735

Val Gln Ala Leu Lys Ala Met Gly Tyr Phe Leu Lys His Arg Pro Pro
            740                 745                 750

Lys Arg Lys Ala Glu Val Met Leu Gly His Gly Leu Phe Ser Leu Leu
        755                 760                 765

Ala Glu Arg Leu Met Leu Gln Thr Asn Leu Ile Thr Met Thr Thr Tyr
770                 775                 780

Asn Val Leu Phe Glu Ile Leu Ile Glu Gln Ile Gly Thr Gln Val Ile
785                 790                 795                 800

His Lys Gln His Pro Asp Pro Asp Ser Ser Val Lys Ile Gln Asn Pro
            805                 810                 815

Gln Ile Leu Lys Val Ile Ala Thr Leu Leu Arg Asn Ser Pro Gln Cys
            820                 825                 830

Pro Glu Ser Met Glu Val Arg Arg Ala Phe Leu Ser Asp Met Ile Lys
        835                 840                 845

Leu Phe Asn Asn Ser Arg Glu Asn Arg Arg Ser Leu Leu Gln Cys Ser
850                 855                 860

Val Trp Gln Glu Trp Met Leu Ser Leu Cys Tyr Phe Asn Pro Lys Asn
865                 870                 875                 880
```

-continued

```
Ser Asp Glu Gln Lys Ile Thr Glu Met Val Tyr Ala Ile Phe Arg Ile
            885                 890                 895

Leu Leu Tyr His Ala Val Lys Tyr Glu Trp Gly Gly Trp Arg Val Trp
            900                 905                 910

Val Asp Thr Leu Ser Ile Thr His Ser Lys Val Thr Phe Glu Ile His
            915                 920                 925

Lys Glu Asn Leu Ala Asn Ile Phe Arg Glu Gln Gly Lys Val Asp
            930                 935                 940

Glu Glu Ile Gly Leu Cys Ser Ser Thr Ser Val Gln Ala Ala Ser Gly
945                 950                 955                 960

Ile Arg Arg Asp Ile Asn Val Ser Val Gly Ser Gln Gln Pro Asp Thr
                965                 970                 975

Lys Asp Ser Pro Val Cys Pro His Phe Thr Thr Asn Gly Asn Glu Asn
            980                 985                 990

Ser Ser Ile Glu Lys Thr Ser Ser  Leu Glu Ser Ala Ser  Asn Ile Glu
            995                 1000                1005

Leu Gln  Thr Thr Asn Thr Ser  Tyr Glu Glu Met Lys   Ala Glu Gln
    1010                1015                1020

Glu Asn  Gln Glu Leu Pro Asp  Glu Gly Thr Leu Glu  Glu Thr Leu
    1025                1030                1035

Thr Asn  Glu Thr Arg Asn Ala  Asp Asp Leu Glu Val  Ser Ser Asp
    1040                1045                1050

Ile Ile  Glu Ala Val Ala Ile  Ser Ser Asn Ser Phe  Ile Thr Thr
    1055                1060                1065

Gly Lys  Asp Ser Met Thr Val  Ser Glu Val Thr Ala  Ser Ile Ser
    1070                1075                1080

Ser Pro  Ser Glu Glu Asp Ala  Ser Glu Met Pro Glu  Phe Leu Asp
    1085                1090                1095

Lys Ser  Ile Val Glu Glu Glu  Asp Asp Asp Tyr  Val Glu Leu
    1100                1105                1110

Lys Val  Glu Gly Ser Pro Thr  Glu Glu Ala Asn Leu  Pro Thr Glu
    1115                1120                1125

Leu Gln  Asp Asn Ser Leu Ser  Pro Ala Ala Ser Glu  Ala Gly Glu
    1130                1135                1140

Lys Leu  Asp Met Phe Gly Asn  Asp Asp Lys Leu Ile  Phe Gln Glu
    1145                1150                1155

Gly Lys  Pro Val Thr Glu Lys  Gln Thr Asp Thr Glu  Thr Gln Asp
    1160                1165                1170

Ser Lys  Asp Ser Gly Ile Gln  Thr Met Thr Ala Ser  Gly Ser Ser
    1175                1180                1185

Ala Met  Ser Pro Glu Thr Thr  Val Ser Gln Ile Ala  Val Glu Ser
    1190                1195                1200

Asp Leu  Gly Gln Met Leu Glu  Gly Lys Lys Ala  Thr Asn Leu
    1205                1210                1215

Thr Arg  Glu Thr Lys Leu Ile  Asn Asp Cys His Gly  Ser Val Ser
    1220                1225                1230

Glu Ala  Ser Ser Glu Gln Lys  Ile Ala Lys Leu Asp  Val Ser Asn
    1235                1240                1245

Val Ala  Thr Asp Thr Glu Arg  Leu Glu Leu Lys Ala  Ser Pro Asn
    1250                1255                1260

Val Glu  Ala Pro Gln Pro His  Arg His Val Leu Glu  Ile Ser Arg
    1265                1270                1275
```

-continued

```
Gln His Glu Gln Pro Gly Gln Gly Ile Ala Pro Asp Ala Val Asn
1280            1285                1290

Gly Gln Arg Arg Asp Ser Arg Ser Thr Val Phe Arg Ile Pro Glu
1295            1300                1305

Phe Asn Trp Ser Gln Met His Gln Arg Leu Leu Thr Asp Leu Leu
1310            1315                1320

Phe Ser Ile Glu Thr Asp Ile Gln Met Trp Arg Ser His Ser Thr
1325            1330                1335

Lys Thr Val Met Asp Phe Val Asn Ser Ser Asp Asn Val Ile Phe
1340            1345                1350

Val His Asn Thr Ile His Leu Ile Ser Gln Val Met Asp Asn Met
1355            1360                1365

Val Met Ala Cys Gly Gly Ile Leu Pro Leu Leu Ser Ala Ala Thr
1370            1375                1380

Ser Ala Thr His Glu Leu Glu Asn Ile Glu Pro Thr Gln Gly Leu
1385            1390                1395

Ser Ile Glu Ala Ser Val Thr Phe Leu Gln Arg Leu Ile Ser Leu
1400            1405                1410

Val Asp Val Leu Ile Phe Ala Ser Ser Leu Gly Phe Thr Glu Ile
1415            1420                1425

Glu Ala Glu Lys Ser Met Ser Ser Gly Ile Leu Arg Gln Cys
1430            1435                1440

Leu Arg Leu Val Cys Ala Val Ala Val Arg Asn Cys Leu Glu Cys
1445            1450                1455

Gln Gln His Ser Gln Leu Lys Thr Arg Gly Asp Lys Ala Leu Lys
1460            1465                1470

Pro Met His Ser Leu Ile Pro Leu Gly Lys Ser Ala Ala Lys Ser
1475            1480                1485

Pro Val Asp Ile Val Thr Gly Gly Ile Ser Pro Val Arg Asp Leu
1490            1495                1500

Asp Arg Leu Leu Gln Asp Met Asp Ile Asn Arg Leu Arg Ala Val
1505            1510                1515

Val Phe Arg Asp Ile Glu Asp Ser Lys Gln Ala Gln Phe Leu Ala
1520            1525                1530

Leu Ala Val Val Tyr Phe Ile Ser Val Leu Met Val Ser Lys Tyr
1535            1540                1545

Arg Asp Ile Leu Glu Pro Gln Asn Glu Arg His Ser Gln Ser Cys
1550            1555                1560

Thr Glu Thr Gly Ser Glu Asn Glu Asn Val Ser Leu Ser Glu Ile
1565            1570                1575

Thr Pro Ala Ala Phe Ser Thr Leu Thr Thr Ala Ser Val Glu Glu
1580            1585                1590

Ser Glu Ser Thr Ser Ser Ala Arg Arg Arg Asp Ser Gly Ile Gly
1595            1600                1605

Glu Glu Thr Ala Thr Gly Leu Gly Ser His Val Glu Val Thr Pro
1610            1615                1620

His Thr Ala Pro Pro Gly Val Ser Ala Gly Pro Asp Ala Ile Ser
1625            1630                1635

Glu Val Leu Ser Thr Leu Leu Glu Val Asn Lys Ser Pro Glu
1640            1645                1650

Thr Lys Asn Asp Arg Gly Asn Asp Leu Asp Thr Lys Ala Thr Pro
1655            1660                1665
```

-continued

```
Ser Val Ser Val Lys Asn Val Asn Val Lys Asp Ile Leu Arg
    1670            1675            1680

Ser Leu Val Asn Ile Pro Ala Asp Gly Val Thr Val Asp Pro Ala
    1685            1690            1695

Leu Leu Pro Pro Ala Cys Leu Gly Ala Leu Gly Asp Leu Ser Val
    1700            1705            1710

Glu Gln Pro Val Gln Phe Arg Ser Phe Asp Arg Ser Val Ile Val
    1715            1720            1725

Ala Ala Lys Lys Ser Ala Val Ser Pro Ser Thr Phe Asn Thr Ser
    1730            1735            1740

Ile Pro Thr Asn Ala Val Ser Val Val Ser Ser Val Asp Ser Ala
    1745            1750            1755

Gln Ala Ser Asp Met Gly Gly Glu Ser Pro Gly Ser Arg Ser Ser
    1760            1765            1770

Asn Ala Lys Leu Pro Ser Val Pro Thr Val Asp Ser Val Ser Gln
    1775            1780            1785

Asp Pro Val Ser Asn Met Ser Ile Thr Glu Arg Leu Glu His Ala
    1790            1795            1800

Leu Glu Lys Ala Ala Pro Leu Leu Arg Glu Ile Phe Val Asp Phe
    1805            1810            1815

Ala Pro Phe Leu Ser Arg Thr Leu Leu Gly Ser His Gly Gln Glu
    1820            1825            1830

Leu Leu Ile Glu Gly Thr Ser Leu Val Cys Met Lys Ser Ser Ser
    1835            1840            1845

Ser Val Val Glu Leu Val Met Leu Leu Cys Ser Gln Glu Trp Gln
    1850            1855            1860

Asn Ser Ile Gln Lys Asn Ala Gly Leu Ala Phe Ile Glu Leu Val
    1865            1870            1875

Asn Glu Gly Arg Leu Leu Ser Gln Thr Met Lys Asp His Leu Val
    1880            1885            1890

Arg Val Ala Asn Glu Ala Glu Phe Ile Leu Ser Arg Gln Arg Ala
    1895            1900            1905

Glu Asp Ile His Arg His Ala Glu Phe Glu Ser Leu Cys Ala Gln
    1910            1915            1920

Tyr Ser Ala Asp Lys Arg Glu Asp Glu Lys Met Cys Asp His Leu
    1925            1930            1935

Ile Arg Ala Ala Lys Tyr Arg Asp His Val Thr Ala Thr Gln Leu
    1940            1945            1950

Ile Gln Lys Ile Ile Asn Ile Leu Thr Asp Lys His Gly Ala Trp
    1955            1960            1965

Gly Asn Ser Ala Val Ser Arg Pro Leu Glu Phe Trp Arg Leu Asp
    1970            1975            1980

Tyr Trp Glu Asp Asp Leu Arg Arg Arg Arg Phe Val Arg Asn
    1985            1990            1995

Pro Leu Gly Ser Thr His Pro Glu Ala Thr Leu Lys Thr Ala Val
    2000            2005            2010

Glu His Val Cys Ile Phe Lys Leu Arg Glu Asn Ser Lys Ala Thr
    2015            2020            2025

Asp Glu Asp Ile Leu Ala Lys Gly Lys Gln Ser Ile Arg Ser Gln
    2030            2035            2040

Ala Leu Gly Asn Gln Asn Ser Glu Asn Glu Ile Leu Leu Glu Gly
    2045            2050            2055
```

-continued

Asp Asp Asp Thr Leu Ser Ser Val Asp Glu Lys Asp Leu Glu Asn
2060             2065             2070

Leu Ala Gly Pro Val Ser Leu Ser Thr Pro Ala Gln Leu Val Ala
2075             2080             2085

Pro Ser Val Val Val Lys Gly Thr Leu Ser Val Thr Ser Ser Glu
2090             2095             2100

Leu Tyr Phe Glu Val Asp Glu Asp Pro Asn Phe Lys Lys Ile
2105             2110             2115

Asp Pro Lys Ile Leu Ala Tyr Thr Glu Gly Leu His Gly Lys Trp
2120             2125             2130

Leu Phe Thr Glu Ile Arg Ser Ile Phe Ser Arg Arg Tyr Leu Leu
2135             2140             2145

Gln Asn Thr Ala Leu Glu Ile Phe Met Ala Asn Arg Val Ala Val
2150             2155             2160

Met Phe Asn Phe Pro Asp Pro Ala Thr Val Lys Lys Val Val Asn
2165             2170             2175

Phe Leu Pro Arg Val Gly Val Gly Thr Ser Phe Gly Leu Pro Gln
2180             2185             2190

Thr Arg Arg Ile Ser Leu Ala Ser Pro Arg Gln Leu Phe Lys Ala
2195             2200             2205

Ser Asn Met Thr Gln Arg Trp Gln His Arg Glu Ile Ser Asn Phe
2210             2215             2220

Glu Tyr Leu Met Phe Leu Asn Thr Ile Ala Gly Arg Ser Tyr Asn
2225             2230             2235

Asp Leu Asn Gln Tyr Pro Val Phe Pro Trp Val Ile Thr Asn Tyr
2240             2245             2250

Glu Ser Glu Glu Leu Asp Leu Thr Leu Pro Thr Asn Phe Arg Asp
2255             2260             2265

Leu Ser Lys Pro Ile Gly Ala Leu Asn Pro Lys Arg Ala Ala Phe
2270             2275             2280

Phe Ala Glu Arg Tyr Glu Ser Trp Glu Asp Asp Gln Val Pro Lys
2285             2290             2295

Phe His Tyr Gly Thr His Tyr Ser Thr Ala Ser Phe Val Leu Ala
2300             2305             2310

Trp Leu Leu Arg Ile Glu Pro Phe Thr Thr Tyr Phe Leu Asn Leu
2315             2320             2325

Gln Gly Gly Lys Phe Asp His Ala Asp Arg Thr Phe Ser Ser Ile
2330             2335             2340

Ser Arg Ala Trp Arg Asn Ser Gln Arg Asp Thr Ser Asp Ile Lys
2345             2350             2355

Glu Leu Ile Pro Glu Phe Tyr Tyr Leu Pro Glu Met Phe Val Asn
2360             2365             2370

Phe Asn Asn Tyr Asn Leu Gly Val Met Asp Asp Gly Thr Val Val
2375             2380             2385

Ser Asp Val Glu Leu Pro Pro Trp Ala Lys Thr Ser Glu Glu Phe
2390             2395             2400

Val His Ile Asn Arg Leu Ala Leu Glu Ser Glu Phe Val Ser Cys
2405             2410             2415

Gln Leu His Gln Trp Ile Asp Leu Ile Phe Gly Tyr Lys Gln Gln
2420             2425             2430

Gly Pro Glu Ala Val Arg Ala Leu Asn Val Phe Tyr Tyr Leu Thr
2435             2440             2445

-continued

```
Tyr Glu Gly Ala Val Asn Leu Asn Ser Ile Thr Asp Pro Val Leu
2450                2455                2460

Arg Glu Ala Val Glu Ala Gln Ile Arg Ser Phe Gly Gln Thr Pro
2465                2470                2475

Ser Gln Leu Leu Ile Glu Pro His Pro Pro Arg Gly Ser Ala Met
2480                2485                2490

Gln Val Ser Pro Leu Met Phe Thr Asp Lys Ala Gln Gln Asp Val
2495                2500                2505

Ile Met Val Leu Lys Phe Pro Ser Asn Ser Pro Val Thr His Val
2510                2515                2520

Ala Ala Asn Thr Gln Pro Gly Leu Ala Thr Pro Ala Val Ile Thr
2525                2530                2535

Val Thr Ala Asn Arg Leu Phe Ala Val Asn Lys Trp His Asn Leu
2540                2545                2550

Pro Ala His Gln Gly Ala Val Gln Asp Gln Pro Tyr Gln Leu Pro
2555                2560                2565

Val Glu Ile Asp Pro Leu Ile Ala Ser Asn Thr Gly Met His Arg
2570                2575                2580

Arg Gln Ile Thr Asp Leu Leu Asp Gln Ser Ile Gln Val His Ser
2585                2590                2595

Gln Cys Phe Val Ile Thr Ser Asp Asn Arg Tyr Ile Leu Val Cys
2600                2605                2610

Gly Phe Trp Asp Lys Ser Phe Arg Val Tyr Ser Thr Asp Thr Gly
2615                2620                2625

Arg Leu Ile Gln Val Val Phe Gly His Trp Asp Val Val Thr Cys
2630                2635                2640

Leu Ala Arg Ser Glu Ser Tyr Ile Gly Gly Asn Cys Tyr Ile Leu
2645                2650                2655

Ser Gly Ser Arg Asp Ala Thr Leu Leu Leu Trp Tyr Trp Asn Gly
2660                2665                2670

Lys Cys Ser Gly Ile Gly Asp Asn Pro Gly Ser Glu Thr Ala Ala
2675                2680                2685

Pro Arg Ala Ile Leu Thr Gly His Asp Tyr Glu Val Thr Cys Ala
2690                2695                2700

Ala Val Cys Ala Glu Leu Gly Leu Val Leu Ser Gly Ser Gln Glu
2705                2710                2715

Gly Pro Cys Leu Ile His Ser Met Asn Gly Asp Leu Leu Arg Thr
2720                2725                2730

Leu Glu Gly Pro Glu Asn Cys Leu Lys Pro Lys Leu Ile Gln Ala
2735                2740                2745

Ser Arg Glu Gly His Cys Val Ile Phe Tyr Glu Asn Gly Leu Phe
2750                2755                2760

Cys Thr Phe Ser Val Asn Gly Lys Leu Gln Ala Thr Met Glu Thr
2765                2770                2775

Asp Asp Asn Ile Arg Ala Ile Gln Leu Ser Arg Asp Gly Gln Tyr
2780                2785                2790

Leu Leu Thr Gly Gly Asp Arg Gly Val Val Val Arg Gln Val
2795                2800                2805

Ser Asp Leu Lys Gln Leu Phe Ala Tyr Pro Gly Cys Asp Ala Gly
2810                2815                2820

Ile Arg Ala Met Ala Leu Ser Tyr Asp Gln Arg Cys Ile Ile Ser
2825                2830                2835
```

```
Gly Met Ala Ser Gly Ser Ile Val Leu Phe Tyr Asn Asp Phe Asn
    2840                2845                2850

Arg Trp His His Glu Tyr Gln Thr Arg Tyr
    2855                2860

<210> SEQ ID NO 9
<211> LENGTH: 69
<212> TYPE: PRT
<213> ORGANISM: Mus musculus
<220> FEATURE:
<221> NAME/KEY: BINDING
<222> LOCATION: (1)..(21)
<223> OTHER INFORMATION: Putative Protein Kinase A RII binding site
<220> FEATURE:
<221> NAME/KEY: BINDING
<222> LOCATION: (50)..(69)
<223> OTHER INFORMATION: Putative Protein Kinase A RII binding site

<400> SEQUENCE: 9

Phe Val His Asn Thr Ile His Leu Ile Ser Gln Val Met Asp Asn Met
1               5                   10                  15

Val Met Ala Cys Gly Gly Ile Leu Pro Leu Leu Ser Ala Ala Thr Ser
            20                  25                  30

Ala Thr His Glu Leu Glu Asn Ile Glu Pro Thr Gln Gly Leu Ser Ile
        35                  40                  45

Glu Ala Ser Val Thr Phe Leu Gln Arg Leu Ile Ser Leu Val Asp Val
    50                  55                  60

Leu Ile Phe Ala Ser
65

<210> SEQ ID NO 10
<211> LENGTH: 69
<212> TYPE: PRT
<213> ORGANISM: Homo sapiens
<220> FEATURE:
<221> NAME/KEY: BINDING
<222> LOCATION: (1)..(21)
<223> OTHER INFORMATION: Putative Protein Kinase A RII binding site
<220> FEATURE:
<221> NAME/KEY: BINDING
<222> LOCATION: (50)..(69)
<223> OTHER INFORMATION: Putative Protein Kinase A RII binding site

<400> SEQUENCE: 10

Phe Val His Asn Thr Ile His Leu Ile Ser Gln Val Met Asp Asn Met
1               5                   10                  15

Val Met Ala Cys Gly Gly Ile Leu Pro Leu Leu Ser Ala Ala Thr Ser
            20                  25                  30

Ala Thr His Glu Leu Glu Asn Ile Glu Pro Thr Gln Gly Leu Ser Ile
        35                  40                  45

Glu Ala Ser Val Thr Phe Leu Gln Arg Leu Ile Ser Leu Val Asp Val
    50                  55                  60

Leu Ile Phe Ala Ser
65

<210> SEQ ID NO 11
<211> LENGTH: 76
<212> TYPE: PRT
<213> ORGANISM: Drosophila melanogaster
<220> FEATURE:
<221> NAME/KEY: BINDING
<222> LOCATION: (1)..(21)
<223> OTHER INFORMATION: Putative Protein Kinase A RII binding site
```

```
<220> FEATURE:
<221> NAME/KEY: BINDING
<222> LOCATION: (57)..(76)
<223> OTHER INFORMATION: Putative Protein Kinase A RII binding site

<400> SEQUENCE: 11

Val Ala Leu Ala Val Arg Asp Ile Val Glu Gln Leu Ile Asp Lys Val
1               5                   10                  15

Ile Asp Ala Thr Glu Ala Glu Ser Ala Ser Gly Thr Lys Thr Glu Thr
            20                  25                  30

Asn Asn Asn Glu Ile Pro Lys Lys Gly Lys Gln Thr Ser Glu Glu Pro
        35                  40                  45

Glu Asp Val Glu Thr Ala Glu Thr Leu Ala Ala Ala Ala Lys Glu Ile
    50                  55                  60

Val Gln Glu Val Val Glu Ala Ala Leu Val Val Val
65                  70                  75

<210> SEQ ID NO 12
<211> LENGTH: 69
<212> TYPE: PRT
<213> ORGANISM: Drosophila melanogaster
<220> FEATURE:
<221> NAME/KEY: BINDING
<222> LOCATION: (1)..(21)
<223> OTHER INFORMATION: Putative Protein Kinase A RII binding site
<220> FEATURE:
<221> NAME/KEY: BINDING
<222> LOCATION: (50)..(69)
<223> OTHER INFORMATION: Putative Protein Kinase A RII binding site

<400> SEQUENCE: 12

Phe Val Val Asn Thr Val His Leu Ile Ser Gln Leu Ala Asp Asn Leu
1               5                   10                  15

Ile Ile Ala Cys Gly Gly Leu Leu Pro Leu Leu Ala Ser Ala Thr Ser
            20                  25                  30

Pro Asn Ser Glu Leu Asp Val Leu Glu Pro Thr Gln Gly Met Pro Leu
        35                  40                  45

Glu Val Ala Val Ser Phe Leu Gln Arg Leu Val Asn Met Ala Asp Val
    50                  55                  60

Leu Ile Phe Ala Thr
65

<210> SEQ ID NO 13
<211> LENGTH: 70
<212> TYPE: PRT
<213> ORGANISM: Caenorhabditis elegans
<220> FEATURE:
<221> NAME/KEY: BINDING
<222> LOCATION: (1)..(21)
<223> OTHER INFORMATION: Putative Protein Kinase A RII binding site
<220> FEATURE:
<221> NAME/KEY: BINDING
<222> LOCATION: (51)..(70)
<223> OTHER INFORMATION: Putative Protein Kinase A RII binding site

<400> SEQUENCE: 13

Phe Val Gly Asn Val Val His Val Ser Gln Leu Ser Asp Ser Leu
1               5                   10                  15

Ile Met Ala Cys Gly Gly Leu Leu Pro Leu Leu Ala Ser Ala Thr Ala
            20                  25                  30

Pro Asn Asn Asp Met Glu Ile Val Asp Pro Cys Gln Gln Gln Leu Pro
        35                  40                  45
```

-continued

```
Ile Ser Val Ser Ala Gly Phe Leu Met Arg Phe Ala Arg Leu Val Asp
 50                  55                  60

Thr Phe Val Leu Ala Ser
 65                  70

<210> SEQ ID NO 14
<211> LENGTH: 972
<212> TYPE: PRT
<213> ORGANISM: Mus musculus
<220> FEATURE:
<221> NAME/KEY: REPEAT
<222> LOCATION: (144)..(187)
<223> OTHER INFORMATION: WDL (WD-like) repeat
<220> FEATURE:
<221> NAME/KEY: REPEAT
<222> LOCATION: (188)..(237)
<223> OTHER INFORMATION: WDL (WD-like) repeat
<220> FEATURE:
<221> NAME/KEY: REPEAT
<222> LOCATION: (238)..(278)
<223> OTHER INFORMATION: WDL (WD-like) repeat
<220> FEATURE:
<221> NAME/KEY: DOMAIN
<222> LOCATION: (308)..(599)
<223> OTHER INFORMATION: BEACH domain
<220> FEATURE:
<221> NAME/KEY: SITE
<222> LOCATION: (345)..(352)
<223> OTHER INFORMATION: Tyrosine kinase recognition site
<220> FEATURE:
<221> NAME/KEY: BINDING
<222> LOCATION: (353)..(356)
<223> OTHER INFORMATION: SH3 binding site
<220> FEATURE:
<221> NAME/KEY: BINDING
<222> LOCATION: (411)..(414)
<223> OTHER INFORMATION: SH2 binding site
<220> FEATURE:
<221> NAME/KEY: REPEAT
<222> LOCATION: (702)..(744)
<223> OTHER INFORMATION: WD repeat
<220> FEATURE:
<221> NAME/KEY: REPEAT
<222> LOCATION: (745)..(803)
<223> OTHER INFORMATION: WD repeat
<220> FEATURE:
<221> NAME/KEY: REPEAT
<222> LOCATION: (804)..(886)
<223> OTHER INFORMATION: WD repeat
<220> FEATURE:
<221> NAME/KEY: REPEAT
<222> LOCATION: (887)..(928)
<223> OTHER INFORMATION: WD repeat
<220> FEATURE:
<221> NAME/KEY: REPEAT
<222> LOCATION: (929)..(972)
<223> OTHER INFORMATION: WD repeat

<400> SEQUENCE: 14

Gly Arg Leu Leu Ser Gln Thr Met Lys Asp His Leu Val Arg Val Ala
 1               5                  10                  15

Asn Glu Ala Glu Phe Ile Leu Ser Arg Gln Arg Ala Glu Asp Ile His
                20                  25                  30

Arg His Ala Glu Phe Glu Ser Leu Cys Ala Gln Tyr Ser Ala Asp Lys
             35                  40                  45

Arg Glu Glu Glu Lys Met Cys Asp His Leu Ile Arg Ala Ala Lys Tyr
         50                  55                  60

Arg Asp His Val Thr Ala Thr Gln Leu Ile Gln Lys Ile Ile Asn Leu
 65                  70                  75                  80

Leu Thr Asp Lys His Gly Ala Trp Gly Ser Ser Ala Val Ser Arg Pro
                 85                  90                  95
```

-continued

```
Arg Glu Phe Trp Arg Leu Asp Tyr Trp Glu Asp Asp Leu Arg Arg Arg
                100                 105                 110
Arg Arg Phe Val Arg Asn Pro Leu Gly Ser Thr His Pro Glu Ala Thr
        115                 120                 125
Leu Lys Thr Ala Val Glu His Ala Ala Asp Glu Asp Ile Leu Ala Lys
    130                 135                 140
Gly Lys Gln Ser Ile Lys Ser Gln Ala Leu Gly Asn Gln Asn Ser Glu
145                 150                 155                 160
Asn Glu Ala Leu Leu Glu Gly Asp Asp Thr Leu Ser Ser Val Asp
                165                 170                 175
Glu Lys Asp Leu Glu Asn Leu Ala Gly Pro Val Ser Leu Ser Thr Pro
            180                 185                 190
Ala Gln Leu Val Ala Pro Ser Val Val Lys Gly Thr Leu Ser Val
        195                 200                 205
Thr Ser Ser Glu Leu Tyr Phe Glu Val Asp Glu Glu Asp Pro Asn Phe
    210                 215                 220
Lys Lys Ile Asp Pro Lys Ile Leu Ala Tyr Thr Glu Gly Leu His Gly
225                 230                 235                 240
Lys Trp Leu Phe Thr Glu Ile Arg Ser Ile Phe Ser Arg Arg Tyr Leu
                245                 250                 255
Leu Gln Asn Thr Ala Leu Glu Ile Phe Met Ala Asn Arg Val Ala Val
            260                 265                 270
Met Phe Asn Phe Pro Asp Pro Ala Thr Val Lys Lys Val Asn Tyr
        275                 280                 285
Leu Pro Arg Val Gly Val Gly Thr Ser Phe Gly Leu Pro Gln Thr Arg
    290                 295                 300
Arg Ile Ser Leu Ala Thr Pro Arg Gln Leu Phe Lys Ala Ser Asn Met
305                 310                 315                 320
Thr Gln Arg Trp Gln His Arg Glu Ile Ser Asn Phe Glu Tyr Leu Met
                325                 330                 335
Phe Leu Asn Thr Ile Ala Gly Arg Ser Tyr Asn Asp Leu Asn Gln Tyr
            340                 345                 350
Pro Val Phe Pro Trp Val Ile Thr Asn Tyr Glu Ser Glu Glu Leu Asp
        355                 360                 365
Leu Thr Leu Pro Ser Asn Phe Arg Asp Leu Ser Lys Pro Ile Gly Ala
    370                 375                 380
Leu Asn Pro Lys Arg Ala Ala Phe Phe Ala Glu Arg Phe Glu Ser Trp
385                 390                 395                 400
Glu Asp Asp Gln Val Pro Lys Phe His Tyr Gly Thr His Tyr Ser Thr
                405                 410                 415
Ala Ser Phe Val Leu Ala Trp Leu Leu Arg Ile Glu Pro Phe Thr Thr
            420                 425                 430
Tyr Phe Leu Asn Leu Gln Gly Gly Lys Phe Asp His Ala Asp Arg Thr
        435                 440                 445
Phe Ser Ser Val Ser Arg Ala Trp Arg Asn Ser Gln Arg Asp Thr Ser
    450                 455                 460
Asp Ile Lys Glu Leu Ile Pro Glu Phe Tyr Tyr Leu Pro Glu Met Phe
465                 470                 475                 480
Val Asn Phe Asn Asn Tyr Asn Leu Gly Val Met Asp Asp Gly Thr Val
                485                 490                 495
Val Ser Asp Val Glu Leu Pro Pro Trp Ala Lys Thr Ser Glu Glu Phe
            500                 505                 510
```

```
Val Arg Ile Asn Arg Leu Ala Leu Glu Ser Glu Phe Val Ser Cys Gln
        515                 520                 525

Leu His Gln Trp Ile Asp Leu Ile Phe Gly Tyr Lys Gln Gln Gly Pro
    530                 535                 540

Glu Ala Val Arg Ala Leu Asn Val Phe Tyr Tyr Leu Thr Tyr Glu Gly
545                 550                 555                 560

Ala Val Asn Leu Asn Ser Ile Thr Asp Pro Val Leu Arg Glu Ala Val
                565                 570                 575

Glu Ala Gln Ile Arg Ser Phe Gly Gln Thr Pro Ser Gln Leu Leu Ile
            580                 585                 590

Glu Pro His Pro Pro Arg Gly Ser Ala Met Gln Ala Ser Pro Leu Met
            595                 600                 605

Phe Thr Asp Gln Ala Gln Gln Asp Val Ile Met Val Leu Lys Phe Pro
        610                 615                 620

Ser Asn Ser Pro Val Thr His Val Ala Ala Asn Thr Gln Pro Gly Leu
625                 630                 635                 640

Ala Met Pro Ala Val Ile Thr Val Thr Ala Asn Arg Leu Phe Ala Val
                645                 650                 655

Asn Lys Trp His Asn Leu Pro Ala His Gln Gly Ala Val Gln Asp Gln
            660                 665                 670

Pro Tyr Gln Leu Pro Val Glu Ile Asp Pro Leu Ile Ala Cys Gly Thr
        675                 680                 685

Gly Thr His Arg Arg Gln Val Thr Asp Leu Leu Asp Gln Ser Ile Gln
    690                 695                 700

Val His Ser Gln Cys Phe Val Ile Thr Ser Asp Asn Arg Tyr Ile Leu
705                 710                 715                 720

Val Cys Gly Phe Trp Asp Lys Ser Phe Arg Val Tyr Ser Thr Asp Thr
                725                 730                 735

Gly Lys Leu Ile Gln Val Val Phe Gly His Trp Asp Val Val Thr Cys
            740                 745                 750

Leu Ala Arg Ser Glu Ser Tyr Ile Gly Gly Asn Cys Tyr Ile Leu Ser
        755                 760                 765

Gly Ser Arg Asp Ala Thr Leu Leu Leu Trp Tyr Trp Asn Gly Lys Ser
    770                 775                 780

Ser Gly Ile Gly Asp Asn Pro Gly Gly Glu Thr Ala Thr Pro Arg Ala
785                 790                 795                 800

Ile Leu Thr Gly His Asp Tyr Glu Ile Thr Cys Ala Ala Val Cys Ala
                805                 810                 815

Glu Leu Gly Leu Val Leu Ser Gly Ser Gln Glu Gly Pro Cys Leu Ile
            820                 825                 830

His Ser Met Asn Gly Asp Leu Leu Arg Thr Leu Glu Gly Pro Glu Asn
        835                 840                 845

Cys Leu Lys Pro Lys Leu Ile Gln Ala Ser Arg Glu Gly His Cys Val
    850                 855                 860

Ile Phe Tyr Glu Asn Gly Cys Phe Cys Thr Phe Ser Val Asn Gly Lys
865                 870                 875                 880

Leu Gln Ala Thr Val Glu Thr Asp Asp His Ile Arg Ala Ile Gln Leu
                885                 890                 895

Ser Arg Asp Gly Gln Tyr Leu Leu Thr Gly Gly Asp Asn Gly Val Val
            900                 905                 910

Ile Val Arg Gln Val Ser Asp Leu Lys Gln Leu Phe Ala Tyr Pro Gly
        915                 920                 925
```

-continued

```
Cys Asp Ala Gly Ile Arg Ala Met Ala Leu Ser Phe Asp Gln Arg Cys
            930                 935                 940

Ile Ile Ser Gly Met Ala Ser Gly Ser Ile Val Leu Phe Tyr Asn Asp
945                 950                 955                 960

Phe Asn Arg Trp His His Glu Tyr Gln Thr Arg Tyr
                965                 970

<210> SEQ ID NO 15
<211> LENGTH: 983
<212> TYPE: PRT
<213> ORGANISM: Homo sapiens
<220> FEATURE:
<221> NAME/KEY: REPEAT
<222> LOCATION: (155)..(198)
<223> OTHER INFORMATION: WDL (WD-like) repeat
<220> FEATURE:
<221> NAME/KEY: REPEAT
<222> LOCATION: (199)..(248)
<223> OTHER INFORMATION: WDL (WD-like) repeat
<220> FEATURE:
<221> NAME/KEY: REPEAT
<222> LOCATION: (249)..(289)
<223> OTHER INFORMATION: WDL (WD-like) repeat
<220> FEATURE:
<221> NAME/KEY: DOMAIN
<222> LOCATION: (319)..(610)
<223> OTHER INFORMATION: BEACH domain
<220> FEATURE:
<221> NAME/KEY: SITE
<222> LOCATION: (356)..(363)
<223> OTHER INFORMATION: Tyrosine kinase recognition site
<220> FEATURE:
<221> NAME/KEY: BINDING
<222> LOCATION: (364)..(367)
<223> OTHER INFORMATION: SH3 binding site
<220> FEATURE:
<221> NAME/KEY: BINDING
<222> LOCATION: (422)..(425)
<223> OTHER INFORMATION: SH2 binding site
<220> FEATURE:
<221> NAME/KEY: REPEAT
<222> LOCATION: (713)..(755)
<223> OTHER INFORMATION: WD repeat
<220> FEATURE:
<221> NAME/KEY: REPEAT
<222> LOCATION: (756)..(814)
<223> OTHER INFORMATION: WD repeat
<220> FEATURE:
<221> NAME/KEY: REPEAT
<222> LOCATION: (815)..(897)
<223> OTHER INFORMATION: WD repeat
<220> FEATURE:
<221> NAME/KEY: REPEAT
<222> LOCATION: (898)..(939)
<223> OTHER INFORMATION: WD repeat
<220> FEATURE:
<221> NAME/KEY: REPEAT
<222> LOCATION: (940)..(983)
<223> OTHER INFORMATION: WD repeat

<400> SEQUENCE: 15

Gly Arg Leu Leu Ser Gln Thr Met Lys Asp His Leu Val Arg Val Ala
1               5                   10                  15

Asn Glu Ala Glu Phe Ile Leu Ser Arg Gln Arg Ala Glu Asp Ile His
            20                  25                  30

Arg His Ala Glu Phe Glu Ser Leu Cys Ala Gln Tyr Ser Ala Asp Lys
        35                  40                  45

Arg Glu Asp Glu Lys Met Cys Asp His Leu Ile Arg Ala Ala Lys Tyr
    50                  55                  60

Arg Asp His Val Thr Ala Thr Gln Leu Ile Gln Lys Ile Ile Asn Ile
65                  70                  75                  80
```

-continued

```
Leu Thr Asp Lys His Gly Ala Trp Gly Asn Ser Ala Val Ser Arg Pro
                 85                  90                  95

Leu Glu Phe Trp Arg Leu Asp Tyr Trp Glu Asp Leu Arg Arg Arg
                100                 105                 110

Arg Arg Phe Val Arg Asn Pro Leu Gly Ser Thr His Pro Glu Ala Thr
            115                 120                 125

Leu Lys Thr Ala Val Glu His Val Cys Ile Phe Lys Leu Arg Glu Asn
        130                 135                 140

Ser Lys Ala Thr Asp Glu Asp Ile Leu Ala Lys Gly Lys Gln Ser Ile
145                 150                 155                 160

Arg Ser Gln Ala Leu Gly Asn Gln Asn Ser Glu Asn Glu Ile Leu Leu
                165                 170                 175

Glu Gly Asp Asp Asp Thr Leu Ser Ser Val Asp Glu Lys Asp Leu Glu
            180                 185                 190

Asn Leu Ala Gly Pro Val Ser Leu Ser Thr Pro Ala Gln Leu Val Ala
        195                 200                 205

Pro Ser Val Val Lys Gly Thr Leu Ser Val Thr Ser Ser Glu Leu
210                 215                 220

Tyr Phe Glu Val Asp Glu Asp Pro Asn Phe Lys Lys Ile Asp Pro
225                 230                 235                 240

Lys Ile Leu Ala Tyr Thr Glu Gly Leu His Gly Lys Trp Leu Phe Thr
                245                 250                 255

Glu Ile Arg Ser Ile Phe Ser Arg Arg Tyr Leu Leu Gln Asn Thr Ala
            260                 265                 270

Leu Glu Ile Phe Met Ala Asn Arg Val Ala Val Met Phe Asn Phe Pro
        275                 280                 285

Asp Pro Ala Thr Val Lys Lys Val Val Asn Phe Leu Pro Arg Val Gly
290                 295                 300

Val Gly Thr Ser Phe Gly Leu Pro Gln Thr Arg Arg Ile Ser Leu Ala
305                 310                 315                 320

Ser Pro Arg Gln Leu Phe Lys Ala Ser Asn Met Thr Gln Arg Trp Gln
                325                 330                 335

His Arg Glu Ile Ser Asn Phe Glu Tyr Leu Met Phe Leu Asn Thr Ile
            340                 345                 350

Ala Gly Arg Ser Tyr Asn Asp Leu Asn Gln Tyr Pro Val Phe Pro Trp
        355                 360                 365

Val Ile Thr Asn Tyr Glu Ser Glu Glu Leu Asp Leu Thr Leu Pro Thr
370                 375                 380

Asn Phe Arg Asp Leu Ser Lys Pro Ile Gly Ala Leu Asn Pro Lys Arg
385                 390                 395                 400

Ala Ala Phe Phe Ala Glu Arg Tyr Glu Ser Trp Glu Asp Asp Gln Val
                405                 410                 415

Pro Lys Phe His Tyr Gly Thr His Tyr Ser Thr Ala Ser Phe Val Leu
            420                 425                 430

Ala Trp Leu Leu Arg Ile Glu Pro Phe Thr Thr Tyr Phe Leu Asn Leu
        435                 440                 445

Gln Gly Gly Lys Phe Asp His Ala Asp Arg Thr Phe Ser Ser Ile Ser
450                 455                 460

Arg Ala Trp Arg Asn Ser Gln Arg Asp Thr Ser Asp Ile Lys Glu Leu
465                 470                 475                 480

Ile Pro Glu Phe Tyr Tyr Leu Pro Glu Met Phe Val Asn Phe Asn Asn
                485                 490                 495
```

```
Tyr Asn Leu Gly Val Met Asp Asp Gly Thr Val Val Ser Asp Val Glu
            500                 505                 510

Leu Pro Pro Trp Ala Lys Thr Ser Glu Glu Phe Val His Ile Asn Arg
        515                 520                 525

Leu Ala Leu Glu Ser Glu Phe Val Ser Cys Gln Leu His Gln Trp Ile
        530                 535                 540

Asp Leu Ile Phe Gly Tyr Lys Gln Gln Gly Pro Glu Ala Val Arg Ala
545                 550                 555                 560

Leu Asn Val Phe Tyr Tyr Leu Thr Tyr Glu Gly Ala Val Asn Leu Asn
                565                 570                 575

Ser Ile Thr Asp Pro Val Leu Arg Glu Ala Val Glu Ala Gln Ile Arg
            580                 585                 590

Ser Phe Gly Gln Thr Pro Ser Gln Leu Leu Ile Glu Pro His Pro Pro
        595                 600                 605

Arg Gly Ser Ala Met Gln Val Ser Pro Leu Met Phe Thr Asp Lys Ala
        610                 615                 620

Gln Gln Asp Val Ile Met Val Leu Lys Phe Pro Ser Asn Ser Pro Val
625                 630                 635                 640

Thr His Val Ala Ala Asn Thr Gln Pro Gly Leu Ala Thr Pro Ala Val
                645                 650                 655

Ile Thr Val Thr Ala Asn Arg Leu Phe Ala Val Asn Lys Trp His Asn
            660                 665                 670

Leu Pro Ala His Gln Gly Ala Val Gln Asp Gln Pro Tyr Gln Leu Pro
        675                 680                 685

Val Glu Ile Asp Pro Leu Ile Ala Ser Asn Thr Gly Met His Arg Arg
        690                 695                 700

Gln Ile Thr Asp Leu Leu Asp Gln Ser Ile Gln Val His Ser Gln Cys
705                 710                 715                 720

Phe Val Ile Thr Ser Asp Asn Arg Tyr Ile Leu Val Cys Gly Phe Trp
                725                 730                 735

Asp Lys Ser Phe Arg Val Tyr Ser Thr Asp Thr Gly Arg Leu Ile Gln
            740                 745                 750

Val Val Phe Gly His Trp Asp Val Thr Cys Leu Ala Arg Ser Glu
        755                 760                 765

Ser Tyr Ile Gly Gly Asn Cys Tyr Ile Leu Ser Gly Ser Arg Asp Ala
        770                 775                 780

Thr Leu Leu Leu Trp Tyr Trp Asn Gly Lys Cys Ser Gly Ile Gly Asp
785                 790                 795                 800

Asn Pro Gly Ser Glu Thr Ala Ala Pro Arg Ala Ile Phe Thr Gly His
                805                 810                 815

Asp Tyr Glu Val Thr Cys Ala Ala Val Cys Ala Glu Leu Gly Leu Val
            820                 825                 830

Leu Ser Gly Ser Gln Glu Gly Pro Cys Leu Ile His Ser Met Asn Gly
        835                 840                 845

Asp Leu Leu Arg Thr Leu Glu Gly Pro Glu Asn Cys Leu Lys Pro Lys
        850                 855                 860

Leu Ile Gln Ala Ser Arg Glu Gly His Cys Val Ile Phe Tyr Glu Asn
865                 870                 875                 880

Gly Leu Phe Cys Thr Phe Ser Val Asn Gly Lys Leu Gln Ala Thr Met
                885                 890                 895

Glu Thr Asp Asp Asn Ile Arg Ala Ile Gln Leu Ser Arg Asp Gly Gln
            900                 905                 910
```

```
Tyr Leu Leu Thr Gly Gly Asp Arg Gly Val Val Val Arg Gln Val
        915                 920                 925

Ser Asp Leu Lys Gln Leu Phe Ala Tyr Pro Gly Cys Asp Ala Gly Ile
    930                 935                 940

Arg Ala Met Ala Leu Ser Tyr Asp Gln Arg Cys Ile Ile Ser Gly Met
945                 950                 955                 960

Ala Ser Gly Ser Ile Val Leu Phe Tyr Asn Asp Phe Asn Arg Trp His
            965                 970                 975

His Glu Tyr Gln Thr Arg Tyr
            980

<210> SEQ ID NO 16
<211> LENGTH: 994
<212> TYPE: PRT
<213> ORGANISM: Drosophila melanogaster
<220> FEATURE:
<221> NAME/KEY: DOMAIN
<222> LOCATION: (320)..(611)
<223> OTHER INFORMATION: BEACH domain
<220> FEATURE:
<221> NAME/KEY: SITE
<222> LOCATION: (357)..(364)
<223> OTHER INFORMATION: Tyrosine kinase recognition site
<220> FEATURE:
<221> NAME/KEY: BINDING
<222> LOCATION: (365)..(368)
<223> OTHER INFORMATION: SH3 binding site
<220> FEATURE:
<221> NAME/KEY: BINDING
<222> LOCATION: (423)..(426)
<223> OTHER INFORMATION: SH2 binding site

<400> SEQUENCE: 16

Gly Arg Leu Leu Ser His Ala Met Lys Asp His Ile Val Arg Val Ala
1               5                   10                  15

Asn Glu Ala Glu Phe Ile Leu Asn Arg Met Arg Ala Asp Asp Val Leu
            20                  25                  30

Lys His Ala Asp Phe Glu Ser Gln Cys Ala Gln Thr Leu Leu Glu Arg
        35                  40                  45

Arg Glu Glu Glu Arg Met Cys Asp His Leu Ile Thr Ala Ala Arg Arg
    50                  55                  60

Arg Asp Asn Val Ile Ala Ser Arg Leu Leu Glu Lys Val Arg Asn Ile
65                  70                  75                  80

Met Cys Asn Arg His Gly Ala Trp Gly Asp Ser Ser Thr Ser Ser
            85                  90                  95

Gly Gly Ala Ile Val Gly Ala Val Gln Lys Ser Pro Tyr Trp Lys Leu
            100                 105                 110

Asp Ala Trp Glu Asp Asp Ala Arg Arg Lys Arg Met Val Gln Asn
        115                 120                 125

Pro Arg Gly Ser Ser His Pro Gln Ala Thr Leu Lys Ala Ala Leu Glu
    130                 135                 140

Asn Gly Gly Pro Glu Asp Ala Ile Leu Gln Thr Arg Asp Glu Phe His
145                 150                 155                 160

Thr Gln Ile Ala Val Ser Arg Thr His Pro Ser Gly Gln His Asn Gly
                165                 170                 175

Glu Leu Leu Asp Asp Ala Glu Leu Leu Ile Glu Asp Arg Glu Leu Asp
            180                 185                 190

Leu Asp Leu Thr Gly Pro Val Asn Ile Ser Thr Lys Ala Arg Leu Ile
        195                 200                 205
```

```
Ala Pro Gly Leu Val Ala Pro Gly Thr Val Ser Ile Thr Ser Thr Glu
210                 215                 220

Met Phe Phe Glu Val Asp Glu Glu His Pro Glu Phe Gln Lys Ile Asp
225                 230                 235                 240

Gly Glu Val Leu Lys Tyr Cys Asp His Leu His Gly Lys Trp Tyr Phe
                245                 250                 255

Ser Glu Val Arg Ala Ile Phe Ser Arg Arg Tyr Leu Leu Gln Asn Val
                260                 265                 270

Ala Leu Glu Ile Phe Leu Ala Ser Arg Thr Ser Ile Leu Phe Ala Phe
            275                 280                 285

Pro Asp Gln His Thr Val Lys Lys Val Ile Lys Ala Leu Pro Arg Val
        290                 295                 300

Gly Val Gly Ile Lys Tyr Gly Ile Pro Gln Thr Arg Arg Ala Ser Met
305                 310                 315                 320

Met Ser Pro Arg Gln Leu Met Arg Asn Ser Asn Met Thr Gln Lys Trp
                325                 330                 335

Gln Arg Arg Glu Ile Ser Asn Phe Glu Tyr Leu Met Phe Leu Asn Thr
                340                 345                 350

Ile Ala Gly Arg Thr Tyr Asn Asp Leu Asn Gln Tyr Pro Ile Phe Pro
            355                 360                 365

Trp Val Leu Thr Asn Tyr Glu Ser Lys Asp Leu Asp Leu Ser Leu Pro
        370                 375                 380

Ser Asn Tyr Arg Asp Leu Ser Lys Pro Ile Gly Ala Leu Asn Pro Ser
385                 390                 395                 400

Arg Arg Ala Tyr Phe Glu Glu Arg Tyr Glu Ser Trp Asp Ser Asp Thr
                405                 410                 415

Ile Pro Pro Phe His Tyr Gly Thr His Tyr Ser Thr Ala Ala Phe Thr
                420                 425                 430

Leu Asn Trp Leu Val Arg Val Glu Pro Phe Thr Thr Met Phe Leu Ala
            435                 440                 445

Leu Gln Gly Gly Lys Phe Asp Tyr Pro Asp Arg Leu Phe Ser Ser Val
        450                 455                 460

Ser Leu Ser Trp Lys Asn Cys Gln Arg Asp Thr Ser Asp Val Lys Glu
465                 470                 475                 480

Leu Ile Pro Glu Trp Tyr Phe Leu Pro Glu Met Phe Tyr Asn Ser Ser
                485                 490                 495

Gly Tyr Arg Leu Gly His Arg Glu Asp Gly Ala Leu Val Asp Asp Ile
            500                 505                 510

Glu Leu Pro Pro Trp Ala Lys Ser Pro Glu Glu Phe Val Arg Ile Asn
        515                 520                 525

Arg Met Ala Leu Glu Ser Glu Phe Val Ser Cys Gln Leu His Gln Trp
530                 535                 540

Ile Asp Leu Ile Phe Gly Tyr Lys Gln Arg Gly Pro Glu Ala Ile Arg
545                 550                 555                 560

Ala Thr Asn Val Phe Tyr Tyr Leu Thr Tyr Glu Gly Ser Val Asp Leu
                565                 570                 575

Asp Gly Val Leu Asp Pro Val Met Arg Glu Ala Val Glu Asn Gln Ile
            580                 585                 590

Arg Asn Phe Gly Gln Thr Pro Ser Gln Leu Leu Met Glu Pro His Pro
        595                 600                 605

Pro Arg Ser Ser Ala Met His Leu Ser Pro Met Met Phe Ser Ala Met
610                 615                 620
```

```
Pro Glu Asp Leu Cys Gln Met Leu Lys Phe Tyr Gln Asn Ser Pro Val
625                 630                 635                 640

Ile His Ile Ser Ala Asn Thr Tyr Pro Gln Leu Ser Leu Pro Ser Val
            645                 650                 655

Val Thr Val Thr Ala Gly His Gln Phe Ala Val Asn Arg Trp Asn Cys
        660                 665                 670

Asn Tyr Thr Ala Ser Val Gln Ser Pro Ser Tyr Ala Glu Ser Pro Gln
    675                 680                 685

Ser Pro Gly Ser Asn Gln Pro Leu Thr Ile Asp Pro Val Leu Ala Val
690                 695                 700

His Gly Thr Asn Asn Asn Ser Asn Ala Ala Ser Arg Arg His Leu Gly
705                 710                 715                 720

Asp Asn Phe Ser Gln Met Leu Lys Ile Arg Ser Asn Cys Phe Val Thr
            725                 730                 735

Thr Val Asp Ser Arg Phe Leu Ile Ala Cys Gly Phe Trp Asp Asn Ser
        740                 745                 750

Phe Arg Val Phe Ala Thr Glu Thr Ala Lys Ile Val Gln Ile Val Phe
    755                 760                 765

Gly His Phe Gly Val Val Thr Cys Met Ala Arg Ser Glu Cys Asn Ile
770                 775                 780

Thr Ser Asp Cys Tyr Ile Ala Ser Gly Ser Ala Asp Cys Thr Val Leu
785                 790                 795                 800

Leu Trp His Trp Asn Ala Arg Thr Gln Ser Ile Val Gly Glu Gly Asp
            805                 810                 815

Val Pro Thr Pro Arg Ala Thr Leu Thr Gly His Glu Gln Ala Val Thr
        820                 825                 830

Ser Val Val Ile Ser Ala Glu Leu Gly Leu Val Val Ser Gly Ser Ser
    835                 840                 845

Asn Gly Pro Val Leu Ile His Thr Thr Phe Gly Asp Leu Leu Arg Ser
850                 855                 860

Leu Asp Pro Pro Ala Glu Phe His Ser Pro Glu Leu Ile Thr Met Ser
865                 870                 875                 880

Arg Glu Gly Phe Ile Val Ile Asn Tyr Asp Lys Gly Asn Val Ala Ala
            885                 890                 895

Tyr Thr Ile Asn Gly Lys Lys Leu Arg His Glu Thr His Asn Asp Asn
        900                 905                 910

Leu Gln Cys Met Leu Leu Ser Arg Asp Gly Glu Tyr Leu Met Thr Ala
    915                 920                 925

Gly Asp Arg Gly Ile Val Glu Val Trp Arg Thr Phe Asn Leu Ala Pro
930                 935                 940

Leu Tyr Ala Phe Pro Ala Cys Asn Ala Gly Ile Arg Ser Leu Ala Leu
945                 950                 955                 960

Thr His Asp Gln Lys Tyr Leu Leu Ala Gly Leu Ser Thr Gly Ser Ile
            965                 970                 975

Ile Val Phe His Ile Asp Phe Asn Arg Trp His His Glu Tyr Gln Gln
        980                 985                 990

Arg Tyr

<210> SEQ ID NO 17
<211> LENGTH: 973
<212> TYPE: PRT
<213> ORGANISM: Homo sapiens
```

```
<220> FEATURE:
<221> NAME/KEY: DOMAIN
<222> LOCATION: (292)..(595)
<223> OTHER INFORMATION: BEACH domain
<220> FEATURE:
<221> NAME/KEY: SITE
<222> LOCATION: (329)..(336)
<223> OTHER INFORMATION: Tyrosine kinase recognition site
<220> FEATURE:
<221> NAME/KEY: BINDING
<222> LOCATION: (337)..(340)
<223> OTHER INFORMATION: SH3 binding site
<220> FEATURE:
<221> NAME/KEY: BINDING
<222> LOCATION: (407)..(410)
<223> OTHER INFORMATION: SH2 binding site

<400> SEQUENCE: 17

Cys Ile Pro Pro Ser Ala Ser Thr Lys Ala Asp Leu Ile Lys Met Ile
1               5                   10                  15

Lys Glu Glu Gln Lys Lys Tyr Glu Thr Glu Glu Gly Val Asn Lys Ala
            20                  25                  30

Ala Trp Gln Lys Thr Val Asn Asn Gln Gln Ser Leu Phe Gln Arg
        35                  40                  45

Leu Asp Ser Lys Ser Lys Asp Ile Ser Lys Ile Ala Ala Asp Ile Thr
    50                  55                  60

Gln Ala Val Ser Leu Ser Gln Gly Asn Glu Arg Lys Lys Val Ile Gln
65                  70                  75                  80

His Ile Arg Gly Met Tyr Lys Val Asp Leu Ser Ala Ser Arg His Trp
                85                  90                  95

Gln Glu Leu Ile Gln Gln Leu Thr His Asp Arg Ala Val Trp Tyr Asp
            100                 105                 110

Pro Ile Tyr Tyr Pro Thr Ser Trp Gln Leu Asp Pro Thr Glu Gly Pro
        115                 120                 125

Asn Arg Glu Arg Arg Leu Gln Arg Cys Tyr Leu Thr Ile Pro Asn
    130                 135                 140

Lys Tyr Leu Leu Arg Asp Arg Gln Lys Ser Glu Asp Val Val Lys Pro
145                 150                 155                 160

Pro Leu Ser Tyr Leu Phe Glu Asp Lys Thr His Ser Ser Phe Ser Ser
                165                 170                 175

Thr Val Lys Asp Lys Ala Ala Ser Glu Ser Ile Arg Val Asn Arg Arg
            180                 185                 190

Cys Ile Ser Val Ala Pro Ser Arg Glu Thr Ala Gly Glu Leu Leu Leu
        195                 200                 205

Gly Lys Cys Gly Met Tyr Phe Val Glu Asp Asn Ala Ser Asp Thr Val
    210                 215                 220

Glu Ser Ser Ser Leu Gln Gly Glu Leu Glu Pro Ala Ser Phe Ser Trp
225                 230                 235                 240

Thr Tyr Glu Glu Ile Lys Glu Val His Lys Arg Trp Trp Gln Leu Arg
                245                 250                 255

Asp Asn Ala Val Glu Ile Phe Leu Thr Asn Gly Arg Thr Leu Leu Leu
            260                 265                 270

Ala Phe Asp Asn Thr Lys Val Arg Asp Asp Val Tyr His Asn Ile Leu
        275                 280                 285

Thr Asn Asn Leu Pro Asn Leu Leu Glu Tyr Gly Asn Ile Thr Ala Leu
    290                 295                 300

Thr Asn Leu Trp Tyr Thr Gly Gln Ile Thr Asn Phe Glu Tyr Leu Thr
305                 310                 315                 320
```

-continued

```
His Leu Asn Lys His Ala Gly Arg Ser Phe Asn Asp Leu Met Gln Tyr
            325                 330                 335

Pro Val Phe Pro Phe Ile Leu Ala Asp Tyr Val Ser Glu Thr Leu Asp
            340                 345                 350

Leu Asn Asp Leu Leu Ile Tyr Arg Asn Leu Ser Lys Pro Ile Ala Val
            355                 360                 365

Gln Tyr Lys Glu Lys Glu Asp Arg Tyr Val Asp Thr Tyr Lys Tyr Leu
            370                 375                 380

Glu Glu Glu Tyr Arg Lys Gly Ala Arg Glu Asp Asp Pro Met Pro Pro
385                 390                 395                 400

Val Gln Pro Tyr His Tyr Gly Ser His Tyr Ser Asn Ser Gly Thr Val
            405                 410                 415

Leu His Phe Leu Val Arg Met Pro Pro Phe Thr Lys Met Phe Leu Ala
            420                 425                 430

Tyr Gln Asp Gln Ser Phe Asp Ile Pro Asp Arg Thr Phe His Ser Thr
            435                 440                 445

Asn Thr Thr Trp Arg Leu Ser Ser Phe Glu Ser Met Thr Asp Val Lys
            450                 455                 460

Glu Leu Ile Pro Glu Phe Phe Tyr Leu Pro Glu Phe Leu Val Asn Arg
465                 470                 475                 480

Glu Gly Phe Asp Phe Gly Val Arg Gln Asn Gly Glu Arg Val Asn His
            485                 490                 495

Val Asn Leu Pro Pro Trp Ala Arg Asn Asp Pro Arg Leu Phe Ile Leu
            500                 505                 510

Ile His Arg Gln Ala Leu Glu Ser Asp Tyr Val Ser Gln Asn Ile Cys
            515                 520                 525

Gln Trp Ile Asp Leu Val Phe Gly Tyr Lys Gln Lys Gly Lys Ala Ser
            530                 535                 540

Val Gln Ala Ile Asn Val Phe His Pro Ala Thr Tyr Phe Gly Met Asp
545                 550                 555                 560

Val Ser Ala Val Glu Asp Pro Val Gln Arg Arg Ala Leu Glu Thr Met
            565                 570                 575

Ile Lys Thr Tyr Gly Gln Thr Pro Arg Gln Leu Phe His Met Ala His
            580                 585                 590

Val Ser Arg Pro Gly Ala Lys Leu Asn Ile Glu Gly Glu Leu Pro Ala
            595                 600                 605

Ala Val Gly Leu Leu Val Gln Phe Ala Phe Arg Glu Thr Arg Glu Gln
            610                 615                 620

Val Lys Glu Ile Thr Tyr Pro Ser Pro Leu Ser Trp Ile Lys Gly Leu
625                 630                 635                 640

Lys Trp Gly Glu Tyr Val Gly Ser Pro Ser Ala Pro Val Pro Val Val
            645                 650                 655

Cys Phe Ser Gln Pro His Gly Glu Arg Phe Gly Ser Leu Gln Ala Leu
            660                 665                 670

Pro Thr Arg Ala Ile Cys Gly Leu Ser Arg Asn Phe Cys Leu Val Met
            675                 680                 685

Thr Tyr Ser Lys Glu Gln Gly Val Arg Ser Met Asn Ser Thr Asp Ile
            690                 695                 700

Gln Trp Ser Ala Ile Leu Ser Trp Gly Tyr Ala Asp Asn Ile Leu Arg
705                 710                 715                 720

Leu Lys Ser Lys Gln Ser Glu Pro Pro Val Asn Phe Ile Gln Ser Ser
            725                 730                 735
```

-continued

```
Gln Gln Tyr Gln Val Thr Ser Cys Ala Trp Val Pro Asp Ser Cys Gln
            740                 745                 750

Leu Phe Thr Gly Ser Lys Cys Gly Val Ile Thr Ala Tyr Thr Asn Arg
        755                 760                 765

Phe Thr Ser Ser Thr Pro Ser Glu Ile Glu Met Glu Thr Gln Ile His
    770                 775                 780

Leu Tyr Gly His Thr Glu Glu Ile Thr Ser Leu Phe Val Cys Lys Pro
785                 790                 795                 800

Tyr Ser Ile Leu Ile Ser Val Ser Arg Asp Gly Thr Cys Ile Ile Trp
                805                 810                 815

Asp Leu Asn Arg Leu Cys Tyr Val Gln Ser Leu Ala Gly His Lys Ser
            820                 825                 830

Pro Val Thr Ala Val Ser Ala Ser Glu Thr Ser Gly Asp Ile Ala Thr
        835                 840                 845

Val Cys Asp Ser Ala Gly Gly Gly Ser Asp Leu Arg Leu Trp Thr Val
    850                 855                 860

Asn Gly Asp Leu Val Gly His Val His Cys Arg Glu Ile Ile Cys Ser
865                 870                 875                 880

Val Ala Phe Ser Asn Gln Pro Glu Gly Val Ser Ile Asn Val Ile Ala
                885                 890                 895

Gly Gly Leu Glu Asn Gly Ile Val Arg Leu Trp Ser Thr Trp Asp Leu
            900                 905                 910

Lys Pro Val Arg Glu Ile Thr Phe Pro Lys Ser Asn Lys Pro Ile Ile
        915                 920                 925

Ser Leu Thr Phe Ser Cys Asp Gly His His Leu Tyr Thr Ala Asn Ser
    930                 935                 940

Asp Gly Thr Val Ile Ala Trp Cys Arg Lys Asp Gln Gln Arg Leu Lys
945                 950                 955                 960

Gln Pro Met Phe Tyr Ser Phe Leu Ser Ser Tyr Ala Ala
                965                 970

<210> SEQ ID NO 18
<211> LENGTH: 907
<212> TYPE: PRT
<213> ORGANISM: Homo sapiens
<220> FEATURE:
<221> NAME/KEY: DOMAIN
<222> LOCATION: (279)..(565)
<223> OTHER INFORMATION: BEACH domain
<220> FEATURE:
<221> NAME/KEY: SITE
<222> LOCATION: (316)..(323)
<223> OTHER INFORMATION: Tyrosine kinase recognition site
<220> FEATURE:
<221> NAME/KEY: BINDING
<222> LOCATION: (324)..(327)
<223> OTHER INFORMATION: SH3 binding site
<220> FEATURE:
<221> NAME/KEY: BINDING
<222> LOCATION: (379)..(382)
<223> OTHER INFORMATION: SH2 binding site

<400> SEQUENCE: 18

Gln Gln Leu Gln Leu Tyr Ser Lys Glu Arg Phe Ser Leu Leu Leu Leu
1               5                   10                  15

Asn Leu Glu Glu Tyr Tyr Phe Glu Gln His Arg Ala Asn His Ile Leu
            20                  25                  30

His Lys Gly Ser His His Glu Arg Lys Ile Arg Gly Ser Leu Lys Ile
        35                  40                  45
```

-continued

```
Cys Ser Lys Ser Val Ile Phe Glu Pro Asp Ser Ile Ser Gln Pro Ile
 50                  55                  60

Ile Lys Ile Pro Leu Arg Asp Cys Ile Lys Ile Gly Lys His Gly Glu
 65                  70                  75                  80

Asn Gly Ala Asn Arg His Phe Thr Lys Ala Lys Ser Gly Gly Ile Ser
                 85                  90                  95

Leu Ile Phe Ser Gln Val Tyr Phe Ile Lys Glu His Asn Val Val Ala
            100                 105                 110

Pro Tyr Lys Ile Glu Arg Gly Lys Met Glu Tyr Val Phe Glu Leu Asp
        115                 120                 125

Val Pro Gly Lys Val Glu Asp Val Val Glu Thr Leu Leu Gln Leu His
130                 135                 140

Arg Ala Ser Cys Leu Asp Lys Leu Gly Asp Gln Thr Ala Met Ile Thr
145                 150                 155                 160

Ala Ile Leu Gln Ser Arg Leu Ala Arg Thr Ser Phe Asp Lys Asn Arg
                165                 170                 175

Phe Gln Asn Ile Ser Glu Lys Leu His Met Glu Cys Lys Ala Glu Met
            180                 185                 190

Val Thr Pro Leu Val Thr Asn Pro Gly His Val Cys Ile Thr Asp Thr
        195                 200                 205

Asn Leu Tyr Phe Gln Pro Leu Asn Gly Tyr Pro Lys Pro Val Val Gln
210                 215                 220

Ile Thr Leu Gln Asp Val Arg Arg Ile Tyr Lys Arg His Gly Leu
225                 230                 235                 240

Met Pro Leu Gly Leu Glu Val Phe Cys Thr Glu Asp Asp Leu Cys Ser
                245                 250                 255

Asp Ile Tyr Leu Lys Phe Tyr Glu Pro Gln Asp Arg Asp Asp Leu Tyr
            260                 265                 270

Phe Tyr Ile Ala Thr Tyr Leu Glu His His Val Ala Glu His Thr Ala
        275                 280                 285

Glu Ser Tyr Met Leu Gln Trp Gln Arg Gly His Leu Ser Asn Tyr Gln
290                 295                 300

Tyr Leu Leu His Leu Asn Asn Leu Ala Asp Arg Ser Cys Asn Asp Leu
305                 310                 315                 320

Ser Gln Tyr Pro Val Phe Pro Trp Ile Ile His Asp Tyr Ser Ser Ser
                325                 330                 335

Glu Leu Asp Leu Ser Asn Pro Gly Thr Phe Arg Asp Leu Ser Lys Pro
            340                 345                 350

Val Gly Ala Leu Asn Lys Glu Arg Leu Glu Arg Leu Leu Thr Arg Tyr
        355                 360                 365

Gln Glu Met Pro Glu Pro Lys Phe Met Tyr Gly Ser His Tyr Ser Ser
370                 375                 380

Pro Gly Tyr Val Leu Phe Tyr Leu Val Arg Ile Ala Pro Glu Tyr Met
385                 390                 395                 400

Leu Cys Leu Gln Asn Gly Arg Phe Asp Asn Ala Asp Arg Met Phe Asn
                405                 410                 415

Ser Ile Ala Glu Thr Trp Lys Asn Cys Leu Asp Gly Ala Thr Asp Phe
            420                 425                 430

Lys Glu Leu Ile Pro Glu Phe Tyr Gly Asp Asp Val Ser Phe Leu Val
        435                 440                 445

Asn Ser Leu Lys Leu Asp Leu Gly Lys Arg Gln Gly Gly Gln Met Val
450                 455                 460
```

-continued

```
Asp Asp Val Glu Leu Pro Pro Trp Ala Ser Ser Pro Glu Asp Phe Leu
465                 470                 475                 480

Gln Lys Ser Lys Asp Ala Leu Glu Ser Asn Tyr Val Ser Glu His Leu
                485                 490                 495

His Glu Trp Ile Asp Leu Ile Phe Gly Tyr Lys Gln Lys Gly Ser Asp
            500                 505                 510

Ala Val Gly Ala His Asn Val Phe His Pro Leu Thr Tyr Glu Gly Gly
            515                 520                 525

Val Asp Leu Asn Ser Ile Gln Asp Pro Asp Glu Lys Val Ala Met Leu
    530                 535                 540

Thr Gln Ile Leu Glu Phe Gly Gln Thr Pro Lys Gln Leu Phe Val Thr
545                 550                 555                 560

Pro His Pro Arg Arg Ile Thr Pro Lys Phe Lys Ser Leu Ser Gln Thr
                565                 570                 575

Ser Ser Tyr Asn Ala Ser Met Ala Asp Ser Pro Gly Glu Glu Ser Phe
                580                 585                 590

Glu Asp Leu Thr Glu Glu Ser Lys Thr Leu Ala Trp Asn Asn Ile Thr
        595                 600                 605

Lys Leu Gln Leu His Glu His Tyr Lys Ile His Lys Gly Ala Val Thr
610                 615                 620

Gly Ile Thr Val Ser Arg Asn Gly Ser Ser Val Phe Thr Thr Ser Gln
625                 630                 635                 640

Asp Ser Thr Leu Lys Met Phe Ser Lys Glu Ser Lys Met Leu Gln Arg
                645                 650                 655

Ser Ile Ser Phe Ser Asn Met Ala Leu Ser Ser Cys Leu Leu Leu Pro
                660                 665                 670

Gly Asp Ala Thr Val Ile Thr Ser Ser Trp Asp Asn Asn Val Tyr Phe
                675                 680                 685

Tyr Ser Ile Ala Phe Gly Arg Arg Gln Asp Thr Leu Met Gly His Asp
690                 695                 700

Asp Ala Val Ser Lys Ile Cys Trp His Asp Asn Arg Leu Tyr Ser Ala
705                 710                 715                 720

Ser Trp Asp Ser Thr Val Lys Val Trp Ser Gly Val Pro Ala Glu Met
                725                 730                 735

Pro Gly Thr Lys Arg His His Phe Asp Leu Leu Ala Glu Leu Glu His
                740                 745                 750

Asp Val Ser Val Asp Thr Ile Ser Leu Asn Ala Ala Ser Thr Leu Leu
                755                 760                 765

Val Ser Gly Thr Lys Glu Gly Thr Val Asn Ile Trp Asp Leu Thr Thr
770                 775                 780

Ala Thr Leu Met His Gln Ile Pro Cys His Ser Gly Ile Val Cys Asp
785                 790                 795                 800

Thr Ala Phe Ser Pro Asp Ser Arg His Val Leu Ser Thr Gly Thr Asp
                805                 810                 815

Gly Cys Leu Asn Val Ile Asp Val Gln Thr Gly Met Leu Ile Ser Ser
                820                 825                 830

Met Thr Ser Asp Glu Pro Gln Thr Cys Phe Val Trp Asp Gly Asn Ser
                835                 840                 845

Val Leu Ser Gly Ser Gln Ser Gly Glu Leu Leu Val Trp Asp Leu Leu
                850                 855                 860

Gly Ala Lys Ile Ser Glu Arg Ile Gln Gly His Thr Gly Ala Val Thr
865                 870                 875                 880
```

Cys Ile Trp Met Asn Glu Gln Cys Ser Ser Ile Ile Thr Gly Gly Glu
                885                 890                 895

Asp Arg Gln Ile Ile Phe Trp Lys Leu Gln Tyr
            900                 905

<210> SEQ ID NO 19
<211> LENGTH: 908
<212> TYPE: PRT
<213> ORGANISM: Mus musculus
<220> FEATURE:
<221> NAME/KEY: REPEAT
<222> LOCATION: (144)..(187)
<223> OTHER INFORMATION: WDL (WD-like) repeat
<220> FEATURE:
<221> NAME/KEY: REPEAT
<222> LOCATION: (188)..(237)
<223> OTHER INFORMATION: WDL (WD-like) repeat
<220> FEATURE:
<221> NAME/KEY: REPEAT
<222> LOCATION: (238)..(278)
<223> OTHER INFORMATION: WDL (WD-like) repeat
<220> FEATURE:
<221> NAME/KEY: DOMAIN
<222> LOCATION: (308)..(599)
<223> OTHER INFORMATION: BEACH domain
<220> FEATURE:
<221> NAME/KEY: SITE
<222> LOCATION: (345)..(352)
<223> OTHER INFORMATION: Tyrosine kinase recognition site
<220> FEATURE:
<221> NAME/KEY: BINDING
<222> LOCATION: (353)..(356)
<223> OTHER INFORMATION: SH3 binding site
<220> FEATURE:
<221> NAME/KEY: BINDING
<222> LOCATION: (411)..(414)
<223> OTHER INFORMATION: SH2 binding site
<220> FEATURE:
<221> NAME/KEY: REPEAT
<222> LOCATION: (702)..(744)
<223> OTHER INFORMATION: WD repeat
<220> FEATURE:
<221> NAME/KEY: REPEAT
<222> LOCATION: (745)..(803)
<223> OTHER INFORMATION: WD repeat
<220> FEATURE:
<221> NAME/KEY: REPEAT
<222> LOCATION: (804)..(886)
<223> OTHER INFORMATION: WD repeat

<400> SEQUENCE: 19

Gly Arg Leu Leu Ser Gln Thr Met Lys Asp His Leu Val Arg Val Ala
1               5                   10                  15

Asn Glu Ala Glu Phe Ile Leu Ser Arg Gln Arg Ala Glu Asp Ile His
            20                  25                  30

Arg His Ala Glu Phe Glu Ser Leu Cys Ala Gln Tyr Ser Ala Asp Lys
        35                  40                  45

Arg Glu Glu Glu Lys Met Cys Asp His Leu Ile Arg Ala Ala Lys Tyr
    50                  55                  60

Arg Asp His Val Thr Ala Thr Gln Leu Ile Gln Lys Ile Ile Asn Leu
65                  70                  75                  80

Leu Thr Asp Lys His Gly Ala Trp Gly Ser Ser Ala Val Ser Arg Pro
                85                  90                  95

Arg Glu Phe Trp Arg Leu Asp Tyr Trp Glu Asp Leu Arg Arg Arg
            100                 105                 110

Arg Arg Phe Val Arg Asn Pro Leu Gly Ser Thr His Pro Glu Ala Thr
        115                 120                 125

-continued

```
Leu Lys Thr Ala Val Glu His Ala Ala Asp Glu Asp Ile Leu Ala Lys
        130                 135                 140

Gly Lys Gln Ser Ile Lys Ser Gln Ala Leu Gly Asn Gln Asn Ser Glu
145                 150                 155                 160

Asn Glu Ala Leu Leu Glu Gly Asp Asp Thr Leu Ser Ser Val Asp
                165                 170                 175

Glu Lys Asp Leu Glu Asn Leu Ala Gly Pro Val Ser Leu Ser Thr Pro
                180                 185                 190

Ala Gln Leu Val Ala Pro Ser Val Val Lys Gly Thr Leu Ser Val
                195                 200                 205

Thr Ser Ser Glu Leu Tyr Phe Glu Val Asp Glu Glu Asp Pro Asn Phe
    210                 215                 220

Lys Lys Ile Asp Pro Lys Ile Leu Ala Tyr Thr Glu Gly Leu His Gly
225                 230                 235                 240

Lys Trp Leu Phe Thr Glu Ile Arg Ser Ile Phe Ser Arg Arg Tyr Leu
                245                 250                 255

Leu Gln Asn Thr Ala Leu Glu Ile Phe Met Ala Asn Arg Val Ala Val
                260                 265                 270

Met Phe Asn Phe Pro Asp Pro Ala Thr Val Lys Lys Val Val Asn Tyr
            275                 280                 285

Leu Pro Arg Val Gly Val Gly Thr Ser Phe Gly Leu Pro Gln Thr Arg
            290                 295                 300

Arg Ile Ser Leu Ala Thr Pro Arg Gln Leu Phe Lys Ala Ser Asn Met
305                 310                 315                 320

Thr Gln Arg Trp Gln His Arg Glu Ile Ser Asn Phe Glu Tyr Leu Met
                325                 330                 335

Phe Leu Asn Thr Ile Ala Gly Arg Ser Tyr Asn Asp Leu Asn Gln Tyr
                340                 345                 350

Pro Val Phe Pro Trp Val Ile Thr Asn Tyr Glu Ser Glu Glu Leu Asp
            355                 360                 365

Leu Thr Leu Pro Ser Asn Phe Arg Asp Leu Ser Lys Pro Ile Gly Ala
    370                 375                 380

Leu Asn Pro Lys Arg Ala Ala Phe Phe Ala Glu Arg Phe Glu Ser Trp
385                 390                 395                 400

Glu Asp Asp Gln Val Pro Lys Phe His Tyr Gly Thr His Tyr Ser Thr
                405                 410                 415

Ala Ser Phe Val Leu Ala Trp Leu Leu Arg Ile Glu Pro Phe Thr Thr
            420                 425                 430

Tyr Phe Leu Asn Leu Gln Gly Gly Lys Phe Asp His Ala Asp Arg Thr
    435                 440                 445

Phe Ser Ser Val Ser Arg Ala Trp Arg Asn Ser Gln Arg Asp Thr Ser
    450                 455                 460

Asp Ile Lys Glu Leu Ile Pro Glu Phe Tyr Leu Pro Glu Met Phe
465                 470                 475                 480

Val Asn Phe Asn Asn Tyr Asn Leu Gly Val Met Asp Asp Gly Thr Val
            485                 490                 495

Val Ser Asp Val Glu Leu Pro Pro Trp Ala Lys Thr Ser Glu Glu Phe
            500                 505                 510

Val Arg Ile Asn Arg Leu Ala Leu Glu Ser Glu Phe Val Ser Cys Gln
            515                 520                 525

Leu His Gln Trp Ile Asp Leu Ile Phe Gly Tyr Lys Gln Gln Gly Pro
    530                 535                 540
```

-continued

```
Glu Ala Val Arg Ala Leu Asn Val Phe Tyr Tyr Leu Thr Tyr Glu Gly
545                 550                 555                 560

Ala Val Asn Leu Asn Ser Ile Thr Asp Pro Val Leu Arg Glu Ala Val
            565                 570                 575

Glu Ala Gln Ile Arg Ser Phe Gly Gln Thr Pro Ser Gln Leu Leu Ile
        580                 585                 590

Glu Pro His Pro Pro Arg Gly Ser Ala Met Gln Ala Ser Pro Leu Met
    595                 600                 605

Phe Thr Asp Gln Ala Gln Gln Asp Val Ile Met Val Leu Lys Phe Pro
610                 615                 620

Ser Asn Ser Pro Val Thr His Val Ala Ala Asn Thr Gln Pro Gly Leu
625                 630                 635                 640

Ala Met Pro Ala Val Ile Thr Val Thr Ala Asn Arg Leu Phe Ala Val
            645                 650                 655

Asn Lys Trp His Asn Leu Pro Ala His Gln Gly Ala Val Gln Asp Gln
        660                 665                 670

Pro Tyr Gln Leu Pro Val Glu Ile Asp Pro Leu Ile Ala Cys Gly Thr
    675                 680                 685

Gly Thr His Arg Arg Gln Val Thr Asp Leu Leu Asp Gln Ser Ile Gln
690                 695                 700

Val His Ser Gln Cys Phe Val Ile Thr Ser Asp Asn Arg Tyr Ile Leu
705                 710                 715                 720

Val Cys Gly Phe Trp Asp Lys Ser Phe Arg Val Tyr Ser Thr Asp Thr
            725                 730                 735

Gly Lys Leu Ile Gln Val Val Phe Gly His Trp Asp Val Val Thr Cys
        740                 745                 750

Leu Ala Arg Ser Glu Ser Tyr Ile Gly Gly Asn Cys Tyr Ile Leu Ser
    755                 760                 765

Gly Ser Arg Asp Ala Thr Leu Leu Leu Trp Tyr Trp Asn Gly Lys Ser
770                 775                 780

Ser Gly Ile Gly Asp Asn Pro Gly Gly Glu Thr Ala Thr Pro Arg Ala
785                 790                 795                 800

Ile Leu Thr Gly His Asp Tyr Glu Ile Thr Cys Ala Ala Val Cys Ala
            805                 810                 815

Glu Leu Gly Leu Val Leu Ser Gly Ser Gln Glu Gly Pro Cys Leu Ile
        820                 825                 830

His Ser Met Asn Gly Asp Leu Leu Arg Thr Leu Glu Gly Pro Glu Asn
    835                 840                 845

Cys Leu Lys Pro Lys Leu Ile Gln Ala Ser Arg Glu Gly His Cys Val
850                 855                 860

Ile Phe Tyr Glu Asn Gly Cys Phe Cys Thr Phe Ser Val Asn Gly Lys
865                 870                 875                 880

Leu Gln Ala Thr Val Glu Thr Asp Asp His Ile Arg Val Ser Ala Val
            885                 890                 895

Gly Ser Thr Leu Phe Leu Leu Leu Gly Ser Ser Lys
        900                 905

<210> SEQ ID NO 20
<211> LENGTH: 695
<212> TYPE: PRT
<213> ORGANISM: Mus musculus
<220> FEATURE:
<221> NAME/KEY: REPEAT
<222> LOCATION: (144)..(187)
<223> OTHER INFORMATION: WDL (WD-like) repeat
```

```
<220> FEATURE:
<221> NAME/KEY: REPEAT
<222> LOCATION: (188)..(237)
<223> OTHER INFORMATION: WDL (WD-like) repeat
<220> FEATURE:
<221> NAME/KEY: REPEAT
<222> LOCATION: (238)..(278)
<223> OTHER INFORMATION: WDL (WD-like) repeat
<220> FEATURE:
<221> NAME/KEY: DOMAIN
<222> LOCATION: (308)..(599)
<223> OTHER INFORMATION: BEACH domain
<220> FEATURE:
<221> NAME/KEY: SITE
<222> LOCATION: (345)..(352)
<223> OTHER INFORMATION: Tyrosine kinase recognition site
<220> FEATURE:
<221> NAME/KEY: BINDING
<222> LOCATION: (353)..(356)
<223> OTHER INFORMATION: SH3 binding site
<220> FEATURE:
<221> NAME/KEY: BINDING
<222> LOCATION: (411)..(414)
<223> OTHER INFORMATION: SH2 binding site

<400> SEQUENCE: 20

Gly Arg Leu Leu Ser Gln Thr Met Lys Asp His Leu Val Arg Val Ala
1               5                   10                  15

Asn Glu Ala Glu Phe Ile Leu Ser Arg Gln Arg Ala Glu Asp Ile His
            20                  25                  30

Arg His Ala Glu Phe Glu Ser Leu Cys Ala Gln Tyr Ser Ala Asp Lys
        35                  40                  45

Arg Glu Glu Glu Lys Met Cys Asp His Leu Ile Arg Ala Ala Lys Tyr
    50                  55                  60

Arg Asp His Val Thr Ala Thr Gln Leu Ile Gln Lys Ile Ile Asn Leu
65                  70                  75                  80

Leu Thr Asp Lys His Gly Ala Trp Gly Ser Ser Ala Val Ser Arg Pro
                85                  90                  95

Arg Glu Phe Trp Arg Leu Asp Tyr Trp Glu Asp Leu Arg Arg Arg
            100                 105                 110

Arg Arg Phe Val Arg Asn Pro Leu Gly Ser Thr His Pro Glu Ala Thr
        115                 120                 125

Leu Lys Thr Ala Val Glu His Ala Ala Asp Glu Asp Ile Leu Ala Lys
    130                 135                 140

Gly Lys Gln Ser Ile Lys Ser Gln Ala Leu Gly Asn Gln Asn Ser Glu
145                 150                 155                 160

Asn Glu Ala Leu Leu Glu Gly Asp Asp Thr Leu Ser Ser Val Asp
                165                 170                 175

Glu Lys Asp Leu Glu Asn Leu Ala Gly Pro Val Ser Leu Ser Thr Pro
            180                 185                 190

Ala Gln Leu Val Ala Pro Ser Val Val Lys Gly Thr Leu Ser Val
        195                 200                 205

Thr Ser Ser Glu Leu Tyr Phe Glu Val Asp Glu Asp Pro Asn Phe
    210                 215                 220

Lys Lys Ile Asp Pro Lys Ile Leu Ala Tyr Thr Glu Gly Leu His Gly
225                 230                 235                 240

Lys Trp Leu Phe Thr Glu Ile Arg Ser Ile Phe Ser Arg Arg Tyr Leu
                245                 250                 255
```

-continued

```
Leu Gln Asn Thr Ala Leu Glu Ile Phe Met Ala Asn Arg Val Ala Val
            260                 265                 270

Met Phe Asn Phe Pro Asp Pro Ala Thr Val Lys Lys Val Val Asn Tyr
        275                 280                 285

Leu Pro Arg Val Gly Val Gly Thr Ser Phe Gly Leu Pro Gln Thr Arg
    290                 295                 300

Arg Ile Ser Leu Ala Thr Pro Arg Gln Leu Phe Lys Ala Ser Asn Met
305                 310                 315                 320

Thr Gln Arg Trp Gln His Arg Glu Ile Ser Asn Phe Glu Tyr Leu Met
            325                 330                 335

Phe Leu Asn Thr Ile Ala Gly Arg Ser Tyr Asn Asp Leu Asn Gln Tyr
        340                 345                 350

Pro Val Phe Pro Trp Val Ile Thr Asn Tyr Glu Ser Glu Glu Leu Asp
    355                 360                 365

Leu Thr Leu Pro Ser Asn Phe Arg Asp Leu Ser Lys Pro Ile Gly Ala
370                 375                 380

Leu Asn Pro Lys Arg Ala Ala Phe Ala Glu Arg Phe Glu Ser Trp
385                 390                 395                 400

Glu Asp Asp Gln Val Pro Lys Phe His Tyr Gly Thr His Tyr Ser Thr
            405                 410                 415

Ala Ser Phe Val Leu Ala Trp Leu Leu Arg Ile Glu Pro Phe Thr Thr
        420                 425                 430

Tyr Phe Leu Asn Leu Gln Gly Gly Lys Phe Asp His Ala Asp Arg Thr
    435                 440                 445

Phe Ser Ser Val Ser Arg Ala Trp Arg Asn Ser Gln Arg Asp Thr Ser
450                 455                 460

Asp Ile Lys Glu Leu Ile Pro Glu Phe Tyr Leu Pro Glu Met Phe
465                 470                 475                 480

Val Asn Phe Asn Asn Tyr Asn Leu Gly Val Met Asp Asp Gly Thr Val
            485                 490                 495

Val Ser Asp Val Glu Leu Pro Pro Trp Ala Lys Thr Ser Glu Glu Phe
        500                 505                 510

Val Arg Ile Asn Arg Leu Ala Leu Glu Ser Glu Phe Val Ser Cys Gln
    515                 520                 525

Leu His Gln Trp Ile Asp Leu Ile Phe Gly Tyr Lys Gln Gln Gly Pro
530                 535                 540

Glu Ala Val Arg Ala Leu Asn Val Phe Tyr Tyr Leu Thr Tyr Glu Gly
545                 550                 555                 560

Ala Val Asn Leu Asn Ser Ile Thr Asp Pro Val Leu Arg Glu Ala Val
            565                 570                 575

Glu Ala Gln Ile Arg Ser Phe Gly Gln Thr Pro Ser Gln Leu Leu Ile
        580                 585                 590

Glu Pro His Pro Pro Arg Gly Ser Ala Met Gln Ala Ser Pro Leu Met
    595                 600                 605

Phe Thr Asp Gln Ala Gln Gln Asp Val Ile Met Val Leu Lys Phe Pro
610                 615                 620

Ser Asn Ser Pro Val Thr His Val Ala Ala Asn Thr Gln Pro Gly Leu
625                 630                 635                 640

Ala Met Pro Ala Val Ile Thr Val Thr Ala Asn Arg Leu Phe Ala Val
            645                 650                 655

Asn Lys Trp His Asn Leu Pro Ala His Gln Gly Ala Val Gln Asp Gln
        660                 665                 670
```

-continued

```
Pro Tyr Gln Leu Pro Val Glu Ile Asp Pro Leu Ile Gly Leu Pro Leu
            675                 680                 685

Leu Ser Leu Phe Ala Ile His
        690                 695

<210> SEQ ID NO 21
<211> LENGTH: 2586
<212> TYPE: PRT
<213> ORGANISM: Homo sapiens
<220> FEATURE:
<221> NAME/KEY: DOMAIN
<222> LOCATION: (1)..(72)
<223> OTHER INFORMATION: G peptide
<220> FEATURE:
<221> NAME/KEY: DOMAIN
<222> LOCATION: (82)..(393)
<223> OTHER INFORMATION: HSH (helix-sheet-helix) domain
<220> FEATURE:
<221> NAME/KEY: DOMAIN
<222> LOCATION: (979)..(1302)
<223> OTHER INFORMATION: SET Domain (Rich in Serine, Glutamic acid and
      Threonine)
<220> FEATURE:
<221> NAME/KEY: DOMAIN
<222> LOCATION: (2035)..(2169)
<223> OTHER INFORMATION: WDL (WD-like) domain
<220> FEATURE:
<221> NAME/KEY: DOMAIN
<222> LOCATION: (2212)..(2489)
<223> OTHER INFORMATION: BEACH domain

<400> SEQUENCE: 21

Met Ala Ser Glu Asp Asn Arg Val Pro Ser Pro Pro Thr Gly Asp
1               5                   10                  15

Asp Gly Gly Gly Gly Arg Glu Glu Thr Pro Thr Glu Gly Gly Ala
            20                  25                  30

Leu Ser Leu Lys Pro Gly Leu Pro Ile Arg Gly Ile Arg Met Lys Phe
        35                  40                  45

Ala Val Leu Thr Gly Leu Val Glu Val Gly Glu Val Ser Asn Arg Asp
    50                  55                  60

Ile Val Glu Thr Val Phe Asn Leu Leu Val Gly Gly Gln Phe Asp Leu
65                  70                  75                  80

Glu Met Asn Phe Ile Ile Gln Glu Gly Glu Ser Ile Asn Cys Met Val
                85                  90                  95

Asp Leu Leu Glu Lys Cys Asp Ile Thr Cys Gln Ala Glu Val Trp Ser
            100                 105                 110

Met Phe Thr Ala Ile Leu Lys Lys Ser Ile Arg Asn Leu Gln Val Cys
        115                 120                 125

Thr Glu Val Gly Leu Val Glu Lys Val Leu Gly Lys Ile Glu Lys Val
    130                 135                 140

Asp Asn Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Arg Trp Pro Pro His Ala Gly Lys Leu Leu Ser
            180                 185                 190

Val Leu Lys His Met Pro Gln Lys Tyr Gly Pro Asp Ala Phe Phe Asn
        195                 200                 205

Phe Pro Gly Lys Ser Ala Ala Ile Ala Leu Pro Pro Ile Ala Lys
    210                 215                 220

Trp Pro Tyr Gln Asn Gly Phe Thr Phe His Thr Trp Leu Arg Met Asp
225                 230                 235                 240
```

-continued

```
Pro Val Asn Asn Ile Asn Val Asp Lys Asp Lys Pro Tyr Leu Tyr Cys
                245                 250                 255

Phe Arg Thr Ser Lys Gly Leu Gly Tyr Ser Ala His Phe Val Gly Gly
            260                 265                 270

Cys Leu Ile Val Thr Ser Ile Lys Ser Lys Gly Lys Gly Phe Gln His
            275                 280                 285

Cys Val Lys Phe Asp Phe Lys Pro Gln Lys Trp Tyr Met Val Thr Ile
            290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
            340                 345                 350

Ala Asn Arg Val Phe Cys Gly Gln Met Thr Ala Val Tyr Leu Phe Ser
            355                 360                 365

Glu Ala Leu Asn Ala Ala Gln Ile Phe Ala Ile Tyr Gln Leu Gly Leu
    370                 375                 380

Gly Tyr Lys Gly Thr Phe Lys Phe Lys Ala Glu Ser Asp Leu Phe Leu
385                 390                 395                 400

Ala Glu His His Lys Leu Leu Tyr Asp Gly Lys Leu Ser Ser Ala
            405                 410                 415

Ile Ala Phe Thr Tyr Asn Pro Arg Ala Thr Asp Ala Gln Leu Cys Leu
            420                 425                 430

Glu Ser Ser Pro Lys Asp Asn Pro Ser Ile Phe Val His Ser Pro His
    435                 440                 445

Ala Leu Met Leu Gln Asp Val Lys Ala Val Leu Thr His Ser Ile Gln
    450                 455                 460

Ser Ala Met His Ser Ile Gly Gly Val Gln Val Leu Phe Pro Leu Phe
465                 470                 475                 480

Ala Gln Leu Asp Tyr Arg Gln Tyr Leu Ser Asp Glu Ile Asp Leu Thr
            485                 490                 495

Ile Cys Ser Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
            515                 520                 525

Gly Tyr Ser Leu Glu Lys Ser Lys Ser His Val Ser Arg Ala Val
            530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Val Leu Leu Asn Pro
            565                 570                 575

Ala Ile Trp Ile His Thr Pro Ala Lys Val Gln Leu Met Leu Tyr Thr
            580                 585                 590

Tyr Leu Ser Thr Glu Phe Ile Gly Thr Val Asn Ile Tyr Asn Thr Ile
            595                 600                 605

Arg Arg Val Gly Thr Val Leu Leu Ile Met His Thr Leu Lys Tyr Tyr
            610                 615                 620

Tyr Trp Ala Val Asn Pro Gln Asp Arg Ser Gly Ile Thr Pro Lys Gly
625                 630                 635                 640

Leu Asp Gly Pro Arg Pro Asn Gln Lys Glu Met Leu Ser Leu Arg Ala
                645                 650                 655
```

-continued

```
Phe Leu Leu Met Phe Ile Lys Gln Leu Val Met Lys Asp Ser Gly Val
            660                 665                 670

Lys Glu Asp Glu Leu Gln Ala Ile Leu Asn Tyr Leu Leu Thr Met His
        675                 680                 685

Glu Asp Asp Asn Leu Met Asp Val Leu Gln Leu Val Ala Leu Met
    690                 695                 700

Ser Glu His Pro Asn Ser Met Ile Pro Ala Phe Asp Gln Arg Asn Gly
705                 710                 715                 720

Leu Arg Val Ile Tyr Lys Leu Leu Ala Ser Lys Ser Glu Gly Ile Arg
                725                 730                 735

Val Gln Ala Leu Lys Ala Met Gly Tyr Phe Leu Lys His Arg Pro Pro
            740                 745                 750

Lys Arg Lys Ala Glu Val Met Leu Gly His Gly Leu Phe Ser Leu Leu
        755                 760                 765

Ala Glu Arg Leu Met Leu Gln Thr Asn Leu Ile Thr Met Thr Thr Tyr
    770                 775                 780

Asn Val Leu Phe Glu Ile Leu Ile Glu Gln Ile Gly Thr Gln Val Ile
785                 790                 795                 800

His Lys Gln His Pro Asp Pro Asp Ser Ser Val Lys Ile Gln Asn Pro
                805                 810                 815

Gln Ile Leu Lys Val Ile Ala Thr Leu Leu Arg Asn Ser Pro Gln Cys
            820                 825                 830

Pro Glu Ser Met Glu Val Arg Arg Ala Phe Leu Ser Asp Met Ile Lys
        835                 840                 845

Leu Phe Asn Asn Ser Arg Glu Asn Arg Arg Ser Leu Leu Gln Cys Ser
    850                 855                 860

Val Trp Gln Glu Trp Met Leu Ser Leu Cys Tyr Phe Asn Pro Lys Asn
865                 870                 875                 880

Ser Asp Glu Gln Lys Ile Thr Glu Met Val Tyr Ala Ile Phe Arg Ile
                885                 890                 895

Leu Leu Tyr His Ala Val Lys Tyr Glu Trp Gly Gly Trp Arg Val Trp
            900                 905                 910

Val Asp Thr Leu Ser Ile Thr His Ser Lys Val Thr Phe Glu Ile His
        915                 920                 925

Lys Glu Asn Leu Ala Asn Ile Phe Arg Glu Gln Gln Gly Lys Val Asp
    930                 935                 940

Glu Glu Ile Gly Leu Cys Ser Ser Thr Val Gln Ala Ala Ser Gly
945                 950                 955                 960

Ile Arg Arg Asp Ile Asn Val Ser Val Gly Ser Gln Gln Pro Asp Thr
                965                 970                 975

Lys Asp Ser Pro Val Cys Pro His Phe Thr Thr Asn Gly Asn Glu Asn
            980                 985                 990

Ser Ser Ile Glu Lys Thr Ser Ser  Leu Glu Ser Ala Ser  Asn Ile Glu
                995                 1000                1005

Leu Gln  Thr Thr Asn Thr Ser  Tyr Glu Glu Met Lys  Ala Glu Gln
    1010                1015                1020

Glu Asn  Gln Glu Leu Pro Asp  Glu Gly Thr Leu Glu  Glu Thr Leu
    1025                1030                1035

Thr Asn  Glu Thr Arg Asn Ala  Asp Asp Leu Glu Val  Ser Ser Asp
    1040                1045                1050

Ile Ile  Glu Ala Val Ala Ile  Ser Ser Asn Ser Phe  Ile Thr Thr
    1055                1060                1065
```

-continued

```
Gly Lys Asp Ser Met Thr Val Ser Glu Val Thr Ala Ser Ile Ser
    1070                1075                1080

Ser Pro Ser Glu Glu Asp Ala Ser Glu Met Pro Glu Phe Leu Asp
    1085                1090                1095

Lys Ser Ile Val Glu Glu Glu Asp Asp Tyr Val Glu Leu
    1100                1105                1110

Lys Val Glu Gly Ser Pro Thr Glu Glu Ala Asn Leu Pro Thr Glu
    1115                1120                1125

Leu Gln Asp Asn Ser Leu Ser Pro Ala Ala Ser Glu Ala Gly Glu
    1130                1135                1140

Lys Leu Asp Met Phe Gly Asn Asp Asp Lys Leu Ile Phe Gln Glu
    1145                1150                1155

Gly Lys Pro Val Thr Glu Lys Gln Thr Asp Thr Glu Thr Gln Asp
    1160                1165                1170

Ser Lys Asp Ser Gly Ile Gln Thr Met Thr Ala Ser Gly Ser Ser
    1175                1180                1185

Ala Met Ser Pro Glu Thr Thr Val Ser Gln Ile Ala Val Glu Ser
    1190                1195                1200

Asp Leu Gly Gln Met Leu Glu Glu Gly Lys Lys Ala Thr Asn Leu
    1205                1210                1215

Thr Arg Glu Thr Lys Leu Ile Asn Asp Cys His Gly Ser Val Ser
    1220                1225                1230

Glu Ala Ser Ser Glu Gln Lys Ile Ala Lys Leu Asp Val Ser Asn
    1235                1240                1245

Val Ala Thr Asp Thr Glu Arg Leu Glu Leu Lys Ala Ser Pro Asn
    1250                1255                1260

Val Glu Ala Pro Gln Pro His Arg His Val Leu Glu Ile Ser Arg
    1265                1270                1275

Gln His Glu Gln Pro Gly Gln Gly Ile Ala Pro Asp Ala Val Asn
    1280                1285                1290

Gly Gln Arg Arg Asp Ser Arg Ser Thr Val Phe Arg Ile Pro Glu
    1295                1300                1305

Phe Asn Trp Ser Gln Met His Gln Arg Leu Leu Thr Asp Leu Leu
    1310                1315                1320

Phe Ser Ile Glu Thr Asp Ile Gln Met Trp Arg Ser His Ser Thr
    1325                1330                1335

Lys Thr Val Met Asp Phe Val Asn Ser Ser Asp Asn Val Ile Phe
    1340                1345                1350

Val His Asn Thr Ile His Leu Ile Ser Gln Val Met Asp Asn Met
    1355                1360                1365

Val Met Ala Cys Gly Gly Ile Leu Pro Leu Leu Ser Ala Ala Thr
    1370                1375                1380

Ser Ala Thr His Glu Leu Glu Asn Ile Glu Pro Thr Gln Gly Leu
    1385                1390                1395

Ser Ile Glu Ala Ser Val Thr Phe Leu Gln Arg Leu Ile Ser Leu
    1400                1405                1410

Val Asp Val Leu Ile Phe Ala Ser Ser Leu Gly Phe Thr Glu Ile
    1415                1420                1425

Glu Ala Glu Lys Ser Met Ser Ser Gly Gly Ile Leu Arg Gln Cys
    1430                1435                1440

Leu Arg Leu Val Cys Ala Val Ala Val Arg Asn Cys Leu Glu Cys
    1445                1450                1455
```

-continued

```
Gln Gln His Ser Gln Leu Lys Thr Arg Gly Asp Lys Ala Leu Lys
    1460                1465                1470

Pro Met His Ser Leu Ile Pro Leu Gly Lys Ser Ala Ala Lys Ser
    1475                1480                1485

Pro Val Asp Ile Val Thr Gly Gly Ile Ser Pro Val Arg Asp Leu
    1490                1495                1500

Asp Arg Leu Leu Gln Asp Met Asp Ile Asn Arg Leu Arg Ala Val
    1505                1510                1515

Val Phe Arg Asp Ile Glu Asp Ser Lys Gln Ala Gln Phe Leu Ala
    1520                1525                1530

Leu Ala Val Val Tyr Phe Ile Ser Val Leu Met Val Ser Lys Tyr
    1535                1540                1545

Arg Asp Ile Leu Glu Pro Gln Asn Glu Arg His Ser Gln Ser Cys
    1550                1555                1560

Thr Glu Thr Gly Ser Glu Asn Glu Asn Val Ser Leu Ser Glu Ile
    1565                1570                1575

Thr Pro Ala Ala Phe Ser Thr Leu Thr Thr Ala Ser Val Glu Glu
    1580                1585                1590

Ser Glu Ser Thr Ser Ser Ala Arg Arg Arg Asp Ser Gly Ile Gly
    1595                1600                1605

Glu Glu Thr Ala Thr Gly Leu Gly Ser His Val Glu Val Thr Pro
    1610                1615                1620

His Thr Ala Pro Pro Gly Val Ser Ala Gly Pro Asp Ala Ile Ser
    1625                1630                1635

Glu Val Leu Ser Thr Leu Ser Leu Glu Val Asn Lys Ser Pro Glu
    1640                1645                1650

Thr Lys Asn Asp Arg Gly Asn Asp Leu Asp Thr Lys Ala Thr Pro
    1655                1660                1665

Ser Val Ser Val Ser Lys Asn Val Asn Val Lys Asp Ile Leu Arg
    1670                1675                1680

Ser Leu Val Asn Ile Pro Ala Asp Gly Val Thr Val Asp Pro Ala
    1685                1690                1695

Leu Leu Pro Pro Ala Cys Leu Gly Ala Leu Gly Asp Leu Ser Val
    1700                1705                1710

Glu Gln Pro Val Gln Phe Arg Ser Phe Asp Arg Ser Val Ile Val
    1715                1720                1725

Ala Ala Lys Lys Ser Ala Val Ser Pro Ser Thr Phe Asn Thr Ser
    1730                1735                1740

Ile Pro Thr Asn Ala Val Ser Val Val Ser Ser Val Asp Ser Ala
    1745                1750                1755

Gln Ala Ser Asp Met Gly Gly Glu Ser Pro Gly Ser Arg Ser Ser
    1760                1765                1770

Asn Ala Lys Leu Pro Ser Val Pro Thr Val Asp Ser Val Ser Gln
    1775                1780                1785

Asp Pro Val Ser Asn Met Ser Ile Thr Glu Arg Leu Glu His Ala
    1790                1795                1800

Leu Glu Lys Ala Ala Pro Leu Leu Arg Glu Ile Phe Val Asp Phe
    1805                1810                1815

Ala Pro Phe Leu Ser Arg Thr Leu Leu Gly Ser His Gly Gln Glu
    1820                1825                1830

Leu Leu Ile Glu Gly Thr Ser Leu Val Cys Met Lys Ser Ser Ser
    1835                1840                1845
```

-continued

Ser Val Val Glu Leu Val Met Leu Leu Cys Ser Gln Glu Trp Gln
1850                    1855                1860

Asn Ser Ile Gln Lys Asn Ala Gly Leu Ala Phe Ile Glu Leu Val
1865                    1870                1875

Asn Glu Gly Arg Leu Leu Ser Gln Thr Met Lys Asp His Leu Val
1880                    1885                1890

Arg Val Ala Asn Glu Ala Glu Phe Ile Leu Ser Arg Gln Arg Ala
1895                    1900                1905

Glu Asp Ile His Arg His Ala Glu Phe Glu Ser Leu Cys Ala Gln
1910                    1915                1920

Tyr Ser Ala Asp Lys Arg Glu Asp Glu Lys Met Cys Asp His Leu
1925                    1930                1935

Ile Arg Ala Ala Lys Tyr Arg Asp His Val Thr Ala Thr Gln Leu
1940                    1945                1950

Ile Gln Lys Ile Ile Asn Ile Leu Thr Asp Lys His Gly Ala Trp
1955                    1960                1965

Gly Asn Ser Ala Val Ser Arg Pro Leu Glu Phe Trp Arg Leu Asp
1970                    1975                1980

Tyr Trp Glu Asp Asp Leu Arg Arg Arg Arg Phe Val Arg Asn
1985                    1990                1995

Pro Leu Gly Ser Thr His Pro Glu Ala Thr Leu Lys Thr Ala Val
2000                    2005                2010

Glu His Val Cys Ile Phe Lys Leu Arg Glu Asn Ser Lys Ala Thr
2015                    2020                2025

Asp Glu Asp Ile Leu Ala Lys Gly Lys Gln Ser Ile Arg Ser Gln
2030                    2035                2040

Ala Leu Gly Asn Gln Asn Ser Glu Asn Glu Ile Leu Leu Glu Gly
2045                    2050                2055

Asp Asp Asp Thr Leu Ser Ser Val Asp Glu Lys Asp Leu Glu Asn
2060                    2065                2070

Leu Ala Gly Pro Val Ser Leu Ser Thr Pro Ala Gln Leu Val Ala
2075                    2080                2085

Pro Ser Val Val Lys Gly Thr Leu Ser Val Thr Ser Ser Glu
2090                    2095                2100

Leu Tyr Phe Glu Val Asp Glu Asp Pro Asn Phe Lys Lys Ile
2105                    2110                2115

Asp Pro Lys Ile Leu Ala Tyr Thr Glu Gly Leu His Gly Lys Trp
2120                    2125                2130

Leu Phe Thr Glu Ile Arg Ser Ile Phe Ser Arg Arg Tyr Leu Leu
2135                    2140                2145

Gln Asn Thr Ala Leu Glu Ile Phe Met Ala Asn Arg Val Ala Val
2150                    2155                2160

Met Phe Asn Phe Pro Asp Pro Ala Thr Val Lys Lys Val Val Asn
2165                    2170                2175

Phe Leu Pro Arg Val Gly Val Gly Thr Ser Phe Gly Leu Pro Gln
2180                    2185                2190

Thr Arg Arg Ile Ser Leu Ala Ser Pro Arg Gln Leu Phe Lys Ala
2195                    2200                2205

Ser Asn Met Thr Gln Arg Trp Gln His Arg Glu Ile Ser Asn Phe
2210                    2215                2220

Glu Tyr Leu Met Phe Leu Asn Thr Ile Ala Gly Arg Ser Tyr Asn
2225                    2230                2235

```
Asp Leu Asn Gln Tyr Pro Val Phe Pro Trp Val Ile Thr Asn Tyr
    2240                2245                2250

Glu Ser Glu Glu Leu Asp Leu Thr Leu Pro Thr Asn Phe Arg Asp
    2255                2260                2265

Leu Ser Lys Pro Ile Gly Ala Leu Asn Pro Lys Arg Ala Ala Phe
    2270                2275                2280

Phe Ala Glu Arg Tyr Glu Ser Trp Glu Asp Asp Gln Val Pro Lys
    2285                2290                2295

Phe His Tyr Gly Thr His Tyr Ser Thr Ala Ser Phe Val Leu Ala
    2300                2305                2310

Trp Leu Leu Arg Ile Glu Pro Phe Thr Thr Tyr Phe Leu Asn Leu
    2315                2320                2325

Gln Gly Gly Lys Phe Asp His Ala Asp Arg Thr Phe Ser Ser Ile
    2330                2335                2340

Ser Arg Ala Trp Arg Asn Ser Gln Arg Asp Thr Ser Asp Ile Lys
    2345                2350                2355

Glu Leu Ile Pro Glu Phe Tyr Tyr Leu Pro Glu Met Phe Val Asn
    2360                2365                2370

Phe Asn Asn Tyr Asn Leu Gly Val Met Asp Asp Gly Thr Val Val
    2375                2380                2385

Ser Asp Val Glu Leu Pro Pro Trp Ala Lys Thr Ser Glu Glu Phe
    2390                2395                2400

Val His Ile Asn Arg Leu Ala Leu Glu Ser Glu Phe Val Ser Cys
    2405                2410                2415

Gln Leu His Gln Trp Ile Asp Leu Ile Phe Gly Tyr Lys Gln Gln
    2420                2425                2430

Gly Pro Glu Ala Val Arg Ala Leu Asn Val Phe Tyr Tyr Leu Thr
    2435                2440                2445

Tyr Glu Gly Ala Val Asn Leu Asn Ser Ile Thr Asp Pro Val Leu
    2450                2455                2460

Arg Glu Ala Val Glu Ala Gln Ile Arg Ser Phe Gly Gln Thr Pro
    2465                2470                2475

Ser Gln Leu Leu Ile Glu Pro His Pro Pro Arg Gly Ser Ala Met
    2480                2485                2490

Gln Val Ser Pro Leu Met Phe Thr Asp Lys Ala Gln Gln Asp Val
    2495                2500                2505

Ile Met Val Leu Lys Phe Pro Ser Asn Ser Pro Val Thr His Val
    2510                2515                2520

Ala Ala Asn Thr Gln Pro Gly Leu Ala Thr Pro Ala Val Ile Thr
    2525                2530                2535

Val Thr Ala Asn Arg Leu Phe Ala Val Asn Lys Trp His Asn Leu
    2540                2545                2550

Pro Ala His Gln Gly Ala Val Gln Asp Gln Pro Tyr Gln Leu Pro
    2555                2560                2565

Val Glu Ile Asp Pro Leu Ile Gly Leu Ser Leu Pro Ser Leu Phe
    2570                2575                2580

Ala Ile His
    2585

<210> SEQ ID NO 22
<211> LENGTH: 2868
<212> TYPE: PRT
<213> ORGANISM: Homo sapiens
```

```
<220> FEATURE:
<221> NAME/KEY: DOMAIN
<222> LOCATION: (1)..(72)
<223> OTHER INFORMATION: G peptide
<220> FEATURE:
<221> NAME/KEY: DOMAIN
<222> LOCATION: (82)..(393)
<223> OTHER INFORMATION: HSH (helix-sheet-helix) domain
<220> FEATURE:
<221> NAME/KEY: DOMAIN
<222> LOCATION: (979)..(1302)
<223> OTHER INFORMATION: SET Domain (Rich in Serine, Glutamic acid and
      Threonine)
<220> FEATURE:
<221> NAME/KEY: DOMAIN
<222> LOCATION: (2035)..(2169)
<223> OTHER INFORMATION: WDL (WD-like) domain
<220> FEATURE:
<221> NAME/KEY: DOMAIN
<222> LOCATION: (2212)..(2489)
<223> OTHER INFORMATION: BEACH domain
<220> FEATURE:
<221> NAME/KEY: REPEAT
<222> LOCATION: (2597)..(2640)
<223> OTHER INFORMATION: WD repeat
<220> FEATURE:
<221> NAME/KEY: REPEAT
<222> LOCATION: (2641)..(2699)
<223> OTHER INFORMATION: WD repeat
<220> FEATURE:
<221> NAME/KEY: REPEAT
<222> LOCATION: (2700)..(2783)
<223> OTHER INFORMATION: WD repeat
<220> FEATURE:
<221> NAME/KEY: REPEAT
<222> LOCATION: (2784)..(2824)
<223> OTHER INFORMATION: WD repeat
<220> FEATURE:
<221> NAME/KEY: REPEAT
<222> LOCATION: (2825)..(2868)
<223> OTHER INFORMATION: WD repeat

<400> SEQUENCE: 22

Met Ala Ser Glu Asp Asn Arg Val Pro Ser Pro Pro Thr Gly Asp
1               5                   10                  15

Asp Gly Gly Gly Gly Arg Glu Glu Thr Pro Thr Glu Gly Gly Ala
            20                  25                  30

Leu Ser Leu Lys Pro Gly Leu Pro Ile Arg Gly Ile Arg Met Lys Phe
            35                  40                  45

Ala Val Leu Thr Gly Leu Val Glu Val Gly Glu Val Ser Asn Arg Asp
        50                  55                  60

Ile Val Glu Thr Val Phe Asn Leu Leu Val Gly Gly Gln Phe Asp Leu
65                  70                  75                  80

Glu Met Asn Phe Ile Ile Gln Glu Gly Glu Ser Ile Asn Cys Met Val
                85                  90                  95

Asp Leu Leu Glu Lys Cys Asp Ile Thr Cys Gln Ala Glu Val Trp Ser
            100                 105                 110

Met Phe Thr Ala Ile Leu Lys Lys Ser Ile Arg Asn Leu Gln Val Cys
        115                 120                 125

Thr Glu Val Gly Leu Val Glu Lys Val Leu Gly Lys Ile Glu Lys Val
    130                 135                 140

Asp Asn Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Arg Trp Pro Pro His Ala Gly Lys Leu Leu Ser
            180                 185                 190
```

```
Val Leu Lys His Met Pro Gln Lys Tyr Gly Pro Asp Ala Phe Phe Asn
        195                 200                 205

Phe Pro Gly Lys Ser Ala Ala Ile Ala Leu Pro Pro Ile Ala Lys
210                 215                 220

Trp Pro Tyr Gln Asn Gly Phe Thr Phe His Thr Trp Leu Arg Met Asp
225                 230                 235                 240

Pro Val Asn Asn Ile Asn Val Asp Lys Asp Lys Pro Tyr Leu Tyr Cys
                245                 250                 255

Phe Arg Thr Ser Lys Gly Leu Gly Tyr Ser Ala His Phe Val Gly Gly
                260                 265                 270

Cys Leu Ile Val Thr Ser Ile Lys Ser Lys Gly Lys Gly Phe Gln His
        275                 280                 285

Cys Val Lys Phe Asp Phe Lys Pro Gln Lys Trp Tyr Met Val Thr Ile
        290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
                340                 345                 350

Ala Asn Arg Val Phe Cys Gly Gln Met Thr Ala Val Tyr Leu Phe Ser
                355                 360                 365

Glu Ala Leu Asn Ala Ala Gln Ile Phe Ala Ile Tyr Gln Leu Gly Leu
                370                 375                 380

Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
                405                 410                 415

Ile Ala Phe Thr Tyr Asn Pro Arg Ala Thr Asp Ala Gln Leu Cys Leu
                420                 425                 430

Glu Ser Ser Pro Lys Asp Asn Pro Ser Ile Phe Val His Ser Pro His
                435                 440                 445

Ala Leu Met Leu Gln Asp Val Lys Ala Val Leu Thr His Ser Ile Gln
                450                 455                 460

Ser Ala Met His Ser Ile Gly Gly Val Gln Val Leu Phe Pro Leu Phe
465                 470                 475                 480

Ala Gln Leu Asp Tyr Arg Gln Tyr Leu Ser Asp Glu Ile Asp Leu Thr
                485                 490                 495

Ile Cys Ser Thr Leu Leu Ala Phe Ile Met Glu Leu Leu Lys Asn Ser
                500                 505                 510

Ile Ala Met Gln Glu Gln Met Leu Ala Cys Lys Gly Phe Leu Val Ile
                515                 520                 525

Gly Tyr Ser Leu Glu Lys Ser Ser Lys Ser His Val Ser Arg Ala Val
                530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Val Leu Leu Asn Pro
                565                 570                 575

Ala Ile Trp Ile His Thr Pro Ala Lys Val Gln Leu Met Leu Tyr Thr
                580                 585                 590

Tyr Leu Ser Thr Glu Phe Ile Gly Thr Val Asn Ile Tyr Asn Thr Ile
                595                 600                 605
```

-continued

```
Arg Arg Val Gly Thr Val Leu Leu Ile Met His Thr Leu Lys Tyr Tyr
    610             615                 620
Tyr Trp Ala Val Asn Pro Gln Asp Arg Ser Gly Ile Thr Pro Lys Gly
625             630                 635                 640
Leu Asp Gly Pro Arg Pro Asn Gln Lys Glu Met Leu Ser Leu Arg Ala
                645                 650                 655
Phe Leu Leu Met Phe Ile Lys Gln Leu Val Met Lys Asp Ser Gly Val
                660                 665                 670
Lys Glu Asp Glu Leu Gln Ala Ile Leu Asn Tyr Leu Leu Thr Met His
    675                 680                 685
Glu Asp Asn Leu Met Asp Val Leu Gln Leu Leu Val Ala Leu Met
690                 695                 700
Ser Glu His Pro Asn Ser Met Ile Pro Ala Phe Asp Gln Arg Asn Gly
705                 710                 715                 720
Leu Arg Val Ile Tyr Lys Leu Leu Ala Ser Lys Ser Glu Gly Ile Arg
                725                 730                 735
Val Gln Ala Leu Lys Ala Met Gly Tyr Phe Leu Lys His Arg Pro Pro
                740                 745                 750
Lys Arg Lys Ala Glu Val Met Leu Gly His Gly Leu Phe Ser Leu Leu
    755                 760                 765
Ala Glu Arg Leu Met Leu Gln Thr Asn Leu Ile Thr Met Thr Thr Tyr
770                 775                 780
Asn Val Leu Phe Glu Ile Leu Ile Glu Gln Ile Gly Thr Gln Val Ile
785                 790                 795                 800
His Lys Gln His Pro Asp Pro Asp Ser Ser Val Lys Ile Gln Asn Pro
                805                 810                 815
Gln Ile Leu Lys Val Ile Ala Thr Leu Leu Arg Asn Ser Pro Gln Cys
                820                 825                 830
Pro Glu Ser Met Glu Val Arg Arg Ala Phe Leu Ser Asp Met Ile Lys
                835                 840                 845
Leu Phe Asn Asn Ser Arg Glu Asn Arg Arg Ser Leu Leu Gln Cys Ser
    850                 855                 860
Val Trp Gln Glu Trp Met Leu Ser Leu Cys Tyr Phe Asn Pro Lys Asn
865                 870                 875                 880
Ser Asp Glu Gln Lys Ile Thr Glu Met Val Tyr Ala Ile Phe Arg Ile
                885                 890                 895
Leu Leu Tyr His Ala Val Lys Tyr Glu Trp Gly Gly Trp Arg Val Trp
                900                 905                 910
Val Asp Thr Leu Ser Ile Thr His Ser Lys Val Thr Phe Glu Ile His
                915                 920                 925
Lys Glu Asn Leu Ala Asn Ile Phe Arg Glu Gln Gln Gly Lys Val Asp
    930                 935                 940
Glu Glu Ile Gly Leu Cys Ser Ser Thr Ser Val Gln Ala Ala Ser Gly
945                 950                 955                 960
Ile Arg Arg Asp Ile Asn Val Ser Val Gly Ser Gln Gln Pro Asp Thr
                965                 970                 975
Lys Asp Ser Pro Val Cys Pro His Phe Thr Thr Asn Gly Asn Glu Asn
                980                 985                 990
Ser Ser Ile Glu Lys Thr Ser Ser  Leu Glu Ser Ala Ser  Asn Ile Glu
        995                 1000                1005
Leu Gln Thr Thr Asn Thr Ser  Tyr Glu Glu Met Lys  Ala Glu Gln
        1010                1015                1020
```

-continued

```
Glu Asn Gln Glu Leu Pro Asp Glu Gly Thr Leu Glu Glu Thr Leu
1025                1030                1035

Thr Asn Glu Thr Arg Asn Ala Asp Asp Leu Glu Val Ser Ser Asp
1040                1045                1050

Ile Ile Glu Ala Val Ala Ile Ser Ser Asn Ser Phe Ile Thr Thr
1055                1060                1065

Gly Lys Asp Ser Met Thr Val Ser Glu Val Thr Ala Ser Ile Ser
1070                1075                1080

Ser Pro Ser Glu Glu Asp Ala Ser Glu Met Pro Glu Phe Leu Asp
1085                1090                1095

Lys Ser Ile Val Glu Glu Glu Asp Asp Tyr Val Glu Leu
1100                1105                1110

Lys Val Glu Gly Ser Pro Thr Glu Glu Ala Asn Leu Pro Thr Glu
1115                1120                1125

Leu Gln Asp Asn Ser Leu Ser Pro Ala Ala Ser Glu Ala Gly Glu
1130                1135                1140

Lys Leu Asp Met Phe Gly Asn Asp Asp Lys Leu Ile Phe Gln Glu
1145                1150                1155

Gly Lys Pro Val Thr Glu Lys Gln Thr Asp Thr Glu Thr Gln Asp
1160                1165                1170

Ser Lys Asp Ser Gly Ile Gln Thr Met Thr Ala Ser Gly Ser Ser
1175                1180                1185

Ala Met Ser Pro Glu Thr Thr Val Ser Gln Ile Ala Val Glu Ser
1190                1195                1200

Asp Leu Gly Gln Met Leu Glu Glu Gly Lys Lys Ala Thr Asn Leu
1205                1210                1215

Thr Arg Glu Thr Lys Leu Ile Asn Asp Cys His Gly Ser Val Ser
1220                1225                1230

Glu Ala Ser Ser Glu Gln Lys Ile Ala Lys Leu Asp Val Ser Asn
1235                1240                1245

Val Ala Thr Asp Thr Glu Arg Leu Glu Leu Lys Ala Ser Pro Asn
1250                1255                1260

Val Glu Ala Pro Gln Pro His Arg His Val Leu Glu Ile Ser Arg
1265                1270                1275

Gln His Glu Gln Pro Gly Gln Gly Ile Ala Pro Asp Ala Val Asn
1280                1285                1290

Gly Gln Arg Arg Asp Ser Arg Ser Thr Val Phe Arg Ile Pro Glu
1295                1300                1305

Phe Asn Trp Ser Gln Met His Gln Arg Leu Leu Thr Asp Leu Leu
1310                1315                1320

Phe Ser Ile Glu Thr Asp Ile Gln Met Trp Arg Ser His Ser Thr
1325                1330                1335

Lys Thr Val Met Asp Phe Val Asn Ser Ser Asp Asn Val Ile Phe
1340                1345                1350

Val His Asn Thr Ile His Leu Ile Ser Gln Val Met Asp Asn Met
1355                1360                1365

Val Met Ala Cys Gly Gly Ile Leu Pro Leu Leu Ser Ala Ala Thr
1370                1375                1380

Ser Ala Thr His Glu Leu Glu Asn Ile Glu Pro Thr Gln Gly Leu
1385                1390                1395

Ser Ile Glu Ala Ser Val Thr Phe Leu Gln Arg Leu Ile Ser Leu
1400                1405                1410
```

-continued

```
Val Asp Val Leu Ile Phe Ala Ser Ser Leu Gly Phe Thr Glu Ile
1415                1420                1425

Glu Ala Glu Lys Ser Met Ser Ser Gly Gly Ile Leu Arg Gln Cys
1430                1435                1440

Leu Arg Leu Val Cys Ala Val Ala Val Arg Asn Cys Leu Glu Cys
1445                1450                1455

Gln Gln His Ser Gln Leu Lys Thr Arg Gly Asp Lys Ala Leu Lys
1460                1465                1470

Pro Met His Ser Leu Ile Pro Leu Gly Lys Ser Ala Ala Lys Ser
1475                1480                1485

Pro Val Asp Ile Val Thr Gly Gly Ile Ser Pro Val Arg Asp Leu
1490                1495                1500

Asp Arg Leu Leu Gln Asp Met Asp Ile Asn Arg Leu Arg Ala Val
1505                1510                1515

Val Phe Arg Asp Ile Glu Asp Ser Lys Gln Ala Gln Phe Leu Ala
1520                1525                1530

Leu Ala Val Val Tyr Phe Ile Ser Val Leu Met Val Ser Lys Tyr
1535                1540                1545

Arg Asp Ile Leu Glu Pro Gln Asn Glu Arg His Ser Gln Ser Cys
1550                1555                1560

Thr Glu Thr Gly Ser Glu Asn Glu Asn Val Ser Leu Ser Glu Ile
1565                1570                1575

Thr Pro Ala Ala Phe Ser Thr Leu Thr Thr Ala Ser Val Glu Glu
1580                1585                1590

Ser Glu Ser Thr Ser Ser Ala Arg Arg Arg Asp Ser Gly Ile Gly
1595                1600                1605

Glu Glu Thr Ala Thr Gly Leu Gly Ser His Val Glu Val Thr Pro
1610                1615                1620

His Thr Ala Pro Pro Gly Val Ser Ala Gly Pro Asp Ala Ile Ser
1625                1630                1635

Glu Val Leu Ser Thr Leu Ser Leu Glu Val Asn Lys Ser Pro Glu
1640                1645                1650

Thr Lys Asn Asp Arg Gly Asn Asp Leu Asp Thr Lys Ala Thr Pro
1655                1660                1665

Ser Val Ser Val Ser Lys Asn Val Asn Val Lys Asp Ile Leu Arg
1670                1675                1680

Ser Leu Val Asn Ile Pro Ala Asp Gly Val Thr Val Asp Pro Ala
1685                1690                1695

Leu Leu Pro Pro Ala Cys Leu Gly Ala Leu Gly Asp Leu Ser Val
1700                1705                1710

Glu Gln Pro Val Gln Phe Arg Ser Phe Asp Arg Ser Val Ile Val
1715                1720                1725

Ala Ala Lys Lys Ser Ala Val Ser Pro Ser Thr Phe Asn Thr Ser
1730                1735                1740

Ile Pro Thr Asn Ala Val Ser Val Val Ser Ser Val Asp Ser Ala
1745                1750                1755

Gln Ala Ser Asp Met Gly Gly Glu Ser Pro Gly Ser Arg Ser Ser
1760                1765                1770

Asn Ala Lys Leu Pro Ser Val Pro Thr Val Asp Ser Val Ser Gln
1775                1780                1785

Asp Pro Val Ser Asn Met Ser Ile Thr Glu Arg Leu Glu His Ala
1790                1795                1800
```

-continued

```
Leu Glu Lys Ala Ala Pro Leu Leu Arg Glu Ile Phe Val Asp Phe
    1805                1810                1815

Ala Pro Phe Leu Ser Arg Thr Leu Leu Gly Ser His Gly Gln Glu
    1820                1825                1830

Leu Leu Ile Glu Gly Thr Ser Leu Val Cys Met Lys Ser Ser Ser
    1835                1840                1845

Ser Val Val Glu Leu Val Met Leu Leu Cys Ser Gln Glu Trp Gln
    1850                1855                1860

Asn Ser Ile Gln Lys Asn Ala Gly Leu Ala Phe Ile Glu Leu Val
    1865                1870                1875

Asn Glu Gly Arg Leu Leu Ser Gln Thr Met Lys Asp His Leu Val
    1880                1885                1890

Arg Val Ala Asn Glu Ala Glu Phe Ile Leu Ser Arg Gln Arg Ala
    1895                1900                1905

Glu Asp Ile His Arg His Ala Glu Phe Glu Ser Leu Cys Ala Gln
    1910                1915                1920

Tyr Ser Ala Asp Lys Arg Glu Asp Glu Lys Met Cys Asp His Leu
    1925                1930                1935

Ile Arg Ala Ala Lys Tyr Arg Asp His Val Thr Ala Thr Gln Leu
    1940                1945                1950

Ile Gln Lys Ile Ile Asn Ile Leu Thr Asp Lys His Gly Ala Trp
    1955                1960                1965

Gly Asn Ser Ala Val Ser Arg Pro Leu Glu Phe Trp Arg Leu Asp
    1970                1975                1980

Tyr Trp Glu Asp Asp Leu Arg Arg Arg Arg Arg Phe Val Arg Asn
    1985                1990                1995

Pro Leu Gly Ser Thr His Pro Glu Ala Thr Leu Lys Thr Ala Val
    2000                2005                2010

Glu His Val Cys Ile Phe Lys Leu Arg Glu Asn Ser Lys Ala Thr
    2015                2020                2025

Asp Glu Asp Ile Leu Ala Lys Gly Lys Gln Ser Ile Arg Ser Gln
    2030                2035                2040

Ala Leu Gly Asn Gln Asn Ser Glu Asn Glu Ile Leu Leu Glu Gly
    2045                2050                2055

Asp Asp Asp Thr Leu Ser Ser Val Asp Glu Lys Asp Leu Glu Asn
    2060                2065                2070

Leu Ala Gly Pro Val Ser Leu Ser Thr Pro Ala Gln Leu Val Ala
    2075                2080                2085

Pro Ser Val Val Val Lys Gly Thr Leu Ser Val Thr Ser Ser Glu
    2090                2095                2100

Leu Tyr Phe Glu Val Asp Glu Glu Asp Pro Asn Phe Lys Lys Ile
    2105                2110                2115

Asp Pro Lys Ile Leu Ala Tyr Thr Glu Gly Leu His Gly Lys Trp
    2120                2125                2130

Leu Phe Thr Glu Ile Arg Ser Ile Phe Ser Arg Arg Tyr Leu Leu
    2135                2140                2145

Gln Asn Thr Ala Leu Glu Ile Phe Met Ala Asn Arg Val Ala Val
    2150                2155                2160

Met Phe Asn Phe Pro Asp Pro Ala Thr Val Lys Lys Val Val Asn
    2165                2170                2175

Phe Leu Pro Arg Val Gly Val Gly Thr Ser Phe Gly Leu Pro Gln
    2180                2185                2190
```

-continued

```
Thr Arg Arg Ile Ser Leu Ala Ser Pro Arg Gln Leu Phe Lys Ala
2195                2200                2205

Ser Asn Met Thr Gln Arg Trp Gln His Arg Glu Ile Ser Asn Phe
2210                2215                2220

Glu Tyr Leu Met Phe Leu Asn Thr Ile Ala Gly Arg Ser Tyr Asn
2225                2230                2235

Asp Leu Asn Gln Tyr Pro Val Phe Pro Trp Val Ile Thr Asn Tyr
2240                2245                2250

Glu Ser Glu Glu Leu Asp Leu Thr Leu Pro Thr Asn Phe Arg Asp
2255                2260                2265

Leu Ser Lys Pro Ile Gly Ala Leu Asn Pro Lys Arg Ala Ala Phe
2270                2275                2280

Phe Ala Glu Arg Tyr Glu Ser Trp Glu Asp Asp Gln Val Pro Lys
2285                2290                2295

Phe His Tyr Gly Thr His Tyr Ser Thr Ala Ser Phe Val Leu Ala
2300                2305                2310

Trp Leu Leu Arg Ile Glu Pro Phe Thr Thr Tyr Phe Leu Asn Leu
2315                2320                2325

Gln Gly Gly Lys Phe Asp His Ala Asp Arg Thr Phe Ser Ser Ile
2330                2335                2340

Ser Arg Ala Trp Arg Asn Ser Gln Arg Asp Thr Ser Asp Ile Lys
2345                2350                2355

Glu Leu Ile Pro Glu Phe Tyr Tyr Leu Pro Glu Met Phe Val Asn
2360                2365                2370

Phe Asn Asn Tyr Asn Leu Gly Val Met Asp Asp Gly Thr Val Val
2375                2380                2385

Ser Asp Val Glu Leu Pro Pro Trp Ala Lys Thr Ser Glu Glu Phe
2390                2395                2400

Val His Ile Asn Arg Leu Ala Leu Glu Ser Glu Phe Val Ser Cys
2405                2410                2415

Gln Leu His Gln Trp Ile Asp Leu Ile Phe Gly Tyr Lys Gln Gln
2420                2425                2430

Gly Pro Glu Ala Val Arg Ala Leu Asn Val Phe Tyr Tyr Leu Thr
2435                2440                2445

Tyr Glu Gly Ala Val Asn Leu Asn Ser Ile Thr Asp Pro Val Leu
2450                2455                2460

Arg Glu Ala Val Glu Ala Gln Ile Arg Ser Phe Gly Gln Thr Pro
2465                2470                2475

Ser Gln Leu Leu Ile Glu Pro His Pro Pro Arg Gly Ser Ala Met
2480                2485                2490

Gln Val Tyr Leu Leu Leu Gln Ser Pro Leu Met Phe Thr Asp Lys
2495                2500                2505

Ala Gln Gln Asp Val Ile Met Val Leu Lys Phe Pro Ser Asn Ser
2510                2515                2520

Pro Val Thr His Val Ala Ala Asn Thr Gln Pro Gly Leu Ala Thr
2525                2530                2535

Pro Ala Val Ile Thr Val Thr Ala Asn Arg Leu Phe Ala Val Asn
2540                2545                2550

Lys Trp His Asn Leu Pro Ala His Gln Gly Ala Val Gln Asp Gln
2555                2560                2565

Pro Tyr Gln Leu Pro Val Glu Ile Asp Pro Leu Ile Ala Ser Asn
2570                2575                2580
```

```
Thr Gly Met His Arg Arg Gln Ile Thr Asp Leu Leu Asp Gln Ser
2585                2590                2595

Ile Gln Val His Ser Gln Cys Phe Val Ile Thr Ser Asp Asn Arg
2600                2605                2610

Tyr Ile Leu Val Cys Gly Phe Trp Asp Lys Ser Phe Arg Val Tyr
2615                2620                2625

Ser Thr Asp Thr Gly Arg Leu Ile Gln Val Val Phe Gly His Trp
2630                2635                2640

Asp Val Val Thr Cys Leu Ala Arg Ser Glu Ser Tyr Ile Gly Gly
2645                2650                2655

Asn Cys Tyr Ile Leu Ser Gly Ser Arg Asp Ala Thr Leu Leu Leu
2660                2665                2670

Trp Tyr Trp Asn Gly Lys Cys Ser Gly Ile Gly Asp Asn Pro Gly
2675                2680                2685

Ser Glu Thr Ala Ala Pro Arg Ala Ile Leu Thr Gly His Asp Tyr
2690                2695                2700

Glu Val Thr Cys Ala Ala Val Cys Ala Glu Leu Gly Leu Val Leu
2705                2710                2715

Ser Gly Ser Gln Glu Gly Pro Cys Leu Ile His Ser Met Asn Gly
2720                2725                2730

Asp Leu Leu Arg Thr Leu Glu Gly Pro Glu Asn Cys Leu Lys Pro
2735                2740                2745

Lys Leu Ile Gln Ala Ser Arg Glu Gly His Cys Val Ile Phe Tyr
2750                2755                2760

Glu Asn Gly Leu Phe Cys Thr Phe Ser Val Asn Gly Lys Leu Gln
2765                2770                2775

Ala Thr Met Glu Thr Asp Asp Asn Ile Arg Ala Ile Gln Leu Ser
2780                2785                2790

Arg Asp Gly Gln Tyr Leu Leu Thr Gly Gly Asp Arg Gly Val Val
2795                2800                2805

Val Val Arg Gln Val Ser Asp Leu Lys Gln Leu Phe Ala Tyr Pro
2810                2815                2820

Gly Cys Asp Ala Gly Ile Arg Ala Met Ala Leu Ser Tyr Asp Gln
2825                2830                2835

Arg Cys Ile Ile Ser Gly Met Ala Ser Gly Ser Ile Val Leu Phe
2840                2845                2850

Tyr Asn Asp Phe Asn Arg Trp His His Glu Tyr Gln Thr Arg Tyr
2855                2860                2865

<210> SEQ ID NO 23
<211> LENGTH: 2411
<212> TYPE: PRT
<213> ORGANISM: Homo sapiens
<220> FEATURE:
<221> NAME/KEY: DOMAIN
<222> LOCATION: (1)..(72)
<223> OTHER INFORMATION: G peptide
<220> FEATURE:
<221> NAME/KEY: DOMAIN
<222> LOCATION: (82)..(393)
<223> OTHER INFORMATION: HSH (helix-sheet-helix) domain
<220> FEATURE:
<221> NAME/KEY: DOMAIN
<222> LOCATION: (979)..(1302)
<223> OTHER INFORMATION: SET Domain (Rich in Serine, Glutamic acid and
      Threonine)
<220> FEATURE:
<221> NAME/KEY: DOMAIN
<222> LOCATION: (2035)..(2169)
<223> OTHER INFORMATION: WDL (WD-like) domain
```

```
<220> FEATURE:
<221> NAME/KEY: DOMAIN
<222> LOCATION: (2212)..(2409)
<223> OTHER INFORMATION: BEACH domain

<400> SEQUENCE: 23
```

| | | | | | | | | | | | | | | | |
|---|---|---|---|---|---|---|---|---|---|---|---|---|---|---|---|
| Met | Ala | Ser | Glu | Asp | Asn | Arg | Val | Pro | Ser | Pro | Pro | Thr | Gly | Asp | |
| 1 | | | | 5 | | | | | 10 | | | | | 15 | |
| Asp | Gly | Gly | Gly | Gly | Arg | Glu | Glu | Thr | Pro | Thr | Glu | Gly | Gly | Ala | |
| | | | 20 | | | | | 25 | | | | | 30 | | |
| Leu | Ser | Leu | Lys | Pro | Gly | Leu | Pro | Ile | Arg | Gly | Ile | Arg | Met | Lys | Phe |
| | | | 35 | | | | | 40 | | | | | 45 | | |
| Ala | Val | Leu | Thr | Gly | Leu | Val | Glu | Val | Gly | Glu | Val | Ser | Asn | Arg | Asp |
| | 50 | | | | | 55 | | | | | 60 | | | | |
| Ile | Val | Glu | Thr | Val | Phe | Asn | Leu | Leu | Val | Gly | Gln | Phe | Asp | Leu | |
| 65 | | | | | 70 | | | | | 75 | | | | | 80 |
| Glu | Met | Asn | Phe | Ile | Ile | Gln | Glu | Gly | Glu | Ser | Ile | Asn | Cys | Met | Val |
| | | | | 85 | | | | | 90 | | | | | 95 | |
| Asp | Leu | Leu | Glu | Lys | Cys | Asp | Ile | Thr | Cys | Gln | Ala | Glu | Val | Trp | Ser |
| | | | 100 | | | | | 105 | | | | | 110 | | |
| Met | Phe | Thr | Ala | Ile | Leu | Lys | Lys | Ser | Ile | Arg | Asn | Leu | Gln | Val | Cys |
| | | | 115 | | | | | 120 | | | | | 125 | | |
| Thr | Glu | Val | Gly | Leu | Val | Glu | Lys | Val | Leu | Gly | Lys | Ile | Glu | Lys | Val |
| | | | 130 | | | | | 135 | | | | | 140 | | |
| Asp | Asn | Met | Ile | Ala | Asp | Leu | Leu | Val | Asp | Met | Leu | Gly | Val | Leu | Ala |
| 145 | | | | | 150 | | | | | 155 | | | | | 160 |
| Ser | Tyr | Asn | Leu | Thr | Val | Arg | Glu | Leu | Lys | Leu | Phe | Phe | Ser | Lys | Leu |
| | | | | 165 | | | | | 170 | | | | | 175 | |
| Gln | Gly | Asp | Lys | Gly | Arg | Trp | Pro | Pro | His | Ala | Gly | Lys | Leu | Leu | Ser |
| | | | 180 | | | | | 185 | | | | | 190 | | |
| Val | Leu | Lys | His | Met | Pro | Gln | Lys | Tyr | Gly | Pro | Asp | Ala | Phe | Phe | Asn |
| | | | 195 | | | | | 200 | | | | | 205 | | |
| Phe | Pro | Gly | Lys | Ser | Ala | Ala | Ala | Ile | Ala | Leu | Pro | Pro | Ile | Ala | Lys |
| | | 210 | | | | | 215 | | | | | 220 | | | |
| Trp | Pro | Tyr | Gln | Asn | Gly | Phe | Thr | Phe | His | Thr | Trp | Leu | Arg | Met | Asp |
| 225 | | | | | 230 | | | | | 235 | | | | | 240 |
| Pro | Val | Asn | Asn | Ile | Asn | Val | Asp | Lys | Asp | Lys | Pro | Tyr | Leu | Tyr | Cys |
| | | | | 245 | | | | | 250 | | | | | 255 | |
| Phe | Arg | Thr | Ser | Lys | Gly | Leu | Gly | Tyr | Ser | Ala | His | Phe | Val | Gly | Gly |
| | | | 260 | | | | | 265 | | | | | 270 | | |
| Cys | Leu | Ile | Val | Thr | Ser | Ile | Lys | Ser | Lys | Gly | Lys | Gly | Phe | Gln | His |
| | | | 275 | | | | | 280 | | | | | 285 | | |
| Cys | Val | Lys | Phe | Asp | Phe | Lys | Pro | Gln | Lys | Trp | Tyr | Met | Val | Thr | Ile |
| | | 290 | | | | | 295 | | | | | 300 | | | |
| Val | His | Ile | Tyr | Asn | Arg | Trp | Lys | Asn | Ser | Glu | Leu | Arg | Cys | Tyr | Val |
| 305 | | | | | 310 | | | | | 315 | | | | | 320 |
| Asn | Gly | Glu | Leu | Ala | Ser | Tyr | Gly | Glu | Ile | Thr | Trp | Phe | Val | Asn | Thr |
| | | | | 325 | | | | | 330 | | | | | 335 | |
| Ser | Asp | Thr | Phe | Asp | Lys | Cys | Phe | Leu | Gly | Ser | Ser | Glu | Thr | Ala | Asp |
| | | | 340 | | | | | 345 | | | | | 350 | | |
| Ala | Asn | Arg | Val | Phe | Cys | Gly | Gln | Met | Thr | Ala | Val | Tyr | Leu | Phe | Ser |
| | | | 355 | | | | | 360 | | | | | 365 | | |
| Glu | Ala | Leu | Asn | Ala | Ala | Gln | Ile | Phe | Ala | Ile | Tyr | Gln | Leu | Gly | Leu |
| | | 370 | | | | | 375 | | | | | 380 | | | |

-continued

```
Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
            405                 410                 415

Ile Ala Phe Thr Tyr Asn Pro Arg Ala Thr Asp Ala Gln Leu Cys Leu
        420                 425                 430

Glu Ser Ser Pro Lys Asp Asn Pro Ser Ile Phe Val His Ser Pro His
            435                 440                 445

Ala Leu Met Leu Gln Asp Val Lys Ala Val Leu Thr His Ser Ile Gln
        450                 455                 460

Ser Ala Met His Ser Ile Gly Gly Val Gln Val Leu Phe Pro Leu Phe
465                 470                 475                 480

Ala Gln Leu Asp Tyr Arg Gln Tyr Leu Ser Asp Glu Ile Asp Leu Thr
            485                 490                 495

Ile Cys Ser Thr Leu Leu Ala Phe Ile Met Glu Leu Leu Lys Asn Ser
        500                 505                 510

Ile Ala Met Gln Glu Gln Met Leu Ala Cys Lys Gly Phe Leu Val Ile
            515                 520                 525

Gly Tyr Ser Leu Glu Lys Ser Ser Lys Ser His Val Ser Arg Ala Val
        530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Val Leu Leu Asn Pro
            565                 570                 575

Ala Ile Trp Ile His Thr Pro Ala Lys Val Gln Leu Met Leu Tyr Thr
        580                 585                 590

Tyr Leu Ser Thr Glu Phe Ile Gly Thr Val Asn Ile Tyr Asn Thr Ile
            595                 600                 605

Arg Arg Val Gly Thr Val Leu Leu Ile Met His Thr Leu Lys Tyr Tyr
610                 615                 620

Tyr Trp Ala Val Asn Pro Gln Asp Arg Ser Gly Ile Thr Pro Lys Gly
625                 630                 635                 640

Leu Asp Gly Pro Arg Pro Asn Gln Lys Glu Met Leu Ser Leu Arg Ala
            645                 650                 655

Phe Leu Leu Met Phe Ile Lys Gln Leu Val Met Lys Asp Ser Gly Val
        660                 665                 670

Lys Glu Asp Glu Leu Gln Ala Ile Leu Asn Tyr Leu Leu Thr Met His
            675                 680                 685

Glu Asp Asp Asn Leu Met Asp Val Leu Gln Leu Leu Val Ala Leu Met
690                 695                 700

Ser Glu His Pro Asn Ser Met Ile Pro Ala Phe Asp Gln Arg Asn Gly
705                 710                 715                 720

Leu Arg Val Ile Tyr Lys Leu Leu Ala Ser Lys Ser Glu Gly Ile Arg
            725                 730                 735

Val Gln Ala Leu Lys Ala Met Gly Tyr Phe Leu Lys His Arg Pro Pro
        740                 745                 750

Lys Arg Lys Ala Glu Val Met Leu Gly His Gly Leu Phe Ser Leu Leu
            755                 760                 765

Ala Glu Arg Leu Met Leu Gln Thr Asn Leu Ile Thr Met Thr Thr Tyr
        770                 775                 780

Asn Val Leu Phe Glu Ile Leu Ile Glu Gln Ile Gly Thr Gln Val Ile
785                 790                 795                 800
```

```
            -continued

His Lys Gln His Pro Asp Pro Asp Ser Ser Val Lys Ile Gln Asn Pro
                        805                 810                 815

Gln Ile Leu Lys Val Ile Ala Thr Leu Leu Arg Asn Ser Pro Gln Cys
                        820                 825                 830

Pro Glu Ser Met Glu Val Arg Arg Ala Phe Leu Ser Asp Met Ile Lys
                        835                 840                 845

Leu Phe Asn Asn Ser Arg Glu Asn Arg Arg Ser Leu Leu Gln Cys Ser
                        850                 855                 860

Val Trp Gln Glu Trp Met Leu Ser Leu Cys Tyr Phe Asn Pro Lys Asn
        865                 870                 875                 880

Ser Asp Glu Gln Lys Ile Thr Glu Met Val Tyr Ala Ile Phe Arg Ile
                        885                 890                 895

Leu Leu Tyr His Ala Val Lys Tyr Glu Trp Gly Gly Trp Arg Val Trp
                        900                 905                 910

Val Asp Thr Leu Ser Ile Thr His Ser Lys Val Thr Phe Glu Ile His
                        915                 920                 925

Lys Glu Asn Leu Ala Asn Ile Phe Arg Glu Gln Gln Gly Lys Val Asp
                        930                 935                 940

Glu Glu Ile Gly Leu Cys Ser Ser Thr Ser Val Gln Ala Ala Ser Gly
        945                 950                 955                 960

Ile Arg Arg Asp Ile Asn Val Ser Val Gly Ser Gln Gln Pro Asp Thr
                        965                 970                 975

Lys Asp Ser Pro Val Cys Pro His Phe Thr Thr Asn Gly Asn Glu Asn
                        980                 985                 990

Ser Ser Ile Glu Lys Thr Ser Ser  Leu Glu Ser Ala Ser  Asn Ile Glu
                        995                 1000                1005

Leu Gln Thr Thr Asn Thr Ser  Tyr Glu Glu Met Lys  Ala Glu Gln
                1010                1015                1020

Glu Asn Gln Glu Leu Pro Asp  Glu Gly Thr Leu Glu  Glu Thr Leu
                1025                1030                1035

Thr Asn Glu Thr Arg Asn Ala  Asp Asp Leu Glu Val  Ser Ser Asp
                1040                1045                1050

Ile Ile Glu Ala Val Ala Ile  Ser Ser Asn Ser Phe  Ile Thr Thr
                1055                1060                1065

Gly Lys Asp Ser Met Thr Val  Ser Glu Val Thr Ala  Ser Ile Ser
                1070                1075                1080

Ser Pro Ser Glu Glu Asp Ala  Ser Glu Met Pro Glu  Phe Leu Asp
                1085                1090                1095

Lys Ser Ile Val Glu Glu Glu  Asp Asp Asp Tyr  Val Glu Leu
                1100                1105                1110

Lys Val Glu Gly Ser Pro Thr  Glu Glu Ala Asn Leu  Pro Thr Glu
                1115                1120                1125

Leu Gln Asp Asn Ser Leu Ser  Pro Ala Ala Ser Glu  Ala Gly Glu
                1130                1135                1140

Lys Leu Asp Met Phe Gly Asn  Asp Asp Lys Leu Ile  Phe Gln Glu
                1145                1150                1155

Gly Lys Pro Val Thr Glu Lys  Gln Thr Asp Thr Glu  Thr Gln Asp
                1160                1165                1170

Ser Lys Asp Ser Gly Ile Gln  Thr Met Thr Ala Ser  Gly Ser Ser
                1175                1180                1185

Ala Met Ser Pro Glu Thr Thr  Val Ser Gln Ile Ala  Val Glu Ser
                1190                1195                1200
```

-continued

```
Asp Leu Gly Gln Met Leu Glu Glu Gly Lys Lys Ala Thr Asn Leu
    1205                1210                1215

Thr Arg Glu Thr Lys Leu Ile Asn Asp Cys His Gly Ser Val Ser
    1220                1225                1230

Glu Ala Ser Ser Glu Gln Lys Ile Ala Lys Leu Asp Val Ser Asn
    1235                1240                1245

Val Ala Thr Asp Thr Glu Arg Leu Glu Leu Lys Ala Ser Pro Asn
    1250                1255                1260

Val Glu Ala Pro Gln Pro His Arg His Val Leu Glu Ile Ser Arg
    1265                1270                1275

Gln His Glu Gln Pro Gly Gln Gly Ile Ala Pro Asp Ala Val Asn
    1280                1285                1290

Gly Gln Arg Arg Asp Ser Arg Ser Thr Val Phe Arg Ile Pro Glu
    1295                1300                1305

Phe Asn Trp Ser Gln Met His Gln Arg Leu Leu Thr Asp Leu Leu
    1310                1315                1320

Phe Ser Ile Glu Thr Asp Ile Gln Met Trp Arg Ser His Ser Thr
    1325                1330                1335

Lys Thr Val Met Asp Phe Val Asn Ser Ser Asp Asn Val Ile Phe
    1340                1345                1350

Val His Asn Thr Ile His Leu Ile Ser Gln Val Met Asp Asn Met
    1355                1360                1365

Val Met Ala Cys Gly Gly Ile Leu Pro Leu Leu Ser Ala Ala Thr
    1370                1375                1380

Ser Ala Thr His Glu Leu Glu Asn Ile Glu Pro Thr Gln Gly Leu
    1385                1390                1395

Ser Ile Glu Ala Ser Val Thr Phe Leu Gln Arg Leu Ile Ser Leu
    1400                1405                1410

Val Asp Val Leu Ile Phe Ala Ser Ser Leu Gly Phe Thr Glu Ile
    1415                1420                1425

Glu Ala Glu Lys Ser Met Ser Ser Gly Gly Ile Leu Arg Gln Cys
    1430                1435                1440

Leu Arg Leu Val Cys Ala Val Ala Val Arg Asn Cys Leu Glu Cys
    1445                1450                1455

Gln Gln His Ser Gln Leu Lys Thr Arg Gly Asp Lys Ala Leu Lys
    1460                1465                1470

Pro Met His Ser Leu Ile Pro Leu Gly Lys Ser Ala Ala Lys Ser
    1475                1480                1485

Pro Val Asp Ile Val Thr Gly Gly Ile Ser Pro Val Arg Asp Leu
    1490                1495                1500

Asp Arg Leu Leu Gln Asp Met Asp Ile Asn Arg Leu Arg Ala Val
    1505                1510                1515

Val Phe Arg Asp Ile Glu Asp Ser Lys Gln Ala Gln Phe Leu Ala
    1520                1525                1530

Leu Ala Val Val Tyr Phe Ile Ser Val Leu Met Val Ser Lys Tyr
    1535                1540                1545

Arg Asp Ile Leu Glu Pro Gln Asn Glu Arg His Ser Gln Ser Cys
    1550                1555                1560

Thr Glu Thr Gly Ser Glu Asn Glu Asn Val Ser Leu Ser Glu Ile
    1565                1570                1575

Thr Pro Ala Ala Phe Ser Thr Leu Thr Thr Ala Ser Val Glu Glu
    1580                1585                1590
```

```
Ser Glu Ser Thr Ser Ser Ala Arg Arg Asp Ser Gly Ile Gly
1595                1600                1605

Glu Glu Thr Ala Thr Gly Leu Gly Ser His Val Glu Val Thr Pro
1610                1615                1620

His Thr Ala Pro Pro Gly Val Ser Ala Gly Pro Asp Ala Ile Ser
1625                1630                1635

Glu Val Leu Ser Thr Leu Ser Leu Glu Val Asn Lys Ser Pro Glu
1640                1645                1650

Thr Lys Asn Asp Arg Gly Asn Asp Leu Asp Thr Lys Ala Thr Pro
1655                1660                1665

Ser Val Ser Val Ser Lys Asn Val Asn Val Lys Asp Ile Leu Arg
1670                1675                1680

Ser Leu Val Asn Ile Pro Ala Asp Gly Val Thr Val Asp Pro Ala
1685                1690                1695

Leu Leu Pro Pro Ala Cys Leu Gly Ala Leu Gly Asp Leu Ser Val
1700                1705                1710

Glu Gln Pro Val Gln Phe Arg Ser Phe Asp Arg Ser Val Ile Val
1715                1720                1725

Ala Ala Lys Lys Ser Ala Val Ser Pro Ser Thr Phe Asn Thr Ser
1730                1735                1740

Ile Pro Thr Asn Ala Val Ser Val Val Ser Ser Val Asp Ser Ala
1745                1750                1755

Gln Ala Ser Asp Met Gly Gly Glu Ser Pro Gly Ser Arg Ser Ser
1760                1765                1770

Asn Ala Lys Leu Pro Ser Val Pro Thr Val Asp Ser Val Ser Gln
1775                1780                1785

Asp Pro Val Ser Asn Met Ser Ile Thr Glu Arg Leu Glu His Ala
1790                1795                1800

Leu Glu Lys Ala Ala Pro Leu Leu Arg Glu Ile Phe Val Asp Phe
1805                1810                1815

Ala Pro Phe Leu Ser Arg Thr Leu Leu Gly Ser His Gly Gln Glu
1820                1825                1830

Leu Leu Ile Glu Gly Thr Ser Leu Val Cys Met Lys Ser Ser Ser
1835                1840                1845

Ser Val Val Glu Leu Val Met Leu Leu Cys Ser Gln Glu Trp Gln
1850                1855                1860

Asn Ser Ile Gln Lys Asn Ala Gly Leu Ala Phe Ile Glu Leu Val
1865                1870                1875

Asn Glu Gly Arg Leu Leu Ser Gln Thr Met Lys Asp His Leu Val
1880                1885                1890

Arg Val Ala Asn Glu Ala Glu Phe Ile Leu Ser Arg Gln Arg Ala
1895                1900                1905

Glu Asp Ile His Arg His Ala Glu Phe Glu Ser Leu Cys Ala Gln
1910                1915                1920

Tyr Ser Ala Asp Lys Arg Glu Asp Glu Lys Met Cys Asp His Leu
1925                1930                1935

Ile Arg Ala Ala Lys Tyr Arg Asp His Val Thr Ala Thr Gln Leu
1940                1945                1950

Ile Gln Lys Ile Ile Asn Ile Leu Thr Asp Lys His Gly Ala Trp
1955                1960                1965

Gly Asn Ser Ala Val Ser Arg Pro Leu Glu Phe Trp Arg Leu Asp
1970                1975                1980
```

```
Tyr Trp Glu Asp Asp Leu Arg Arg Arg Arg Phe Val Arg Asn
    1985                1990                1995

Pro Leu Gly Ser Thr His Pro Glu Ala Thr Leu Lys Thr Ala Val
    2000                2005                2010

Glu His Val Cys Ile Phe Lys Leu Arg Glu Asn Ser Lys Ala Thr
    2015                2020                2025

Asp Glu Asp Ile Leu Ala Lys Gly Lys Gln Ser Ile Arg Ser Gln
    2030                2035                2040

Ala Leu Gly Asn Gln Asn Ser Glu Asn Glu Ile Leu Leu Glu Gly
    2045                2050                2055

Asp Asp Asp Thr Leu Ser Ser Val Asp Glu Lys Asp Leu Glu Asn
    2060                2065                2070

Leu Ala Gly Pro Val Ser Leu Ser Thr Pro Ala Gln Leu Val Ala
    2075                2080                2085

Pro Ser Val Val Lys Gly Thr Leu Ser Val Thr Ser Ser Glu
    2090                2095                2100

Leu Tyr Phe Glu Val Asp Glu Asp Pro Asn Phe Lys Lys Ile
    2105                2110                2115

Asp Pro Lys Ile Leu Ala Tyr Thr Glu Gly Leu His Gly Lys Trp
    2120                2125                2130

Leu Phe Thr Glu Ile Arg Ser Ile Phe Ser Arg Arg Tyr Leu Leu
    2135                2140                2145

Gln Asn Thr Ala Leu Glu Ile Phe Met Ala Asn Arg Val Ala Val
    2150                2155                2160

Met Phe Asn Phe Pro Asp Pro Ala Thr Val Lys Lys Val Val Asn
    2165                2170                2175

Phe Leu Pro Arg Val Gly Val Gly Thr Ser Phe Gly Leu Pro Gln
    2180                2185                2190

Thr Arg Arg Ile Ser Leu Ala Ser Pro Arg Gln Leu Phe Lys Ala
    2195                2200                2205

Ser Asn Met Thr Gln Arg Trp Gln His Arg Glu Ile Ser Asn Phe
    2210                2215                2220

Glu Tyr Leu Met Phe Leu Asn Thr Ile Ala Gly Arg Ser Tyr Asn
    2225                2230                2235

Asp Leu Asn Gln Tyr Pro Val Phe Pro Trp Val Ile Thr Asn Tyr
    2240                2245                2250

Glu Ser Glu Glu Leu Asp Leu Thr Leu Pro Thr Asn Phe Arg Asp
    2255                2260                2265

Leu Ser Lys Pro Ile Gly Ala Leu Asn Pro Lys Arg Ala Ala Phe
    2270                2275                2280

Phe Ala Glu Arg Tyr Glu Ser Trp Glu Asp Asp Gln Val Pro Lys
    2285                2290                2295

Phe His Tyr Gly Thr His Tyr Ser Thr Ala Ser Phe Val Leu Ala
    2300                2305                2310

Trp Leu Leu Arg Ile Glu Pro Phe Thr Thr Tyr Phe Leu Asn Leu
    2315                2320                2325

Gln Gly Gly Lys Phe Asp His Ala Asp Arg Thr Phe Ser Ser Ile
    2330                2335                2340

Ser Arg Ala Trp Arg Asn Ser Gln Arg Asp Thr Ser Asp Ile Lys
    2345                2350                2355

Glu Leu Ile Pro Glu Phe Tyr Tyr Leu Pro Glu Met Phe Val Asn
    2360                2365                2370
```

```
Phe Asn Asn Tyr Asn Leu Gly Val Met Asp Asp Gly Thr Val Val
    2375                2380                2385

Ser Asp Val Glu Leu Pro Pro Trp Ala Lys Thr Ser Glu Glu Phe
    2390                2395                2400

Val His Ile Asn Arg Leu Val Arg
    2405                2410

<210> SEQ ID NO 24
<211> LENGTH: 72
<212> TYPE: PRT
<213> ORGANISM: Homo sapiens
<220> FEATURE:
<221> NAME/KEY: DOMAIN
<222> LOCATION: (1)..(72)
<223> OTHER INFORMATION: G peptide

<400> SEQUENCE: 24

Met Ala Ser Glu Asp Asn Arg Val Pro Ser Pro Pro Thr Gly Asp
1               5                   10                  15

Asp Gly Gly Gly Gly Arg Glu Glu Thr Pro Thr Glu Gly Gly Ala
                20                  25                  30

Leu Ser Leu Lys Pro Gly Leu Pro Ile Arg Gly Ile Arg Met Lys Phe
            35                  40                  45

Ala Val Leu Thr Gly Leu Val Glu Val Gly Glu Val Ser Asn Arg Asp
        50                  55                  60

Ile Val Glu Thr Val Phe Asn Leu
65                  70

<210> SEQ ID NO 25
<211> LENGTH: 341
<212> TYPE: PRT
<213> ORGANISM: Mus musculus

<400> SEQUENCE: 25

Leu Thr Gly Leu Val Glu Val Gly Glu Val Ser Asn Arg Asp Ile Val
1               5                   10                  15

Glu Thr Val Phe Asn Leu Leu Val Gly Gly Gln Phe Asp Leu Glu Met
                20                  25                  30

Asn Phe Ile Ile Gln Glu Gly Glu Ser Ile Met Cys Met Val Glu Leu
            35                  40                  45

Leu Glu Lys Cys Asp Val Thr Cys Gln Ala Glu Val Trp Ser Met Phe
        50                  55                  60

Thr Ala Ile Leu Lys Lys Ser Ile Arg Asn Leu Gln Val Cys Thr Glu
65                  70                  75                  80

Val Gly Leu Val Glu Lys Val Leu Gly Lys Ile Glu Lys Val Asp Ser
                85                  90                  95

Met Ile Ala Asp Leu Leu Val Asp Met Leu Gly Val Leu Ala Ser Tyr
            100                 105                 110

Asn Leu Thr Val Arg Glu Leu Lys Leu Phe Ser Lys Leu Gln Gly
        115                 120                 125

Asp Lys Gly Gln Trp Pro Pro His Ala Gly Lys Leu Leu Ser Val Leu
    130                 135                 140

Lys His Met Pro Gln Lys Tyr Gly Pro Asp Ala Phe Asn Phe Pro
145                 150                 155                 160

Gly Lys Ser Ala Ala Ala Ile Ala Leu Pro Pro Ile Ala Arg Trp Pro
                165                 170                 175

Tyr Gln Asn Gly Phe Thr Phe His Thr Trp Leu Arg Met Asp Pro Val
            180                 185                 190
```

```
Asn Asn Ile Asn Val Asp Lys Asp Lys Pro Tyr Leu Tyr Cys Phe Arg
            195                 200                 205

Thr Ser Lys Gly Leu Gly Tyr Ser Ala His Phe Val Gly Gly Cys Leu
    210                 215                 220

Ile Ile Thr Ser Ile Lys Ser Lys Gly Lys Gly Phe Gln His Cys Val
225                 230                 235                 240

Lys Phe Asp Phe Lys Pro Gln Lys Trp Tyr Met Val Thr Ile Val His
                245                 250                 255

Ile Tyr Asn Arg Trp Lys Asn Ser Glu Leu Arg Cys Tyr Val Asn Gly
            260                 265                 270

Glu Leu Ala Ser Tyr Gly Glu Ile Thr Trp Phe Val Asn Thr Ser Asp
        275                 280                 285

Thr Phe Asp Lys Cys Phe Leu Gly Ser Ser Glu Thr Ala Asp Ala Asn
290                 295                 300

Arg Val Phe Cys Gly Gln Met Thr Ala Val Tyr Leu Phe Ser Asp Ala
305                 310                 315                 320

Leu Asn Ala Ala Gln Ile Phe Ala Ile Tyr Gln Leu Gly Leu Gly Tyr
                325                 330                 335

Lys Gly Thr Phe Lys
            340

<210> SEQ ID NO 26
<211> LENGTH: 341
<212> TYPE: PRT
<213> ORGANISM: Homo sapiens

<400> SEQUENCE: 26

Leu Thr Gly Leu Val Glu Val Gly Val Ser Asn Arg Asp Ile Val
1               5                   10                  15

Glu Thr Val Phe Asn Leu Leu Val Gly Gly Gln Phe Asp Leu Glu Met
            20                  25                  30

Asn Phe Ile Ile Gln Glu Gly Glu Ser Ile Asn Cys Met Val Asp Leu
        35                  40                  45

Leu Glu Lys Cys Asp Ile Thr Cys Gln Ala Glu Val Trp Ser Met Phe
50                  55                  60

Thr Ala Ile Leu Lys Lys Ser Ile Arg Asn Leu Gln Val Cys Thr Glu
65                  70                  75                  80

Val Gly Leu Val Glu Lys Val Leu Gly Lys Ile Glu Lys Val Asp Asn
                85                  90                  95

Met Ile Ala Asp Leu Leu Val Asp Met Leu Gly Val Leu Ala Ser Tyr
            100                 105                 110

Asn Leu Thr Val Arg Glu Leu Lys Leu Phe Phe Ser Lys Leu Gln Gly
        115                 120                 125

Asp Lys Gly Arg Trp Pro Pro His Ala Gly Lys Leu Leu Ser Val Leu
130                 135                 140

Lys His Met Pro Gln Lys Tyr Gly Pro Asp Ala Phe Phe Asn Phe Pro
145                 150                 155                 160

Gly Lys Ser Ala Ala Ile Ala Leu Pro Pro Ile Ala Lys Trp Pro
                165                 170                 175

Tyr Gln Asn Gly Phe Thr Phe His Thr Trp Leu Arg Met Asp Pro Val
            180                 185                 190

Asn Asn Ile Asn Val Asp Lys Asp Lys Pro Tyr Leu Tyr Cys Phe Arg
        195                 200                 205

Thr Ser Lys Gly Leu Gly Tyr Ser Ala His Phe Val Gly Gly Cys Leu
    210                 215                 220
```

```
Ile Val Thr Ser Ile Lys Ser Lys Gly Lys Gly Phe Gln His Cys Val
225                 230                 235                 240

Lys Phe Asp Phe Lys Pro Gln Lys Trp Tyr Met Val Thr Ile Val His
                245                 250                 255

Ile Tyr Asn Arg Trp Lys Asn Ser Glu Leu Arg Cys Tyr Val Asn Gly
            260                 265                 270

Glu Leu Ala Ser Tyr Gly Glu Ile Thr Trp Phe Val Asn Thr Ser Asp
        275                 280                 285

Thr Phe Asp Lys Cys Phe Leu Gly Ser Ser Glu Thr Ala Asp Ala Asn
    290                 295                 300

Arg Val Phe Cys Gly Gln Met Thr Ala Val Tyr Leu Phe Ser Glu Ala
305                 310                 315                 320

Leu Asn Ala Ala Gln Ile Phe Ala Ile Tyr Gln Leu Gly Leu Gly Tyr
                325                 330                 335

Lys Gly Thr Phe Lys
            340

<210> SEQ ID NO 27
<211> LENGTH: 206
<212> TYPE: PRT
<213> ORGANISM: Drosophila melanogaster

<400> SEQUENCE: 27

Leu Leu Phe Asn Ile Ala Leu Val Val Lys Phe Glu Leu Leu Leu Ile
1               5                   10                  15

Ala Phe Arg Ser His Phe Arg Phe Arg Phe Thr Phe Val Gln Ala Met
            20                  25                  30

Val Leu Pro Pro Leu Ala Lys Trp Pro Tyr Glu Asn Gly Phe Thr Phe
        35                  40                  45

Thr Thr Trp Cys Arg Leu Asp Pro Ile Asn Ser Val Asn Ile Glu Arg
    50                  55                  60

Glu Lys Pro Tyr Leu Tyr Ser Phe Lys Thr Ser Lys Gly Val Gly Tyr
65                  70                  75                  80

Thr Ala His Phe Val Gly Asn Cys Leu Val Leu Thr Ser Met Lys Val
                85                  90                  95

Lys Gly Lys Gly Phe Gln His Cys Val Lys Tyr Glu Phe Gln Pro Pro
            100                 105                 110

Lys Trp Tyr Met Ile Ala Ile Val Tyr Ile Tyr Asn Arg Trp Thr Lys
        115                 120                 125

Ser Glu Ile Lys Cys Leu Val Asn Gly Gln Leu Ala Ser Ser Thr Glu
    130                 135                 140

Met Ala Trp Phe Val Ser Thr Asn Asp Pro Phe Asp Lys Cys Tyr Ile
145                 150                 155                 160

Gly Ala Thr Pro Glu Leu Asp Glu Glu Arg Val Phe Cys Gly Gln Met
                165                 170                 175

Ser Ala Ile Tyr Leu Phe Ser Glu Ala Leu Thr Thr Gln Gln Ile Cys
            180                 185                 190

Ala Met His Arg Leu Gly Pro Gly Tyr Lys Ser Gln Phe Arg
        195                 200                 205

<210> SEQ ID NO 28
<211> LENGTH: 333
<212> TYPE: PRT
<213> ORGANISM: Caenorhabditis elegans
```

-continued

```
<400> SEQUENCE: 28

Val Val Asp Asn Leu Phe Asn Leu Leu Val Gly Gly His Phe Asp Gln
1               5                   10                  15

Glu Ser Lys Phe Val Ile Glu Asp Ala Ala Asn Val Asp His Met Leu
            20                  25                  30

Thr Leu Leu Ser His Cys Asp Tyr Asp Leu Gln Asn Glu Ile Trp Ser
        35                  40                  45

Leu Phe Leu Ala Val Met Lys Lys Ser Asn Arg Asn Leu Glu Ala Cys
    50                  55                  60

Thr Arg Val Gly Leu Ile Ser Lys Thr Gln Leu Phe Phe Arg Val Leu
65                  70                  75                  80

Asp Ile Leu Pro Glu Ala Pro Pro Leu Leu Ala Asp Leu Leu Val Gln
                85                  90                  95

Ile Ile Ala Ala Leu Val Ala Tyr Ser Ile Asn Val Lys Gln Thr Lys
            100                 105                 110

His Leu Leu Arg Ala Leu Lys Ser Thr Lys Glu Gln Trp Pro Pro Asn
        115                 120                 125

Ser Leu Lys Leu Leu His Val Leu Lys Glu Met Pro Gln His Asp Ser
    130                 135                 140

Ala Asp Val Phe Phe Ser Phe Pro Gly Lys Asp Gln Ser Gly Ile Ile
145                 150                 155                 160

Leu Pro Pro Ile Lys Thr Met Pro Tyr Gln Gln Gly Trp Thr Phe Ala
                165                 170                 175

Thr Trp Leu Arg Met Glu Pro Leu Asn Ser Val Thr Phe Glu Lys Glu
            180                 185                 190

Gln Pro Val Leu Tyr Ser Phe Arg Thr Ser Lys Gly Val Gly Tyr Ser
        195                 200                 205

Cys His Phe Thr Gly Asn Cys Leu Val Val Asn Val Glu Lys Thr Lys
    210                 215                 220

Gly Lys Glu Gln Ser Arg Cys Val Arg Ala Glu Leu Gly Ala Arg Lys
225                 230                 235                 240

Trp His His Ile Ala Ile Ala His Cys Tyr Ser Arg Trp Gly Arg Ser
                245                 250                 255

Asp Ile Lys Cys Phe Ile Asp Gly Gln Leu Ala Glu Thr Ile Glu Leu
            260                 265                 270

Ser Trp Val Val Thr Ser Ala Thr Asn Trp Asp Arg Cys Ser Ile Gly
        275                 280                 285

Val Ser Ala Asp Gly Thr Ala Asn Ser Ala Phe Cys Gly Gln Met Gly
    290                 295                 300

Ala Met Tyr Leu Phe Ala Glu Ala Leu Thr Leu Gln Gln Ala Asn Ser
305                 310                 315                 320

Leu Phe Cys Leu Gly Pro Val Tyr Gln Ser Thr Phe Lys
                325                 330

<210> SEQ ID NO 29
<211> LENGTH: 328
<212> TYPE: PRT
<213> ORGANISM: Arabidopsis thaliana

<400> SEQUENCE: 29

Ile Leu Pro Ser Cys Thr Arg Asn Arg Ala Met Cys Ser Thr Ala Gly
1               5                   10                  15

Leu Leu Gly Val Leu Leu Arg Ser Val Glu Ala Ile Thr Ser Lys Asp
            20                  25                  30
```

```
Val Asp Met Lys Trp Asn Ala Ala Ile Leu Leu Leu Cys Ile Gln
         35                  40                  45

His Leu Ala Gly His Ser Leu Ser Val Asp Asp Leu His Arg Trp Leu
 50                  55                  60

Gln Val Ile Lys Ala Ala Ile Thr Thr Ala Trp Ser Ser Pro Leu Met
65                  70                  75                  80

Leu Ala Leu Glu Lys Ala Met Ser Gly Lys Glu Ser Arg Gly Pro Ala
                 85                  90                  95

Cys Thr Phe Glu Phe Asp Gly Glu Ser Ser Gly Leu Leu Gly Pro Gly
                100                 105                 110

Glu Ser Arg Trp Pro Phe Thr Asn Gly Tyr Ala Phe Ala Thr Trp Ile
            115                 120                 125

Tyr Ile Glu Ser Phe Ala Asp Thr Leu Asn Ala Thr Ala Ala Ala
130                 135                 140

Ala Ile Ala Ala Ala Ala Ala Lys Ser Gly Lys Thr Ser Ala Met
145                 150                 155                 160

Ser Ala Ala Ala Ala Ser Ala Leu Ala Gly Gly Thr Ala His
                165                 170                 175

Met Pro Arg Leu Phe Ser Phe Leu Ser Ala Asp Asn Gln Gly Ile Glu
            180                 185                 190

Ala Tyr Phe His Ala Gln Phe Leu Val Val Glu Ser Gly Ser Gly Lys
        195                 200                 205

Gly Arg Lys Ser Ser Leu His Phe Thr His Ala Phe Lys Pro Gln Cys
    210                 215                 220

Trp Tyr Phe Ile Gly Leu Glu His Ser Cys Lys Gln Gly Leu Leu Gly
225                 230                 235                 240

Lys Ala Glu Ser Glu Leu Arg Leu Tyr Ile Asp Gly Ser Leu Tyr Glu
                245                 250                 255

Ser Arg Pro Phe Asp Phe Pro Arg Ile Ser Lys Pro Leu Ser Phe Cys
                260                 265                 270

Cys Ile Gly Thr Asn Pro Pro Thr Met Ala Gly Leu Gln Arg Arg
            275                 280                 285

Arg Arg Cys Cys Pro Leu Phe Ala Glu Met Gly Pro Val Tyr Ile Phe
290                 295                 300

Lys Glu Pro Ile Gly Pro Glu Arg Met Ala Arg Leu Ala Ser Arg Gly
305                 310                 315                 320

Gly Asp Val Leu Pro Cys Phe Gly
                325

<210> SEQ ID NO 30
<211> LENGTH: 373
<212> TYPE: PRT
<213> ORGANISM: Dictyostelium discoideum

<400> SEQUENCE: 30

Ile Met Thr Gly Val Leu Gly Thr Glu Phe Ser Lys Ser Val Val Asp
1               5                   10                  15

Phe Ile Phe Asp Met Val Thr Glu Asn Leu Asn Ala Ser Asp Gln Ile
                20                  25                  30

Ser Asn Gln Met Ile Ile Asn Asn Val Glu Ser Phe Asn Val Ile Leu
            35                  40                  45

Asp Ile Ile Pro His Ile Glu Asn Lys Asp Phe Arg Leu Gln Ile Ile
    50                  55                  60

Ser Arg Ile Asn Lys Met Ala Glu Tyr Gly Arg Tyr Asn Gln Glu Ala
65                  70                  75                  80
```

```
Leu Ser Lys Leu Ser Ile Pro Ile Trp Ile Leu Ser Arg Phe Pro Ser
                85                  90                  95

Asn Leu Ser Asn Ala Asn Asp Pro Leu Gln Pro Leu Leu Ser Leu
            100                 105                 110

Ile Gln Thr Val Gly Ala Asn Cys Leu Ser Gly Ser Glu Leu Arg Gln
            115                 120                 125

Phe Val Lys Leu Leu Gln Pro Glu His Ser Pro Glu Val Leu Leu Lys
        130                 135                 140

Ile Leu Ser Ser Met Ala Lys Ser Pro Pro Thr Pro Pro Tyr Phe Glu
145                 150                 155                 160

Phe Asn Leu Ser Lys Ile Pro Phe Gly Tyr Ile Arg Val Pro Ile Thr
                165                 170                 175

Glu Arg Ala Trp Pro Pro Thr Asn Gly Tyr Thr Ile Met Phe Trp Leu
            180                 185                 190

Tyr Ile Asp Lys Phe Pro Thr Val Asn Asn Asn Asn Asn Asn Asn Asn
        195                 200                 205

Ser Ser Asn Asn Ser Asn Asn Ser Asn Ser Asn Asn Asn Asn Asn Asn
        210                 215                 220

Asn Asn Asn Asn Asn Asp Gln Ile Asp Leu Val His Ile Tyr Ser Asp
225                 230                 235                 240

Asp Lys Lys Ser Ser Leu Tyr Ile Tyr Leu Lys Asn Gly Ile Ile Thr
                245                 250                 255

Val Asn Ile Ile Asn Ser Ser Lys Tyr Val Ile Glu Ile Pro Ser Tyr
            260                 265                 270

Lys Phe Val Glu Gly Lys Trp Tyr His Ile Gly Ile Val His Ala Arg
        275                 280                 285

Arg Leu Leu Gly Gly Thr Asp Phe Lys Leu Phe Val Asp Gly Phe Leu
290                 295                 300

Lys Tyr Thr Ala Thr Lys Ala Gln Tyr Pro Ala Gln Ile Thr Ser Gly
305                 310                 315                 320

Ser Met Leu Ile Cys Asp Ile Gly Val Ser Asn Gln Asn Arg Phe Pro
                325                 330                 335

Thr Asp Ser Ile Trp Arg Ile Gly Thr Phe Tyr Leu Leu Glu Asp Ser
            340                 345                 350

Leu Gly Ala Lys His Ile Asn Thr Ile Tyr Phe Leu Gly Pro Asn Tyr
        355                 360                 365

Ala Ser Asn Phe Lys
    370

<210> SEQ ID NO 31
<211> LENGTH: 374
<212> TYPE: PRT
<213> ORGANISM: Arabidopsis thaliana

<400> SEQUENCE: 31

Thr Ala Leu Ala Thr Ile Pro Glu Asn Glu Asn Thr Thr Phe Val Val
1               5                   10                  15

Thr Thr Pro Ser Gly Gln Phe Asn Pro Asp Lys Glu Arg Ile Tyr Asn
            20                  25                  30

Ala Gly Ala Val Arg Val Leu Ile Arg Ser Leu Leu Leu Phe Ser Pro
        35                  40                  45

Lys Met Gln Leu Glu Phe Leu Arg Leu Leu Glu Ser Leu Ala Arg Ala
    50                  55                  60

Ser Pro Phe Asn Gln Glu Asn Leu Thr Ser Ile Gly Cys Val Glu Leu
65                  70                  75                  80
```

```
Leu Leu Glu Ile Ile Tyr Pro Phe Leu Ala Gly Ser Ser Pro Phe Leu
             85                  90                  95

Ser Tyr Ala Leu Lys Ile Val Glu Ile Leu Gly Ala Tyr Arg Leu Ser
            100                 105                 110

Pro Ser Glu Leu Arg Met Leu Phe Arg Tyr Val Leu Gln Met Arg Ile
        115                 120                 125

Met Asn Ser Gly His Ala Ile Val Gly Met Met Glu Lys Leu Ile Leu
    130                 135                 140

Met Glu Asp Thr Ala Leu Glu His Leu Ser Leu Ala Pro Phe Val Glu
145                 150                 155                 160

Leu Asp Met Ser Lys Thr Gly His Ala Ser Val Gln Val Ser Leu Gly
                165                 170                 175

Glu Arg Ser Trp Pro Ala Ala Gly Tyr Ser Phe Val Cys Trp Phe
            180                 185                 190

Gln Phe Arg Asn Phe Leu Thr Thr Gln Gly Lys Glu Ser Glu Ala Ser
        195                 200                 205

Lys Ala Gly Gly Ser Ser Lys Thr Arg Met Thr Ser Ala Gln Gln His
    210                 215                 220

Glu Gln Asn Ile Phe Arg Met Phe Ser Val Gly Ala Val Ser Asn Glu
225                 230                 235                 240

Ser Pro Phe Tyr Ala Glu Leu Tyr Phe Gln Glu Asp Gly Ile Leu Thr
                245                 250                 255

Leu Ala Thr Ser Asn Ser His Ser Leu Ser Phe Ser Gly Leu Glu Ile
                260                 265                 270

Glu Glu Gly Arg Trp His His Leu Ala Val Val His Ser Lys Pro Asn
            275                 280                 285

Ala Leu Ala Gly Leu Phe Gln Ala Ser Val Ala Tyr Val Tyr Leu Asp
    290                 295                 300

Gly Lys Leu Arg His Thr Gly Lys Leu Gly Tyr Ser Pro Ser Pro Val
305                 310                 315                 320

Gly Lys Ser Leu Gln Val Thr Val Gly Thr Pro Ala Thr Cys Ala Arg
                325                 330                 335

Val Ser Asp Leu Thr Trp Lys Thr Arg Ser Cys Tyr Leu Phe Glu Glu
                340                 345                 350

Val Leu Thr Ser Gly Cys Ile Gly Phe Met Tyr Ile Leu Gly Arg Gly
            355                 360                 365

Tyr Lys Gly Leu Phe Gln
        370

<210> SEQ ID NO 32
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: inserted amino acid sequence in human LRBA-g

<400> SEQUENCE: 32

Tyr Leu Leu Leu Gln
1               5

<210> SEQ ID NO 33
<211> LENGTH: 646
<212> TYPE: DNA
<213> ORGANISM: Homo sapiens
```

```
<220> FEATURE:
<221> NAME/KEY: misc_feature
<222> LOCATION: (248)..(250)
<223> OTHER INFORMATION: translation initiation codon
<220> FEATURE:
<221> NAME/KEY: misc_feature
<222> LOCATION: (248)..(466)
<223> OTHER INFORMATION: ORF encodes the first 73 amino acids of the
      lrba protein
<220> FEATURE:
<221> NAME/KEY: misc_feature
<222> LOCATION: (464)..(466)
<223> OTHER INFORMATION: in-frame translation termination codon
<220> FEATURE:
<221> NAME/KEY: misc_feature
<222> LOCATION: (484)..(486)
<223> OTHER INFORMATION: out-of-frame translation termination codon
<220> FEATURE:
<221> NAME/KEY: misc_feature
<222> LOCATION: (466)..(598)
<223> OTHER INFORMATION: extra exon interrupting LRBA sequence
<220> FEATURE:
<221> NAME/KEY: misc_feature
<222> LOCATION: (487)..(489)
<223> OTHER INFORMATION: out-of-frame translation termination codon
<220> FEATURE:
<221> NAME/KEY: misc_feature
<222> LOCATION: (492)..(494)
<223> OTHER INFORMATION: out-of-frame translation termination codon
<220> FEATURE:
<221> NAME/KEY: misc_feature
<222> LOCATION: (499)..(501)
<223> OTHER INFORMATION: out-of-frame translation termination codon
<220> FEATURE:
<221> NAME/KEY: misc_feature
<222> LOCATION: (517)..(519)
<223> OTHER INFORMATION: out-of-frame translation termination codon
<220> FEATURE:
<221> NAME/KEY: misc_feature
<222> LOCATION: (551)..(553)
<223> OTHER INFORMATION: in-frame translation termination codon
<220> FEATURE:
<221> NAME/KEY: misc_feature
<222> LOCATION: (566)..(568)
<223> OTHER INFORMATION: in-frame translation termination codon
<220> FEATURE:
<221> NAME/KEY: misc_feature
<222> LOCATION: (570)..(572)
<223> OTHER INFORMATION: out-of-frame translation termination codon
<220> FEATURE:
<221> NAME/KEY: misc_feature
<222> LOCATION: (590)..(592)
<223> OTHER INFORMATION: in-frame translation termination codon

<400> SEQUENCE: 33
ggggtgagga cgagtccgga gtatctgggg tttggcgttg ttgtcagcct cggggagaga    60
gattggacaa atattctcca agaggaggag ggcgacgcca aggactttcc acatcaactg   120
ctttggggta tctccacaag ttggaagagg daccctttcg tttcattg cgtgtgttgt   180 gctcattacc agtgcagcga ctgccgtccc agggtgactc tgagttgtcc tttatcgtga   240
gctagcaatg gctagcgaag acaatcgtgt cccttccccg ccaccaacag gtgatgacgg   300
gggaggtgga gggagagaag aaacccctac tgaaggggt gcattgtctc tgaaaccagg   360
gctccccatc aggggcatca gaatgaaatt tgccgtgttg accggtttgg ttgaagttgg   420
agaagtatcc aatagggata ttgtagaaac tgtctttaac ctgtgagaaa cagaaatttg   480
tggtagtaat ataatccata attacttatt tgtgtgtgaa gacacaacat cttttggcag   540
aaggaggatt tgaactcctg ttctttagaa tgtgctgtgt tggagtggat gaccaaactt   600
ggtaggagga cagtttgatc tggaaatgaa tttcattatc caagaa             646
```

```
<210> SEQ ID NO 34
<211> LENGTH: 72
<212> TYPE: PRT
<213> ORGANISM: Homo sapiens

<400> SEQUENCE: 34

Met Ala Ser Glu Asp Asn Arg Val Pro Ser Pro Pro Thr Gly Asp
1               5                   10                  15

Asp Gly Gly Gly Gly Arg Glu Glu Thr Pro Thr Glu Gly Gly Ala
            20                  25                  30

Leu Ser Leu Lys Pro Gly Leu Pro Ile Arg Gly Ile Arg Met Lys Phe
        35                  40                  45

Ala Val Leu Thr Gly Leu Val Glu Val Gly Glu Val Ser Asn Arg Asp
    50                  55                  60

Ile Val Glu Thr Val Phe Asn Leu
65                  70

<210> SEQ ID NO 35
<211> LENGTH: 7
<212> TYPE: PRT
<213> ORGANISM: Homo sapiens

<400> SEQUENCE: 35

Met Asn Phe Ile Ile Gln Glu
1               5

<210> SEQ ID NO 36
<211> LENGTH: 9
<212> TYPE: PRT
<213> ORGANISM: Homo sapiens

<400> SEQUENCE: 36

Leu Val Gly Gly Gln Phe Asp Leu Glu
1               5

<210> SEQ ID NO 37
<211> LENGTH: 1920
<212> TYPE: DNA
<213> ORGANISM: Homo sapiens
<220> FEATURE:
<221> NAME/KEY: protein_bind
<222> LOCATION: (786)..(793)
<223> OTHER INFORMATION: E2F transcription binding site
<220> FEATURE:
<221> NAME/KEY: protein_bind
<222> LOCATION: (824)..(831)
<223> OTHER INFORMATION: E2F transcription binding site
<220> FEATURE:
<221> NAME/KEY: protein_bind
<222> LOCATION: (1066)..(1073)
<223> OTHER INFORMATION: E2F transcription binding site
<220> FEATURE:
<221> NAME/KEY: protein_bind
<222> LOCATION: (1187)..(1196)
<223> OTHER INFORMATION: Sp1 transcription binding site
<220> FEATURE:
<221> NAME/KEY: protein_bind
<222> LOCATION: (1290)..(1299)
<223> OTHER INFORMATION: Sp1 transcription binding site
<220> FEATURE:
<221> NAME/KEY: protein_bind
<222> LOCATION: (1295)..(1304)
<223> OTHER INFORMATION: Sp1 transcription binding site
<220> FEATURE:
<221> NAME/KEY: protein_bind
<222> LOCATION: (1303)..(1312)
<223> OTHER INFORMATION: c-ETs transcription binding site
```

```
<220> FEATURE:
<221> NAME/KEY: protein_bind
<222> LOCATION: (1411)..(1416)
<223> OTHER INFORMATION: AML-1a transcription binding site
<220> FEATURE:
<221> NAME/KEY: misc_feature
<222> LOCATION: (1353)..(1353)
<223> OTHER INFORMATION: transcription start site
<220> FEATURE:
<221> NAME/KEY: protein_bind
<222> LOCATION: (1533)..(1546)
<223> OTHER INFORMATION: Tst-1 transcription binding site
<220> FEATURE:
<221> NAME/KEY: protein_bind
<222> LOCATION: (1537)..(1543)
<223> OTHER INFORMATION: CdxA transcription binding site
<220> FEATURE:
<221> NAME/KEY: protein_bind
<222> LOCATION: (1541)..(1550)
<223> OTHER INFORMATION: HSF2 transcription binding site
<220> FEATURE:
<221> NAME/KEY: protein_bind
<222> LOCATION: (1543)..(1549)
<223> OTHER INFORMATION: CdxA transcription binding site
<220> FEATURE:
<221> NAME/KEY: misc_feature
<222> LOCATION: (1566)..(1566)
<223> OTHER INFORMATION: transcription start site
<220> FEATURE:
<221> NAME/KEY: protein_bind
<222> LOCATION: (1614)..(1622)
<223> OTHER INFORMATION: Sp1 transcription binding site
<220> FEATURE:
<221> NAME/KEY: misc_feature
<222> LOCATION: (1621)..(1621)
<223> OTHER INFORMATION: transcription start site
<220> FEATURE:
<221> NAME/KEY: protein_bind
<222> LOCATION: (1646)..(1651)
<223> OTHER INFORMATION: AML-1a transcription binding site
<220> FEATURE:
<221> NAME/KEY: protein_bind
<222> LOCATION: (1651)..(1658)
<223> OTHER INFORMATION: E2F transcription binding site
<220> FEATURE:
<221> NAME/KEY: protein_bind
<222> LOCATION: (1676)..(1691)
<223> OTHER INFORMATION: C/EBPa transcription binding site
<220> FEATURE:
<221> NAME/KEY: protein_bind
<222> LOCATION: (1679)..(1687)
<223> OTHER INFORMATION: GATA-3 transcription binding site
<220> FEATURE:
<221> NAME/KEY: misc_feature
<222> LOCATION: (1680)..(1680)
<223> OTHER INFORMATION: transcription start site
<220> FEATURE:
<221> NAME/KEY: misc_feature
<222> LOCATION: (1868)..(1870)
<223> OTHER INFORMATION: translation initiation codon

<400> SEQUENCE: 37
cccggcttct gtccacttct caaggccatc tcaaataact ttttcttcag gaaactattt      60
ctcaaaccac tataatttt tcctaagttc tctagaattc ttcctttgtt taatcccact     120
ttttgcttca ctttcatttt aggagctagg cgtatttta aaaaggcct ttgacctcaa      180 aggatacacg tgggtgaaaa accaccttcc tctaaattta tttttcactc actaggaaga     240
atggtttact gttaatagcg ggtggaaaga agggacactg agtatgagga cctatctgta     300
ctacctaata taatttatct tttgatctac tctgagaatg acgcgagcct aatcttcaca     360
ttggaaaatc acgagaggaa aaaacccttc ggaggtctac aggcacaagg aaccctgtct     420
ccacgctgtt tatagcagct gtctcaggaa tcctctgcct agaatgaatg tgggagaggt     480
```

| | | |
|---|---|---|
| ttcgtggcgc ggcagctgca aagcaaggaa tctttcccat tcctcgtcga ctcggtcccc | 540 | |
| tcccctcccc tcccgaatgg cggcagctgc cgaggtatcc cagtggaaat ctccaagtct | 600 | |
| ccgccgagag cggcgggcgg gcaacagctg aaagcagcca ggggtgggga ctcctcgctc | 660 | |
| ccattgggca gggacagcag cctcactggc tccagcgccg tcacctctct ggctcgtaga | 720 | |
| ggtgcctcag gtgttcttct ccaagtccaa tgagacacct aggcaacgca gcgcgtgttc | 780 | |
| cctccgcgcc aagagaccct acggtaactt aacaacagca ggagcgccaa aatccccgcc | 840 | |
| tcaggacttg gcagaagcac ctcccgaggt ccgagagtgg gagaggggaa agtgtaggcc | 900 | |
| ctcggacgga agggtctctc ctcgccgggc cgggtacaca cctggtgcta ccagagcagc | 960 | |
| gcgcctagtg cagccggaag ccccagccca gcactccggc tggctcgggg ccccccttggc | 1020 | |
| tgtccgcgcg tgtaaccgcg cccccggccg cgcgggtggc tccgctttgg cgccctcccc | 1080 | |
| gcccgcgcac tcgcgctcgc gcacgcgcac gccgcgcccg gcagcactcg gcgctgtcat | 1140 | |
| ggcggccgga agcagcttca gtgggcacac gacagccgcg cgacccgtgg cggggcgagc | 1200 | |
| tgtggcagta gcatcctcac cactcgcagc agcctcagcc gcggcgcccg tagcgccagc | 1260 | |
| agcggctgct tttgcaaagg ctgagcgcag gggcggggcg ggccaggaag ccatggagtt | 1320 | |
| ctgtgcagcc gcggactccc ggggagcgga ctagggaaac ttggaggctg cgaccaggtg | 1380 | |
| cactgacctc tctgtcctcc cttctctccc tgccgtggcc gctgggtttc tctggccgct | 1440 | |
| cccctccctt cctgccacca cacacacctc cccaccccctt cccgtcgaat ctcaggtgcc | 1500 | |
| tgagagaggt gcttcactcc tcccactggg ccgagcattt agaataatca ccgccccctt | 1560 | |
| ccccgccctt ttcctgccct ggatctccgc cgccacctcg gtctcgctgc tcctgggcgg | 1620 | |
| ggggtgagga cgagtccgga gtatctgggg tttggcgttg ttgtcagcct cggggagaga | 1680 | |
| gattggacaa atattctcca agaggaggag ggcgacgcca aggactttcc acatcaactg | 1740 | |
| ctttggggta tctccacaag ttggaagagg gacccttttcg ttttgcattg cgtgtgttgt | 1800 | |
| gctcattacc agtgcagcga ctgccgtccc agggtgactc tgagttgtcc tttatcgtga | 1860 | |
| gctagcaatg gctagcgaag acaatcgtgt cccttccccg ccaccaacag gtgatgacgg | 1920 | |

<210> SEQ ID NO 38
<211> LENGTH: 21
<212> TYPE: DNA
<213> ORGANISM: Artificial Sequence
<220> FEATURE:
<223> OTHER INFORMATION: lrba siRNA antisense strand
<220> FEATURE:
<221> NAME/KEY: misc_feature
<222> LOCATION: (1)..(21)
<223> OTHER INFORMATION: combined DNA/RNA sequence
<220> FEATURE:
<221> NAME/KEY: misc_feature
<222> LOCATION: (20)..(21)
<223> OTHER INFORMATION: deoxythymidine

<400> SEQUENCE: 38
uagccaagac cuuugcuggt t                                          21

<210> SEQ ID NO 39
<211> LENGTH: 21
<212> TYPE: DNA
<213> ORGANISM: Artificial Sequence
<220> FEATURE:
<223> OTHER INFORMATION: lrba siRNA (siRNA2)
<220> FEATURE:
<221> NAME/KEY: misc_feature
<222> LOCATION: (1)..(21)
<223> OTHER INFORMATION: combined DNA/RNA sequence

```
<220> FEATURE:
<221> NAME/KEY: misc_feature
<222> LOCATION: (20)..(21)
<223> OTHER INFORMATION: deoxythymidine

<400> SEQUENCE: 39
gggcacucuu ucugucacct t                                               21

<210> SEQ ID NO 40
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 40
agagaagagg agaagatgtg tgatc                                           25

<210> SEQ ID NO 41
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 41
ccaggctcca tgcttgtctg tgag                                            24

<210> SEQ ID NO 42
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 42
agcaagttca gcctggttaa gt                                              22

<210> SEQ ID NO 43
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 43
ttatgagtat ttcttccagg g                                               21

<210> SEQ ID NO 44
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 44
actgcagcaa gctcctcctg ttttctc                                         27

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide
```

```
<400> SEQUENCE: 45
tgggcgaaga gcggaaacag aac                                    23

<210> SEQ ID NO 46
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 46
gagtgatgga tgatgggaca gtggtg                                 26

<210> SEQ ID NO 47
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 47
gccacctccg tctcgctgc                                         19

<210> SEQ ID NO 48
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 48
gggcactggg gagaatttcg aagtagg                                27

<210> SEQ ID NO 49
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 49
ttcaggcagt tttcaggacc ctccaag                                27

<210> SEQ ID NO 50
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 50
tagtgtctga tgttgaactt cctcctg                                27

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 51
ggcacaacct tcctgctcac                                        20
```

```
<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
cctgtccccc atttgaaccc                                               20

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
acggctgctt ctgcaccttc                                               20

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
ttttgggaca gggcttctct g                                             21

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
ggcacaacct tcctgctcac                                               20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 56
gcagatgctc tcctcgctcc                                               20

<210> SEQ ID NO 57
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 57
cacacagagc attgtagcaa gctcctc                                       27

<210> SEQ ID NO 58
<211> LENGTH: 19
<212> TYPE: DNA
<213> ORGANISM: Artificial Sequence
<220> FEATURE:
<223> OTHER INFORMATION: synthetic oligonucleotide
```

```
<400> SEQUENCE: 58
tgcagacttg aagattccg                                              19

<210> SEQ ID NO 59
<211> LENGTH: 57
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (56)..(56)
<223> OTHER INFORMATION: v = a, g, or c
<220> FEATURE:
<221> NAME/KEY: misc_feature
<222> LOCATION: (57)..(57)
<223> OTHER INFORMATION: n = a, c, g, or t

<400> SEQUENCE: 59
aagcagtggt atcaacgcag agtactttt tttttttttt tttttttttt tttttvn     57

<210> SEQ ID NO 60
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 60
gagtgatgga tgatgggaca gtagtg                                      26

<210> SEQ ID NO 61
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 61
cgagaagatg agaagatgtg tgatc                                       25

<210> SEQ ID NO 62
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 1 5' spice donor

<400> SEQUENCE: 62
agtatctggg tgaggaag                                               18

<210> SEQ ID NO 63
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 2 5' spice donor

<400> SEQUENCE: 63
tttaacctgg taagtcca                                               18
```

```
<210> SEQ ID NO 64
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 3 5' spice donor

<400> SEQUENCE: 64
tgatagcagg tatgattt                                                 18

<210> SEQ ID NO 65
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 4 5' spice donor

<400> SEQUENCE: 65
ggacgatggg taaaaaaa                                                 18

<210> SEQ ID NO 66
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Exon 5 5' spice donor

<400> SEQUENCE: 66
agtgctgcag taagtaa                                                  17

<210> SEQ ID NO 67
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 6 5' spice donor

<400> SEQUENCE: 67
tttgtattgg tatgtatt                                                 18

<210> SEQ ID NO 68
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 7 5' spice donor

<400> SEQUENCE: 68
ccacaaaagg tacatgat                                                 18

<210> SEQ ID NO 69
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 8 5' spice donor
```

```
<400> SEQUENCE: 69
actagcgatg taagtagt                                               18

<210> SEQ ID NO 70
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 9 5' spice donor

<400> SEQUENCE: 70
ggatacaagg tagtttgc                                               18

<210> SEQ ID NO 71
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 10 5' spice donor

<400> SEQUENCE: 71
atgctccagg tactaact                                               18

<210> SEQ ID NO 72
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 11 5' spice donor

<400> SEQUENCE: 72
gactatatgg tgagtgcc                                               18

<210> SEQ ID NO 73
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 12 5' spice donor

<400> SEQUENCE: 73
cttgaaaagg taaagtat                                               18

<210> SEQ ID NO 74
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 13 5' spice donor

<400> SEQUENCE: 74
ccagccaagg taatatat                                               18

<210> SEQ ID NO 75
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Exon 14 5' spice donor

<400> SEQUENCE: 75
aaggattagg tatataat                                                 18

<210> SEQ ID NO 76
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 15 5' spice donor

<400> SEQUENCE: 76
gtgatgaagg taggttca                                                 18

<210> SEQ ID NO 77
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 16 5' spice donor

<400> SEQUENCE: 77
atgcatgagg taatatat                                                 18

<210> SEQ ID NO 78
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 17 5' spice donor

<400> SEQUENCE: 78
tgggttacgg taagagtt                                                 18

<210> SEQ ID NO 79
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 18 5' spice donor

<400> SEQUENCE: 79
ggccccaaag taagtatg                                                 18

<210> SEQ ID NO 80
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 19 5' spice donor

<400> SEQUENCE: 80
ctgtttgagg taggaatg                                                 18
```

```
<210> SEQ ID NO 81
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 20 5' spice donor

<400> SEQUENCE: 81
aaacccctcg tatgtatg                                                18

<210> SEQ ID NO 82
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 21 5' spice donor

<400> SEQUENCE: 82
aaacaggagg taagctga                                                18

<210> SEQ ID NO 83
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 22 5' spice donor

<400> SEQUENCE: 83
cattcaaagg taagtttc                                                18

<210> SEQ ID NO 84
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 23 5' spice donor

<400> SEQUENCE: 84
gtgcttgagg tgatttta                                                18

<210> SEQ ID NO 85
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 24 5' spice donor

<400> SEQUENCE: 85
gtggagaagg tttgtcta                                                18

<210> SEQ ID NO 86
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 25 5' spice donor
```

```
<400> SEQUENCE: 86
tcggctacag taaggact                                                18

<210> SEQ ID NO 87
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 26 5' spice donor

<400> SEQUENCE: 87
tccgactagg tgagctgc                                                18

<210> SEQ ID NO 88
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 27 5' spice donor

<400> SEQUENCE: 88
gcagcgaagg taagtata                                                18

<210> SEQ ID NO 89
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 28 5' spice donor

<400> SEQUENCE: 89
agagacatag taagttac                                                18

<210> SEQ ID NO 90
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 29 5' spice donor

<400> SEQUENCE: 90
cactctctgg taagtttg                                                18

<210> SEQ ID NO 91
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 30 5' spice donor

<400> SEQUENCE: 91
ttttgacagg tactgata                                                18

<210> SEQ ID NO 92
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Exon 31 5' spice donor

<400> SEQUENCE: 92
aatcaccagg tgagttag                                                       18

<210> SEQ ID NO 93
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 32 5' spice donor

<400> SEQUENCE: 93
aaatatgagg tatttaag                                                       18

<210> SEQ ID NO 94
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 33 5' spice donor

<400> SEQUENCE: 94
aaggaacaag taagtggt                                                       18

<210> SEQ ID NO 95
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 34 5' spice donor

<400> SEQUENCE: 95
tgttctcagg tgagtggc                                                       18

<210> SEQ ID NO 96
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 35 5' spice donor

<400> SEQUENCE: 96
atgaggaagg taatttat                                                       18

<210> SEQ ID NO 97
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 36 5' spice donor

<400> SEQUENCE: 97
gaatttgagg taggttac                                                       18
```

```
<210> SEQ ID NO 98
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 37 5' spice donor

<400> SEQUENCE: 98
tgcagtgagg taaaggga                                                   18

<210> SEQ ID NO 99
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Exon 38 5' spice donor

<400> SEQUENCE: 99
tggaacatgg tcagtgg                                                    17

<210> SEQ ID NO 100
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 39 5' spice donor

<400> SEQUENCE: 100
acagcaaagg taagcatt                                                   18

<210> SEQ ID NO 101
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 40 5' spice donor

<400> SEQUENCE: 101
atcttgccgg taaatttg                                                   18

<210> SEQ ID NO 102
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Exon 41 5' spice donor

<400> SEQUENCE: 102
gaccccaagg t                                                          11

<210> SEQ ID NO 103
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 42 5' spice donor
```

```
<400> SEQUENCE: 103
caaacagagg taatgtgt                                                18

<210> SEQ ID NO 104
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 43 5' spice donor

<400> SEQUENCE: 104
tcaaaccagg tactgttt                                                18

<210> SEQ ID NO 105
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 44 5' spice donor

<400> SEQUENCE: 105
cgatagcagg taacctaa                                                18

<210> SEQ ID NO 106
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 45 5' spice donor

<400> SEQUENCE: 106
ttgtccaagg taatttct                                                18

<210> SEQ ID NO 107
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 46 5' spice donor

<400> SEQUENCE: 107
ctaagaatag taagttca                                                18

<210> SEQ ID NO 108
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 47 5' spice donor

<400> SEQUENCE: 108
gatattaagg tacagaaa                                                18

<210> SEQ ID NO 109
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Exon 48 5' spice donor

<400> SEQUENCE: 109
aacagattgg taagataa                                                 18

<210> SEQ ID NO 110
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 49 5' spice donor

<400> SEQUENCE: 110
ttgagagagg taagttat                                                 18

<210> SEQ ID NO 111
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 50 5' spice donor

<400> SEQUENCE: 111
atgcaagtgg taagtgct                                                 18

<210> SEQ ID NO 112
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 51 5' spice donor

<400> SEQUENCE: 112
accttcctgg taagtaaa                                                 18

<210> SEQ ID NO 113
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 52 5' spice donor

<400> SEQUENCE: 113
ctctcatagg tctgtcac                                                 18

<210> SEQ ID NO 114
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 53 5' spice donor

<400> SEQUENCE: 114
cagacacagg taattttc                                                 18
```

```
<210> SEQ ID NO 115
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 54 5' spice donor

<400> SEQUENCE: 115
acccaggcag taagtatg                                                 18

<210> SEQ ID NO 116
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 55 5' spice donor

<400> SEQUENCE: 116
gttcacaagg taaacctg                                                 18

<210> SEQ ID NO 117
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 56 5' spice donor

<400> SEQUENCE: 117
aacataagag tgagtgcc                                                 18

<210> SEQ ID NO 118
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Exon 57 5' spice donor

<400> SEQUENCE: 118
cgaccagagg taacactg                                                 18

<210> SEQ ID NO 119
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 1 3' splice acceptor

<400> SEQUENCE: 119
tccaataagg gtttggcg                                                 18

<210> SEQ ID NO 120
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 2 3' splice acceptor
```

```
<400> SEQUENCE: 120
ccttgtaagt tggtagga                                               18

<210> SEQ ID NO 121
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 3 3' splice acceptor

<400> SEQUENCE: 121
tgtttccaga tcttttgg                                               18

<210> SEQ ID NO 122
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 4 3' splice acceptor

<400> SEQUENCE: 122
tcttcatagc ctccacat                                               18

<210> SEQ ID NO 123
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 5 3' splice acceptor

<400> SEQUENCE: 123
ttcctttagg ctattgca                                               18

<210> SEQ ID NO 124
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 6 3' splice acceptor

<400> SEQUENCE: 124
tctttatagt ttcagaac                                               18

<210> SEQ ID NO 125
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 7 3' splice acceptor

<400> SEQUENCE: 125
cttctgcagt ggtatatg                                               18

<210> SEQ ID NO 126
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Intron 8 3' splice acceptor

<400> SEQUENCE: 126
cttttacaga cctttgac                                                  18

<210> SEQ ID NO 127
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 9 3' splice acceptor

<400> SEQUENCE: 127
ttcttagagg gtacattt                                                  18

<210> SEQ ID NO 128
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 10 3' splice acceptor

<400> SEQUENCE: 128
tcttacaagg atgtaaag                                                  18

<210> SEQ ID NO 129
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 11 3' splice acceptor

<400> SEQUENCE: 129
aaattctagt tcaacctt                                                  18

<210> SEQ ID NO 130
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 12 3' splice acceptor

<400> SEQUENCE: 130
tttttgcagt cttccaaa                                                  18

<210> SEQ ID NO 131
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 13 3' splice acceptor

<400> SEQUENCE: 131
attctgtagg ttcaactg                                                  18
```

```
<210> SEQ ID NO 132
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 14 3' splice acceptor

<400> SEQUENCE: 132
ttttaaaaga tggaccgc                                                 18

<210> SEQ ID NO 133
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 15 3' splice acceptor

<400> SEQUENCE: 133
tttttgaagg attctgga                                                 18

<210> SEQ ID NO 134
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 16 3' splice acceptor

<400> SEQUENCE: 134
tgattatagg atgacaat                                                 18

<210> SEQ ID NO 135
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 17 3' splice acceptor

<400> SEQUENCE: 135
ttcattcagt gttatcta                                                 18

<210> SEQ ID NO 136
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 18 3' splice acceptor

<400> SEQUENCE: 136
taattgcagg aggaaagc                                                 18

<210> SEQ ID NO 137
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 19 3' splice acceptor
```

```
<400> SEQUENCE: 137
cttctgtaga ttcttata                                                18

<210> SEQ ID NO 138
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 20 3' splice acceptor

<400> SEQUENCE: 138
agattacaga gatactaa                                                18

<210> SEQ ID NO 139
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 21 3' splice acceptor

<400> SEQUENCE: 139
aattttcagg agcttgct                                                18

<210> SEQ ID NO 140
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 22 3' splice acceptor

<400> SEQUENCE: 140
ttcacctagg tcactttt                                                18

<210> SEQ ID NO 141
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 23 3' splice acceptor

<400> SEQUENCE: 141
tgtattaaga tatcaagg                                                18

<210> SEQ ID NO 142
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 24 3' splice acceptor

<400> SEQUENCE: 142
tttggacagc cattcaac                                                18

<210> SEQ ID NO 143
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Intron 25 3' splice acceptor

<400> SEQUENCE: 143
tctttacagc atgaactg                                                 18

<210> SEQ ID NO 144
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 26 3' splice acceptor

<400> SEQUENCE: 144
aaattacagt ttgtgcag                                                 18

<210> SEQ ID NO 145
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 27 3' splice acceptor

<400> SEQUENCE: 145
cttaaataga gcccagtg                                                 18

<210> SEQ ID NO 146
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 28 3' splice acceptor

<400> SEQUENCE: 146
ttttcccagg aggatagc                                                 18

<210> SEQ ID NO 147
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 29 3' splice acceptor

<400> SEQUENCE: 147
atgatataga aatcacac                                                 18

<210> SEQ ID NO 148
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 30 3' splice acceptor

<400> SEQUENCE: 148
ttattacaga agtgtcat                                                 18
```

```
<210> SEQ ID NO 149
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 31 3' splice acceptor

<400> SEQUENCE: 149
cttttatagg cagtagat                                                  18

<210> SEQ ID NO 150
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 32 3' splice acceptor

<400> SEQUENCE: 150
tttccttagt attacaga                                                  18

<210> SEQ ID NO 151
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 33 3' splice acceptor

<400> SEQUENCE: 151
ttaaaatagg tctggttt                                                  18

<210> SEQ ID NO 152
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 34 3' splice acceptor

<400> SEQUENCE: 152
tttttatagg agtggcaa                                                  18

<210> SEQ ID NO 153
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 35 3' splice acceptor

<400> SEQUENCE: 153
ttcttacagg ttgcttag                                                  18

<210> SEQ ID NO 154
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 36 3' splice acceptor
```

```
<400> SEQUENCE: 154
ctctccaagt cactgtgt                                                       18

<210> SEQ ID NO 155
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Intron 37 3' splice acceptor

<400> SEQUENCE: 155
cattgtagtc gtcctct                                                        17

<210> SEQ ID NO 156
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 38 3' splice acceptor

<400> SEQUENCE: 156
atgttttagt gtgcattt                                                       18

<210> SEQ ID NO 157
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 39 3' splice acceptor

<400> SEQUENCE: 157
tcatttcagc cacagatg                                                       18

<210> SEQ ID NO 158
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 40 3' splice acceptor

<400> SEQUENCE: 158
ttttggcagg tcctgtta                                                       18

<210> SEQ ID NO 159
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 41 3' splice acceptor

<400> SEQUENCE: 159
cctcattaga tcttggca                                                       18

<210> SEQ ID NO 160
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Intron 42 3' splice acceptor

<400> SEQUENCE: 160
ctgttgtagt tgctgtga                                                 18

<210> SEQ ID NO 161
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 43 3' splice acceptor

<400> SEQUENCE: 161
ttcttgcaga cgtatttc                                                 18

<210> SEQ ID NO 162
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 44 3' splice acceptor

<400> SEQUENCE: 162
ccctatcagg acggagtt                                                 18

<210> SEQ ID NO 163
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 45 3' splice acceptor

<400> SEQUENCE: 163
tattggcagc caatagga                                                 18

<210> SEQ ID NO 164
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 46 3' splice acceptor

<400> SEQUENCE: 164
attttttagg aacccttt                                                 18

<210> SEQ ID NO 165
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 47 3' splice acceptor
```

```
<400> SEQUENCE: 165
tttatatagg agttgatc                                              18

<210> SEQ ID NO 166
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 48 3' splice acceptor

<400> SEQUENCE: 166 tttttttcagg ccctggag                                             18

<210> SEQ ID NO 167
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 49 3' splice acceptor

<400> SEQUENCE: 167
ccttttcagg ctgttgaa                                              18

<210> SEQ ID NO 168
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 50 3' splice acceptor

<400> SEQUENCE: 168
ctcctgcaga gtccattg                                              18

<210> SEQ ID NO 169
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 51 3' splice acceptor

<400> SEQUENCE: 169
gaattccagc tcatcaag                                              18

<210> SEQ ID NO 170
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 52 3' splice acceptor

<400> SEQUENCE: 170
ttcttacagc cagcaata                                              18

<210> SEQ ID NO 171
<211> LENGTH: 18
<212> TYPE: DNA
<213> ORGANISM: Homo sapiens
```

```
<220> FEATURE:
<221> NAME/KEY: misc_feature
<222> LOCATION: (1)..(18)
<223> OTHER INFORMATION: Intron 53 3' splice acceptor

<400> SEQUENCE: 171
gcattacagg aagattga                                                 18

<210> SEQ ID NO 172
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 54 3' splice acceptor

<400> SEQUENCE: 172
ttcctaaagg tgagactg                                                 18

<210> SEQ ID NO 173
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 55 3' splice acceptor

<400> SEQUENCE: 173
tcttctcaga aggaccat                                                 18

<210> SEQ ID NO 174
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 56 3' splice acceptor

<400> SEQUENCE: 174
gtctcacagg ccatccag                                                 18

<210> SEQ ID NO 175
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Intron 57 3' splice acceptor

<400> SEQUENCE: 175
ttctcctagg tgcatcat                                                 18

<210> SEQ ID NO 176
<211> LENGTH: 8
<212> TYPE: PRT
<213> ORGANISM: Artificial Sequence
<220> FEATURE:
<223> OTHER INFORMATION: p21 RAS motif

<400> SEQUENCE: 176

Leu Leu Gly Val Gly Gly Phe Asp
1               5
```

```
<210> SEQ ID NO 177
<211> LENGTH: 19
<212> TYPE: RNA
<213> ORGANISM: Artificial Sequence
<220> FEATURE:
<223> OTHER INFORMATION: lrba siRNA (siRNA1)

<400> SEQUENCE: 177
ccagcaaagg ucuuggcua                                                19

<210> SEQ ID NO 178
<211> LENGTH: 19
<212> TYPE: RNA
<213> ORGANISM: Artificial Sequence
<220> FEATURE:
<223> OTHER INFORMATION: lrba siRNA

<400> SEQUENCE: 178
cagucggguu ugcgacugg                                                19

<210> SEQ ID NO 179
<211> LENGTH: 19
<212> TYPE: RNA
<213> ORGANISM: Artificial Sequence
<220> FEATURE:
<223> OTHER INFORMATION: lrba siRNA antisense strand

<400> SEQUENCE: 179
uagccaagac cuuugcugg                                                19

<210> SEQ ID NO 180
<211> LENGTH: 19
<212> TYPE: RNA
<213> ORGANISM: Artificial Sequence
<220> FEATURE:
<223> OTHER INFORMATION: lrba siRNA (siRNA2)

<400> SEQUENCE: 180
gggcacucuu ucugucacc                                                19

<210> SEQ ID NO 181
<211> LENGTH: 165
<212> TYPE: RNA
<213> ORGANISM: Homo sapiens

<400> SEQUENCE: 181
ugagaaacag aaauuugugg uaguaauaua auccauaauu acuuauuugu gugugaagac      60
acaacaucuu uuggcagaag gaggauuuga acuccuguuc uuuagaaugu gcuguguugg     120
aguggaugac caaacuuggu aggaggacag uuugaucugg aaaug                    165

<210> SEQ ID NO 182
<211> LENGTH: 2818
<212> TYPE: PRT
<213> ORGANISM: Homo sapiens

<400> SEQUENCE: 182

Met Ala Ser Glu Asp Asn Arg Val Pro Ser Pro Pro Thr Gly Asp
1               5                   10                  15

Asp Gly Gly Gly Gly Arg Glu Gly Thr Pro Thr Glu Gly Gly Ala
                20                  25                  30

Leu Ser Leu Lys Pro Gly Leu Pro Ile Arg Gly Ile Arg Met Lys Phe
                35                  40                  45
```

-continued

```
Ala Val Leu Thr Gly Leu Val Glu Val Gly Glu Val Ser Asn Arg Asp
     50                  55                  60
Ile Val Glu Thr Val Phe Asn Leu Leu Val Gly Gln Phe Asp Leu
 65                  70                  75                  80
Glu Met Asn Phe Ile Ile Gln Glu Gly Glu Ser Ile Asn Cys Met Val
                     85                  90                  95
Asp Leu Leu Glu Lys Cys Asp Ile Thr Cys Gln Ala Glu Val Trp Ser
                100                 105                 110
Met Phe Thr Ala Ile Leu Lys Lys Ser Ile Arg Asn Leu Gln Val Cys
                115                 120                 125
Thr Glu Val Gly Leu Val Glu Lys Val Leu Gly Lys Ile Glu Lys Val
     130                 135                 140
Asp Asn Met Ile Ala Asp Leu Leu Val Asp Met Leu Gly Val Leu Ala
145                 150                 155                 160
Ser Tyr Asn Leu Thr Val Arg Glu Leu Lys Leu Phe Phe Ser Lys Leu
                165                 170                 175
Gln Gly Asp Lys Gly Arg Trp Pro Pro His Ala Gly Lys Leu Leu Ser
                180                 185                 190
Val Leu Lys His Met Pro Gln Lys Tyr Gly Pro Asp Ala Phe Phe Asn
                195                 200                 205
Phe Pro Gly Lys Ser Ala Ala Ala Ile Ala Leu Pro Pro Ile Ala Lys
     210                 215                 220
Trp Pro Tyr Gln Asn Gly Phe Thr Phe His Thr Trp Leu Arg Met Asp
225                 230                 235                 240
Pro Val Asn Asn Ile Asn Val Asp Lys Asp Lys Pro Tyr Leu Tyr Cys
                245                 250                 255
Phe Arg Thr Ser Lys Gly Leu Gly Tyr Ser Ala His Phe Val Gly Gly
                260                 265                 270
Cys Leu Ile Val Thr Ser Ile Lys Ser Lys Gly Lys Gly Phe Gln His
                275                 280                 285
Cys Val Lys Phe Asp Phe Lys Pro Gln Lys Trp Tyr Met Val Thr Ile
                290                 295                 300
Val His Ile Tyr Asn Arg Trp Lys Asn Ser Glu Leu Arg Cys Tyr Val
305                 310                 315                 320
Asn Gly Glu Leu Ala Ser Tyr Gly Glu Ile Thr Trp Phe Val Asn Thr
                325                 330                 335
Ser Asp Thr Phe Asp Lys Cys Phe Leu Gly Ser Ser Glu Thr Ala Asp
                340                 345                 350
Ala Asn Arg Val Phe Cys Gly Gln Met Thr Ala Val Tyr Leu Phe Ser
                355                 360                 365
Glu Ala Leu Asn Ala Ala Gln Ile Phe Ala Ile Tyr Gln Leu Gly Leu
     370                 375                 380
Gly Tyr Lys Gly Thr Phe Lys Phe Lys Ala Glu Ser Asp Leu Phe Leu
385                 390                 395                 400
Ala Glu His His Lys Leu Leu Leu Tyr Asp Gly Lys Leu Ser Ser Ala
                405                 410                 415
Ile Ala Phe Thr Tyr Asn Pro Arg Ala Thr Asp Ala Gln Leu Cys Leu
                420                 425                 430
Glu Ser Ser Pro Lys Asp Asn Pro Ser Ile Phe Val His Ser Pro His
                435                 440                 445
Ala Leu Met Leu Gln Asp Val Lys Ala Val Leu Thr His Ser Ile Gln
     450                 455                 460
```

-continued

```
Ser Ala Met His Ser Ile Gly Val Gln Val Leu Phe Pro Leu Phe
465                 470                 475                 480

Ala Gln Leu Asp Tyr Arg Gln Tyr Leu Ser Asp Glu Ile Asp Leu Thr
                485                 490                 495

Ile Cys Ser Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
            515                 520                 525

Gly Tyr Ser Leu Glu Lys Ser Ser Lys Ser His Val Ser Arg Ala Val
        530                 535                 540

Leu Glu Leu Cys Leu Ala Phe Ser Lys Tyr Leu Ser Asn Leu Gln Asn
545                 550                 555                 560

Gly Met Pro Leu Leu Lys Gln Leu Cys Asp His Val Leu Leu Asn Pro
                565                 570                 575

Ala Ile Trp Ile His Thr Pro Ala Lys Val Gln Leu Met Leu Tyr Thr
                580                 585                 590

Tyr Leu Ser Thr Glu Phe Ile Gly Thr Val Asn Ile Tyr Asn Thr Ile
            595                 600                 605

Arg Arg Val Gly Thr Val Leu Leu Ile Met His Thr Leu Lys Tyr Tyr
            610                 615                 620

Tyr Trp Ala Val Asn Pro Gln Asp Arg Ser Gly Ile Thr Pro Lys Gly
625                 630                 635                 640

Leu Asp Gly Pro Arg Pro Asn Gln Lys Glu Met Leu Ser Leu Arg Ala
                645                 650                 655

Phe Leu Leu Met Phe Ile Lys Gln Leu Val Met Lys Asp Ser Gly Val
                660                 665                 670

Lys Glu Asp Glu Leu Gln Ala Ile Leu Asn Tyr Leu Leu Thr Met His
            675                 680                 685

Glu Asp Asp Asn Leu Met Asp Val Leu Gln Leu Leu Val Ala Leu Met
690                 695                 700

Ser Glu His Pro Asn Ser Met Ile Pro Ala Phe Asp Gln Arg Asn Gly
705                 710                 715                 720

Leu Arg Val Ile Tyr Lys Leu Leu Ala Ser Lys Ser Glu Gly Ile Arg
                725                 730                 735

Val Gln Ala Leu Lys Ala Met Gly Tyr Phe Leu Lys His Arg Pro Pro
            740                 745                 750

Lys Arg Lys Ala Glu Val Met Leu Gly His Gly Leu Phe Ser Leu Leu
            755                 760                 765

Ala Glu Arg Leu Met Leu Gln Thr Asn Leu Ile Thr Met Thr Thr Tyr
            770                 775                 780

Asn Val Leu Phe Glu Ile Leu Ile Glu Gln Ile Gly Thr Gln Val Ile
785                 790                 795                 800

His Lys Gln His Pro Asp Pro Asp Ser Ser Val Lys Ile Gln Asn Pro
                805                 810                 815

Gln Ile Leu Lys Val Ile Ala Thr Leu Leu Arg Asn Ser Pro Gln Cys
                820                 825                 830

Pro Glu Ser Met Glu Val Arg Arg Ala Phe Leu Ser Asp Met Ile Lys
            835                 840                 845

Leu Phe Asn Asn Ser Arg Glu Asn Arg Arg Ser Leu Leu Gln Cys Ser
            850                 855                 860

Val Trp Gln Glu Trp Met Leu Ser Leu Cys Tyr Phe Asn Pro Lys Asn
865                 870                 875                 880
```

-continued

```
Ser Asp Glu Gln Lys Ile Thr Glu Met Val Tyr Ala Ile Phe Arg Ile
            885                 890                 895

Leu Leu Tyr His Ala Val Lys Tyr Glu Trp Gly Gly Trp Arg Val Trp
            900                 905                 910

Val Asp Thr Leu Ser Ile Thr His Ser Lys Val Thr Phe Glu Ile His
            915                 920                 925

Lys Glu Asn Leu Ala Asn Ile Phe Arg Glu Gln Gln Gly Lys Val Asp
            930                 935                 940

Glu Glu Ile Gly Leu Cys Ser Ser Thr Ser Val Gln Ala Ala Ser Gly
945                 950                 955                 960

Ile Arg Arg Asp Ile Asn Val Ser Val Gly Ser Gln Gln Pro Asp Thr
            965                 970                 975

Lys Asp Ser Pro Val Cys Pro His Phe Thr Thr Asn Gly Asn Glu Asn
            980                 985                 990

Ser Ser Ile Glu Lys Thr Ser Ser  Leu Glu Ser Ala Ser  Asn Ile Glu
            995                 1000                1005

Leu Gln  Thr Thr Asn Thr Ser  Tyr Glu Glu Met Lys  Ala Glu Gln
    1010                1015                1020

Glu Asn  Gln Glu Leu Pro Asp  Glu Gly Thr Leu Glu  Glu Thr Leu
    1025                1030                1035

Thr Asn  Glu Thr Arg Asn Ala  Asp Asp Leu Glu Val  Ser Ser Asp
    1040                1045                1050

Ile Ile  Glu Ala Val Ala Ile  Ser Ser Asn Ser Phe  Ile Thr Thr
    1055                1060                1065

Gly Lys  Asp Ser Met Thr Val  Ser Glu Val Thr Ala  Ser Ile Ser
    1070                1075                1080

Ser Pro  Ser Glu Glu Asp Ala  Ser Glu Met Pro Glu  Phe Leu Asp
    1085                1090                1095

Lys Ser  Ile Val Glu Glu Glu  Asp Asp Asp Tyr  Val Glu Leu
    1100                1105                1110

Lys Val  Glu Gly Ser Pro Thr  Glu Glu Ala Asn Leu  Pro Thr Glu
    1115                1120                1125

Leu Gln  Asp Asn Ser Leu Ser  Pro Ala Ala Ser Glu  Ala Gly Glu
    1130                1135                1140

Lys Leu  Asp Met Phe Gly Asn  Asp Asp Lys Leu Ile  Phe Gln Glu
    1145                1150                1155

Gly Lys  Pro Val Thr Glu Lys  Gln Thr Asp Thr Glu  Thr Gln Asp
    1160                1165                1170

Ser Lys  Asp Ser Gly Ile Gln  Thr Met Thr Ala Ser  Gly Ser Ser
    1175                1180                1185

Ala Met  Ser Pro Glu Thr Thr  Val Ser Gln Ile Ala  Val Glu Ser
    1190                1195                1200

Asp Leu  Gly Gln Met Leu Glu  Gly Lys Lys Ala  Thr Asn Leu
    1205                1210                1215

Thr Arg  Glu Thr Lys Leu Ile  Asn Asp Cys His Gly  Ser Val Ser
    1220                1225                1230

Glu Ala  Ser Ser Glu Gln Lys  Ile Ala Lys Leu Asp  Val Ser Asn
    1235                1240                1245

Val Ala  Thr Asp Thr Glu Arg  Leu Glu Leu Lys Ala  Ser Pro Asn
    1250                1255                1260

Val Glu  Ala Pro Gln Pro His  Arg His Val Leu Glu  Ile Ser Arg
    1265                1270                1275
```

-continued

Gln His Glu Gln Pro Gly Gln Gly Ile Ala Pro Asp Ala Val Asn
1280                1285                1290

Gly Gln Arg Arg Asp Ser Arg Ser Thr Val Phe Arg Ile Pro Glu
    1295                1300                1305

Phe Asn Trp Ser Gln Met His Gln Arg Leu Leu Thr Asp Leu Leu
1310                1315                1320

Phe Ser Ile Glu Thr Asp Ile Gln Met Trp Arg Ser His Ser Thr
1325                1330                1335

Lys Thr Val Met Asp Phe Val Asn Ser Ser Asp Asn Val Ile Phe
1340                1345                1350

Val His Asn Thr Ile His Leu Ile Ser Gln Val Met Asp Asn Met
1355                1360                1365

Val Met Ala Cys Gly Gly Ile Leu Pro Leu Leu Ser Ala Ala Thr
1370                1375                1380

Ser Ala Thr His Glu Leu Glu Asn Ile Glu Pro Thr Gln Gly Leu
1385                1390                1395

Ser Ile Glu Ala Ser Val Thr Phe Leu Gln Arg Leu Ile Ser Leu
1400                1405                1410

Val Asp Val Leu Ile Phe Ala Ser Ser Leu Gly Phe Thr Glu Ile
1415                1420                1425

Glu Ala Glu Lys Ser Met Ser Ser Gly Gly Ile Leu Arg Gln Cys
1430                1435                1440

Leu Arg Leu Val Cys Ala Val Ala Val Arg Asn Cys Leu Glu Cys
1445                1450                1455

Gln Gln His Ser Gln Leu Lys Thr Arg Gly Asp Lys Ala Leu Lys
1460                1465                1470

Pro Met His Ser Leu Ile Pro Leu Gly Lys Ser Ala Ala Lys Ser
1475                1480                1485

Pro Val Asp Ile Val Thr Gly Gly Ile Ser Pro Val Arg Asp Leu
1490                1495                1500

Asp Arg Leu Leu Gln Asp Met Asp Ile Asn Arg Leu Arg Ala Val
1505                1510                1515

Val Phe Arg Asp Ile Glu Asp Ser Lys Gln Ala Gln Phe Leu Ala
1520                1525                1530

Leu Ala Val Val Tyr Phe Ile Ser Val Leu Met Val Ser Lys Tyr
1535                1540                1545

Arg Asp Ile Leu Glu Pro Gln Asn Glu Arg His Ser Gln Ser Cys
1550                1555                1560

Thr Glu Thr Gly Ser Glu Asn Glu Asn Val Ser Leu Ser Glu Ile
1565                1570                1575

Thr Pro Ala Ala Phe Ser Thr Leu Thr Thr Ala Ser Val Glu Glu
1580                1585                1590

Ser Glu Ser Thr Ser Ser Ala Arg Arg Arg Asp Ser Gly Ile Gly
1595                1600                1605

Glu Glu Thr Ala Thr Gly Leu Gly Ser His Val Glu Val Thr Pro
1610                1615                1620

His Thr Ala Pro Pro Gly Val Ser Ala Gly Pro Asp Ala Ile Ser
1625                1630                1635

Glu Val Leu Ser Thr Leu Leu Glu Val Asn Lys Ser Pro Glu
1640                1645                1650

Thr Lys Asn Asp Arg Gly Asn Asp Leu Asp Thr Lys Ala Thr Pro
1655                1660                1665

```
Ser Val Ser Val Lys Asn Val Asn Val Lys Asp Ile Leu Arg
    1670            1675            1680

Ser Leu Val Asn Ile Pro Ala Asp Gly Val Thr Val Asp Pro Ala
    1685            1690            1695

Leu Leu Pro Pro Ala Cys Leu Gly Ala Leu Gly Asp Leu Ser Val
    1700            1705            1710

Glu Gln Pro Val Gln Phe Arg Ser Phe Asp Arg Ser Val Ile Val
    1715            1720            1725

Ala Ala Lys Lys Ser Ala Val Ser Pro Ser Thr Phe Asn Thr Ser
    1730            1735            1740

Ile Pro Thr Asn Ala Val Ser Val Val Ser Ser Val Asp Ser Ala
    1745            1750            1755

Gln Ala Ser Asp Met Gly Gly Glu Ser Pro Gly Ser Arg Ser Ser
    1760            1765            1770

Asn Ala Lys Leu Pro Ser Val Pro Thr Val Asp Ser Val Ser Gln
    1775            1780            1785

Asp Pro Val Ser Asn Met Ser Ile Thr Glu Arg Leu Glu His Ala
    1790            1795            1800

Leu Glu Lys Ala Ala Pro Leu Leu Arg Glu Ile Phe Val Asp Phe
    1805            1810            1815

Ala Pro Phe Leu Ser Arg Thr Leu Leu Gly Ser His Gly Gln Glu
    1820            1825            1830

Leu Leu Ile Glu Gly Thr Ser Leu Val Cys Met Lys Ser Ser Ser
    1835            1840            1845

Ser Val Val Glu Leu Val Met Leu Leu Cys Ser Gln Glu Trp Gln
    1850            1855            1860

Asn Ser Ile Gln Lys Asn Ala Gly Leu Ala Phe Ile Glu Leu Val
    1865            1870            1875

Asn Glu Gly Arg Leu Leu Ser Gln Thr Met Lys Asp His Leu Val
    1880            1885            1890

Arg Val Ala Asn Glu Ala Glu Phe Ile Leu Ser Arg Gln Arg Ala
    1895            1900            1905

Glu Asp Ile His Arg His Ala Glu Phe Glu Ser Leu Cys Ala Gln
    1910            1915            1920

Tyr Ser Ala Asp Lys Arg Glu Asp Glu Lys Met Cys Asp His Leu
    1925            1930            1935

Ile Arg Ala Ala Lys Tyr Arg Asp His Val Thr Ala Thr Gln Leu
    1940            1945            1950

Ile Gln Lys Ile Ile Asn Ile Leu Thr Asp Lys His Gly Ala Trp
    1955            1960            1965

Gly Asn Ser Ala Val Ser Arg Pro Leu Glu Phe Trp Arg Leu Asp
    1970            1975            1980

Tyr Trp Glu Asp Asp Leu Arg Arg Arg Arg Phe Val Arg Asn
    1985            1990            1995

Pro Leu Gly Ser Thr His Pro Glu Ala Thr Leu Lys Thr Ala Val
    2000            2005            2010

Glu His Val Cys Ile Phe Lys Leu Arg Glu Asn Ser Lys Ala Thr
    2015            2020            2025

Asp Glu Asp Ile Leu Ala Lys Gly Lys Gln Ser Ile Arg Ser Gln
    2030            2035            2040

Ala Leu Gly Asn Gln Asn Ser Glu Asn Glu Ile Leu Leu Glu Gly
    2045            2050            2055
```

-continued

```
Asp Asp Asp Thr Leu Ser Ser Val Asp Glu Lys Asp Leu Glu Asn
2060                2065                2070

Leu Ala Gly Pro Val Ser Leu Ser Thr Pro Ala Gln Leu Val Ala
2075                2080                2085

Pro Ser Val Val Val Lys Gly Thr Leu Ser Val Thr Ser Ser Glu
2090                2095                2100

Leu Tyr Phe Glu Val Asp Glu Asp Pro Asn Phe Lys Lys Ile
2105                2110                2115

Asp Pro Lys Ile Leu Ala Tyr Thr Glu Gly Leu His Gly Lys Trp
2120                2125                2130

Leu Phe Thr Glu Ile Arg Ser Ile Phe Ser Arg Arg Tyr Leu Leu
2135                2140                2145

Gln Asn Thr Ala Leu Glu Ile Phe Met Ala Asn Arg Val Ala Val
2150                2155                2160

Met Phe Asn Phe Pro Asp Pro Ala Thr Val Lys Lys Val Val Asn
2165                2170                2175

Phe Leu Pro Arg Val Gly Val Gly Thr Ser Phe Gly Leu Pro Gln
2180                2185                2190

Thr Arg Arg Ile Ser Leu Ala Ser Pro Arg Gln Leu Phe Lys Ala
2195                2200                2205

Ser Asn Met Thr Gln Arg Trp Gln His Arg Glu Ile Ser Asn Phe
2210                2215                2220

Glu Tyr Leu Met Phe Leu Asn Thr Ile Ala Gly Arg Ser Tyr Asn
2225                2230                2235

Asp Leu Asn Gln Tyr Pro Val Phe Pro Trp Val Ile Thr Asn Tyr
2240                2245                2250

Glu Ser Glu Glu Leu Asp Leu Thr Leu Pro Thr Asn Phe Arg Asp
2255                2260                2265

Leu Ser Lys Pro Ile Gly Ala Leu Asn Pro Lys Arg Ala Ala Phe
2270                2275                2280

Phe Ala Glu Arg Tyr Glu Ser Trp Glu Asp Asp Gln Val Pro Lys
2285                2290                2295

Phe His Tyr Gly Thr His Tyr Ser Thr Ala Ser Phe Val Leu Ala
2300                2305                2310

Trp Leu Leu Arg Ile Glu Pro Phe Thr Thr Tyr Phe Leu Asn Leu
2315                2320                2325

Gln Gly Gly Lys Phe Asp His Ala Asp Arg Thr Phe Ser Ser Ile
2330                2335                2340

Ser Arg Ala Trp Arg Asn Ser Gln Arg Asp Thr Ser Asp Ile Lys
2345                2350                2355

Glu Leu Ile Pro Glu Phe Tyr Tyr Leu Pro Glu Met Phe Val Asn
2360                2365                2370

Phe Asn Asn Tyr Asn Leu Gly Val Met Asp Asp Gly Thr Val Val
2375                2380                2385

Ser Asp Val Glu Leu Pro Pro Trp Ala Lys Thr Ser Glu Glu Phe
2390                2395                2400

Val His Ile Asn Arg Leu Val Arg Ala Leu Glu Ser Glu Phe Val
2405                2410                2415

Ser Cys Gln Leu His Gln Trp Ile Asp Leu Ile Phe Gly Tyr Lys
2420                2425                2430

Gln Gln Gly Pro Glu Ala Val Arg Ala Leu Asn Val Phe Tyr Tyr
2435                2440                2445
```

-continued

```
Leu Thr Tyr Glu Gly Ala Val Asn Leu Asn Ser Ile Thr Asp Pro
    2450                2455                2460

Val Leu Arg Glu Ala Val Glu Ala Gln Ile Arg Ser Phe Gly Gln
    2465                2470                2475

Thr Pro Ser Gln Leu Leu Ile Glu Pro His Pro Pro Arg Gly Ser
    2480                2485                2490

Ala Met Gln Val Tyr Leu Leu Leu Gln Ser Pro Leu Met Phe Thr
    2495                2500                2505

Asp Lys Ala Gln Gln Asp Val Ile Met Val Leu Lys Phe Pro Ser
    2510                2515                2520

Asn Ser Pro Val Thr His Val Ala Ala Asn Thr Gln Pro Gly Leu
    2525                2530                2535

Ala Thr Pro Ala Val Ile Thr Val Thr Ala Asn Arg Leu Phe Ala
    2540                2545                2550

Val Asn Lys Trp His Asn Leu Pro Ala His Gln Gly Ala Val Gln
    2555                2560                2565

Asp Gln Pro Tyr Gln Leu Pro Val Glu Ile Asp Pro Leu Ile Gly
    2570                2575                2580

Leu Ser Leu Pro Ser Leu Phe Ala Ile His Ala Ser Asn Thr Gly
    2585                2590                2595

Met His Arg Arg Gln Ile Thr Asp Leu Leu Asp Gln Ser Ile Gln
    2600                2605                2610

Val His Ser Gln Cys Phe Val Ile Thr Ser Asp Asn Arg Tyr Ile
    2615                2620                2625

Leu Val Cys Gly Phe Trp Asp Lys Ser Phe Arg Val Tyr Ser Thr
    2630                2635                2640

Asp Thr Gly Arg Leu Ile Gln Val Val Phe Gly His Trp Asp Val
    2645                2650                2655

Val Thr Cys Leu Ala Arg Ser Glu Ser Tyr Ile Gly Gly Asn Cys
    2660                2665                2670

Tyr Ile Leu Ser Gly Ser Arg Asp Ala Thr Leu Leu Leu Trp Tyr
    2675                2680                2685

Trp Asn Gly Lys Cys Ser Gly Ile Gly Asp Asn Pro Gly Ser Glu
    2690                2695                2700

Thr Ala Ala Pro Arg Ala Ile Leu Thr Gly His Asp Tyr Glu Val
    2705                2710                2715

Thr Cys Ala Ala Val Cys Ala Glu Leu Gly Leu Val Leu Ser Gly
    2720                2725                2730

Ser Gln Glu Gly Pro Cys Leu Ile His Ser Met Asn Gly Asp Leu
    2735                2740                2745

Leu Arg Thr Leu Glu Gly Pro Glu Asn Cys Leu Lys Pro Lys Leu
    2750                2755                2760

Ile Gln Ala Ser Arg Glu Gly His Cys Val Ile Phe Tyr Glu Asn
    2765                2770                2775

Gly Leu Phe Cys Thr Phe Ser Val Asn Gly Lys Leu Gln Ala Thr
    2780                2785                2790

Met Glu Thr Asp Asp Asn Ile Arg Ala Ile Gln Leu Ser Arg Asp
    2795                2800                2805

Gly Gln Tyr Leu Leu Thr Gly Gly Asp Arg
    2810                2815
```